United States Patent
Tahri et al.

(10) Patent No.: US 9,845,321 B2
(45) Date of Patent: *Dec. 19, 2017

(54) 1,3-DIHYDRO-2H-BENZIMIDAZOL-2-ONE DERIVATIVES SUBSTITUTED WITH HETEROCYCLES AS RESPIRATORY SYNCYTIAL VIRUS ANTIVIRAL AGENTS

(71) Applicant: JANSSEN SCIENCES IRELAND UC, Little Island, County Cork (IE)

(72) Inventors: Abdellah Tahri, Anderlecht (BE); Tim Hugo Maria Jonckers, Heist-op-den-Berg (BE); Pierre Jean-Marie Bernard Raboisson, Rosieres (BE); Sandrine Marie Helene Vendeville, Woluwe-Saint-Pierre (BE); Lili Hu, Mechelen (BE); Samuel Dominique Demin, Antwerp (BE); Ludwig Paul Cooymans, Beerse (BE)

(73) Assignee: Janssen Sciences Ireland UC, Co Cork (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/991,815

(22) Filed: Jan. 8, 2016

(65) Prior Publication Data

US 2016/0122346 A1    May 5, 2016

Related U.S. Application Data

(63) Continuation of application No. 14/407,134, filed as application No. PCT/EP2013/062322 on Jun. 14, 2013, now abandoned.

(30) Foreign Application Priority Data

Jun. 15, 2012   (EP) ..................... 12172271
Aug. 31, 2012   (EP) ..................... 12182550

(51) Int. Cl.
| | | |
|---|---|---|
| C07D 471/02 | (2006.01) | |
| C07D 471/04 | (2006.01) | |
| C07D 403/14 | (2006.01) | |
| C07D 417/14 | (2006.01) | |
| C07D 519/00 | (2006.01) | |

(52) U.S. Cl.
CPC ......... *C07D 471/04* (2013.01); *C07D 403/14* (2013.01); *C07D 417/14* (2013.01); *C07D 519/00* (2013.01)

(58) Field of Classification Search
CPC .................................................. C07D 471/04
USPC ..................................................... 546/113
See application file for complete search history.

(56) References Cited

U.S. PATENT DOCUMENTS

| | | | |
|---|---|---|---|
| 6,489,338 B2 | 12/2002 | Yu et al. | |
| 6,506,738 B1 | 1/2003 | Yu et al. | |
| 6,534,535 B1 | 3/2003 | Zhu et al. | |
| 6,919,331 B2 | 7/2005 | Yu et al. | |
| 7,361,657 B2 | 4/2008 | Janssens et al. | |
| 7,528,149 B2 | 5/2009 | Janssens et al. | |
| 8,846,672 B2 | 9/2014 | Cooymans | |
| 8,865,705 B2 | 10/2014 | Cooymans et al. | |
| 8,921,560 B2* | 12/2014 | Cooymans ........... | C07D 471/04 546/113 |
| 8,927,720 B2 | 1/2015 | Cooymans | |
| 9,051,317 B2 | 6/2015 | Cooymans et al. | |
| 9,321,767 B2 | 4/2016 | Cooymans et al. | |
| 9,321,768 B2 | 4/2016 | Cooymans et al. | |
| 9,339,494 B2 | 5/2016 | Cooymans et al. | |
| 2002/0016309 A1 | 2/2002 | Yu et al. | |
| 2004/0166137 A1 | 8/2004 | Lackey | |
| 2011/0009444 A1 | 1/2011 | Dubois et al. | |

(Continued)

FOREIGN PATENT DOCUMENTS

| | | |
|---|---|---|
| FR | 2926556 | 7/2009 |
| JP | 2008522968 | 6/2006 |

(Continued)

OTHER PUBLICATIONS

Venkatesh et al., J. Pharm. Sci. 89, 145-54 (2000) (p. 146, left column).*
West (Solid-State Chemistry and Its Applications, 1984, John Wiley & Sons.*
Banker, et al., Modern Pharmaceutics, 3 edition, 1996, pp. 451 and 596.
Wang, et al., "Respiratory Syncytial virus Fusion Inhibitors. Part 5: Optimization of Benzimidazole Substitution Patterns Towards Derivatives with Improved Activity", Biorganic and Medicinal Chemistry Letters, vol. 17, 2007, pp. 4592-4598.
Beaulieu, et al., "Improved Replicon Cellular Activity of Non-Nucleoside Allosteric Inhibitors of HCV NS5B Polymerase: From Benzimidazole to Indole Scaffolds", Biorganic & Medicinal Chemistry letters 16, 2006, pp. 4987-4993.

(Continued)

*Primary Examiner* — Nizal Chandrakumar

(57) ABSTRACT

The present invention is concerned with novel 1,3-dihydro-2H-benzimidazol-2-one derivatives substituted with heterocycles having formula (I)

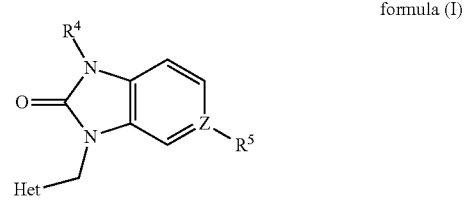

formula (I)

stereoisomeric forms thereof, and the pharmaceutically acceptable addition salts, and the solvates thereof, wherein $R^4$, $R^5$, Z and Het have the meaning defined in the claims. The compounds according to the present invention are useful as inhibitors on the replication of the respiratory syncytial virus (RSV). The invention further concerns the preparation of such novel compounds, compositions comprising these compounds, and the compounds for use in the treatment of respiratory syncytial virus infection.

18 Claims, No Drawings

(56) References Cited

U.S. PATENT DOCUMENTS

| | | |
|---|---|---|
| 2013/0261151 A1 | 10/2013 | Cooymans et al. |
| 2013/0267508 A1 | 10/2013 | Cooymans et al. |
| 2013/0267555 A1 | 10/2013 | Cooymans et al. |
| 2013/0267556 A1 | 10/2013 | Cooymans et al. |
| 2013/0324527 A1 | 12/2013 | Cooymans et al. |
| 2015/0073012 A1 | 3/2015 | Cooymans et al. |
| 2015/0073013 A1 | 3/2015 | Cooymans et al. |
| 2015/0111868 A1 | 4/2015 | Tahri et al. |
| 2015/0158862 A1 | 6/2015 | Tahri et al. |
| 2015/0166533 A1 | 6/2015 | Tahri et al. |
| 2015/0175608 A1 | 6/2015 | Tahri et al. |
| 2015/0231119 A1 | 8/2015 | Cooymans et al. |
| 2015/0259367 A1 | 9/2015 | Tahri et al. |
| 2016/0122346 A1 | 5/2016 | Tahri et al. |
| 2016/0237083 A1 | 8/2016 | Cooymans et al. |
| 2016/0237096 A1 | 8/2016 | Cooymans et al. |
| 2016/0251377 A1 | 9/2016 | Cooymans et al. |

FOREIGN PATENT DOCUMENTS

| | | |
|---|---|---|
| WO | WO 98/01428 | 1/1998 |
| WO | WO 00/20400 | 4/2000 |
| WO | 0035886 A2 | 6/2000 |
| WO | 0157019 A1 | 8/2001 |
| WO | 0157020 | 8/2001 |
| WO | WO 01/95910 | 12/2001 |
| WO | WO 02/26228 | 4/2002 |
| WO | WO 03/053344 | 4/2003 |
| WO | 03049688 A2 | 6/2003 |
| WO | 03056344 A2 | 7/2003 |
| WO | WO 2004069256 | 8/2004 |
| WO | 2006062465 A1 | 6/2006 |
| WO | 2006062565 A1 | 6/2006 |
| WO | WO 2008/147697 | 12/2008 |
| WO | 2012080447 | 6/2012 |
| WO | 2012080449 A1 | 6/2012 |
| WO | 2012080450 A1 | 6/2012 |
| WO | 2012080451 A1 | 6/2012 |
| WO | 2012080481 A1 | 6/2012 |
| WO | WO 2012080446 | 6/2012 |
| WO | 2013186335 A1 | 12/2013 |

OTHER PUBLICATIONS

Goodman, et al, Biotransformation of Drugs:, The Pharmacological Basis of Therapeutics, 8$^{th}$ ed., 1992, pp. 13-15.
Giampieri, et al., "Antiviral Activity of Indole Derivatives", Antiviral Research, vol. 83, 2009, pp. 179-185.
Wyde, et al., AWY Dentiviral Research, vol. 38, 1998, pp. 31-42.
Wolff, et al., "Burger's Medicinal Chemistry, 5$^{th}$ edition", Part I, pp. 975-977.
Wermuth, "Molecular Variations Based on Isosteric Replacements", Practice of Medicinal Chemistry 3$^{rd}$ edition, 2008, pp. 290-342.
Yu, et al., "Respiratory Syncytial Virus Fusion Inhibitors. Part 4: Optimization for Oral Bioavailability" Biorganic & Medicinal Chemistry letters, vol. 17, 2007, pp. 895-901.
Yu, et al., "Respiratory syncytial virus inhibitors. Part 2: Benzimidazol-2-one derivative" Biorg & Med Chem Letters, vol. 14 pp. 1133-1137.
Silverman, et al., The Organic of Drug Design and Drug Action, pp. 29-34.
Pearce, et al., "E-Novo: An Automated Workflow for efficient Structure-Based Lead Optimization" J. Chem. Inf. Model, 2009, vol. 49, pp. 1797-1809.
Ito, et al., "A Medium-Term Rat Liver Bioassay for Rapid in Vivo Detection of Carcinogenic Potential of Chemicals" Cancer Science, 94(1) 2003, pp. 3-8.

Database Registry Chemical Abstracts Service, Columbus, Ohio, Assession No. RN 941045-14-3 and RN 931665-23-5.Entered STN: Jul. 4, 2007 and Apr. 22, 2007.
Mackman, et al., "Discovery of an Oral Respiratory Syncytial Virus (RSV) Fusion Inhibitor (GS-5806) and Clinical Proof of Concept in a Human RSV Challenge Study", Journal of Medicinal Chemistry, 2015, vol. 58, pp. 1630-1643.
International Search Report—PCT/EP2011/073008, dated, Mar. 28, 2012.
International Search Report—PCT/EP2011/073011, dated, Mar. 27, 2012.
International Search Report—PCT/EP2011/073014, dated Mar. 28, 2012.
International Search Report—PCT/EP2011/073016, dated Mar. 27, 2012.
International Search Report—PCT/EP2011/073017, dated Mar. 28, 2012.
International Search Report—PCT/EP2013/062321, dated Jul. 16, 2013.
International Search Report—PCT/EP2013/062322, dated Aug. 21, 2013.
International Search Report—PCT/EP2013/062324, dated Jul. 18, 2013.
International Search Report—PCT/EP2013/062325, dated Jul. 18, 2013.
Provencal et al. Organic Process Research & Development (2004), 8(6), 903-908.
West, Solid-State Chemistry and Its Applications, 1984, John Wiley & Sons.
Ciapetti et al. In Chapter 15 Wermuth's the Practice of Medicinal Chemistry, 2008, 290-342.
Giampieri, et al., "Antiviral Activity of Indole Derivatives", Antiviral Research, vol. 83: pp. 179-185 (2009).
Goodman, et al, "Desymmetrization of Dichloroazaheterocycles", Tetrahedron, vol. 55: pp. 15067-15070 (1999).
Greene, et al., "Protection for the Hydroxyl Group Including 1,2- and 1,3-diols." Protective Groups in Organic Synthesis, 3rd edition, pp. 119-121 (1999). XP002670712.
Hallack, et al., "Glycosaminoglycan Sulfation Requirements for Respiratory Syncytial Virus Infection", Journal of Virology, vol. 74(22):pp. 10508-10513 (Nov. 2000).
Negishi, "3 Fluorine as an Organic Compound", Flourine Chemistry Towards New Functionality, pp. 89-90 (Jun. 30, 1988).
Nozaki, et al., "Chapter 5: Structure-Activity Relationship and Drug Design", Medicinal Chemistry, pp. 98-99 (Jul. 1, 1995).
Qidong, et al., Pharmaceutical Chemistry, Chemical Industry Press, Jan. 2004, pp. 32-34, 2004.
Tonelli, et al., Antiviral Activiey of Benzimidazole Derivatives I., Chemistry & Biodiversity, vol. 5(11):pp. 2386-2401 (2008).
Wang, et al., "Synthesis and Evaluation of Benzothiazole-Based Analogues as Novel, Potent, and Selective Fatty Acid Amide Hydrolase Inhibitors", J. Med. Chem., vol. 52: pp. 170-180 (2009).
Wermuth (Editor), "The Latest Medicinal Chemistry : Chapter 13—Molecular Variations based on Isosteric Replacement", The Latest Medicinal Chemistry, 1998, pp. 235-271, vol. 1.
Wermuth (Editor), "The Practice of Medicial Chemistry", The Lastest Medicinal Chemistry, 1993, pp. 375-380, vol. 1.
Wermuth, et al, The Practice of Medicinal Chemistry, Designing Prodrugs and Bioprecursors I: Carrier Prodrugs, 1996, pp. 672-696, vol. 31, Academic Press Limited.
Wolff, et al, Burger's Medicinal Chemistry and Drug Discovery, -, 1994, pp. 975-977, 5th Edition, vol. 1.
Yamanaka (Editor), "Introduction to Fluorine Chemistry: The Role of Fluorine Chemistry in Cutty Edge Technology", Japan Society for the Promotion of Science, 2005, pp. 398-403.

* cited by examiner

1,3-DIHYDRO-2H-BENZIMIDAZOL-2-ONE DERIVATIVES SUBSTITUTED WITH HETEROCYCLES AS RESPIRATORY SYNCYTIAL VIRUS ANTIVIRAL AGENTS

CROSS REFERENCE TO RELATED APPLICATIONS

This application is a continuation of U.S. application Ser. No. 14/407,134, filed Dec. 11, 2014, which is the national stage entry under 35 U.S.C. 371 of PCT Application No. PCT/EP2013/062322, filed Jun. 14, 2013, which application claims priority from European Patent Application No. EP 12182550.9, filed Aug. 31, 2012, which application claims priority from European Patent Application No. EP 12172271.4 filed Jun. 15, 2012, the entire disclosures of which are hereby incorporated by reference in their entirety.

FIELD OF THE INVENTION

The invention concerns novel 1,3-dihydro-2H-benzimidazol-2-one derivatives substituted with heterocycles having antiviral activity, in particular, having an inhibitory activity on the replication of the respiratory syncytial virus (RSV). The invention further concerns the preparation of such novel compounds, compositions comprising these compounds, and the compounds for use in the treatment of respiratory syncytial virus infection.

BACKGROUND

Human RSV or Respiratory Syncytial Virus is a large RNA virus, member of the family of Paramyxoviridae, subfamily pneumoviridae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue that provides an aerosol treatment for serious RSV infection in hospitalized children. The aerosol route of administration, the toxicity (risk of teratogenicity), the cost and the highly variable efficacy limit its use. The other two drugs, RespiGam® (RSV-IG) and Synagis® (palivizumab), polyclonal and monoclonal antibody immunostimulants, are intended to be used in a preventive way. Both are very expensive, and require parenteral administration.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication. It would be particularly preferred to provide drugs against RSV replication that could be administered perorally.

A reference on benzimidazole antiviral agents is WO-01/95910. Herein compounds are presented to have antiviral activity, yet with $EC_{50}$ values over a wide range of from 0.001 µm to as high as 50 µM (which does not normally represent the desired biological activity). Another reference, relating to substituted 2-methyl-benzimidazole RSV antiviral agents, in the same range of activities is WO-03/053344. Another related background reference on compounds in the same range of activities, is WO-02/26228 regarding benzimidazolone antiviral agents. A reference on structure-activity relations, in respect of RSV inhibition, of 5-substituted benzimidazole compounds is Kuo-Long Yu et al., Bioorganic and Medicinal Chemistry Letters 14 (2004) 1133-1137, Kuo-Long Yu et al., Bioorganic and Medicinal Chemistry Letters 17 (2007) 895-901, and X. A. Wang et al., Bioorganic and Medicinal Chemistry Letters 17 (2007) 4592-4598.

WO-2004/069256 discloses 2-cyanopyrrolopyrimidines as capthepsin K or S inhibitors useful in the treatment of various pain disorders. WO-2008/147697 discloses benzimidazole derivatives as chymase inhibitors.

WO-2012/080446, WO-2012/080447, WO-2012/080449, WO-2012/080450 and WO-2012/080481 all filed on 16 Dec. 2011 and published on 21 Jun. 2012 disclose benzimidazole derivatives having antiviral activity against respiratory syncytial virus.

It is desired to provide new drugs that have antiviral activity. Particularly, it would be desired to provide new drugs that have RSV replication inhibitory activity. Further, it would be desired to retrieve compound structures that allow obtaining antiviral biological activities of the order of magnitude in the stronger regions of the prior art (i.e. at the bottom of the above-mentioned range of up to 50 µM), and preferably at a level of about the most active, more preferably of even stronger activity, than the compounds disclosed in the art. A further desire is to find compounds having oral antiviral activity.

SUMMARY OF THE INVENTION

In order to better address one or more of the foregoing desires, the invention, in one aspect, presents antiviral compounds represented by formula (I),

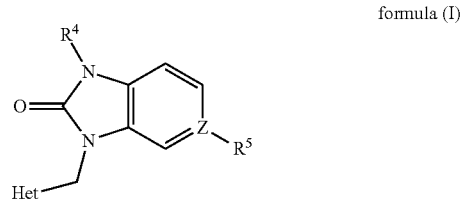

formula (I)

and stereoisomeric forms thereof, wherein
Het is a heterocycle having formula (b), (c), (d) or (e)

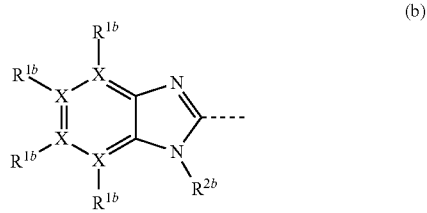

(b)

-continued

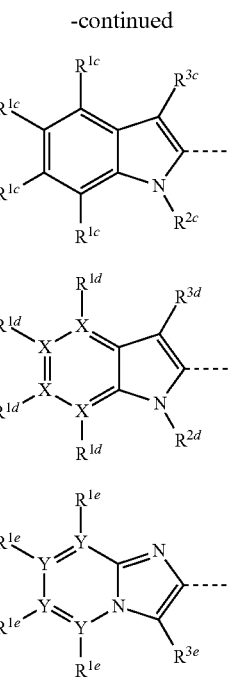

(c)

(d)

(e)

each X independently is C or N; provided that at least one X is N;
R$^{1b}$ is present when Het has formula (b) and X is C; each R$^{1b}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; R$^{1b}$ is absent when the X to which it is bound is N;
R$^{2b}$ is —(CR$^8$R$^9$)$_m$—R$^{10b}$;
each R$^6$ is independently selected from the group consisting of H, C$_1$-C$_6$alkyl, COOCH$_3$ and CONHSO$_2$CH$_3$;
each R$^7$ is independently selected from the group consisting of OH, C$_1$-C$_6$alkyloxy, NH$_2$, NHSO$_2$N(C$_1$-C$_6$alkyl)$_2$, NHSO$_2$NHCH$_3$, NHSO$_2$(C$_1$-C$_6$alkyl), NHSO$_2$(C$_3$-C$_7$cycloalkyl) and N(C$_1$-C$_6$-alkyl)$_2$;
each R$^8$ and R$^9$ are independently chosen from the group consisting of H, C$_1$-C$_{10}$alkyl and C$_3$-C$_7$cycloalkyl; or R$^8$ and R$^9$ taken together form a 4 to 6 membered aliphatic ring that optionally contains one or more heteroatoms selected from the group consisting of N, S and O;
R$^{10b}$ is selected from the group consisting of H, R$^{11}$, OH, CN, F, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, O-Benzyl, NR$^8$SO$_2$R$^9$, SO$_2$NR$^8$R$^9$, SO$_2$R$^8$, OCONR$^8$R$^9$, OCONR$^8$R$^{12}$, N(R$^8$)CON(R$^8$R$^9$), N(R$^8$)COOR$^{12}$, and a 4 to 6 membered saturated ring containing one oxygen atom;
m is an integer from 2 to 6;
R$^{11}$ is selected from the group consisting of C$_1$-C$_6$ alkyl, C$_3$-C$_7$cycloalkyl, phenyl, pyridinyl and pyrazolyl; each optionally substituted with one or more substituents each independently selected from the group consisting of CF$_3$, CH$_3$, OCH$_3$, OCF$_3$ and halogen;
R$^{12}$ is selected from the group consisting of phenyl, pyridinyl and pyrazolyl; each optionally substituted with one or more substituents each independently selected from the group consisting of CF$_3$, CH$_3$, OCH$_3$, OCF$_3$ and halogen; or R$^{12}$ is C$_1$-C$_6$ alkyl or C$_3$-C$_7$cycloalkyl; each substituted with one or more substituents each independently selected from the group consisting of CF$_3$, CH$_3$, OCH$_3$, OCF$_3$ and halogen;

R$^{1c}$ is present when Het has formula (c);
each R$^{1c}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^{7c}$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$;
R$^{3c}$ is selected from the group consisting of H, halogen, C$_1$-C$_6$alkyl, C$_3$-C$_7$cycloalkyl, C$_1$-C$_6$alkyloxy and CO(R$^{7c}$);
R$^{2c}$ is (CR$^8$R$^9$)$_m$—R$^{10c}$;
R$^{7c}$ is selected from the group consisting of OH, O(C$_1$-C$_6$alkyl), NH$_2$, NHSO$_2$N(C$_1$-C$_6$alkyl)$_2$, NHSO$_2$NHCH$_3$, NHSO$_2$(C$_1$-C$_6$alkyl), NHSO$_2$(C$_3$-C$_7$cycloalkyl), N(C$_1$-C$_6$-alkyl)$_2$, NR$^8$R$^9$ and NR$^9$R$^{10c}$;
R$^{10c}$ is selected from the group consisting of H, R$^{11}$, OH, CN, F, CF$_2$H, CF$_3$, C(=NOH)NH$_2$, CONR$^8$R$^9$, COOR$^8$, CONR$^8$SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$ and a 4 to 6 membered saturated ring containing one oxygen atom;
R$^{1d}$ is present when Het has formula (d) and X is C; each R$^{1d}$ is selected independently from the group consisting of H, OH, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; R$^{1d}$ is absent when the X to which it is bound is N;
R$^{3d}$ is selected from the group consisting of H, halogen, C$_1$-C$_6$alkyl, C$_3$-C$_7$cycloalkyl, C$_1$-C$_6$alkyloxy, and CO(R$^7$);
R$^{2d}$ is —(CR$^8$R$^9$)$_m$—R$^{10d}$;
R$^{10d}$ is selected from the group consisting of H, R$^{11}$, OH, CN, F, CF$_2$H, CF$_3$, CONR$^8$R$^9$, COOR$^8$, CONR$^8$SO$_2$R$^9$, CON(R$^8$)SO$_2$N(R$^8$R$^9$), NR$^8$R$^9$, NR$^8$COOR$_9$, OCOR$^8$, NR$^8$SO$_2$R$^9$, SO$_2$NR$^8$R$^9$, SO$_2$R$^8$ and a 4 to 6 membered saturated ring containing one oxygen atom;
each Y independently is C or N;
R$^{1e}$ is present when Het has formula (e) and Y is C; each R$^{1e}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; R$^{1e}$ is absent when the Y to which it is bound is N;
R$^{3e}$ is selected from the group consisting of H, halogen, —(CR$^8$R$^9$)$_m$—R$^{10e}$, C=C—CH$_2$—R$^{10e}$, C≡C—R$^{10e}$ and C=C—R$^{10e}$;
R$^{10e}$ is selected from the group consisting of H, R$^{11}$, C$_1$-C$_6$alkyloxy, OH, CN, F, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$ and a 4 to 6 membered saturated ring containing one oxygen atom;
R$^4$ is selected from the group consisting of tert-butyl, Het$^1$, aryl, Het$^2$, CH(CH$_3$)(CF$_3$), and C$_3$-C$_7$cycloalkyl substituted with one or more substituents selected from the group consisting of halo and C$_1$-C$_4$alkyl;
aryl represents phenyl or naphthalenyl; said aryl optionally being substituted with one or more substituents each independently selected from the group consisting of halo, C$_1$-C$_4$alkyloxy, C$_1$-C$_4$alkyl, OH, CN, CF$_2$H, CF$_3$, CF$_3$O, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$, OCONR$^8$R$^9$, OCONR$^8$R$^{12}$, N(R$^8$)CON(R$^8$R$^9$), N(R$^8$)COOR$^{12}$, or C$_{1-4}$alkyloxy, C$_{1-4}$alkyloxy;

Het$^1$ represents a 4 to 6 membered saturated ring containing one N atom, optionally being substituted with one or more substituents each independently selected from the group consisting of halo, $C_1$-$C_4$alkyloxy, $SO_2R^8$, $C_1$-$C_4$alkylcarbonyl, CO(aryl), COHet$^2$, $C_1$-$C_4$alkyloxycarbonyl, pyridinyl, $CF_3$, $SO_2N(C_1$-$C_4$alkyl)$_2$, $SO_2NH(C_1$-$C_4$alkyl), (C=O)NH($C_{1-4}$alkyl), (C=S)NH($C_{1-4}$alkyl), $C_1$-$C_4$alkyl and $C_1$-$C_4$alkyl substituted with one hydroxy; or Het$^1$ represents a 4 to 6 membered saturated ring containing one O atom, substituted with one or more substituents each independently selected from the group consisting of halo, $C_1$-$C_4$alkyloxy, $CF_3$, NH(C=O)($C_{1-4}$alkyl), (C=O)NH($C_{1-4}$alkyl) and $C_1$-$C_4$alkyl; or Het$^1$ represents a bicyclic 7 to 11 membered non-aromatic heterocycle containing one or two heteroatoms each independently selected from the group consisting of O, S and N, optionally substituted with one or more substituents each independently selected from the group consisting of halo, $C_1$-$C_4$alkyloxy, $SO_2R^8$, $C_1$-$C_4$alkylcarbonyl, CO(aryl), COHet$^2$, $C_1$-$C_4$alkyloxycarbonyl, pyridinyl, $CF_3$, $SO_2N(C_1$-$C_4$alkyl)$_2$, $SO_2NH(C_1$-$C_4$alkyl), (C=O)NH($C_{1-4}$alkyl), (C=S)NH($C_{1-4}$alkyl), $C_1$-$C_4$alkyl and $C_1$-$C_4$alkyl substituted with one hydroxy;

Het$^2$ represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N; said Het$^2$ optionally being substituted with one or more substituents each independently selected from the group consisting of halo, $C_1$-$C_4$alkyloxy, $C_1$-$C_4$alkyl, OH, CN, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$, $OCONR^8R^9$, $OCONR^8R^{12}$, $N(R^8)CON(R^8R^9)$, $N(R^8)COOR^{12}$;

Z is C or N; $R^5$ is present where Z is C, whereby $R^5$ is selected form the group consisting of hydrogen, $CF_3$ and halogen; $R^5$ is absent where Z is N;

and the pharmaceutically acceptable addition salts, and the solvates thereof.

In another aspect, the invention relates to the foregoing compounds for use in the treatment of RSV infections in warm-blooded animals, preferably humans. In yet another aspect, the invention presents a method of treatment of viral RSV infections in a subject in need thereof, comprising administering to said subject an effective amount of a compound as defined above. In still another aspect, the invention resides in the use of a compound as defined above, for the manufacture of a medicament in the treatment of RSV infections.

In a further aspect, the invention relates to a pharmaceutical composition comprising a compound as defined above, and a pharmaceutically acceptable excipient.

In a still further aspect, the invention provides methods for preparing the compounds defined above.

DETAILED DESCRIPTION OF THE INVENTION

The invention, in a broad sense, is based on the judicious recognition that the compounds of Formula (I) generally possess an interesting RSV inhibitory activity. Moreover, these compounds enable access to anti-RSV activities at the higher regions (lower end of the $EC_{50}$ values) of the range available in the aforementioned references. Particularly, on the basis of these compounds, molecular structures can be uncovered that even outperform the reference compounds in terms of biological activities.

The present invention will further be described with respect to particular embodiments and with reference to certain examples but the invention is not limited thereto but only by the claims. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Whenever the term "substituted" is used in the present invention, it is meant, unless otherwise is indicated or is clear from the context, to indicate that one or more hydrogens, in particular from 1 to 4 hydrogens, preferably from 1 to 3 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

As used herein "$C_1$-$C_4$alkyl" or "$C_{1-4}$alkyl" as a group or part of a group defines straight or branched chain saturated hydrocarbon radicals having from 1 to 4 carbon atoms such as methyl, ethyl, propyl, 1-methylethyl, butyl and the like.

As used herein "$C_1$-$C_6$alkyl" as a group or part of a group defines straight or branched chain saturated hydrocarbon radicals having from 1 to 6 carbon atoms such as methyl, ethyl, propyl, 1-methylethyl, butyl, pentyl, hexyl, 2-methylbutyl and the like.

"$C_1$-$C_{10}$alkyl" as a group or part of a group defines straight or branched chain saturated hydrocarbon radicals having from 1 to 10 carbon atoms such as the groups defined for $C_1$-$C_6$alkyl and heptyl, octyl, nonyl, 2-methylhexyl, 2-methylheptyl, decyl, 2-methylnonyl, and the like.

The term "$C_2$-$C_{10}$alkenyl" used herein as a group or part of a group is meant to comprise straight or branched chain unsaturated hydrocarbon radicals having at least one double bond, and preferably having one double bond, and from 2 to 10 carbon atoms such as ethenyl, propenyl, buten-1-yl, buten-2-yl, penten-1-yl, penten-2-yl, hexen-1-yl, hexen-2-yl, hexen-3-yl, 2-methylbuten-1-yl, hepten-1-yl, hepten-2-yl, hepten-3-yl, hepten-4-yl, 2-methylhexen-1-yl, octen-1-yl, octen-2-yl, octen-3-yl, octen-4-yl, 2-methylhepten-1-yl, nonen-1-yl, nonen-2-yl, nonen-3-yl, nonen-4-yl, nonen-5-yl, 2-methylocten-1-yl, decen-1-yl, decen-2-yl, decen-3-yl, decen-4-yl, decen-5-yl, 2-methylnonen-1-yl, and the like.

Whenever a "$C_2$-$C_{10}$alkenyl" group is linked to a heteroatom it preferably is linked via a saturated carbon atom.

"$C_1$-$C_4$alkyloxy" or "$C_1$-$C_4$alkoxy", as a group or part of a group defines an O—$C_1$-$C_4$alkyl radical, wherein $C_1$-$C_4$alkyl has, independently, the meaning given above.

"$C_1$-$C_6$alkyloxy" or "$C_1$-$C_6$alkoxy", as a group or part of a group defines an O—$C_1$-$C_6$alkyl radical, wherein $C_1$-$C_6$alkyl has, independently, the meaning given above.

The term "$C_3$-$C_7$cycloalkyl" alone or in combination, refers to a cyclic saturated hydrocarbon radical having from 3 to 7 carbon atoms. Non-limiting examples of suitable $C_3$-$C_7$cycloalkyl include cyclopropyl, cyclobutyl, cyclopentyl, cyclohexyl and cycloheptyl.

The term "—$(CR^8R^9)_m$—" used herein defines m repetitions of the $CR^8R^9$ subgroup, wherein each of these subgroups is independently defined.

The term "halo" or "halogen" as a group or part of a group is generic for fluoro, chloro, bromo, iodo unless otherwise is indicated or is clear from the context.

A term of the form NRCOOR is identical to N(R)COOR.

Examples of (but not limited to) a 4 to 6 membered aliphatic ring optionally containing one or more heteroatoms selected from the group consisting of N, S and O, as used in the definitions of $R^8$ and $R^9$, are cyclobutyl, cyclopentyl, cyclohexyl, piperidinyl, oxetanyl, tetrahydrofuranyl, tetrahydropyranyl, piperidinyl, azetidinyl, thiolanyl, piperazinyl, pyrrolidinyl.

An example of (but not limited to) $Het^2$ is thiazolyl or quinolinyl.

An example of (but not limited to) $Het^1$ is azetidinyl.

It should be noted that the radical positions on any molecular moiety used in the definitions may be anywhere on such moiety as long as it is chemically stable. Radicals used in the definitions of the variables include all possible isomers unless otherwise indicated. For instance pentyl includes 1-pentyl, 2-pentyl and 3-pentyl.

When any variable occurs more than one time in any constituent, each definition is independent.

Hereinbefore and hereinafter, the term "compound of formula (I)" or "compounds of formula (I)" is meant to include the stereoisomeric forms thereof, and the pharmaceutically acceptable addition salts, and the solvates thereof.

The terms "stereoisomers", "stereoisomeric forms" or "stereochemically isomeric forms" hereinbefore or hereinafter are used interchangeably.

The term "stereochemically isomeric forms" as used hereinbefore defines all the possible compounds made up of the same atoms bonded by the same sequence of bonds but having different three-dimensional structures which are not interchangeable, which the compounds of formula (I) may possess.

It will be appreciated that some of the compounds of formula (I) may contain one or more centers of chirality and exist as stereochemically isomeric forms.

The invention includes all stereoisomers of the compound of Formula (I), either as a pure stereoisomer or as a mixture of two or more stereoisomers.

Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof, whenever chemically possible.

The absolute configuration is specified according to the Cahn-Ingold-Prelog system. The configuration at an asymmetric atom is specified by either R or S. Resolved compounds whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

Some of the compounds according to formula (I) may also exist in their tautomeric form. Such forms although not explicitly indicated in the above formula are intended to be included within the scope of the present invention.

Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

For some of the compounds of formula (I) and stereoisomeric forms thereof, and the pharmaceutically acceptable addition salts, and the solvates thereof; and intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butane-dioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term solvate comprises the hydrates and solvent addition forms which the compounds of Formula (I) are able to form, as well as the salts thereof. Examples of such forms are e.g. hydrates, alcoholates and the like.

It will be appreciated that the compounds of the invention, with reference to the aforementioned left- and right-hand parts of formula I, present a wide variety of modification.

Without detracting from the overall scope of the invention, certain embodiments are discussed in more detail below.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to Formula (I) which contains at least one radioactive atom. For example, a compound can be labelled with positron or with gamma emitting radioactive isotopes. For radioligand-binding techniques, the $^3$H-atom or the $^{125}$I-atom is the atom of choice to be replaced. For imaging, the most commonly used positron emitting (PET) radioactive isotopes are $^{11}$C, $^{18}$F, $^{15}$O and $^{13}$N, all of which are accelerator produced and have half-lives of 20, 100, 2 and 10 minutes (min) respectively. Since the half-lives of these radioactive isotopes are so short, it is only feasible to use them at institutions which have an accelerator on site for their production, thus limiting their use. The most widely used of these are $^{18}$F, $^{99m}$Tc, $^{201}$Tl and $^{123}$I. The handling of these radioactive isotopes, their production, isolation and incorporation in a molecule are known to the skilled person.

In particular, the radioactive atom is selected from the group of hydrogen, carbon, nitrogen, sulfur, oxygen and halogen. In particular, the radioactive isotope is selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br.

The terms described above and others used in the specification are well understood to those in the art.

Preferred features of the compounds of this invention are now set forth.

In an embodiment, the present invention concerns novel compounds of Formula (I) and stereoisomeric forms thereof, wherein Het is a heterocycle having formula (b), (c), (d) or (e);

each X independently is C or N; provided that at least one X is N;

$R^{1b}$ is present when Het has formula (b) and X is C; each $R^{1b}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, $CN$, $C(=NOH)NH_2$, $C(=NOCH_3)NH_2$, $C(=NH)NH_2$, $CF_3$, $OCF_3$, $B(OH)_2$ and $B(O-C_1-C_6alkyl)_2$; $R^{1b}$ is absent when the X to which it is bound is N;

$R^{2b}$ is —$(CR^8R^9)_m$—$R^{10b}$;

each $R^6$ is independently selected from the group consisting of H, $C_1$-$C_6$alkyl, $COOCH_3$ and $CONHSO_2CH_3$;

each $R^7$ is independently selected from the group consisting of OH, $C_1$-$C_6$alkyloxy, $NH_2$, $NHSO_2N(C_1$-$C_6$alkyl$)_2$, $NHSO_2NHCH_3$, $NHSO_2(C_1$-$C_6$alkyl), $NHSO_2(C_3$-$C_7$cycloalkyl) and $N(C_1$-$C_6$-alkyl$)_2$;

each $R^8$ and $R^9$ are independently chosen from the group consisting of H, $C_1$-$C_{10}$alkyl and $C_3$-$C_7$cycloalkyl; or $R^8$ and $R^9$ taken together form a 4 to 6 membered aliphatic ring that optionally contains one or more heteroatoms selected from the group consisting of N, S and O;

$R^{10b}$ is selected from the group consisting of H, $R^{11}$, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, O-Benzyl, $NR^8SO_2R^9$, $SO_2NR^8R^9$, $SO_2R^8$, $OCONR^8R^9$, $OCONR^8R^{12}$, $N(R^8)CON(R^8R^9)$, $N(R^8)COOR^{12}$, and a 4 to 6 membered saturated ring containing one oxygen atom;

m is an integer from 2 to 6;

$R^{11}$ is selected from the group consisting of $C_1$-$C_6$ alkyl, $C_3$-$C_7$cycloalkyl, phenyl, pyridinyl and pyrazolyl; each optionally substituted with one or more substituents each independently selected from the group consisting of $CF_3$, $CH_3$, $OCH_3$, $OCF_3$ and halogen;

$R^{12}$ is selected from the group consisting of phenyl, pyridinyl and pyrazolyl; each optionally substituted with one or more substituents each independently selected from the group consisting of $CF_3$, $CH_3$, $OCH_3$, $OCF_3$ and halogen; or $R^{12}$ is $C_1$-$C_6$ alkyl or $C_3$-$C_7$cycloalkyl; each substituted with one or more substituents each independently selected from the group consisting of $CF_3$, $CH_3$, $OCH_3$, $OCF_3$ and halogen;

$R^{1c}$ is present when Het has formula (c);

each $R^{1c}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^{7c})$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O-C_1-C_6alkyl)_2$;

$R^{3c}$ is selected from the group consisting of H, halogen, $C_1$-$C_6$alkyl, $C_3$-$C_7$cycloalkyl, $C_1$-$C_6$alkyloxy and $CO(R^{7c})$;

$R^{2c}$ is —$(CR^8R^9)_m$—$R^{10c}$;

$R^{7c}$ is selected from the group consisting of OH, $O(C_1$-$C_6$alkyl), $NH_2$, $NHSO_2N(C_1$-$C_6$alkyl$)_2$, $NHSO_2NHCH_3$, $NHSO_2(C_1$-$C_6$alkyl), $NHSO_2(C_3$-$C_7$cycloalkyl), $N(C_1$-$C_6$-alkyl$)_2$, $NR^8R^9$ and $NR^9R^{10c}$;

$R^{10c}$ is selected from the group consisting of H, $C_1$-$C_6$alkyl, OH, CN, F, $CF_2H$, $CF_3$, $C(=NOH)NH_2$, $CONR^8R^9$, $COOR^8$, $CONR^8SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$ and a 4 to 6 membered saturated ring containing one oxygen atom;

$R^{1d}$ is present when Het has formula (d) and X is C; each $R^{1d}$ is selected independently from the group consisting of H, OH, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O$—$C_1$-$C_6$alkyl$)_2$; $R^{1d}$ is absent when the X to which it is bound is N;

$R^{3d}$ is selected from the group consisting of H, halogen, $C_1$-$C_6$alkyl, $C_3$-$C_7$cycloalkyl, $C_1$-$C_6$alkyloxy, and $CO(R^7)$;

$R^{2d}$ is —$(CR^8R^9)_m$—$R^{10d}$;

$R^{10d}$ is selected from the group consisting of H, $C_1$-$C_6$alkyl, OH, CN, F, $CF_2H$, $CF_3$, $CONR^8R^9$, $COOR^8$, $CONR^8SO_2R^9$, $CON(R^8)SO_2N(R^8R^9)$, $NR^8R^9$, $NR^8COOR_9$, $OCOR^8$, $NR^8SO_2R^9$, $SO_2NR^8R^9$, $SO_2R^8$ and a 4 to 6 membered saturated ring containing one oxygen atom;

each Y independently is C or N;

$R^{1e}$ is present when Het has formula (e) and Y is C; each $R^{1e}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O$—$C_1$-$C_6$alkyl$)_2$; $R^{1e}$ is absent when the Y to which it is bound is N;

$R^{3e}$ is selected from the group consisting of H, halogen, —$(CR^8R^9)_m$—$R^{10e}$ $C=C$—$CH_2$—$R^{10e}$, $C\equiv C$—$R^{10e}$ and $C=C$—$R^{10e}$;

$R^{10e}$ is selected from the group consisting of H, $C_1$-$C_6$alkyl, $C_1$-$C_6$alkyloxy, $C_3$-$C_7$cycloalkyl, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$ and a 4 to 6 membered saturated ring containing one oxygen atom;

$R^4$ is selected from the group consisting of tert-butyl, $Het^1$, aryl, $Het^2$, $CH(CH_3)(CF_3)$, and $C_3$-$C_7$cycloalkyl substituted with one or more substituents selected from the group consisting of halo and $C_1$-$C_4$alkyl;

aryl represents phenyl or naphthalenyl; said aryl optionally being substituted with one or more substituents each independently selected from the group consisting of halo, $C_1$-$C_4$alkyloxy, $C_1$-$C_4$alkyl, OH, CN, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$, $OCONR^8R^9$, $OCONR^8R^{12}$, $N(R^8)CON(R^8R^9)$, $N(R^8)COOR^{12}$;

$Het^1$ represents a 4 to 6 membered saturated ring containing one N atom, optionally being substituted with one or more substituents each independently selected from the group consisting of halo, $C_1$-$C_4$alkyloxy, $SO_2R^8$, $C_1$-$C_4$alkylcarbonyl, CO(aryl), $COHet^2$, $C_1$-$C_4$alkyloxycarbonyl, pyridinyl, $CF_3$, $SO_2N(C_1$-$C_4$alkyl$)_2$, $SO_2NH(C_1$-$C_4$alkyl), $(C=O)NH(C_{1-4}$alkyl), $(C=S)NH(C_{1-4}$alkyl), $C_1$-$C_4$alkyl and $C_1$-$C_4$alkyl substituted with one hydroxy; or $Het^1$ represents a 4 to 6 membered saturated ring containing one O atom, substituted with one or more substituents each independently selected from the group consisting of halo, $C_1$-$C_4$alkyloxy, $CF_3$, $NH(C=O)(C_{1-4}$alkyl), $(C=O)NH(C_{1-4}$alkyl) and $C_1$-$C_4$alkyl; or $Het^1$ represents a bicyclic 7 to 11 membered non-aromatic heterocycle containing one or two heteroatoms each independently selected from the group consisting of O, S and N, optionally substituted with one or more substituents each independently selected from the group consisting of halo, $C_1$-$C_4$alkyloxy, $SO_2R^8$, $C_1$-$C_4$alkylcarbonyl, CO(aryl), $COHet^2$, $C_1$-$C_4$alkyloxycarbonyl, pyridinyl, $CF_3$, $SO_2N(C_1$-$C_4$alkyl$)_2$, $SO_2NH(C_1$-$C_4$alkyl), $(C=O)NH(C_{1-4}$alkyl), $(C=S)NH(C_{1-4}$alkyl), $C_1$-$C_4$alkyl and $C_1$-$C_4$alkyl substituted with one hydroxy;

$Het^2$ represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N; said $Het^2$ optionally being substituted with one or more substituents each independently selected from the group consisting of halo, $C_1$-$C_4$alkyloxy, $C_1$-$C_4$alkyl, OH, CN, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$, $OCONR^8R^9$, $OCONR^8R^{12}$, $N(R^8)CON(R^8R^9)$, $N(R^8)COOR^{12}$;

Z is C or N; $R^5$ is present where Z is C, whereby $R^5$ is selected form the group consisting of hydrogen, $CF_3$ and halogen; $R^5$ is absent where Z is N;

and the pharmaceutically acceptable addition salts, and the solvates thereof.

In an embodiment, the present invention concerns novel compounds of Formula (I) and stereoisomeric forms thereof, wherein Het is a heterocycle having formula (b), (c), (d) or (e);

each X independently is C or N; provided that at least one X is N;

$R^{1b}$ is present when Het has formula (b) and X is C; each $R^{1b}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O$—$C_1$-$C_6$alkyl$)_2$; $R^{1b}$ is absent when the X to which it is bound is N;

$R^{2b}$ is —$(CR^8R^9)_m$—$R^{10b}$;

each $R^6$ is independently selected from the group consisting of H, $C_1$-$C_6$alkyl, $COOCH_3$ and $CONHSO_2CH_3$;

each $R^7$ is independently selected from the group consisting of OH, $C_1$-$C_6$alkyloxy, $NH_2$, $NHSO_2N(C_1$-$C_6$alkyl$)_2$, $NHSO_2NHCH_3$, $NHSO_2(C_1$-$C_6$alkyl), $NHSO_2(C_3$-$C_7$cycloalkyl) and $N(C_1$-$C_6$-alkyl$)_2$;

each $R^8$ and $R^9$ are independently chosen from the group consisting of H, $C_1$-$C_{10}$alkyl and $C_3$-$C_7$cycloalkyl; or $R^8$ and $R^9$ taken together form a 4 to 6 membered aliphatic ring that optionally contains one or more heteroatoms selected from the group consisting of N, S and O;

$R^{10b}$ is selected from the group consisting of H, $R^{11}$, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, O-Benzyl, $NR^8SO_2R^9$, $SO_2NR^8R^9$, $SO_2R^8$, $OCONR^8R^9$, $OCONR^8R^{12}$, $N(R^8)CON(R^8R^9)$, $N(R^8)COOR^{12}$, and a 4 to 6 membered saturated ring containing one oxygen atom;

m is an integer from 2 to 6;

$R^{11}$ is selected from the group consisting of $C_1$-$C_6$ alkyl, $C_3$-$C_7$cycloalkyl, phenyl, pyridinyl and pyrazolyl; each optionally substituted with one or more substituents each independently selected from the group consisting of $CF_3$, $CH_3$, $OCH_3$, $OCF_3$ and halogen;

$R^{12}$ is selected from the group consisting of phenyl, pyridinyl and pyrazolyl; each optionally substituted with one or more substituents each independently selected from the group consisting of $CF_3$, $CH_3$, $OCH_3$, $OCF_3$ and halogen; or $R^{12}$ is $C_1$-$C_6$ alkyl or $C_3$-$C_7$cycloalkyl; each substituted with one or more substituents each independently selected from the group consisting of $CF_3$, $CH_3$, $OCH_3$, $OCF_3$ and halogen;

$R^{1c}$ is present when Het has formula (c);

each $R^{1c}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^{7c})$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O\text{---}C_1\text{-}C_6alkyl)_2$;

$R^{3c}$ is selected from the group consisting of H, halogen, $C_1$-$C_6$alkyl, $C_3$-$C_7$cycloalkyl, $C_1$-$C_6$alkyloxy and $CO(R^{7c})$;

$R^{2c}$ is ---$(CR^8R^9)_m$---$R^{10c}$;

$R^{7c}$ is selected from the group consisting of OH, $O(C_1$-$C_6$alkyl), $NH_2$, $NHSO_2N(C_1$-$C_6$alkyl$)_2$, $NHSO_2NHCH_3$, $NHSO_2(C_1$-$C_6$alkyl), $NHSO_2(C_3$-$C_7$cycloalkyl), $N(C_1$-$C_6$-alkyl$)_2$, $NR^8R^9$ and $NR^9R^{10c}$;

$R^{10c}$ is selected from the group consisting of H, $C_1$-$C_6$alkyl, OH, CN, F, $CF_2H$, $CF_3$, $C(=NOH)NH_2$, $CONR^8R^9$, $COOR^8$, $CONR^8SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$ and a 4 to 6 membered saturated ring containing one oxygen atom;

$R^{1d}$ is present when Het has formula (d) and X is C; each $R^{1d}$ is selected independently from the group consisting of H, OH, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O\text{---}C_1\text{-}C_6alkyl)_2$; $R^{1d}$ is absent when the X to which it is bound is N;

$R^{3d}$ is selected from the group consisting of H, halogen, $C_1$-$C_6$alkyl, $C_3$-$C_7$cycloalkyl, $C_1$-$C_6$alkyloxy, and $CO(R^7)$;

$R^{2d}$ is ---$(CR^8R^9)_m$---$R^{10d}$;

$R^{10d}$ is selected from the group consisting of H, $C_1$-$C_6$alkyl, OH, CN, F, $CF_2H$, $CF_3$, $CONR^8R^9$, $COOR^8$, $CONR^8SO_2R^9$, $CON(R^8)SO_2N(R^8R^9)$, $NR^8R^9$, $NR^8COOR_9$, $OCOR^8$, $NR^8SO_2R^9$, $SO_2NR^8R^9$, $SO_2R^8$ and a 4 to 6 membered saturated ring containing one oxygen atom;

each Y independently is C or N;

$R^{1e}$ is present when Het has formula (e) and Y is C; each $R^{1e}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O\text{---}C_1\text{-}C_6alkyl)_2$; $R^{1e}$ is absent when the Y to which it is bound is N;

$R^{3e}$ is selected from the group consisting of H, halogen, ---$(CR^8R^9)_m$---$R^{10e}$, $C=C\text{---}CH_2R^{10e}$, $C=C\text{---}R^{10e}$ and $C=C\text{---}R^{10e}$;

$R^{10e}$ is selected from the group consisting of H, $C_1$-$C_6$alkyl, $C_1$-$C_6$alkyloxy, $C_3$-$C_7$cycloalkyl, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$ and a 4 to 6 membered saturated ring containing one oxygen atom;

$R^4$ is selected from the group consisting of tert-butyl, $Het^1$, aryl, $Het^2$, $CH(CH_3)(CF_3)$, and $C_3$-$C_7$cycloalkyl substituted with one or more substituents selected from the group consisting of halo and $C_1$-$C_4$alkyl;

aryl represents phenyl or naphthalenyl; said aryl optionally being substituted with one or more substituents each independently selected from the group consisting of halo, $C_1$-$C_4$alkyloxy, $C_1$-$C_4$alkyl, OH, CN, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$, $OCONR^8R^9$, $OCONR^8R^{12}$, $N(R^8)CON(R^8R^9)$, $N(R^8)COOR^{12}$;

$Het^1$ represents a 4 to 6 membered saturated ring containing one N atom, optionally being substituted with one or more substituents each independently selected from the group consisting of halo, $C_1$-$C_4$alkyloxy, $SO_2R^8$, $C_1$-$C_4$alkylcarbonyl, CO(aryl), $COHet^2$, $C_1$-$C_4$alkyloxycarbonyl, pyridinyl, $CF_3$, $SO_2N(C_1$-$C_4$alkyl$)_2$, $SO_2NH(C_1$-$C_4$alkyl), $(C=O)NH(C_{1-4}$alkyl), $(C=S)NH(C_{1-4}$alkyl), $C_1$-$C_4$alkyl and $C_1$-$C_4$alkyl substituted with one hydroxy; or $Het^1$ represents a 4 to 6 membered saturated ring containing one O atom, substituted with one or more substituents each independently selected from the group consisting of halo, $C_1$-$C_4$alkyloxy, $CF_3$, $NH(C=O)(C_{1-4}$alkyl), $(C=O)NH(C_{1-4}$alkyl) and $C_1$-$C_4$alkyl;

$Het^2$ represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N; said $Het^2$ optionally being substituted with one or more substituents each independently selected from the group consisting of halo, $C_1$-$C_4$alkyloxy, $C_1$-$C_4$alkyl, OH, CN, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$, $OCONR^8R^9$, $OCONR^8R^{12}$, $N(R^8)CON(R^8R^9)$, $N(R^8)COOR^{12}$;

Z is C or N; $R^5$ is present where Z is C, whereby $R^5$ is selected form the group consisting of hydrogen, $CF_3$ and halogen; $R^5$ is absent where Z is N;

and the pharmaceutically acceptable addition salts, and the solvates thereof.

In an embodiment, the present invention concerns novel compounds of Formula (I) and stereoisomeric forms thereof, wherein Het is a heterocycle having formula (b), (c), (d) or (e);

each X independently is C or N; provided that at least one X is N;

$R^{1b}$ is present when Het has formula (b) and X is C; each $R^{1b}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O\text{---}C_1\text{-}C_6alkyl)_2$; $R^{1b}$ is absent when the X to which it is bound is N;

$R^{2b}$ is ---$(CR^8R^9)_m$---$R^{10b}$;

each $R^6$ is independently selected from the group consisting of H, $C_1$-$C_6$alkyl, $COOCH_3$ and $CONHSO_2CH_3$;

each $R^7$ is independently selected from the group consisting of OH, $C_1$-$C_6$alkyloxy, $NH_2$, $NHSO_2N(C_1$-$C_6$alkyl$)_2$, $NHSO_2NHCH_3$, $NHSO_2(C_1$-$C_6$alkyl), $NHSO_2(C_3$-$C_7$cycloalkyl) and $N(C_1$-$C_6$-alkyl$)_2$;

each $R^8$ and $R^9$ are independently chosen from the group consisting of H, $C_1$-$C_{10}$alkyl and $C_3$-$C_7$cycloalkyl; or $R^8$ and $R^9$ taken together form a 4 to 6 membered aliphatic ring that optionally contains one or more heteroatoms selected from the group consisting of N, S and O;

$R^{10b}$ is selected from the group consisting of H, $R^{11}$, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, O-Benzyl, $NR^8SO_2R^9$, $SO_2NR^8R^9$, $SO_2R^8$, $OCONR^8R^9$, OCONR$^8$R$^{12}$, N(R$^8$)CON(R$^8$R$^9$), N(R$^8$)COOR$^{12}$, and a 4 to 6 membered saturated ring containing one oxygen atom;

m is an integer from 2 to 6;

R$^{11}$ is selected from the group consisting of C$_1$-C$_6$ alkyl, C$_3$-C$_7$cycloalkyl, phenyl, pyridinyl and pyrazolyl; each optionally substituted with one or more substituents each independently selected from the group consisting of CF$_3$, CH$_3$, OCH$_3$, OCF$_3$ and halogen;

R$^{12}$ is selected from the group consisting of phenyl, pyridinyl and pyrazolyl; each optionally substituted with one or more substituents each independently selected from the group consisting of CF$_3$, CH$_3$, OCH$_3$, OCF$_3$ and halogen; or R$^{12}$ is C$_1$-C$_6$ alkyl or C$_3$-C$_7$cycloalkyl; each substituted with one or more substituents each independently selected from the group consisting of CF$_3$, CH$_3$, OCH$_3$, OCF$_3$ and halogen;

R$^{1c}$ is present when Het has formula (c);

each R$^{1c}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^{7c}$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$;

R$^{3c}$ is selected from the group consisting of H, halogen, C$_1$-C$_6$alkyl, C$_3$-C$_7$cycloalkyl, C$_1$-C$_6$alkyloxy and CO(R$^{7c}$);

R$^{2c}$ is —(CR$^8$R$^9$)$_m$—R$^{10e}$,

R$^{7c}$ is selected from the group consisting of OH, O(C$_1$-C$_6$alkyl), NH$_2$, NHSO$_2$N(C$_1$-C$_6$alkyl)$_2$, NHSO$_2$NHCH$_3$, NHSO$_2$(C$_1$-C$_6$alkyl), NHSO$_2$(C$_3$-C$_7$cycloalkyl), N(C$_1$-C$_6$-alkyl)$_2$, NR$^8$R$^9$ and NR$^9$R$^{10c}$;

R$^{10c}$ is selected from the group consisting of H, C$_1$-C$_6$alkyl, OH, CN, F, CF$_2$H, CF$_3$, C(=NOH)NH$_2$, CONR$^8$R$^9$, COOR$^8$, CONR$^8$SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$ and a 4 to 6 membered saturated ring containing one oxygen atom;

R$^{1d}$ is present when Het has formula (d) and X is C; each R$^{1d}$ is selected independently from the group consisting of H, OH, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; R$^{1d}$ is absent when the X to which it is bound is N;

R$^{3d}$ is selected from the group consisting of H, halogen, C$_1$-C$_6$alkyl, C$_3$-C$_7$cycloalkyl, C$_1$-C$_6$alkyloxy, and CO(R$^7$);

R$^{2d}$ is —(CR$^8$R$^9$)$_m$—R$^{10d}$;

R$^{10d}$ is selected from the group consisting of H, C$_1$-C$_6$alkyl, OH, CN, F, CF$_2$H, CF$_3$, CONR$^8$R$^9$, COOR$^8$, CONR$^8$SO$_2$R$^9$, CON(R$^8$)SO$_2$N(R$^8$R$^9$), NR$^8$R$^9$, NR$^8$COOR$_9$, OCOR$^8$, NR$^8$SO$_2$R$^9$, SO$_2$NR$^8$R$^9$, SO$_2$R$^8$ and a 4 to 6 membered saturated ring containing one oxygen atom;

each Y independently is C or N;

R$^{1e}$ is present when Het has formula (e) and Y is C; each R$^{1e}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; R$^{1e}$ is absent when the Y to which it is bound is N;

R$^{3e}$ is selected from the group consisting of H, halogen, —(CR$^8$R$^9$)$_m$—R$^{10e}$, C=C—CH$_2$—R$^{10e}$, C≡C—R$^{10e}$ and C=C—R$^{10e}$;

R$^{10e}$ is selected from the group consisting of H, C$_1$-C$_6$alkyl, C$_1$-C$_6$alkyloxy, C$_3$-C$_7$cycloalkyl, OH, CN, F, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$ and a 4 to 6 membered saturated ring containing one oxygen atom;

R$^4$ is selected from the group consisting of tert-butyl, Het$^1$, aryl, Het$^2$, CH(CH$_3$)(CF$_3$), and C$_3$-C$_7$cycloalkyl substituted with one or more substituents selected from the group consisting of halo and C$_1$-C$_4$alkyl;

aryl represents phenyl or naphthalenyl; said aryl optionally being substituted with one or more substituents each independently selected from the group consisting of halo, C$_1$-C$_4$alkyloxy, C$_1$-C$_4$alkyl, OH, CN, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$, OCONR$^8$R$^9$, OCONR$^8$R$^{12}$, N(R$^8$)CON(R$^8$R$^9$), N(R$^8$)COOR$^{12}$;

Het$^1$ represents a 4 to 6 membered saturated ring containing one N atom, optionally being substituted with one or more substituents each independently selected from the group consisting of halo, C$_1$-C$_4$alkyloxy, SO$_2$R$^8$, C$_1$-C$_4$alkylcarbonyl, CO(aryl), COHet$^2$, C$_1$-C$_4$alkyloxycarbonyl, pyridinyl, CF$_3$, SO$_2$N(C$_1$-C$_4$alkyl)$_2$, SO$_2$NH(C$_1$-C$_4$alkyl), (C=O)NH(C$_{1-4}$alkyl), (C=S)NH(C$_{1-4}$alkyl), C$_1$-C$_4$alkyl and C$_1$-C$_4$alkyl substituted with one hydroxy; or Het$^1$ represents a 4 to 6 membered saturated ring containing one O atom, substituted with one or more substituents each independently selected from the group consisting of halo, C$_1$-C$_4$alkyloxy, CF$_3$, NH(C=O)(C$_{1-4}$alkyl), (C=O)NH(C$_{1-4}$alkyl) and C$_1$-C$_4$alkyl;

Het$^2$ represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N; said Het$^2$ optionally being substituted with one or more substituents each independently selected from the group consisting of halo, C$_1$-C$_4$alkyloxy, C$_1$-C$_4$alkyl, OH, CN, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$, OCONR$^8$R$^9$, OCONR$^8$R$^{12}$, N(R$^8$)CON(R$^8$R$^9$), N(R$^8$)COOR$^{12}$;

Z is C or N; R$^5$ is present where Z is C, whereby R$^5$ is selected form the group consisting of CF$_3$ and halogen; R$^5$ is absent where Z is N;

and the pharmaceutically acceptable addition salts, and the solvates thereof.

In an embodiment, the present invention concerns novel compounds of Formula (I) and stereoisomeric forms thereof, wherein Het is a heterocycle having formula (b), (c), (d) or (e);

each X independently is C or N; provided that at least one X is N;

R$^{1b}$ is present when Het has formula (b) and X is C; each R$^{1b}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; R$^{1b}$ is absent when the X to which it is bound is N;

R$^{2b}$ is —(CR$^8$R$^9$)$_m$—R$^{10b}$;

each R$^6$ is independently selected from the group consisting of H, C$_1$-C$_6$alkyl, COOCH$_3$ and CONHSO$_2$CH$_3$;

each R$^7$ is independently selected from the group consisting of OH, C$_1$-C$_6$alkyloxy, NH$_2$, NHSO$_2$N(C$_1$-C$_6$alkyl)$_2$, $NHSO_2NHCH_3$, $NHSO_2(C_1$-$C_6$alkyl), $NHSO_2(C_3$-$C_7$cycloalkyl) and $N(C_1$-$C_6$-alkyl)$_2$;

each $R^8$ and $R^9$ are independently chosen from the group consisting of H, $C_1$-$C_{10}$alkyl and $C_3$-$C_7$cycloalkyl; or $R^8$ and $R^9$ taken together form a 4 to 6 membered aliphatic ring that optionally contains one or more heteroatoms selected from the group consisting of N, S and O;

$R^{10b}$ is selected from the group consisting of H, $R^{11}$, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, O-Benzyl, $NR^8SO_2R^9$, $SO_2NR^8R^9$, $SO_2R^8$, $OCONR^8R^9$, $OCONR^8R^{12}$, $N(R^8)CON(R^8R^9)$, $N(R^8)COOR^{12}$, and a 4 to 6 membered saturated ring containing one oxygen atom;

m is an integer from 2 to 6;

$R^{11}$ is selected from the group consisting of $C_1$-$C_6$ alkyl, $C_3$-$C_7$cycloalkyl, phenyl, pyridinyl and pyrazolyl; each optionally substituted with one or more substituents each independently selected from the group consisting of $CF_3$, $CH_3$, $OCH_3$, $OCF_3$ and halogen;

$R^{12}$ is selected from the group consisting of phenyl, pyridinyl and pyrazolyl; each optionally substituted with one or more substituents each independently selected from the group consisting of $CF_3$, $CH_3$, $OCH_3$, $OCF_3$ and halogen; or $R^{12}$ is $C_1$-$C_6$ alkyl or $C_3$-$C_7$cycloalkyl; each substituted with one or more substituents each independently selected from the group consisting of $CF_3$, $CH_3$, $OCH_3$, $OCF_3$ and halogen;

$R^{1c}$ is present when Het has formula (c);

each $R^{1c}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^{7c})$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O-C_1$-$C_6$alkyl)$_2$;

$R^{3c}$ is selected from the group consisting of H, halogen, $C_1$-$C_6$alkyl, $C_3$-$C_7$cycloalkyl, $C_1$-$C_6$alkyloxy and $CO(R^{7c})$;

$R^{2c}$ is $-(CR^8R^9)_m-R^{10c}$;

$R^{7c}$ is selected from the group consisting of OH, O($C_1$-$C_6$alkyl), $NH_2$, $NHSO_2N(C_1$-$C_6$alkyl)$_2$, $NHSO_2NHCH_3$, $NHSO_2(C_1$-$C_6$alkyl), $NHSO_2(C_3$-$C_7$cycloalkyl), $N(C_1$-$C_6$-alkyl)$_2$, $NR^8R^9$ and $NR^9R^{10c}$;

$R^{10c}$ is selected from the group consisting of H, $C_1$-$C_6$alkyl, OH, CN, F, $CF_2H$, $CF_3$, $C(=NOH)NH_2$, $CONR^8R^9$, $COOR^8$, $CONR^8SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$ and a 4 to 6 membered saturated ring containing one oxygen atom;

$R^{1d}$ is present when Het has formula (d) and X is C; each $R^{1d}$ is selected independently from the group consisting of H, OH, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O-C_1$-$C_6$alkyl)$_2$; $R^{1d}$ is absent when the X to which it is bound is N;

$R^{3d}$ is selected from the group consisting of H, halogen, $C_1$-$C_6$alkyl, $C_3$-$C_7$cycloalkyl, $C_1$-$C_6$alkyloxy, and $CO(R^7)$;

$R^{3d}$ is $-(CR^8R^9)_m-R^{10d}$;

$R^{10d}$ is selected from the group consisting of H, $C_1$-$C_6$alkyl, OH, CN, F, $CF_2H$, $CF_3$, $CONR^8R^9$, $COOR^8$, $CONR^8SO_2R^9$, $CON(R^8)SO_2N(R^8R^9)$, $NR^8R^9$, $NR^8COOR_9$, $OCOR^8$, $NR^8SO_2R^9$, $SO_2NR^8R^9$, $SO_2R^8$ and a 4 to 6 membered saturated ring containing one oxygen atom;

each Y independently is C or N;

$R^{1e}$ is present when Het has formula (e) and Y is C; each $R^{1e}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O-C_1$-$C_6$alkyl)$_2$; $R^{1e}$ is absent when the Y to which it is bound is N;

$R^{3e}$ is selected from the group consisting of H, halogen, $-(CR^8R^9)_m-R^{10e}$, $C=C-CH_2-R^{10e}$, $C\equiv C-R^{10e}$ and $C=C-R^{10e}$;

$R^{10e}$ is selected from the group consisting of H, $C_1$-$C_6$alkyl, $C_1$-$C_6$alkyloxy, $C_3$-$C_7$cycloalkyl, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$ and a 4 to 6 membered saturated ring containing one oxygen atom;

$R^4$ is Het$^1$;

aryl represents phenyl or naphthalenyl; said aryl optionally being substituted with one or more substituents each independently selected from the group consisting of halo, $C_1$-$C_4$alkyloxy, $C_1$-$C_4$alkyl, OH, CN, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$, $OCONR^8R^9$, $OCONR^8R^{12}$, $N(R^8)CON(R^8R^9)$, $N(R^8)COOR^{12}$;

Het$^1$ represents a 4 to 6 membered saturated ring containing one N atom, optionally being substituted with one or more substituents each independently selected from the group consisting of halo, $C_1$-$C_4$alkyloxy, $SO_2R^8$, $C_1$-$C_4$alkylcarbonyl, CO(aryl), COHet$^2$, $C_1$-$C_4$alkyloxycarbonyl, pyridinyl, $CF_3$, $SO_2N(C_1$-$C_4$alkyl)$_2$, $SO_2NH(C_1$-$C_4$alkyl), $(C=O)NH(C_{1-4}$alkyl), $(C=S)NH(C_{1-4}$alkyl), $C_1$-$C_4$alkyl and $C_1$-$C_4$alkyl substituted with one hydroxy; or Het$^1$ represents a 4 to 6 membered saturated ring containing one O atom, substituted with one or more substituents each independently selected from the group consisting of halo, $C_1$-$C_4$alkyloxy, $CF_3$, $NH(C=O)(C_{1-4}$alkyl), $(C=O)NH(C_{1-4}$alkyl) and $C_1$-$C_4$alkyl;

Het$^2$ represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N; said Het$^2$ optionally being substituted with one or more substituents each independently selected from the group consisting of halo, $C_1$-$C_4$alkyloxy, $C_1$-$C_4$alkyl, OH, CN, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$, $OCONR^8R^9$, $OCONR^8R^{12}$, $N(R^8)CON(R^8R^9)$, $N(R^8)COOR^{12}$;

Z is C or N; $R^5$ is present where Z is C, whereby $R^5$ is selected form the group consisting of hydrogen, $CF_3$ and halogen; $R^5$ is absent where Z is N;

and the pharmaceutically acceptable addition salts, and the solvates thereof.

In an embodiment, the present invention concerns novel compounds of Formula (I) and stereoisomeric forms thereof, wherein Het is a heterocycle having formula (b), (c), (d) or (e);

each X independently is C or N; provided that at least one X is N;

$R^{1b}$ is present when Het has formula (b) and X is C; each $R^{1b}$ is selected independently from the group consisting of H, halogen, $C_1$-$C_6$alkyl, $C_3$-$C_7$cycloalkyl, $C_1$-$C_6$alkyloxy, N($R^6$)$_2$, CO($R^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; $R^{1b}$ is absent when the X to which it is bound is N;

$R^{2b}$ is —(CR$^8$R$^9$)$_m$—R$^{10b}$;

each $R^6$ is independently selected from the group consisting of H, C$_1$-C$_6$alkyl, COOCH$_3$ and CONHSO$_2$CH$_3$;

each $R^7$ is independently selected from the group consisting of OH, C$_1$-C$_6$alkyloxy, NH$_2$, NHSO$_2$N(C$_1$-C$_6$alkyl)$_2$, NHSO$_2$NHCH$_3$, NHSO$_2$(C$_1$-C$_6$alkyl), NHSO$_2$(C$_3$-C$_7$cycloalkyl) and N(C$_1$-C$_6$-alkyl)$_2$;

each $R^8$ and $R^9$ are independently chosen from the group consisting of H, C$_1$-C$_{10}$alkyl and C$_3$-C$_7$cycloalkyl; or $R^8$ and $R^9$ taken together form a 4 to 6 membered aliphatic ring that optionally contains one or more heteroatoms selected from the group consisting of N, S and O;

$R^{10b}$ is selected from the group consisting of H, $R^{11}$, OH, CN, F, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, O-Benzyl, NR$^8$SO$_2$R$^9$, SO$_2$NR$^8$R$^9$, SO$_2$R$^8$, OCONR$^8$R$^9$, OCONR$^8$R$^{12}$, N(R$^8$)CON(R$^8$R$^9$), N(R$^8$)COOR$^{12}$, and a 4 to 6 membered saturated ring containing one oxygen atom;

m is an integer from 2 to 6;

$R^{11}$ is selected from the group consisting of C$_1$-C$_6$ alkyl, C$_3$-C$_7$cycloalkyl, phenyl, pyridinyl and pyrazolyl; each optionally substituted with one or more substituents each independently selected from the group consisting of CF$_3$, CH$_3$, OCH$_3$, OCF$_3$ and halogen;

$R^{12}$ is selected from the group consisting of phenyl, pyridinyl and pyrazolyl; each optionally substituted with one or more substituents each independently selected from the group consisting of CF$_3$, CH$_3$, OCH$_3$, OCF$_3$ and halogen; or $R^{12}$ is C$_1$-C$_6$ alkyl or C$_3$-C$_7$cycloalkyl; each substituted with one or more substituents each independently selected from the group consisting of CF$_3$, CH$_3$, OCH$_3$, OCF$_3$ and halogen;

$R^{1c}$ is present when Het has formula (c);

each $R^{1c}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^{7c}$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$;

$R^{3c}$ is selected from the group consisting of H, halogen, C$_1$-C$_6$alkyl, C$_3$-C$_7$cycloalkyl, C$_1$-C$_6$alkyloxy and CO(R$^{7c}$);

$R^{2c}$ is —(CR$^8$R$^9$)$_m$—R$^{10c}$;

$R^{7c}$ is selected from the group consisting of OH, O(C$_1$-C$_6$alkyl), NH$_2$, NHSO$_2$N(C$_1$-C$_6$alkyl)$_2$, NHSO$_2$NHCH$_3$, NHSO$_2$(C$_1$-C$_6$alkyl), NHSO$_2$(C$_3$-C$_7$cycloalkyl), N(C$_1$-C$_6$-alkyl)$_2$, NR$^8$R$^9$ and NR$^9$R$^{10c}$;

$R^{10c}$ is selected from the group consisting of H, C$_1$-C$_6$alkyl, OH, CN, F, CF$_2$H, CF$_3$, C(=NOH)NH$_2$, CONR$^8$R$^9$, COOR$^8$, CONR$^8$SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$ and a 4 to 6 membered saturated ring containing one oxygen atom;

$R^{1d}$ is present when Het has formula (d) and X is C; each $R^{1d}$ is selected independently from the group consisting of H, OH, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; $R^{1d}$ is absent when the X to which it is bound is N;

$R^{3d}$ is selected from the group consisting of H, halogen, C$_1$-C$_6$alkyl, C$_3$-C$_7$cycloalkyl, C$_1$-C$_6$alkyloxy, and CO(R$^7$);

$R^{2d}$ is —(CR$^8$R$^9$)$_m$—R$^{10d}$;

$R^{10d}$ is selected from the group consisting of H, C$_1$-C$_6$alkyl, OH, CN, F, CF$_2$H, CF$_3$, CONR$^8$R$^9$, COOR$^8$, CONR$^8$SO$_2$R$^9$, CON(R$^8$)SO$_2$N(R$^8$R$^9$), NR$^8$R$^9$, NR$^8$COOR$_9$, OCOR$^8$, NR$^8$SO$_2$R$^9$, SO$_2$NR$^8$R$^9$, SO$_2$R$^8$ and a 4 to 6 membered saturated ring containing one oxygen atom;

each Y independently is C or N;

$R^{1e}$ is present when Het has formula (e) and Y is C; each $R^{1e}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; $R^{1e}$ is absent when the Y to which it is bound is N;

$R^{3e}$ is selected from the group consisting of H, halogen, —(CR$^8$R$^9$)$_m$—R$^{10e}$, C≡C—CH$_2$—R$^{10e}$, C≡C—R$^{10e}$ and C=C—R$^{10e}$;

$R^{10e}$ is selected from the group consisting of H, C$_1$-C$_6$alkyl, C$_1$-C$_6$alkyloxy, C$_3$-C$_7$cycloalkyl, OH, CN, F, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$ and a 4 to 6 membered saturated ring containing one oxygen atom;

$R^4$ is Het$^1$;

Het$^1$ represents a 4 to 6 membered saturated ring containing one N atom, optionally being substituted with one or more substituents each independently selected from the group consisting of halo, C$_1$-C$_4$alkyloxy, SO$_2$R$^8$, C$_1$-C$_4$alkylcarbonyl, C$_1$-C$_4$alkyloxycarbonyl, pyridinyl, CF$_3$, SO$_2$N(C$_1$-C$_4$alkyl)$_2$, SO$_2$NH(C$_1$-C$_4$alkyl), (C=O)NH(C$_{1-4}$alkyl), (C=S)NH(C$_{1-4}$alkyl), C$_1$-C$_4$alkyl and C$_1$-C$_4$alkyl substituted with one hydroxy; or Het$^1$ represents a 4 to 6 membered saturated ring containing one O atom, substituted with one or more substituents each independently selected from the group consisting of halo, C$_1$-C$_4$alkyloxy, CF$_3$, NH(C=O)(C$_{1-4}$alkyl), (C=O)NH(C$_{1-4}$alkyl) and C$_1$-C$_4$alkyl;

Z is C or N; $R^5$ is present where Z is C, whereby $R^5$ is selected form the group consisting of hydrogen, CF$_3$ and halogen; $R^5$ is absent where Z is N;

and the pharmaceutically acceptable addition salts, and the solvates thereof.

In an embodiment, the present invention concerns novel compounds of Formula (I) and stereoisomeric forms thereof, wherein Het is a heterocycle having formula (b), (c), (d) or (e);

each X independently is C or N; provided that at least one X is N;

$R^{1b}$ is present when Het has formula (b) and X is C; each $R^{1b}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; $R^{1b}$ is absent when the X to which it is bound is N;

$R^{2b}$ is —(CR$^8$R$^9$)$_m$—R$^{10b}$;

each $R^6$ is independently selected from the group consisting of H, C$_1$-C$_6$alkyl, COOCH$_3$ and CONHSO$_2$CH$_3$;

each $R^7$ is independently selected from the group consisting of OH, C$_1$-C$_6$alkyloxy, NH$_2$, NHSO$_2$N(C$_1$-C$_6$alkyl)$_2$, NHSO$_2$NHCH$_3$, NHSO$_2$(C$_1$-C$_6$alkyl), NHSO$_2$(C$_3$-C$_7$cycloalkyl) and N(C$_1$-C$_6$-alkyl)$_2$;

each $R^8$ and $R^9$ are independently chosen from the group consisting of H, C$_1$-C$_{10}$alkyl and C$_3$-C$_7$cycloalkyl; or $R^8$ and $R^9$ taken together form a 4 to 6 membered aliphatic ring that optionally contains one or more heteroatoms selected from the group consisting of N, S and O;

$R^{10b}$ is selected from the group consisting of H, $R^{11}$, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, O-Benzyl, $NR^8SO_2R^9$, $SO_2NR^8R^9$, $SO_2R^8$, $OCONR^8R^9$, $OCONR^8R^{12}$, $N(R^8)CON(R^8R^9)$, $N(R^8)COOR^{12}$, and a 4 to 6 membered saturated ring containing one oxygen atom;

m is an integer from 2 to 6;

$R^{11}$ is selected from the group consisting of $C_1$-$C_6$ alkyl, $C_3$-$C_7$cycloalkyl, phenyl, pyridinyl and pyrazolyl; each optionally substituted with one or more substituents each independently selected from the group consisting of $CF_3$, $CH_3$, $OCH_3$, $OCF_3$ and halogen;

$R^{12}$ is selected from the group consisting of phenyl, pyridinyl and pyrazolyl; each optionally substituted with one or more substituents each independently selected from the group consisting of $CF_3$, $CH_3$, $OCH_3$, $OCF_3$ and halogen; or $R^{12}$ is $C_1$-$C_6$ alkyl or $C_3$-$C_7$cycloalkyl; each substituted with one or more substituents each independently selected from the group consisting of $CF_3$, $CH_3$, $OCH_3$, $OCF_3$ and halogen;

$R^{1c}$ is present when Het has formula (c);

each $R^{1c}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^{7c})$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O-C_1-C_6alkyl)_2$;

$R^{3c}$ is selected from the group consisting of H, halogen, $C_1$-$C_6$alkyl, $C_3$-$C_7$cycloalkyl, $C_1$-$C_6$alkyloxy and $CO(R^{7c})$;

$R^{2c}$ is $-(CR^8R^9)_m-R^{10e}$, $R^{7c}$ is selected from the group consisting of OH, $O(C_1$-$C_6alkyl)$, $NH_2$, $NHSO_2N(C_1$-$C_6alkyl)_2$, $NHSO_2NHCH_3$, $NHSO_2(C_1$-$C_6alkyl)$, $NHSO_2(C_3$-$C_7cycloalkyl)$, $N(C_1$-$C_6$-$alkyl)_2$, $NR^8R^9$ and $NR^9R^{10c}$;

$R^{10c}$ is selected from the group consisting of H, $C_1$-$C_6$alkyl, OH, CN, F, $CF_2H$, $CF_3$, $C(=NOH)NH_2$, $CONR^8R^9$, $COOR^8$, $CONR^8SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$ and a 4 to 6 membered saturated ring containing one oxygen atom;

$R^{1d}$ is present when Het has formula (d) and X is C; each $R^{1d}$ is selected independently from the group consisting of H, OH, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O-C_1-C_6alkyl)_2$; $R^{1d}$ is absent when the X to which it is bound is N;

$R^{1d}$ is selected from the group consisting of H, halogen, $C_1$-$C_6$alkyl, $C_3$-$C_7$cycloalkyl, $C_1$-$C_6$alkyloxy, and $CO(R^7)$;

$R^{2d}$ is $-(CR^8R^9)_m-R^{10d}$;

$R^{10d}$ is selected from the group consisting of H, $C_1$-$C_6$alkyl, OH, CN, F, $CF_2H$, $CF_3$, $CONR^8R^9$, $COOR^8$, $CONR^8SO_2R^9$, $CON(R^8)SO_2N(R^8R^9)$, $NR^8R^9$, $NR^8COOR_9$, $OCOR^8$, $NR^8SO_2R^9$, $SO_2NR^8R^9$, $SO_2R^8$ and a 4 to 6 membered saturated ring containing one oxygen atom;

each Y independently is C or N;

$R^{1e}$ is present when Het has formula (e) and Y is C; each $R^{1e}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O-C_1-C_6alkyl)_2$; $R^{1e}$ is absent when the Y to which it is bound is N;

$R^{3e}$ is selected from the group consisting of H, halogen, $-(CR^8R^9)_m-R^{10e}$, $C=C-CH_2-R^{10e}$, $C≡C-R^{10e}$ and $C≡C-R^{10e}$;

$R^{10e}$ is selected from the group consisting of H, $C_1$-$C_6$alkyl, $C_1$-$C_6$alkyloxy, $C_3$-$C_7$cycloalkyl, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$ and a 4 to 6 membered saturated ring containing one oxygen atom;

$R^4$ is selected from the group consisting of aryl and $Het^2$; in particular $Het^2$;

aryl represents phenyl or naphthalenyl; said aryl optionally being substituted with one or more substituents each independently selected from the group consisting of halo, $C_1$-$C_4$alkyloxy, $C_1$-$C_4$alkyl, OH, CN, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$, $OCONR^8R^9$, $OCONR^8R^{12}$, $N(R^8)CON(R^8R^9)$, $N(R^8)COOR^{12}$;

$Het^2$ represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N; said $Het^2$ optionally being substituted with one or more substituents each independently selected from the group consisting of halo, $C_1$-$C_4$alkyloxy, $C_1$-$C_4$alkyl, OH, CN, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$, $OCONR^8R^9$, $OCONR^8R^{12}$, $N(R^8)CON(R^8R^9)$, $N(R^8)COOR^{12}$;

Z is C or N; $R^5$ is present where Z is C, whereby $R^5$ is selected form the group consisting of hydrogen, $CF_3$ and halogen; $R^5$ is absent where Z is N;

and the pharmaceutically acceptable addition salts, and the solvates thereof.

In an embodiment, the present invention concerns novel compounds of Formula (I) and stereoisomeric forms thereof, wherein Het is a heterocycle having formula (b), (c), (d) or (e);

each X independently is C or N; provided that at least one X is N;

$R^{1b}$ is present when Het has formula (b) and X is C; each $R^{1b}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O-C_1-C_6alkyl)_2$; $R^{1b}$ is absent when the X to which it is bound is N;

$R^{2b}$ is $-(CR^8R^9)_m-R^{10b}$;

each $R^6$ is independently selected from the group consisting of H, $COOCH_3$ and $CONHSO_2CH_3$;

each $R^7$ is independently selected from the group consisting of OH, $C_1$-$C_6$alkyloxy, $NH_2$, $NHSO_2N(C_1$-$C_6alkyl)_2$, $NHSO_2NHCH_3$, $NHSO_2(C_1$-$C_6alkyl)$, $NHSO_2(C_3$-$C_7cycloalkyl)$ and $N(C_1$-$C_6$-$alkyl)_2$;

each $R^8$ and $R^9$ are independently chosen from the group consisting of H, and $C_3$-$C_7$cycloalkyl;

$R^{10b}$ is selected from the group consisting of H, $R^{11}$, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, O-Benzyl, $NR^8SO_2R^9$, $SO_2NR^8R^9$, $SO_2R^8$, $OCONR^8R^9$, OCONR$^8$R$^{12}$, N(R$^8$)CON(R$^8$R$^9$), N(R$^8$)COOR$^{12}$, and a 4 to 6 membered saturated ring containing one oxygen atom;

m is an integer from 2 to 6;

R$^{11}$ is selected from the group consisting of C$_1$-C$_6$ alkyl, C$_3$-C$_7$cycloalkyl, phenyl, pyridinyl and pyrazolyl; each optionally substituted with one or more substituents each independently selected from the group consisting of CF$_3$, CH$_3$, OCH$_3$, OCF$_3$ and halogen;

R$^{12}$ is selected from the group consisting of phenyl, pyridinyl and pyrazolyl; each optionally substituted with one or more substituents each independently selected from the group consisting of CF$_3$, CH$_3$, OCH$_3$, OCF$_3$ and halogen; or R$^{12}$ is C$_1$-C$_6$ alkyl or C$_3$-C$_7$cycloalkyl; each substituted with one or more substituents each independently selected from the group consisting of CF$_3$, CH$_3$, OCH$_3$, OCF$_3$ and halogen;

R$^{1c}$ is present when Het has formula (c);

each R$^{1c}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^{7c}$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$;

R$^{1c}$ is selected from the group consisting of H, halogen, C$_1$-C$_6$alkyl, C$_3$-C$_7$cycloalkyl, C$_1$-C$_6$alkyloxy and CO(R$^{7c}$);

R$^2$ is —(CR$^8$R$^9$)$_m$—R$^{10c}$;

R$^{7c}$ is selected from the group consisting of OH, O(C$_1$-C$_6$alkyl), NH$_2$, NHSO$_2$N(C$_1$-C$_6$alkyl)$_2$, NHSO$_2$NHCH$_3$, NHSO$_2$(C$_1$-C$_6$alkyl), NHSO$_2$(C$_3$-C$_7$cycloalkyl), N(C$_1$-C$_6$-alkyl)$_2$, NR$^8$R$^9$ and NR$^9$R$^{10c}$;

R$^{10c}$ is selected from the group consisting of H, C$_1$-C$_6$alkyl, OH, CN, F, CF$_2$H, CF$_3$, C(=NOH)NH$_2$, CONR$^8$R$^9$, COOR$^8$, CONR$^8$SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$ and a 4 to 6 membered saturated ring containing one oxygen atom;

R$^{1d}$ is present when Het has formula (d) and X is C; each R$^{1d}$ is selected independently from the group consisting of H, OH, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; R$^{1d}$ is absent when the X to which it is bound is N;

R$^{3d}$ is selected from the group consisting of H, halogen, C$_1$-C$_6$alkyl, C$_3$-C$_7$cycloalkyl, C$_1$-C$_6$alkyloxy, and CO(R$^7$);

R$^{2d}$ is —(CR$^8$R$^9$)$_m$—R$^{10d}$;

R$^{10d}$ is selected from the group consisting of H, C$_1$-C$_6$alkyl, OH, CN, F, CF$_2$H, CF$_3$, CONR$^8$R$^9$, COOR$^8$, CONR$^8$SO$_2$R$^9$, CON(R$^8$)SO$_2$N(R$^8$R$^9$), NR$^8$R$^9$, NR$^8$COOR$_9$, OCOR$^8$, NR$^8$SO$_2$R$^9$, SO$_2$NR$^8$R$^9$, SO$_2$R$^8$ and a 4 to 6 membered saturated ring containing one oxygen atom;

each Y independently is C or N;

R$^{1e}$ is present when Het has formula (e) and Y is C; each R$^{1e}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; R$^{1e}$ is absent when the Y to which it is bound is N;

R$^{3e}$ is selected from the group consisting of H, halogen, —(CR$^8$R$^9$)$_m$—R$^{10e}$, C=C—CH$_2$—R$^{10e}$, C≡C—R$^{10e}$ and C=C—R$^{10e}$;

R$^{10e}$ is selected from the group consisting of H, C$_1$-C$_6$alkyl, C$_1$-C$_6$alkyloxy, C$_3$-C$_7$cycloalkyl, OH, CN, F, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$ and a 4 to 6 membered saturated ring containing one oxygen atom;

R$^4$ is selected from the group consisting of tert-butyl, Het$^1$, aryl, Het$^2$, CH(CH$_3$)(CF$_3$), and C$_3$-C$_7$cycloalkyl substituted with one or more substituents selected from the group consisting of halo and C$_1$-C$_4$alkyl;

aryl represents phenyl or naphthalenyl; said aryl optionally being substituted with one or more substituents each independently selected from the group consisting of halo, C$_1$-C$_4$alkyloxy, C$_1$-C$_4$alkyl, OH, CN, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$, OCONR$^8$R$^9$, OCONR$^8$R$^{12}$, N(R$^8$)CON(R$^8$R$^9$), N(R$^8$)COOR$^{12}$;

Het$^1$ represents a 4 to 6 membered saturated ring containing one N atom, optionally being substituted with one or more substituents each independently selected from the group consisting of halo, C$_1$-C$_4$alkyloxy, SO$_2$R$^8$, C$_1$-C$_4$alkylcarbonyl, CO(aryl), COHet$^2$, C$_1$-C$_4$alkyloxycarbonyl, pyridinyl, CF$_3$, SO$_2$N(C$_1$-C$_4$alkyl)$_2$, SO$_2$NH(C$_1$-C$_4$alkyl), (C=O)NH(C$_{1-4}$alkyl), (C=S)NH(C$_{1-4}$alkyl), C$_1$-C$_4$alkyl and C$_1$-C$_4$alkyl substituted with one hydroxy; or Het$^1$ represents a 4 to 6 membered saturated ring containing one O atom, substituted with one or more substituents each independently selected from the group consisting of halo, C$_1$-C$_4$alkyloxy, CF$_3$, NH(C=O)(C$_{1-4}$alkyl), (C=O)NH(C$_{1-4}$alkyl) and C$_1$-C$_4$alkyl;

Het$^2$ represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N; said Het$^2$ optionally being substituted with one or more substituents each independently selected from the group consisting of halo, C$_1$-C$_4$alkyloxy, C$_1$-C$_4$alkyl, OH, CN, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$, OCONR$^8$R$^9$, OCONR$^8$R$^{12}$, N(R$^8$)CON(R$^8$R$^9$), N(R$^8$)COOR$^{12}$;

Z is C or N; R$^5$ is present where Z is C, whereby R$^5$ is selected form the group consisting of hydrogen, CF$_3$ and halogen; R$^5$ is absent where Z is N;

and the pharmaceutically acceptable addition salts, and the solvates thereof.

In an embodiment, the present invention concerns novel compounds of Formula (I) and stereoisomeric forms thereof, wherein Het is a heterocycle having formula (b), (c), (d) or (e);

each X independently is C or N; provided that at least one X is N;

R$^{1b}$ is present when Het has formula (b) and X is C; each R$^{1b}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; R$^{1b}$ is absent when the X to which it is bound is N;

R$^{2b}$ is —(CR$^8$R$^9$)$_m$—R$^{10b}$;

each R$^6$ is independently selected from the group consisting of H, C$_1$-C$_6$alkyl, COOCH$_3$ and CONHSO$_2$CH$_3$;

each R$^7$ is independently selected from the group consisting of OH, C$_1$-C$_6$alkyloxy, NH$_2$, NHSO$_2$N(C$_1$-C$_6$alkyl)$_2$, NHSO$_2$NHCH$_3$, NHSO$_2$(C$_1$-C$_6$alkyl), NHSO$_2$(C$_3$-C$_7$cycloalkyl) and N(C$_1$-C$_6$-alkyl)$_2$;

each R$^8$ and R$^9$ are independently chosen from the group consisting of H;

R$^{10b}$ is selected from the group consisting of H, R$^{11}$, OH, CN, F, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, O-Benzyl, NR$^8$SO$_2$R$^9$, SO$_2$NR$^8$R$^9$, SO$_2$CH$_3$, OCONR$^8$R$^9$, OCONR$^8$R$^{12}$, N(R$^8$)CON(R$^8$R$^9$), N(R$^8$)COOR$^{12}$, and a 4 to 6 membered saturated ring containing one oxygen atom;

m is an integer from 2 to 6;

R$^{11}$ is selected from the group consisting of C$_1$-C$_6$ alkyl, C$_3$-C$_7$cycloalkyl, phenyl, pyridinyl and pyrazolyl; each optionally substituted with one or more substituents each independently selected from the group consisting of CF$_3$, CH$_3$, OCH$_3$, OCF$_3$ and halogen;

R$^{12}$ is selected from the group consisting of phenyl, pyridinyl and pyrazolyl; each optionally substituted with one or more substituents each independently selected from the group consisting of CF$_3$, CH$_3$, OCH$_3$, OCF$_3$ and halogen; or R$^{12}$ is C$_1$-C$_6$ alkyl or C$_3$-C$_7$cycloalkyl; each substituted with one or more substituents each independently selected from the group consisting of CF$_3$, CH$_3$, OCH$_3$, OCF$_3$ and halogen;

R$^{1c}$ is present when Het has formula (c);

each R$^{1c}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^{7c}$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$;

R$^{3c}$ is selected from the group consisting of H, halogen, C$_1$-C$_6$alkyl, C$_3$-C$_7$cycloalkyl, C$_1$-C$_6$alkyloxy and CO(R$^{7c}$);

R$^{2c}$ is —(CR$^8$R$^9$)$_m$—R$^{10c}$;

R$^{7c}$ is selected from the group consisting of OH, O(C$_1$-C$_6$alkyl), NH$_2$, NHSO$_2$N(C$_1$-C$_6$alkyl)$_2$, NHSO$_2$NHCH$_3$, NHSO$_2$(C$_1$-C$_6$alkyl), NHSO$_2$(C$_3$-C$_7$cycloalkyl), N(C$_1$-C$_6$-alkyl)$_2$, NR$^8$R$^9$ and NR$^9$R$^{10c}$;

R$^{10c}$ is selected from the group consisting of H, C$_1$-C$_6$alkyl, OH, CN, F, CF$_2$H, CF$_3$, C(=NOH)NH$_2$, CONR$^8$R$^9$, COOR$^8$, CONR$^8$SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$CH$_3$ and a 4 to 6 membered saturated ring containing one oxygen atom;

R$^{10d}$ is present when Het has formula (d) and X is C; each R$^{1d}$ is selected independently from the group consisting of H, OH, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; R$^{1d}$ is absent when the X to which it is bound is N;

R$^{3d}$ is selected from the group consisting of H, halogen, C$_1$-C$_6$alkyl, C$_3$-C$_7$cycloalkyl, C$_1$-C$_6$alkyloxy, and CO(R$^7$);

R$^{2c}$ is —(CR$^8$R$^9$)$_m$—R$^{10d}$;

R$^{10d}$ is selected from the group consisting of H, C$_1$-C$_6$alkyl, OH, CN, F, CF$_2$H, CF$_3$, CONR$^8$R$^9$, COOR$^8$, CONR$^8$SO$_2$R$^9$, CON(R$^8$)SO$_2$N(R$^8$R$^9$), NR$^8$R$^9$, NR$^8$COOR$_9$, OCOR$^8$, NR$^8$SO$_2$R$^9$, SO$_2$NR$^8$R$^9$, SO$_2$CH$_3$ and a 4 to 6 membered saturated ring containing one oxygen atom;

each Y independently is C or N;

R$^{1e}$ is present when Het has formula (e) and Y is C; each R$^{1e}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; R$^{1e}$ is absent when the Y to which it is bound is N;

R$^{3e}$ is selected from the group consisting of H, halogen, —(CR$^8$R$^9$)$_m$—R$^{10e}$, C=C—CH$_2$—R$^{10e}$, C=C—R$^{10e}$ and C=C—R$^{10e}$;

R$^{10e}$ is selected from the group consisting of H, C$_1$-C$_6$alkyloxy, C$_3$-C$_7$cycloalkyl, OH, CN, F, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$CH$_3$ and a 4 to 6 membered saturated ring containing one oxygen atom;

R$^4$ is selected from the group consisting of tert-butyl, Het$^1$, aryl, Het$^2$, CH(CH$_3$)(CF$_3$), and C$_3$-C$_7$cycloalkyl substituted with one or more substituents selected from the group consisting of halo and C$_1$-C$_4$alkyl;

aryl represents phenyl or naphthalenyl; said aryl optionally being substituted with one or more substituents each independently selected from the group consisting of halo, C$_1$-C$_4$alkyloxy, C$_1$-C$_4$alkyl, OH, CN, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$CH$_3$, OCONR$^8$R$^9$, OCONR$^8$R$^{12}$, N(R$^8$)CON(R$^8$R$^9$), N(R$^8$)COOR$^{12}$;

Het$^1$ represents a 4 to 6 membered saturated ring containing one N atom, optionally being substituted with one or more substituents each independently selected from the group consisting of halo, C$_1$-C$_4$alkyloxy, SO$_2$CH$_3$, C$_1$-C$_4$alkylcarbonyl, CO(aryl), COHet$^2$, C$_1$-C$_4$alkyloxycarbonyl, pyridinyl, CF$_3$, SO$_2$N(C$_1$-C$_4$alkyl)$_2$, SO$_2$NH(C$_1$-C$_4$alkyl), (C=O)NH(C$_{1-4}$alkyl), (C=S)NH(C$_{1-4}$alkyl), C$_1$-C$_4$alkyl and C$_1$-C$_4$alkyl substituted with one hydroxy; or Het$^1$ represents a 4 to 6 membered saturated ring containing one O atom, substituted with one or more substituents each independently selected from the group consisting of halo, C$_1$-C$_4$alkyloxy, CF$_3$, NH(C=O)(C$_{1-4}$alkyl), (C=O)NH(C$_{1-4}$alkyl) and C$_1$-C$_4$alkyl;

Het$^2$ represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N; said Het$^2$ optionally being substituted with one or more substituents each independently selected from the group consisting of halo, C$_1$-C$_4$alkyloxy, C$_1$-C$_4$alkyl, OH, CN, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$CH$_3$, OCONR$^8$R$^9$, OCONR$^8$R$^{12}$, N(R$^8$)CON(R$^8$R$^9$), N(R$^8$)COOR$^{12}$;

Z is C or N; R$^5$ is present where Z is C, whereby R$^5$ is selected form the group consisting of hydrogen, CF$_3$ and halogen; R$^5$ is absent where Z is N;

and the pharmaceutically acceptable addition salts, and the solvates thereof.

In an embodiment, the present invention concerns novel compounds of Formula (I) and stereoisomeric forms thereof, wherein Het is a heterocycle having formula (b), (c), (d) or (e); in particular (b) or (c);

each X independently is C or N; provided that at least one X is N;

R$^{1b}$ is present when Het has formula (b) and X is C; each R$^{1b}$ is selected independently from the group consisting of H, halogen, $C_1$-$C_6$alkyl, $C_3$-$C_7$cycloalkyl, $C_1$-$C_6$alkyloxy, $CF_3$ and $OCF_3$; $R^{1b}$ is absent when the X to which it is bound is N;

$R^{2b}$ is —$(CR^8R^9)_m$—$R^{10b}$;

each $R^8$ and $R^9$ are independently chosen from the group consisting of H and $C_1$-$C_{10}$alkyl;

$R^{10b}$ is selected from the group consisting of H, $R^{11}$, OH, CN, F, $CF_2H$, $CF_3$, $NR^8R^9$, $SO_2NR^8R^9$, $SO_2R^8$;

m is an integer from 2 to 6;

$R^{11}$ is selected from the group consisting of $C_1$-$C_6$ alkyl, $C_3$-$C_7$cycloalkyl, phenyl, pyridinyl and pyrazolyl; each optionally substituted with one or more substituents each independently selected from the group consisting of $CF_3$, $CH_3$, $OCH_3$, $OCF_3$ and halogen; in particular $C_1$-$C_6$ alkyl;

$R^{12}$ is selected from the group consisting of phenyl, pyridinyl and pyrazolyl; each optionally substituted with one or more substituents each independently selected from the group consisting of $CF_3$, $CH_3$, $OCH_3$, $OCF_3$ and halogen; or $R^{12}$ is $C_1$-$C_6$ alkyl or $C_3$-$C_7$cycloalkyl; each substituted with one or more substituents each independently selected from the group consisting of $CF_3$, $CH_3$, $OCH_3$, $OCF_3$ and halogen;

$R^{1c}$ is present when Het has formula (c);

each $R^{1c}$ is selected independently from the group consisting of H, halogen, $C_1$-$C_6$alkyl, $C_3$-$C_7$cycloalkyl, $C_1$-$C_6$alkyloxy, $CF_3$ and $OCF_3$;

$R^{3c}$ is selected from the group consisting of H, halogen, $C_1$-$C_6$alkyl;

$R^{2c}$ is —$(CR^8R^9)_m$—$R^{10c}$;

$R^{10c}$ is selected from the group consisting of H, OH, CN, F, $CF_2H$, $CF_3$, $NR^8R^9$, $SO_2NR^8R^9$, $SO_2R^8$;

$R^{1d}$ is present when Het has formula (d) and X is C; each $R^{1d}$ is selected independently from the group consisting of H, halogen, $C_1$-$C_6$alkyl, $C_3$-$C_7$cycloalkyl, $C_1$-$C_6$alkyloxy, $CF_3$ and $OCF_3$; $R^{1d}$ is absent when the X to which it is bound is N;

$R^{3d}$ is selected from the group consisting of H, halogen, $C_1$-$C_6$alkyl;

$R^{2d}$ is —$(CR^8R^9)_m$—$R^{10d}$;

$R^{10d}$ is selected from the group consisting of H, OH, CN, F, $CF_2H$, $CF_3$, $NR^8R^9$, $SO_2NR^8R^9$, $SO_2R^8$;

each Y independently is C or N;

$R^{1e}$ is present when Het has formula (e) and Y is C; each $R^{1e}$ is selected independently from the group consisting of H, halogen, $C_1$-$C_6$alkyl, $C_3$-$C_7$cycloalkyl, $C_1$-$C_6$alkyloxy, $CF_3$ and $OCF_3$; $R^{1e}$ is absent when the Y to which it is bound is N;

$R^{3e}$ is selected from the group consisting of H, halogen;

$R^4$ is selected from the group consisting of tert-butyl, $Het^1$, aryl, $Het^2$, $CH(CH_3)(CF_3)$, and $C_3$-$C_7$cycloalkyl substituted with one or more substituents selected from the group consisting of halo and $C_1$-$C_4$alkyl;

aryl represents phenyl or naphthalenyl; said aryl optionally being substituted with one or more substituents each independently selected from the group consisting of halo, $C_1$-$C_4$alkyloxy, $C_1$-$C_4$alkyl, OH, CN, $CF_2H$, $CF_3$, $CONR^8R^9$, $NR^8R^9$, $NR^8COOR^9$, $SO_2NR^8R^9$, $SO_2R^8$, $OCONR^8R^9$, $OCONR^8R^{12}$, $N(R^8)COOR^{12}$;

$Het^1$ represents a 4 to 6 membered saturated ring containing one N atom, optionally being substituted with one or more substituents each independently selected from the group consisting of halo, $C_1$-$C_4$alkyloxy, $SO_2R^8$, $C_1$-$C_4$alkylcarbonyl, $C_1$-$C_4$alkyloxycarbonyl, pyridinyl, $CF_3$, $SO_2N(C_1$-$C_4$alkyl)$_2$, $SO_2NH(C_1$-$C_4$alkyl), (C=O)NH($C_{1-4}$alkyl), (C=S)NH($C_{1-4}$alkyl), $C_1$-$C_4$alkyl and $C_1$-$C_4$alkyl substituted with one hydroxy; or $Het^1$ represents a 4 to 6 membered saturated ring containing one O atom, substituted with one or more substituents each independently selected from the group consisting of halo, $C_1$-$C_4$alkyloxy, $CF_3$, NH(C=O)($C_{1-4}$alkyl), (C=O)NH($C_{1-4}$alkyl) and $C_1$-$C_4$alkyl;

$Het^2$ represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N; said $Het^2$ optionally being substituted with one or more substituents each independently selected from the group consisting of halo, $C_1$-$C_4$alkyloxy, $C_1$-$C_4$alkyl, OH, CN, $CF_2H$, $CF_3$, $CONR^8R^9$, $NR^8R^9$, $NR^8COOR^9$, $SO_2NR^8R^9$, $SO_2R^8$, $OCONR^8R^9$, $OCONR^8R^{12}$, $N(R^8)COOR^{12}$;

Z is C or N; $R^5$ is present where Z is C, whereby $R^5$ is selected form the group consisting of hydrogen, $CF_3$ and halogen; in particular $R^5$ is selected form the group consisting of $CF_3$ and halogen; $R^5$ is absent where Z is N;

and the pharmaceutically acceptable addition salts, and the solvates thereof.

In an embodiment, the present invention concerns novel compounds of Formula (I) and stereoisomeric forms thereof, wherein Het is a heterocycle having formula (b), (c), (d) or (e); in particular (b) or (c);

each X independently is C or N; provided that at least one X is N;

$R^{1b}$ is present when Het has formula (b) and X is C; each $R^{1b}$ is selected independently from the group consisting of H, halogen, $C_1$-$C_6$alkyl, $C_3$-$C_7$cycloalkyl, $C_1$-$C_6$alkyloxy, $CF_3$ and $OCF_3$; $R^{1b}$ is absent when the X to which it is bound is N;

$R^{2b}$ is —$(CR^8R^9)_m$—$R^{10b}$;

each $R^8$ and $R^9$ are independently chosen from the group consisting of H and $C_1$-$C_{10}$alkyl;

$R^{10b}$ is selected from the group consisting of H, $R^{11}$, OH, CN, F, $CF_2H$, $CF_3$, $NR^8R^9$, $SO_2NR^8R^9$, $SO_2R^8$;

m is an integer from 2 to 6;

$R^{11}$ is selected from the group consisting of $C_1$-$C_6$ alkyl, $C_3$-$C_7$cycloalkyl, phenyl, pyridinyl and pyrazolyl; each optionally substituted with one or more substituents each independently selected from the group consisting of $CF_3$, $CH_3$, $OCH_3$, $OCF_3$ and halogen; in particular $C_1$-$C_6$ alkyl;

$R^{1c}$ is present when Het has formula (c);

each $R^{1c}$ is selected independently from the group consisting of H, halogen, $C_1$-$C_6$alkyl, $C_3$-$C_7$cycloalkyl, $C_1$-$C_6$alkyloxy, $CF_3$ and $OCF_3$;

$R^{3c}$ is selected from the group consisting of H, halogen, $C_1$-$C_6$alkyl;

$R^{2c}$ is —$(CR^8R^9)_m$—$R^{10c}$;

$R^{10c}$ is selected from the group consisting of H, $C_1$-$C_6$alkyl, OH, CN, F, $CF_2H$, $CF_3$, $NR^8R^9$, $SO_2NR^8R^9$, $SO_2R^8$;

$R^{1d}$ is present when Het has formula (d) and X is C; each $R^{1d}$ is selected independently from the group consisting of H, halogen, $C_1$-$C_6$alkyl, $C_3$-$C_7$cycloalkyl, $C_1$-$C_6$alkyloxy, $CF_3$ and $OCF_3$; $R^{1d}$ is absent when the X to which it is bound is N;

$R^{3d}$ is selected from the group consisting of H, halogen, $C_1$-$C_6$alkyl;

$R^{2d}$ is —$(CR^8R^9)_m$—$R^{10d}$;

$R^{10d}$ is selected from the group consisting of H, $C_1$-$C_6$alkyl, OH, CN, F, $CF_2H$, $CF_3$, $NR^8R^9$, $SO_2NR^8R^9$, $SO_2R^8$;

each Y independently is C or N;

$R^{3e}$ is present when Het has formula (e) and Y is C; each $R^{1e}$ is selected independently from the group consisting of H, halogen, $C_1$-$C_6$alkyl, $C_3$-$C_7$cycloalkyl, $C_1$-$C_6$alkyloxy, $CF_3$ and $OCF_3$; $R^{1e}$ is absent when the Y to which it is bound is N;

$R^{3e}$ is selected from the group consisting of H, halogen;

$R^4$ is selected from the group consisting of tert-butyl, $Het^1$, aryl, $Het^2$, $CH(CH_3)(CF_3)$, and $C_3$-$C_7$cycloalkyl substituted with one or more substituents selected from the group consisting of halo and $C_1$-$C_4$alkyl;

aryl represents phenyl or naphthalenyl; said aryl optionally being substituted with one or more substituents each independently selected from the group consisting of halo, $C_1$-$C_4$alkyloxy, $C_1$-$C_4$alkyl;

$Het^1$ represents a 4 to 6 membered saturated ring containing one N atom, optionally being substituted with one or more substituents each independently selected from the group consisting of halo, $C_1$-$C_4$alkyloxy, $SO_2R^8$, $C_1$-$C_4$alkylcarbonyl, $C_1$-$C_4$alkyloxycarbonyl, pyridinyl, $CF_3$, $C_1$-$C_4$alkyl and $C_1$-$C_4$alkyl substituted with one hydroxy; or $Het^1$ represents a 4 to 6 membered saturated ring containing one O atom, substituted with one or more substituents each independently selected from the group consisting of halo, $C_1$-$C_4$alkyloxy, $CF_3$ and $C_1$-$C_4$alkyl;

$Het^2$ represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N; said $Het^2$ optionally being substituted with one or more substituents each independently selected from the group consisting of halo, $C_1$-$C_4$alkyloxy, $C_1$-$C_4$alkyl;

Z is C or N; $R^5$ is present where Z is C, whereby $R^5$ is selected form the group consisting of hydrogen, $CF_3$ and halogen; in particular $R^5$ is selected form the group consisting of $CF_3$ and halogen; $R^5$ is absent where Z is N;

and the pharmaceutically acceptable addition salts, and the solvates thereof.

In an embodiment, the present invention concerns novel compounds of Formula (I) and stereoisomeric forms thereof, wherein Het is a heterocycle having formula (b), (c), (d) or (e);

each X independently is C or N; provided that at least one X is N;

$R^{1b}$ is present when Het has formula (b) and X is C; each $R^{1b}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O—C_1$-$C_6$alkyl$)_2$; $R^{1b}$ is absent when the X to which it is bound is N;

$R^{2b}$ is —$(CR^8R^9)_m$—$R^{10b}$;

each $R^6$ is independently selected from the group consisting of H, $COOCH_3$ and $CONHSO_2CH_3$;

each $R^7$ is independently selected from the group consisting of OH, $C_1$-$C_6$alkyloxy, $NH_2$, $NHSO_2N(C_1$-$C_6$alkyl$)_2$, $NHSO_2NHCH_3$, $NHSO_2(C_1$-$C_6$alkyl), $NHSO_2(C_3$-$C_7$cycloalkyl) and $N(C_1$-$C_6$-alkyl$)_2$;

each $R^8$ and $R^9$ are independently chosen from the group consisting of H, and $C_3$-$C_7$cycloalkyl; or $R^8$ and $R^9$ taken together form a 4 to 6 membered aliphatic ring that optionally contains one or more heteroatoms selected from the group consisting of N, S and O;

$R^{10b}$ is selected from the group consisting of H, $R^{11}$, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, O-Benzyl, $NR^8SO_2R^9$, $SO_2NR^8R^9$, $SO_2R^8$, $OCONR^8R^9$, $OCONR^8R^{12}$, $N(R^8)CON(R^8R^9)$, $N(R^8)COOR^{12}$, and a 4 to 6 membered saturated ring containing one oxygen atom;

m is an integer from 2 to 6;

$R^{11}$ is selected from the group consisting of $C_1$-$C_6$ alkyl, $C_3$-$C_7$cycloalkyl, phenyl, pyridinyl and pyrazolyl; each optionally substituted with one or more substituents each independently selected from the group consisting of $CF_3$, $CH_3$, $OCH_3$, $OCF_3$ and halogen;

$R^{12}$ is selected from the group consisting of phenyl, pyridinyl and pyrazolyl; each optionally substituted with one or more substituents each independently selected from the group consisting of $CF_3$, $CH_3$, $OCH_3$, $OCF_3$ and halogen;

or $R^{12}$ is $C_1$-$C_6$ alkyl or $C_3$-$C_7$cycloalkyl; each substituted with one or more substituents each independently selected from the group consisting of $CF_3$, $CH_3$, $OCH_3$, $OCF_3$ and halogen;

$R^{1c}$ is present when Het has formula (c);

each $R^{1c}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^{7c})$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O—C_1$-$C_6$alkyl$)_2$;

$R^{3c}$ is selected from the group consisting of H, halogen, $C_1$-$C_6$alkyl, $C_3$-$C_7$cycloalkyl, $C_1$-$C_6$alkyloxy and $CO(R^{7c})$;

$R^{2c}$ is —$(CR^8R^9)_m$—$R^{10c}$;

$R^{7c}$ is selected from the group consisting of OH, $O(C_1$-$C_6$alkyl), $NH_2$, $NHSO_2N(C_1$-$C_6$alkyl$)_2$, $NHSO_2NHCH_3$, $NHSO_2(C_1$-$C_6$alkyl), $NHSO_2(C_3$-$C_7$cycloalkyl), $N(C_1$-$C_6$-alkyl$)_2$, $NR^8R^9$ and $NR^9R^{10c}$;

$R^{10c}$ is selected from the group consisting of H, $C_1$-$C_6$alkyl, OH, CN, F, $CF_2H$, $CF_3$, $C(=NOH)NH_2$, $CONR^8R^9$, $COOR^8$, $CONR^8SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$ and a 4 to 6 membered saturated ring containing one oxygen atom;

$R^{1d}$ is present when Het has formula (d) and X is C; each $R^{1d}$ is selected independently from the group consisting of H, OH, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O—C_1$-$C_6$alkyl$)_2$; $R^{1d}$ is absent when the X to which it is bound is N;

$R^{3d}$ is selected from the group consisting of H, halogen, $C_1$-$C_6$alkyl, $C_3$-$C_7$cycloalkyl, $C_1$-$C_6$alkyloxy, and $CO(R^7)$;

$R^{2d}$ is —$(CR^8R^9)_m$—$R^{10d}$;

$R^{10d}$ is selected from the group consisting of H, $C_1$-$C_6$alkyl, OH, CN, F, $CF_2H$, $CF_3$, $CONR^8R^9$, $COOR^8$, $CONR^8SO_2R^9$, $CON(R^8)SO_2N(R^8R^9)$, $NR^8R^9$, $NR^8COOR_9$, $OCOR^8$, $NR^8SO_2R^9$, $SO_2NR^8R^9$, $SO_2R^8$ and a 4 to 6 membered saturated ring containing one oxygen atom;

each Y independently is C or N;

$R^{1e}$ is present when Het has formula (e) and Y is C; each $R^{1e}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O—C_1$-$C_6$alkyl$)_2$; $R^{1e}$ is absent when the Y to which it is bound is N;

$R^{3e}$ is selected from the group consisting of H, halogen, —$(CR^8R^9)_m$—$R^{10e}$, $C=C—CH_2$—$R^{10e}$, $C\equiv C—R^{10e}$ and $C=C—R^{10e}$;

$R^{10e}$ is selected from the group consisting of H, $C_1$-$C_6$alkyl, $C_1$-$C_6$alkyloxy, $C_3$-$C_7$cycloalkyl, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$ and a 4 to 6 membered saturated ring containing one oxygen atom;

$R^4$ is selected from the group consisting of $Het^1$, aryl, $Het^2$, and $C_3$-$C_7$cycloalkyl substituted with one or more substituents selected from the group consisting of halo and $C_1$-$C_4$alkyl; in particular $Het^1$, $Het^2$, and $C_3$-$C_7$cycloalkyl substituted with one or more substituents selected from the group consisting of halo and $C_1$-$C_4$alkyl;

aryl represents phenyl or naphthalenyl; said aryl optionally being substituted with one or more substituents each independently selected from the group consisting of halo, $C_1$-$C_4$alkyloxy, $C_1$-$C_4$alkyl, OH, CN, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$, $OCONR^8R^9$, $OCONR^8R^{12}$, $N(R^8)CON(R^8R^9)$, $N(R^8)COOR^{12}$;

$Het^1$ represents a 4 to 6 membered saturated ring containing one N atom, optionally being substituted with one or more substituents each independently selected from the group consisting of halo, $C_1$-$C_4$alkyloxy, $SO_2R^8$, $C_1$-$C_4$alkylcarbonyl, CO(aryl), $COHet^2$, $C_1$-$C_4$alkyloxycarbonyl, pyridinyl, $CF_3$, $SO_2N(C_1$-$C_4$alkyl$)_2$, $SO_2NH(C_1$-$C_4$alkyl), (C=O)NH($C_{1-4}$alkyl), (C=S)NH($C_{1-4}$alkyl), $C_1$-$C_4$alkyl and $C_1$-$C_4$alkyl substituted with one hydroxy; or $Het^1$ represents a 4 to 6 membered saturated ring containing one O atom, substituted with one or more substituents each independently selected from the group consisting of halo, $C_1$-$C_4$alkyloxy, $CF_3$, NH(C=O)($C_{1-4}$alkyl), (C=O)NH($C_{1-4}$alkyl) and $C_1$-$C_4$alkyl;

$Het^2$ represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N; said $Het^2$ optionally being substituted with one or more substituents each independently selected from the group consisting of halo, $C_1$-$C_4$alkyloxy, $C_1$-$C_4$alkyl, OH, CN, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$, $OCONR^8R^9$, $OCONR^8R^{12}$, $N(R^8)CON(R^8R^9)$, $N(R^8)COOR^{12}$;

Z is C or N; $R^5$ is present where Z is C, whereby $R^5$ is selected form the group consisting of hydrogen, $CF_3$ and halogen; $R^5$ is absent where Z is N;

and the pharmaceutically acceptable addition salts, and the solvates thereof.

In an embodiment, the present invention concerns novel compounds of Formula (I) and stereoisomeric forms thereof, wherein Het is a heterocycle having formula (b), (c), (d) or (e);

each X independently is C or N; provided that at least one X is N;

$R^{1b}$ is present when Het has formula (b) and X is C; each $R^{1b}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, C(=NOH)$NH_2$, C(=NOCH$_3$)$NH_2$, C(=NH)$NH_2$, $CF_3$, $OCF_3$, $B(OH)_2$ and B(O—$C_1$-$C_6$alkyl)$_2$; $R^{1b}$ is absent when the X to which it is bound is N;

$R^{2b}$ is —(CR$^8$R$^9$)$_m$—R$^{10b}$;

each $R^6$ is independently selected from the group consisting of H, $C_1$-$C_6$alkyl, $COOCH_3$ and $CONHSO_2CH_3$;

each $R^7$ is independently selected from the group consisting of OH, $C_1$-$C_6$alkyloxy, $NH_2$, $NHSO_2N(C_1$-$C_6$alkyl)$_2$, $NHSO_2NHCH_3$, $NHSO_2(C_1$-$C_6$alkyl), $NHSO_2(C_3$-$C_7$cycloalkyl) and N($C_1$-$C_6$-alkyl)$_2$;

each $R^8$ and $R^9$ are independently chosen from the group consisting of H, $C_1$-$C_{10}$alkyl and $C_3$-$C_7$cycloalkyl; or $R^8$ and $R^9$ taken together form a 4 to 6 membered aliphatic ring that optionally contains one or more heteroatoms selected from the group consisting of N, S and O;

$R^{10b}$ is selected from the group consisting of H, $R^{11}$, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, O-Benzyl, $NR^8SO_2R^9$, $SO_2NR^8R^9$, $SO_2R^8$, $OCONR^8R^9$, $OCONR^8R^{12}$, $N(R^8)CON(R^8R^9)$, $N(R^8)COOR^{12}$, and a 4 to 6 membered saturated ring containing one oxygen atom;

m is an integer from 2 to 6;

$R^{11}$ is selected from the group consisting of $C_1$-$C_6$ alkyl, $C_3$-$C_7$cycloalkyl, phenyl, pyridinyl and pyrazolyl; each optionally substituted with one or more substituents each independently selected from the group consisting of $CF_3$, $CH_3$, $OCH_3$, $OCF_3$ and halogen;

$R^{12}$ is selected from the group consisting of phenyl, pyridinyl and pyrazolyl; each optionally substituted with one or more substituents each independently selected from the group consisting of $CF_3$, $CH_3$, $OCH_3$, $OCF_3$ and halogen; or $R^{12}$ is $C_1$-$C_6$ alkyl or $C_3$-$C_7$cycloalkyl; each substituted with one or more substituents each independently selected from the group consisting of $CF_3$, $CH_3$, $OCH_3$, $OCF_3$ and halogen;

$R^{1c}$ is present when Het has formula (c);

each $R^{1c}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^{7c})$, $CH_2NH_2$, $CH_2OH$, CN, C(=NOH)$NH_2$, C(=NOCH$_3$)$NH_2$, C(=NH)$NH_2$, $CF_3$, $OCF_3$, $B(OH)_2$ and B(O—$C_1$-$C_6$alkyl)$_2$;

$R^{3c}$ is selected from the group consisting of H, halogen, $C_1$-$C_6$alkyl, $C_3$-$C_7$cycloalkyl, $C_1$-$C_6$alkyloxy and CO($R^{7c}$);

$R^{2c}$ is —(CR$^8$R$^9$)$_m$—R$^{10c}$;

$R^{7c}$ is selected from the group consisting of OH, O($C_1$-$C_6$alkyl), $NH_2$, $NHSO_2N(C_1$-$C_6$alkyl)$_2$, $NHSO_2NHCH_3$, $NHSO_2(C_1$-$C_6$alkyl), $NHSO_2(C_3$-$C_7$cycloalkyl), N($C_1$-$C_6$-alkyl)$_2$, $NR^8R^9$ and $NR^9R^{10c}$;

$R^{10c}$ is selected from the group consisting of H, $C_1$-$C_6$alkyl, OH, CN, F, $CF_2H$, $CF_3$, C(=NOH)$NH_2$, $CONR^8R^9$, $COOR^8$, $CONR^8SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$ and a 4 to 6 membered saturated ring containing one oxygen atom;

$R^{1d}$ is present when Het has formula (d) and X is C; each $R^{1d}$ is selected independently from the group consisting of H, OH, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, C(=NOH)$NH_2$, C(=NOCH$_3$)$NH_2$, C(=NH)$NH_2$, $CF_3$, $OCF_3$, $B(OH)_2$ and B(O—$C_1$-$C_6$alkyl)$_2$; $R^{1d}$ is absent when the X to which it is bound is N;

$R^{3d}$ is selected from the group consisting of H, halogen, $C_1$-$C_6$alkyl, $C_3$-$C_7$cycloalkyl, $C_1$-$C_6$alkyloxy, and CO($R^7$);

$R^{2d}$ is —(CR$^8$R$^9$)$_m$—R$^{10d}$;

$R^{10d}$ is selected from the group consisting of H, $C_1$-$C_6$alkyl, OH, CN, F, $CF_2H$, $CF_3$, $CONR^8R^9$, $COOR^8$, $CONR^8SO_2R^9$, $CON(R^8)SO_2N(R^8R^9)$, $NR^8R^9$, $NR^8COOR_9$, $OCOR^8$, $NR^8SO_2R^9$, $SO_2NR^8R^9$, $SO_2R^8$ and a 4 to 6 membered saturated ring containing one oxygen atom;

each Y independently is C or N;

$R^{1e}$ is present when Het has formula (e) and Y is C; each $R^{1e}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O-C_1$-$C_6$alkyl$)_2$; $R^{1e}$ is absent when the Y to which it is bound is N;

$R^{3e}$ is selected from the group consisting of H, halogen, $-(CR^8R^9)_m-R^{10e}$, $C=C-CH_2-R^{10e}$, $C=C-R^{10e}$ and $C=C-R^{10e}$;

$R^{10e}$ is selected from the group consisting of H, $C_1$-$C_6$alkyl, $C_1$-$C_6$alkyloxy, $C_3$-$C_7$cycloalkyl, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$ and a 4 to 6 membered saturated ring containing one oxygen atom;

$R^4$ is selected from the group consisting of tert-butyl, $Het^1$, aryl, $Het^2$, $CH(CH_3)(CF_3)$, and $C_3$-$C_7$cycloalkyl substituted with one or more substituents selected from the group consisting of halo and $C_1$-$C_4$alkyl;

aryl represents phenyl or naphthalenyl; said aryl optionally being substituted with one or more substituents each independently selected from the group consisting of halo, $C_1$-$C_4$alkyloxy, $C_1$-$C_4$alkyl, $SO_2CH_3$, $CF_3$, $SO_2N(C_1$-$C_4$alkyl$)_2$, $SO_2NH(C_1$-$C_4$alkyl), CN, $(C=O)NH(C_1$-$C_4$alkyl), $(C=O)N(C_1$-$C_4$alkyl$)_2$, $NH(C=O)O(C_{1-4}$alkyl), $O(C=O)NH(C_1$-$C_4$alkyl) and $O(C=O)N(C_1$-$C_4$alkyl$)_2$;

$Het^1$ represents a 4 to 6 membered saturated ring containing one N atom, optionally being substituted with one or more substituents each independently selected from the group consisting of halo, $C_1$-$C_4$alkyloxy, $SO_2CH_3$, $C_1$-$C_4$alkylcarbonyl, $C_1$-$C_4$alkyloxycarbonyl, pyridinyl, $CF_3$, $SO_2N(C_1$-$C_4$alkyl$)_2$, $SO_2NH(C_1$-$C_4$alkyl), $(C=O)NH(C_{1-4}$alkyl), $C_1$-$C_4$alkyl and $C_1$-$C_4$alkyl substituted with one hydroxy; or $Het^1$ represents a 4 to 6 membered saturated ring containing one O atom, substituted with one or more substituents each independently selected from the group consisting of halo, $C_1$-$C_4$alkyloxy, $CF_3$, $NH(C=O)(C_{1-4}$alkyl), $(C=O)NH(C_{1-4}$alkyl) and $C_1$-$C_4$alkyl;

$Het^2$ represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N; said $Het^2$ optionally being substituted with one or more substituents each independently selected from the group consisting of halo, $C_1$-$C_4$alkyloxy, $C_1$-$C_4$alkyl, $SO_2CH_3$, $CF_3$, $SO_2N(C_1$-$C_4$alkyl$)_2$, $SO_2NH(C_1$-$C_4$alkyl), CN, $(C=O)NH(C_1$-$C_4$alkyl), $(C=O)N(C_1$-$C_4$alkyl$)_2$, $NH(C=O)O(C_{1-4}$alkyl), $O(C=O)NH(C_1$-$C_4$alkyl) and $O(C=O)N(C_1$-$C_4$alkyl$)_2$;

Z is C or N; $R^5$ is present where Z is C, whereby $R^5$ is selected form the group consisting of hydrogen, $CF_3$ and halogen; $R^5$ is absent where Z is N;

and the pharmaceutically acceptable addition salts, and the solvates thereof.

In an embodiment, the present invention concerns novel compounds of Formula (I) and stereoisomeric forms thereof, Het is a heterocycle having formula (b), (c), (d) or (e); in particular (b) or (c); each X independently is C or N; provided that at least one X is N;

$R^{1b}$ is present when Het has formula (b) and X is C; each $R^{1b}$ is selected independently from the group consisting of H, halogen, $C_1$-$C_6$alkyl, $C_3$-$C_7$cycloalkyl, $C_1$-$C_6$alkyloxy, $CH_2NH_2$, $CH_2OH$, CN, $CF_3$, $OCF_3$;

$R^{1b}$ is absent when the X to which it is bound is N;

$R^{2b}$ is $-(CR^8R^9)_m-R^{10b}$;

each $R^8$ and $R^9$ are independently chosen from the group consisting of H, $C_1$-$C_{10}$alkyl and $C_3$-$C_7$cycloalkyl;

$R^{10b}$ is selected from the group consisting of H, $R^{11}$, OH, CN, F, $CF_2H$, $CF_3$, $SO_2R^8$;

m is an integer from 2 to 6;

$R^{11}$ is selected from the group consisting of $C_1$-$C_6$ alkyl optionally substituted with one or more substituents each independently selected from the group consisting of $CF_3$, $CH_3$, $OCH_3$, $OCF_3$ and halogen;

$R^{1c}$ is present when Het has formula (c);

each $R^{1c}$ is selected independently from the group consisting of H, halogen, $C_1$-$C_6$alkyl, $C_3$-$C_7$cycloalkyl, $C_1$-$C_6$alkyloxy, $CH_2NH_2$, $CH_2OH$, CN, $CF_3$, $OCF_3$;

$R^{1c}$ is selected from the group consisting of H;

$R^{2c}$ is $-(CR^8R^9)_m-R^{10c}$;

$R^{10c}$ is selected from the group consisting of H, $C_1$-$C_6$alkyl, OH, CN, F, $CF_2H$, $CF_3$, $SO_2R^8$;

$R^{1d}$ is present when Het has formula (d) and X is C; each $R^{1d}$ is selected independently from the group consisting of H, OH, halogen, $C_1$-$C_6$alkyl, $C_3$-$C_7$cycloalkyl, $C_1$-$C_6$alkyloxy, $CH_2NH_2$, $CH_2OH$, CN, $CF_3$, $OCF_3$;

$R^{1d}$ is absent when the X to which it is bound is N;

$R^{3d}$ is selected from the group consisting of H;

$R^{2d}$ is $-(CR^8R^9)_m-R^{10d}$;

$R^{10d}$ is selected from the group consisting of H, $C_1$-$C_6$alkyl, OH, CN, F, $CF_2H$, $CF_3$, $SO_2R^8$;

each Y independently is C or N;

$R^{1e}$ is present when Het has formula (e) and Y is C; each $R^{1e}$ is selected independently from the group consisting of H, halogen, $C_1$-$C_6$alkyl, $C_3$-$C_7$cycloalkyl, $C_1$-$C_6$alkyloxy, $CH_2NH_2$, $CH_2OH$, CN, $CF_3$, $OCF_3$;

$R^{1e}$ is absent when the Y to which it is bound is N;

$R^{3e}$ is selected from the group consisting of $-(CR^8R^9)_m-R^{10e}$;

$R^{10e}$ is selected from the group consisting of H, $C_1$-$C_6$alkyloxy, $C_3$-$C_7$cycloalkyl, OH, CN, F, $CF_2H$, $CF_3$, $SO_2R^8$;

$R^4$ is selected from the group consisting of tert-butyl, $Het^1$, aryl, $Het^2$, $CH(CH_3)(CF_3)$, and $C_3$-$C_7$cycloalkyl substituted with one or more substituents selected from the group consisting of halo and $C_1$-$C_4$alkyl;

aryl represents phenyl or naphthalenyl; said aryl optionally being substituted with one or more substituents each independently selected from the group consisting of halo, $C_1$-$C_4$alkyloxy, $SO_2CH_3$, $CF_3$, $SO_2N(C_1$-$C_4$alkyl$)_2$, $SO_2NH(C_1$-$C_4$alkyl), CN, $(C=O)NH(C_1$-$C_4$alkyl), $(C=O)N(C_1$-$C_4$alkyl$)_2$, $NH(C=O)O(C_{1-4}$alkyl), $O(C=O)NH(C_1$-$C_4$alkyl) and $O(C=O)N(C_1$-$C_4$alkyl$)_2$;

$Het^1$ represents a 4 to 6 membered saturated ring containing one N atom, optionally being substituted with one or more substituents each independently selected from the group consisting of halo, $C_1$-$C_4$alkyloxy, $SO_2CH_3$, $C_1$-$C_4$alkylcarbonyl, $C_1$-$C_4$alkyloxycarbonyl, pyridinyl, $CF_3$, $SO_2N(C_1$-$C_4$alkyl$)_2$, $SO_2NH(C_1$-$C_4$alkyl), $(C=O)NH(C_{1-4}$alkyl), $C_1$-$C_4$alkyl and $C_1$-$C_4$alkyl substituted with one hydroxy; or $Het^1$ represents a 4 to 6 membered saturated ring containing one O atom, substituted with one or more substituents each independently selected from the group consisting of halo, $C_1$-$C_4$alkyloxy, $CF_3$, $NH(C=O)(C_{1-4}alkyl)$, $(C=O)NH(C_{1-4}alkyl)$ and $C_1$-$C_4$alkyl;

$Het^2$ represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N; said $Het^2$ optionally being substituted with one or more substituents each independently selected from the group consisting of halo, $C_1$-$C_4$alkyloxy, $C_1$-$C_4$alkyl, $SO_2CH_3$, $CF_3$, $SO_2N(C_1$-$C_4alkyl)_2$, $SO_2NH(C_1$-$C_4alkyl)$, CN, $(C=O)NH(C_1$-$C_4alkyl)$, $(C=O)N(C_1$-$C_4alkyl)_2$, $NH(C=O)O(C_{1-4}alkyl)$, $O(C=O)NH(C_1$-$C_4alkyl)$ and $O(C=O)N(C_1$-$C_4alkyl)_2$;

Z is C or N; $R^5$ is present where Z is C, whereby $R^5$ is selected form the group consisting of hydrogen, $CF_3$ and halogen; $R^5$ is absent where Z is N;

and the pharmaceutically acceptable addition salts, and the solvates thereof.

In an embodiment, the present invention relates to those compounds of formula (I), or any subgroup thereof as mentioned in any of the other embodiments, wherein each $R^8$ and $R^9$ are independently chosen from the group consisting of H, and $C_3$-$C_7$cycloalkyl.

In an embodiment, the present invention relates to those compounds of formula (I), or any subgroup thereof as mentioned in any of the other embodiments, wherein $R^4$ is $Het^1$.

In an embodiment, the present invention relates to those compounds of formula (I), or any subgroup thereof as mentioned in any of the other embodiments, wherein $R^4$ is aryl or $Het^2$; in particular $Het^2$.

In an embodiment, the present invention relates to those compounds of formula (I), or any subgroup thereof as mentioned in any of the other embodiments, aryl represents phenyl or naphthalenyl; said aryl optionally being substituted with one or more substituents each independently selected from the group consisting of halo, $C_1$-$C_4$alkyloxy, $C_1$-$C_4$alkyl;

$Het^1$ represents a 4 to 6 membered saturated ring containing one N atom, optionally being substituted with one or more substituents each independently selected from the group consisting of halo, $C_1$-$C_4$alkyloxy, $SO_2R^8$, $C_1$-$C_4$alkylcarbonyl, $C_1$-$C_4$alkyloxycarbonyl, pyridinyl, $CF_3$, $C_1$-$C_4$alkyl and $C_1$-$C_4$alkyl substituted with one hydroxy; or $Het^1$ represents a 4 to 6 membered saturated ring containing one O atom, substituted with one or more substituents each independently selected from the group consisting of halo, $C_1$-$C_4$alkyloxy, $CF_3$ and $C_1$-$C_4$alkyl;

$Het^2$ represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N; said $Het^2$ optionally being substituted with one or more substituents each independently selected from the group consisting of halo, $C_1$-$C_4$alkyloxy, $C_1$-$C_4$alkyl;

Z is C or N; $R^5$ is present where Z is C, whereby $R^5$ is selected form the group consisting of hydrogen, $CF_3$ and halogen; in particular $R^5$ is selected form the group consisting of $CF_3$ and halogen; $R^5$ is absent where Z is N.

In an embodiment, the present invention relates to those compounds of formula (I), or any subgroup thereof as mentioned in any of the other embodiments, wherein aryl represents phenyl or naphthalenyl; said aryl optionally being substituted with one or more substituents each independently selected from the group consisting of halo, $C_1$-$C_4$alkyloxy, $C_1$-$C_4$alkyl, $SO_2CH_3$, $CF_3$, $SO_2N(C_1$-$C_4alkyl)_2$, $SO_2NH(C_1$-$C_4alkyl)$, CN, $(C=O)NH(C_1$-$C_4alkyl)$, $(C=O)N(C_1$-$C_4alkyl)_2$, $NH(C=O)O(C_{1-4}alkyl)$, $O(C=O)NH(C_1$-$C_4alkyl)$ and $O(C=O)N(C_1$-$C_4alkyl)_2$;

$Het^1$ represents a 4 to 6 membered saturated ring containing one N atom, optionally being substituted with one or more substituents each independently selected from the group consisting of halo, $C_1$-$C_4$alkyloxy, $SO_2CH_3$, $C_1$-$C_4$alkylcarbonyl, $C_1$-$C_4$alkyloxycarbonyl, pyridinyl, $CF_3$, $SO_2N(C_1$-$C_4alkyl)_2$, $SO_2NH(C_1$-$C_4alkyl)$, $(C=O)NH(C_{1-4}alkyl)$, $C_1$-$C_4$alkyl and $C_1$-$C_4$alkyl substituted with one hydroxy; or $Het^1$ represents a 4 to 6 membered saturated ring containing one O atom, substituted with one or more substituents each independently selected from the group consisting of halo, $C_1$-$C_4$alkyloxy, $CF_3$, $NH(C=O)(C_{1-4}alkyl)$, $(C=O)NH(C_{1-4}alkyl)$ and $C_1$-$C_4$alkyl;

$Het^2$ represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N; said $Het^2$ optionally being substituted with one or more substituents each independently selected from the group consisting of halo, $C_1$-$C_4$alkyloxy, $C_1$-$C_4$alkyl, $SO_2CH_3$, $CF_3$, $SO_2N(C_1$-$C_4alkyl)_2$, $SO_2NH(C_1$-$C_4alkyl)$, CN, $(C=O)NH(C_1$-$C_4alkyl)$, $(C=O)N(C_1$-$C_4alkyl)_2$, $NH(C=O)O(C_{1-4}alkyl)$, $O(C=O)NH(C_1$-$C_4alkyl)$ and $O(C=O)N(C_1$-$C_4alkyl)_2$.

In an embodiment, the present invention concerns novel compounds of Formula (I) and stereoisomeric forms thereof, wherein Het is a heterocycle having formula (b), (c), (d) or (e);

each X independently is C or N; provided that at least one X is N;

$R^{1b}$ is present when Het has formula (b) and X is C; each $R^{1b}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O-C_1$-$C_6alkyl)_2$; $R^{1b}$ is absent when the X to which it is bound is N;

$R^{2b}$ is —$(CR^8R^9)_m$—$R^{10b}$;

each $R^6$ is independently selected from the group consisting of H, $COOCH_3$ and $CONHSO_2CH_3$;

each $R^7$ is independently selected from the group consisting of OH, $C_1$-$C_6$alkyloxy, $NH_2$, $NHSO_2N(C_1$-$C_6alkyl)_2$, $NHSO_2NHCH_3$, $NHSO_2(C_1$-$C_6alkyl)$, $NHSO_2(C_3$-$C_7cycloalkyl)$ and $N(C_1$-$C_6$-$alkyl)_2$;

each $R^8$ and $R^9$ are independently chosen from the group consisting of H, and $C_3$-$C_7$cycloalkyl; or $R^8$ and $R^9$ taken together form a 4 to 6 membered aliphatic ring that optionally contains one or more heteroatoms selected from the group consisting of N, S and O;

$R^{10b}$ is selected from the group consisting of H, $R^{11}$, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, O-Benzyl, $NR^8SO_2R^9$, $SO_2NR^8R^9$, $SO_2R^8$, $OCONR^8R^9$, OCONR$^8$R$^{12}$, N(R$^8$)CON(R$^8$R$^9$), N(R$^8$)COOR$^{12}$, and a 4 to 6 membered saturated ring containing one oxygen atom;

m is an integer from 2 to 6;

R$^{11}$ is selected from the group consisting of C$_1$-C$_6$ alkyl, C$_3$-C$_7$cycloalkyl, phenyl, pyridinyl and pyrazolyl; each optionally substituted with one or more substituents each independently selected from the group consisting of CF$_3$, CH$_3$, OCH$_3$, OCF$_3$ and halogen;

R$^{12}$ is selected from the group consisting of phenyl, pyridinyl and pyrazolyl; each optionally substituted with one or more substituents each independently selected from the group consisting of CF$_3$, CH$_3$, OCH$_3$, OCF$_3$ and halogen; or R$^{12}$ is C$_1$-C$_6$ alkyl or C$_3$-C$_7$cycloalkyl; each substituted with one or more substituents each independently selected from the group consisting of CF$_3$, CH$_3$, OCH$_3$, OCF$_3$ and halogen;

R$^{1c}$ is present when Het has formula (c);

each R$^{1c}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^{7c}$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$;

R$^{3c}$ is selected from the group consisting of H, halogen, C$_1$-C$_6$alkyl, C$_3$-C$_7$cycloalkyl, C$_1$-C$_6$alkyloxy and CO(R$^{7c}$);

R$^{2c}$ is —(CR$^8$R$^9$)$_m$—R$^{10c}$;

R$^{7c}$ is selected from the group consisting of OH, O(C$_1$-C$_6$alkyl), NH$_2$, NHSO$_2$N(C$_1$-C$_6$alkyl)$_2$, NHSO$_2$NHCH$_3$, NHSO$_2$(C$_1$-C$_6$alkyl), NHSO$_2$(C$_3$-C$_7$cycloalkyl), N(C$_1$-C$_6$-alkyl)$_2$, NR$^8$R$^9$ and NR$^9$R$^{10c}$;

R$^{10c}$ is selected from the group consisting of H, C$_1$-C$_6$alkyl, OH, CN, F, CF$_2$H, CF$_3$, C(=NOH)NH$_2$, CONR$^8$R$^9$, COOR$^8$, CONR$^8$SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$ and a 4 to 6 membered saturated ring containing one oxygen atom;

R$^{1d}$ is present when Het has formula (d) and X is C; each R$^{1d}$ is selected independently from the group consisting of H, OH, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; R$^{1d}$ is absent when the X to which it is bound is N;

R$^{3d}$ is selected from the group consisting of H, halogen, C$_1$-C$_6$alkyl, C$_3$-C$_7$cycloalkyl, C$_1$-C$_6$alkyloxy, and CO(R$^7$);

R$^{2d}$ is —(CR$^8$R$^9$)$_m$—R$^{10d}$;

R$^{10d}$ is selected from the group consisting of H, C$_1$-C$_6$alkyl, OH, CN, F, CF$_2$H, CF$_3$, CONR$^8$R$^9$, COOR$^8$, CONR$^8$SO$_2$R$^9$, CON(R$^8$)SO$_2$N(R$^8$R$^9$), NR$^8$R$^9$, NR$^8$COOR$_9$, OCOR$^8$, NR$^8$SO$_2$R$^9$, SO$_2$NR$^8$R$^9$, SO$_2$R$^8$ and a 4 to 6 membered saturated ring containing one oxygen atom;

each Y independently is C or N;

R$^{1e}$ is present when Het has formula (e) and Y is C; each R$^{1e}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; R$^{1e}$ is absent when the Y to which it is bound is N;

R$^{3e}$ is selected from the group consisting of H, halogen, —(CR$^8$R$^9$)$_m$—R$^{10e}$, C=C—CH$_2$—R$^{10e}$, C≡C—R$^{10e}$ and C=C—R$^{10e}$;

R$^{10e}$ is selected from the group consisting of H, C$_1$-C$_6$alkyl, C$_1$-C$_6$alkyloxy, C$_3$-C$_7$cycloalkyl, OH, CN, F, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$ and a 4 to 6 membered saturated ring containing one oxygen atom;

R$^4$ is selected from the group consisting of Het$^1$ and C$_3$-C$_7$cycloalkyl substituted with one or more substituents selected from the group consisting of halo and C$_1$-C$_4$alkyl; in particular R$^4$ is Het$^1$;

Het$^1$ represents a 4 to 6 membered saturated ring containing one N atom, optionally being substituted with one or more substituents each independently selected from the group consisting of halo, C$_1$-C$_4$alkyloxy, SO$_2$R$^8$, C$_1$-C$_4$alkylcarbonyl, CO(aryl), COHet$^2$, C$_1$-C$_4$alkyloxycarbonyl, pyridinyl, CF$_3$, SO$_2$N(C$_1$-C$_4$alkyl)$_2$, SO$_2$NH(C$_1$-C$_4$alkyl), (C=O)NH(C$_{1-4}$alkyl), (C=S)NH(C$_{1-4}$alkyl), C$_1$-C$_4$alkyl and C$_1$-C$_4$alkyl substituted with one hydroxy; or Het$^1$ represents a 4 to 6 membered saturated ring containing one O atom, substituted with one or more substituents each independently selected from the group consisting of halo, C$_1$-C$_4$alkyloxy, CF$_3$, NH(C=O)(C$_{1-4}$alkyl), (C=O)NH(C$_{1-4}$alkyl) and C$_1$-C$_4$alkyl;

aryl represents phenyl or naphthalenyl; said aryl optionally being substituted with one or more substituents each independently selected from the group consisting of halo, C$_1$-C$_4$alkyloxy, C$_1$-C$_4$alkyl, OH, CN, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$, OCONR$^8$R$^9$, OCONR$^8$R$^{12}$, N(R$^8$)CON(R$^8$R$^9$), N(R$^8$)COOR$^{12}$;

Het$^2$ represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N; said Het$^2$ optionally being substituted with one or more substituents each independently selected from the group consisting of halo, C$_1$-C$_4$alkyloxy, C$_1$-C$_4$alkyl, OH, CN, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$, OCONR$^8$R$^9$, OCONR$^8$R$^{12}$, N(R$^8$)CON(R$^8$R$^9$), N(R$^8$)COOR$^{12}$;

Z is C or N; R$^5$ is present where Z is C, whereby R$^5$ is selected form the group consisting of hydrogen, CF$_3$ and halogen; R$^5$ is absent where Z is N;

and the pharmaceutically acceptable addition salts, and the solvates thereof.

In an embodiment, the present invention concerns novel compounds of Formula (I) and stereoisomeric forms thereof, wherein Het is a heterocycle having formula (b), (c), (d) or (e);

each X independently is C or N; provided that at least one X is N;

R$^{1b}$ is present when Het has formula (b) and X is C; each R$^{1b}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; R$^{1b}$ is absent when the X to which it is bound is N;

R$^{2b}$ is —(CR$^8$R$^9$)$_m$—R$^{10b}$;

each R$^6$ is independently selected from the group consisting of H, COOCH$_3$ and CONHSO$_2$CH$_3$;

each R$^7$ is independently selected from the group consisting of OH, C$_1$-C$_6$alkyloxy, NH$_2$, NHSO$_2$N(C$_1$-C$_6$alkyl)$_2$, NHSO$_2$NHCH$_3$, NHSO$_2$(C$_1$-C$_6$alkyl), NHSO$_2$(C$_3$-C$_7$cycloalkyl) and N(C$_1$-C$_6$-alkyl)$_2$;

each R$^8$ and R$^9$ are independently chosen from the group consisting of H, and C$_3$-C$_7$cycloalkyl; or R$^8$ and R$^9$ taken together form a 4 to 6 membered aliphatic ring that optionally contains one or more heteroatoms selected from the group consisting of N, S and O;

R$^{10b}$ is selected from the group consisting of H, R$^{11}$, OH, CN, F, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, O-Benzyl, NR$^8$SO$_2$R$^9$, SO$_2$NR$^8$R$^9$, SO$_2$R$^8$, OCONR$^8$R$^9$, OCONR$^8$R$^{12}$, N(R$^8$)CON(R$^8$R$^9$), N(R$^8$)COOR$^{12}$, and a 4 to 6 membered saturated ring containing one oxygen atom;

m is an integer from 2 to 6;

R$^{11}$ is selected from the group consisting of C$_1$-C$_6$ alkyl, C$_3$-C$_7$cycloalkyl, phenyl, pyridinyl and pyrazolyl; each optionally substituted with one or more substituents each independently selected from the group consisting of CF$_3$, CH$_3$, OCH$_3$, OCF$_3$ and halogen;

R$^{12}$ is selected from the group consisting of phenyl, pyridinyl and pyrazolyl; each optionally substituted with one or more substituents each independently selected from the group consisting of CF$_3$, CH$_3$, OCH$_3$, OCF$_3$ and halogen; or R$^{12}$ is C$_1$-C$_6$ alkyl or C$_3$-C$_7$cycloalkyl; each substituted with one or more substituents each independently selected from the group consisting of CF$_3$, CH$_3$, OCH$_3$, OCF$_3$ and halogen;

R$^{1c}$ is present when Het has formula (c);

each R$^{1c}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^{7c}$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$;

R$^{3c}$ is selected from the group consisting of H, halogen, C$_1$-C$_6$alkyl, C$_3$-C$_7$cycloalkyl, C$_1$-C$_6$alkyloxy and CO(R$^{7c}$);

R$^{2c}$ is —(CR$^8$R$^9$)$_m$—R$^{10c}$;

R$^{7c}$ is selected from the group consisting of OH, O(C$_1$-C$_6$alkyl), NH$_2$, NHSO$_2$N(C$_1$-C$_6$alkyl)$_2$, NHSO$_2$NHCH$_3$, NHSO$_2$(C$_1$-C$_6$alkyl), NHSO$_2$(C$_3$-C$_7$cycloalkyl), N(C$_1$-C$_6$-alkyl)$_2$, NR$^8$R$^9$ and NR$^9$R$^{10c}$;

R$^{10c}$ is selected from the group consisting of H, C$_1$-C$_6$alkyl, OH, CN, F, CF$_2$H, CF$_3$, C(=NOH)NH$_2$, CONR$^8$R$^9$, COOR$^8$, CONR$^8$SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$ and a 4 to 6 membered saturated ring containing one oxygen atom;

R$^{10d}$ is present when Het has formula (d) and X is C; each R$^{1d}$ is selected independently from the group consisting of H, OH, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; R$^{1d}$ is absent when the X to which it is bound is N;

R$^{3d}$ is selected from the group consisting of H, halogen, C$_1$-C$_6$alkyl, C$_3$-C$_7$cycloalkyl, C$_1$-C$_6$alkyloxy, and CO(R$^7$);

R$^{2d}$ is —(CR$^8$R$^9$)$_m$—R$^{10d}$;

R$^{10d}$ is selected from the group consisting of H, C$_1$-C$_6$alkyl, OH, CN, F, CF$_2$H, CF$_3$, CONR$^8$R$^9$, COOR$^8$, CONR$^8$SO$_2$R$^9$, CON(R$^8$)SO$_2$N(R$^8$R$^9$), NR$^8$R$^9$, NR$^8$COOR$_9$, OCOR$^8$, NR$^8$SO$_2$R$^9$, SO$_2$NR$^8$R$^9$, SO$_2$R$^8$ and a 4 to 6 membered saturated ring containing one oxygen atom;

each Y independently is C or N;

R$^{1e}$ is present when Het has formula (e) and Y is C; each R$^{1e}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; R$^{1e}$ is absent when the Y to which it is bound is N;

R$^{3e}$ is selected from the group consisting of H, halogen, —(CR$^8$R$^9$)$_m$—R$^{10e}$, C=C—CH$_2$—R$^{10e}$, C≡C—R$^{10e}$ and C=C—R$^{10e}$;

R$^{10e}$ is selected from the group consisting of H, C$_1$-C$_6$alkyl, C$_1$-C$_6$alkyloxy, C$_3$-C$_7$cycloalkyl, OH, CN, F, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$ and a 4 to 6 membered saturated ring containing one oxygen atom;

R$^4$ is selected from the group consisting of Het$^1$ and C$_3$-C$_7$cycloalkyl substituted with one or more substituents selected from the group consisting of halo and C$_1$-C$_4$alkyl; in particular R$^4$ is Het$^1$;

Het$^1$ represents a 4 to 6 membered saturated ring containing one N atom, optionally being substituted with one or more substituents each independently selected from the group consisting of halo, C$_1$-C$_4$alkyloxy, SO$_2$R$^8$, C$_1$-C$_4$alkylcarbonyl, C$_1$-C$_4$alkyloxycarbonyl, pyridinyl, CF$_3$, SO$_2$N(C$_1$-C$_4$alkyl)$_2$, SO$_2$NH(C$_1$-C$_4$alkyl), (C=O)NH(C$_{1-4}$alkyl), (C=S)NH(C$_{1-4}$alkyl), C$_1$-C$_4$alkyl and C$_1$-C$_4$alkyl substituted with one hydroxy; or Het$^1$ represents a 4 to 6 membered saturated ring containing one O atom, substituted with one or more substituents each independently selected from the group consisting of halo, C$_1$-C$_4$alkyloxy, CF$_3$, NH(C=O)(C$_{1-4}$alkyl), (C=O)NH(C$_{1-4}$alkyl) and C$_1$-C$_4$alkyl;

Z is C or N; R$^5$ is present where Z is C, whereby R$^5$ is selected form the group consisting of hydrogen, CF$_3$ and halogen; R$^5$ is absent where Z is N;

and the pharmaceutically acceptable addition salts, and the solvates thereof.

In an embodiment, the present invention concerns novel compounds of Formula (I) and stereoisomeric forms thereof, wherein Het is a heterocycle having formula (b), (c), (d) or (e);

each X independently is C or N; provided that at least one X is N;

R$^{1b}$ is present when Het has formula (b) and X is C; each R$^{1b}$ is selected independently from the group consisting of H, halogen, C$_1$-C$_6$alkyl, C$_3$-C$_7$cycloalkyl, C$_1$-C$_6$alkyloxy, N(R$^6$)$_2$, CO(R$^7$), CH$_2$NH$_2$, CH$_2$OH, CN, C(=NOH)NH$_2$, C(=NOCH$_3$)NH$_2$, C(=NH)NH$_2$, CF$_3$, OCF$_3$, B(OH)$_2$ and B(O—C$_1$-C$_6$alkyl)$_2$; R$^{1b}$ is absent when the X to which it is bound is N;

R$^{2b}$ is —(CR$^8$R$^9$)$_m$—R$^{10b}$;

each R$^6$ is independently selected from the group consisting of H, C$_1$-C$_6$alkyl, COOCH$_3$ and CONHSO$_2$CH$_3$;

each R$^7$ is independently selected from the group consisting of OH, C$_1$-C$_6$alkyloxy, NH$_2$, NHSO$_2$N(C$_1$-C$_6$alkyl)$_2$, NHSO$_2$NHCH$_3$, NHSO$_2$(C$_1$-C$_6$alkyl), NHSO$_2$(C$_3$-C$_7$cycloalkyl) and N(C$_1$-C$_6$-alkyl)$_2$;

each R$^8$ and R$^9$ are independently chosen from the group consisting of H, C$_1$-C$_{10}$alkyl and C$_3$-C$_7$cycloalkyl; or R$^8$ and R$^9$ taken together form a 4 to 6 membered aliphatic ring that optionally contains one or more heteroatoms selected from the group consisting of N, S and O;

R$^{10b}$ is selected from the group consisting of H, R$^{11}$, OH, CN, F, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, O-Benzyl, $NR^8SO_2R^9$, $SO_2NR^8R^9$, $SO_2R^8$, $OCONR^8R^9$, $OCONR^8R^{12}$, $N(R^8)CON(R^8R^9)$, $N(R^8)COOR^{12}$, and a 4 to 6 membered saturated ring containing one oxygen atom;

m is an integer from 2 to 6;

$R^{11}$ is selected from the group consisting of $C_1$-$C_6$ alkyl, $C_3$-$C_7$cycloalkyl, phenyl, pyridinyl and pyrazolyl; each optionally substituted with one or more substituents each independently selected from the group consisting of $CF_3$, $CH_3$, $OCH_3$, $OCF_3$ and halogen;

$R^{12}$ is selected from the group consisting of phenyl, pyridinyl and pyrazolyl; each optionally substituted with one or more substituents each independently selected from the group consisting of $CF_3$, $CH_3$, $OCH_3$, $OCF_3$ and halogen; or $R^{12}$ is $C_1$-$C_6$ alkyl or $C_3$-$C_7$cycloalkyl; each substituted with one or more substituents each independently selected from the group consisting of $CF_3$, $CH_3$, $OCH_3$, $OCF_3$ and halogen;

$R^{1c}$ is present when Het has formula (c);

each $R^{1c}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^{7c})$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O-C_1-C_6alkyl)_2$;

$R^{3c}$ is selected from the group consisting of H, halogen, $C_1$-$C_6$alkyl, $C_3$-$C_7$cycloalkyl, $C_1$-$C_6$alkyloxy and $CO(R^{7c})$;

$R^{2c}$ is $-(CR^8R^9)_m-R^{10c}$;

$R^{7c}$ is selected from the group consisting of OH, $O(C_1$-$C_6$alkyl), $NH_2$, $NHSO_2N(C_1$-$C_6$alkyl$)_2$, $NHSO_2NHCH_3$, $NHSO_2(C_1$-$C_6$alkyl), $NHSO_2(C_3$-$C_7$cycloalkyl), $N(C_1$-$C_6$-alkyl$)_2$, $NR^8R^9$ and $NR^9R^{10c}$;

$R^{10c}$ is selected from the group consisting of H, $C_1$-$C_6$alkyl, OH, CN, F, $CF_2H$, $CF_3$, $C(=NOH)NH_2$, $CONR^8R^9$, $COOR^8$, $CONR^8SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$ and a 4 to 6 membered saturated ring containing one oxygen atom;

$R^{1d}$ is present when Het has formula (d) and X is C; each $R^{1d}$ is selected independently from the group consisting of H, OH, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O-C_1-C_6alkyl)_2$; $R^{1d}$ is absent when the X to which it is bound is N;

$R^{3d}$ is selected from the group consisting of H, halogen, $C_1$-$C_6$alkyl, $C_3$-$C_7$cycloalkyl, $C_1$-$C_6$alkyloxy, and $CO(R^7)$;

$R^{2d}$ is $-(CR^8R^9)_m-R^{10d}$;

$R^{10d}$ is selected from the group consisting of H, $C_1$-$C_6$alkyl, OH, CN, F, $CF_2H$, $CF_3$, $CONR^8R^9$, $COOR^8$, $CONR^8SO_2R^9$, $CON(R^8)SO_2N(R^8R^9)$, $NR^8R^9$, $NR^8COOR_9$, $OCOR^8$, $NR^8SO_2R^9$, $SO_2NR^8R^9$, $SO_2R^8$ and a 4 to 6 membered saturated ring containing one oxygen atom;

each Y independently is C or N;

$R^{1e}$ is present when Het has formula (e) and Y is C; each $R^{1e}$ is selected independently from the group consisting of H, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O-C_1-C_6alkyl)_2$; $R^{1e}$ is absent when the Y to which it is bound is N;

$R^{3e}$ is selected from the group consisting of H, halogen, $-(CR^8R^9)_m-R^{10e}$, $C=C-CH_2-R^{10e}$, $C\equiv C-R^{10e}$ and $C=C-R^{10e}$;

$R^{10e}$ is selected from the group consisting of H, $C_1$-$C_6$alkyl, $C_1$-$C_6$alkyloxy, $C_3$-$C_7$cycloalkyl, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$ and a 4 to 6 membered saturated ring containing one oxygen atom;

$R^4$ is selected from the group consisting of $Het^1$ and $C_3$-$C_7$cycloalkyl substituted with one or more substituents selected from the group consisting of halo and $C_1$-$C_4$alkyl; in particular $R^4$ is Het1;

$Het^1$ represents a 4 to 6 membered saturated ring containing one N atom, optionally being substituted on the nitrogen atom with one substituent selected from the group consisting of halo, $C_1$-$C_4$alkyloxy, $SO_2R^8$, $C_1$-$C_4$alkylcarbonyl, $C_1$-$C_4$alkyloxycarbonyl, pyridinyl, $CF_3$, $SO_2N(C_1$-$C_4$alkyl$)_2$, $SO_2NH(C_1$-$C_4$alkyl), $(C=O)NH(C_{1-4}$alkyl), $(C=S)NH(C_{1-4}$alkyl), $C_1$-$C_4$alkyl and $C_1$-$C_4$alkyl substituted with one hydroxy; or $Het^1$ represents a 4 to 6 membered saturated ring containing one O atom, wherein the carbon atom attached to the remainder of the molecule is substituted with one substituent selected from the group consisting of halo, $C_1$-$C_4$alkyloxy, $CF_3$, $NH(C=O)(C_{1-4}$alkyl), $(C=O)NH(C_{1-4}$alkyl) and $C_1$-$C_4$alkyl; in particular $C_1$-$C_4$alkyl; more in particular methyl;

Z is C or N; $R^5$ is present where Z is C, whereby $R^5$ is selected form the group consisting of hydrogen, $CF_3$ and halogen; $R^5$ is absent where Z is N;

and the pharmaceutically acceptable addition salts, and the solvates thereof.

In an embodiment, the present invention relates to those compounds of formula (I), or any subgroup thereof as mentioned in any of the other embodiments, wherein $Het^1$ represents a 4 to 6 membered saturated ring containing one N atom, optionally being substituted on the nitrogen atom with one substituent selected from the group consisting of halo, $C_1$-$C_4$alkyloxy, $SO_2R^8$, $C_1$-$C_4$alkylcarbonyl, CO(aryl), $COHet^2$, $C_1$-$C_4$alkyloxycarbonyl, pyridinyl, $CF_3$, $SO_2N(C_1$-$C_4$alkyl$)_2$, $SO_2NH(C_1$-$C_4$alkyl), $(C=O)NH(C_{1-4}$alkyl), $(C=S)NH(C_{1-4}$alkyl), $C_1$-$C_4$alkyl and $C_1$-$C_4$alkyl substituted with one hydroxy; or $Het^1$ represents a 4 to 6 membered saturated ring containing one O atom, wherein the carbon atom attached to the remainder of the molecule is substituted with one substituent selected from the group consisting of halo, $C_1$-$C_4$alkyloxy, $CF_3$, $NH(C=O)(C_{1-4}$alkyl), $(C=O)NH(C_{1-4}$alkyl) and $C_1$-$C_4$alkyl; in particular $C_1$-$C_4$alkyl; more in particular In an embodiment, the present invention relates to those compounds of formula (I), or any subgroup thereof as mentioned in any of the other embodiments, wherein $R^4$ is selected from the group consisting of $Het^1$ and $C_3$-$C_7$cycloalkyl substituted with one or more substituents selected from the group consisting of halo and $C_1$-$C_4$alkyl; in particular $R^4$ is Het1.

In an embodiment, the present invention relates to those compounds of formula (I), or any subgroup thereof as mentioned in any of the other embodiments, wherein $R^{10b}$ is selected from the group consisting of H, $R^{11}$, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, O-Benzyl, $NR^8SO_2R^9$, $SO_2NR^8R^9$, $SO_2CH_3$, $OCONR^8R^9$, $OCONR^8R^{12}$, $N(R^8)CON(R^8R^9)$, $N(R^8)COOR^{12}$, and a 4 to 6 membered saturated ring containing one oxygen atom;

$R^{10c}$ is selected from the group consisting of H, $R^{11}$, OH, CN, F, $CF_2H$, $CF_3$, C(=NOH)$NH_2$, $CONR^8R^9$, $COOR^8$, $CONR^8SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2CH_3$ and a 4 to 6 membered saturated ring containing one oxygen atom;

$R^{10d}$ is selected from the group consisting of H, $R^{11}$, OH, CN, F, $CF_2H$, $CF_3$, $CONR^8R^9$, $COOR^8$, $CONR^8SO_2R^9$, $CON(R^8)SO_2N(R^8R^9)$, $NR^8R^9$, $NR^8COOR_9$, $OCOR^8$, $NR^8SO_2R^9$, $SO_2NR^8R^9$, $SO_2CH_3$ and a 4 to 6 membered saturated ring containing one oxygen atom;

$R^{10e}$ is selected from the group consisting of H, $R^{11}$, $C_1$-$C_6$alkyloxy, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2CH_3$ and a 4 to 6 membered saturated ring containing one oxygen atom.

In an embodiment, the present invention relates to those compounds of formula (I), or any subgroup thereof as mentioned in any of the other embodiments, wherein $SO_2R^8$ is restricted to $SO_2CH^3$ or $SO_2C_3$-$C_7$cycloalkyl; in particular $SO_2CH^3$.

In an embodiment, the present invention relates to those compounds of formula (I), or any subgroup thereof as mentioned in any of the other embodiments, wherein $R^4$ is selected from the group consisting of $Het^1$, aryl, $Het^2$, and $C_3$-$C_7$cycloalkyl substituted with one or more substituents selected from the group consisting of halo and $C_1$-$C_4$alkyl; in particular $Het^1$, $Het^2$, and $C_3$-$C_7$cycloalkyl substituted with one or more substituents selected from the group consisting of halo and $C_1$-$C_4$alkyl.

In an embodiment, the present invention relates to those compounds of formula (I), or any subgroup thereof as mentioned in any of the other embodiments, wherein $R^4$ is selected from the group consisting of $Het^1$ and $C_3$-$C_7$cycloalkyl substituted with one or more substituents selected from the group consisting of halo and $C_1$-$C_4$alkyl; in particular $R^4$ is Het1; and wherein $Het^1$ represents a 4 to 6 membered saturated ring containing one N atom, optionally being substituted on the nitrogen atom with one substituent selected from the group consisting of halo, $C_1$-$C_4$alkyloxy, $SO_2R^8$, $C_1$-$C_4$alkylcarbonyl, CO(aryl), $COHet^2$, $C_1$-$C_4$alkyloxycarbonyl, pyridinyl, $CF_3$, $SO_2N(C_1$-$C_4$alkyl$)_2$, $SO_2NH(C_1$-$C_4$alkyl), (C=O)NH($C_{1-4}$alkyl), (C=S)NH($C_{1-4}$alkyl), $C_1$-$C_4$alkyl and $C_1$-$C_4$alkyl substituted with one hydroxy; or $Het^1$ represents a 4 to 6 membered saturated ring containing one O atom, wherein the carbon atom attached to the remainder of the molecule is substituted with one substituent selected from the group consisting of halo, $C_1$-$C_4$alkyloxy, $CF_3$, NH(C=O)($C_{1-4}$alkyl), (C=O)NH($C_{1-4}$alkyl) and $C_1$-$C_4$alkyl; in particular $C_1$-$C_4$alkyl; more in particular methyl.

In an embodiment, the present invention relates to those compounds of formula (I), or any subgroup thereof as mentioned in any of the other embodiments, wherein $R^4$ is $Het^1$, and wherein $Het^1$ represents a 4 to 6 membered saturated ring containing one N atom, optionally being substituted on the nitrogen atom with one substituent selected from the group consisting of halo, $C_1$-$C_4$alkyloxy, $SO_2R^8$, $C_1$-$C_4$alkylcarbonyl, CO(aryl), $COHet^2$, $C_1$-$C_4$alkyloxycarbonyl, pyridinyl, $CF_3$, $SO_2N(C_1$-$C_4$alkyl$)_2$, $SO_2NH(C_1$-$C_4$alkyl), (C=O)NH($C_{1-4}$alkyl), (C=S)NH($C_{1-4}$alkyl), $C_1$-$C_4$alkyl and $C_1$-$C_4$alkyl substituted with one hydroxy; or $Het^1$ represents a 4 to 6 membered saturated ring containing one O atom, wherein the carbon atom attached to the remainder of the molecule is substituted with one substituent selected from the group consisting of halo, $C_1$-$C_4$alkyloxy, $CF_3$, NH(C=O)($C_{1-4}$alkyl), (C=O)NH($C_{1-4}$alkyl) and $C_1$-$C_4$alkyl; in particular methyl.

In an embodiment, the present invention relates to those compounds of formula (I), or any subgroup thereof as mentioned in any of the other embodiments, wherein $R^4$ is $Het^1$, and wherein $Het^1$ represents a 4 to 6 membered saturated ring containing one O atom, wherein the carbon atom attached to the remainder of the molecule is substituted with one substituent selected from the group consisting of halo, $C_1$-$C_4$alkyloxy, $CF_3$, NH(C=O)($C_{1-4}$alkyl), (C=O)NH($C_{1-4}$alkyl) and $C_1$-$C_4$alkyl; in particular $C_1$-$C_4$alkyl; more in particular methyl.

In an embodiment, the present invention relates to those compounds of formula (I), or any subgroup thereof as mentioned in any of the other embodiments, wherein $R^4$ is $Het^1$, and wherein $Het^1$ represents a 4 membered saturated ring containing one O atom, wherein the carbon atom attached to the remainder of the molecule is substituted with one methyl group.

In an embodiment, the present invention concerns novel compounds of Formula (I) and stereoisomeric forms thereof, wherein Het is a heterocycle having formula (b) or (c), each X independently is C or N; provided that at least one X is N;

$R^{1b}$ is present when Het has formula (b) and X is C; each $R^{1b}$ is selected independently from the group consisting of H and halogen; $R^{1b}$ is absent when the X to which it is bound is N;

$R^{2b}$ is —$(CR^8R^9)_m$—$R^{10b}$;

each $R^8$ and $R^9$ are independently chosen from the group consisting of H and $C_1$-$C_{10}$alkyl; in particular H and $C_1$-$C_6$ alkyl;

$R^{10b}$ is selected from the group consisting of F, $C_1$-$C_6$ alkyl, $CF_3$, $SO_2R^8$;

m is an integer from 2 to 4;

$R^{1c}$ is present when Het has formula (c);

each $R^{1c}$ is selected independently from the group consisting of H and halogen;

$R^{1c}$ is H;

$R^{2c}$ is —$(CR^8R^9)_m$—$R^{10c}$;

$R^{10c}$ is selected from the group consisting of F and $SO_2R^8$;

$R^4$ is selected from the group consisting of tert-butyl, $Het^1$, $Het^2$, and $C_3$-$C_7$cycloalkyl substituted with one or more substituents selected from the group consisting of halo and $C_1$-$C_4$alkyl;

$Het^1$ represents a 4 membered saturated ring containing one N atom, optionally being substituted with one or more substituents each independently selected from the group consisting of $SO_2R^8$, $C_1$-$C_4$alkylcarbonyl, $C_1$-$C_4$alkyloxycarbonyl and $C_1$-$C_4$alkyl substituted with one hydroxy; or $Het^1$ represents a 4 membered saturated ring containing one O atom, substituted with one or more substituents each independently selected from the group consisting of $C_1$-$C_4$alkyl;

$Het^2$ represents a monocyclic 5 membered aromatic heterocycle containing one or more heteroatoms each independently selected from the group consisting of S and N; or a bicyclic 10-membered aromatic heterocycle containing one N-atom;

Z is C or N; R$^5$ is present where Z is C, whereby R$^5$ is halogen; R$^5$ is absent where Z is N;

and the pharmaceutically acceptable addition salts, and the solvates thereof.

In an embodiment, the present invention concerns novel compounds of Formula (I) and stereoisomeric forms thereof, wherein Het is a heterocycle having formula (b) or (c), each X independently is C or N; provided that at least one X is N;

R$^{1b}$ is present when Het has formula (b) and X is C; each R$^{1b}$ is selected independently from the group consisting of H and halogen; R$^{1b}$ is absent when the X to which it is bound is N;

R$^{2b}$ is —(CR$^8$R$^9$)$_m$—R$^{10b}$;

each R$^8$ and R$^9$ are independently chosen from the group consisting of H and C$_1$-C$_{10}$alkyl; in particular H and C$_1$-C$_6$ alkyl;

R$^{10b}$ is selected from the group consisting of F, C$_1$-C$_6$ alkyl, CF$_3$, SO$_2$R$_8$;

m is an integer from 2 to 4;

R$^{1c}$ is present when Het has formula (c);

each R$^{1c}$ is selected independently from the group consisting of H and halogen;

R$^{3c}$ is H;

R$^{2c}$ is —(CR$^8$R$^9$)$_m$—R$^{10c}$;

R$^{10c}$ is selected from the group consisting of F and SO$_2$R$^8$;

R$^4$ is selected from the group consisting of tert-butyl, Het$^1$, Het$^2$, and C$_3$-C$_7$cycloalkyl substituted with one or more substituents selected from the group consisting of halo and C$_1$-C$_4$alkyl;

Het$^1$ represents a 4 membered saturated ring containing one N atom, optionally being substituted with one or more substituents each independently selected from the group consisting of SO$_2$R$^8$, C$_1$-C$_4$alkylcarbonyl, C$_1$-C$_4$alkyloxycarbonyl and C$_1$-C$_4$alkyl substituted with one hydroxy;

Het$^2$ represents a monocyclic 5 membered aromatic heterocycle containing one or more heteroatoms each independently selected from the group consisting of S and N; or a bicyclic 10-membered aromatic heterocycle containing one N-atom;

Z is C or N; R$^5$ is present where Z is C, whereby R$^5$ is halogen; R$^5$ is absent where Z is N;

and the pharmaceutically acceptable addition salts, and the solvates thereof.

In an embodiment, the present invention concerns novel compounds of Formula (I) and stereoisomeric forms thereof, wherein Het is a heterocycle having formula (b) or (c), each X independently is C or N; provided that at least one X is N;

R$^{1b}$ is present when Het has formula (b) and X is C; each R$^{1b}$ is selected independently from the group consisting of H and halogen; R$^{1b}$ is absent when the X to which it is bound is N;

R$^{2b}$ is —(CR$^8$R$^9$)$_m$—R$^{10b}$;

each R$^8$ and R$^9$ are H;

R$^{10b}$ is selected from the group consisting of F, C$_1$-C$_6$ alkyl, CF$_3$, SO$_2$CH$_3$;

m is an integer from 2 to 4;

R$^{1c}$ is present when Het has formula (c);

each R$^{1c}$ is selected independently from the group consisting of H and halogen;

R$^{3c}$ is H;

R$^{2c}$ is —(CR$^8$R$^9$)$_m$—R$^{10c}$;

R$^{10c}$ is selected from the group consisting of F and SO$_2$CH$_3$;

R$^4$ is selected from the group consisting of tert-butyl, Het$^1$, Het$^2$, and C$_3$-C$_7$cycloalkyl substituted with one or more substituents selected from the group consisting of halo and C$_1$-C$_4$alkyl;

Het$^1$ represents a 4 membered saturated ring containing one N atom, optionally being substituted with one or more substituents each independently selected from the group consisting of SO$_2$CH$_3$, C$_1$-C$_4$alkylcarbonyl, C$_1$-C$_4$alkyloxycarbonyl and C$_1$-C$_4$alkyl substituted with one hydroxy;

Het$^2$ represents a monocyclic 5 membered aromatic heterocycle containing one or more heteroatoms each independently selected from the group consisting of S and N; or a bicyclic 10-membered aromatic heterocycle containing one N-atom;

Z is C or N; R$^5$ is present where Z is C, whereby R$^5$ is halogen; R$^5$ is absent where Z is N;

and the pharmaceutically acceptable addition salts, and the solvates thereof.

In an embodiment, the present invention concerns novel compounds of Formula (I) and stereoisomeric forms thereof, wherein Het is a heterocycle having formula (b-1a) or (c-1a),

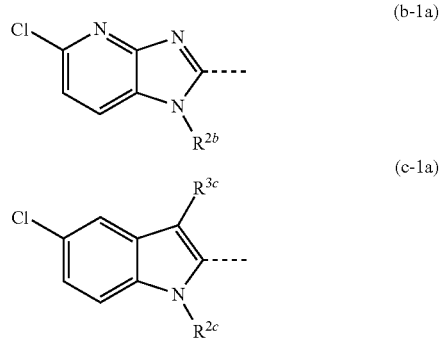

R$^{2b}$ is —(CR$^8$R$^9$)$_m$—R$^{10b}$;

each R$^8$ and R$^9$ are H;

R$^{10b}$ is selected from the group consisting of F, isopropyl, CF$_3$, SO$_2$CH$_3$;

m is an integer from 2 to 4;

R$^{3c}$ is H;

R$^{2c}$ is —(CR$^8$R$^9$)$_m$—R$^{10c}$;

R$^{10c}$ is selected from the group consisting of F and SO$_2$CH$_3$;

R$^4$ is selected from the group consisting of tert-butyl, Het$^1$, Het$^2$, and C$_3$-C$_7$cycloalkyl substituted with one or more substituents selected from the group consisting of halo and C$_1$-C$_4$alkyl;

Het$^1$ represents a 4 membered saturated ring containing one N atom, optionally being substituted on the nitrogen atom with one substituent selected from the group consisting of SO$_2$CH$_3$, methylcarbonyl, tert-butyloxycarbonyl and C$_1$-C$_4$alkyl substituted with one hydroxy;

Het$^2$ represents a monocyclic 5 membered aromatic heterocycle containing one or more heteroatoms each independently selected from the group consisting of S and N; or a bicyclic 10-membered aromatic heterocycle containing one N-atom;

Z is C or N; R$^5$ is present where Z is C, whereby R$^5$ is fluoro; R$^5$ is absent where Z is N;

and the pharmaceutically acceptable addition salts, and the solvates thereof.

In an embodiment, the present invention relates to those compounds of formula (I), or any subgroup thereof as mentioned in any of the other embodiments, wherein $R^5$ is selected from the group consisting of $CF_3$ and halogen.

In an embodiment, the present invention relates to those compounds of formula (I), or any subgroup thereof as mentioned in any of the other embodiments, wherein $R^{3e}$ is $-(CR^8R^9)_m-R^{10e}$.

In an embodiment, the present invention relates to those compounds of formula (I), or any subgroup thereof as mentioned in any of the other embodiments, wherein Het has formula (b) or (c).

In an embodiment, the present invention relates to those compounds of formula (I), or any subgroup thereof as mentioned in any of the other embodiments, wherein Het has formula (b).

In an embodiment, the present invention relates to those compounds of formula (I), or any subgroup thereof as mentioned in any of the other embodiments, wherein Het has formula (c).

In an embodiment, the present invention relates to those compounds of formula (I), or any subgroup thereof as mentioned in any of the other embodiments, wherein Het has formula (d).

In an embodiment, the present invention relates to those compounds of formula (I), or any subgroup thereof as mentioned in any of the other embodiments, wherein Het has formula (e).

In an embodiment, the present invention relates to those compounds of formula (I), or any subgroup thereof as mentioned in any of the other embodiments, wherein Het is a heterocycle having formula (bb), (cc), (dd) or (ee); in particular (bb) or (cc); more in particular (bb); more in particular (cc); more in particular (dd); more in particular (ee);

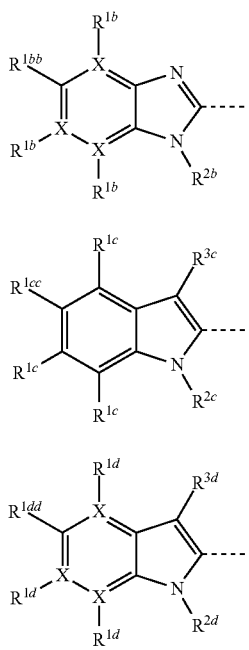

(bb)

(cc)

(dd)

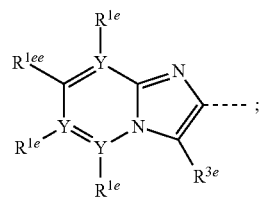

(ee)

wherein $R^{1bb}$, $R^{1cc}$, $R1^{dd}$ or $R^{1ee}$ are chloro or bromo; in particular chloro;

wherein $R^{1b}$, $R^{1c}$, $R^{1d}$, $R^{1e}$ and the other substituents are defined according to any of the other embodiments;

in a particular embodiment $R^{1bb}$, $R^{1cc}$, $R1^{dd}$ or $R^{1ee}$ are chloro; $R^{1b}$, $R^{1c}$, $R^{1d}$, $R^{1e}$ if present are H; and the other substituents are defined according to any of the other embodiments.

In an embodiment, the present invention relates to those compounds of formula (I), or any subgroup thereof as mentioned in any of the other embodiments, wherein Het is a heterocycle having formula (b-1) or (c-1); in particular (b-1); also in particular (c-1);

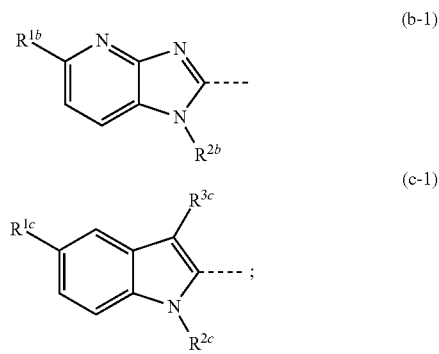

(b-1)

(c-1)

wherein $R^{1b}$ and $R^{1c}$ are chloro or bromo.

In an embodiment, the present invention relates to those compounds of formula (I), or any subgroup thereof as mentioned in any of the other embodiments, wherein Het is a heterocycle having formula (b-1a) or (c-1a); in particular (b-1a); also in particular (c-1a);

(b-1a)

(c-1a)

In an embodiment, the present invention relates to those compounds of formula (I), or any subgroup thereof as mentioned in any of the other embodiments, wherein $R^4$ is selected from the group consisting of tert-butyl, azetidinyl substituted on the N atom with one substituent selected from the group consisting of $C_1$-$C_4$alkylcarbonyl and $C_1$-$C_4$alkyloxycarbonyl,
phenyl substituted with one substituent selected from the group consisting of F and $C_1$-$C_4$alkyloxy, and
cyclopropyl substituted with one substituent selected from the group consisting of $C_1$-$C_4$alkyl and F;
Z is C or N; $R^5$ is present where Z is C, whereby $R^5$ is halogen; $R^5$ is absent where Z is N.

In an embodiment, the present invention relates to those compounds of formula (I), or any subgroup thereof as mentioned in any of the other embodiments, wherein
$R^4$ is selected from the group consisting of tert-butyl, $Het^1$, $Het^2$, and $C_3$-$C_7$cycloalkyl substituted with one or more substituents selected from the group consisting of halo and $C_1$-$C_4$alkyl;
$Het^1$ represents a 4 membered saturated ring containing one N atom, optionally being substituted on the nitrogen atom with one substituent selected from the group consisting of $SO_2CH_3$, $C_1$-$C_4$alkylcarbonyl, $C_1$-$C_4$alkyloxycarbonyl and $C_1$-$C_4$alkyl substituted with one hydroxy;
$Het^2$ represents a monocyclic 5 membered aromatic heterocycle containing one or more heteroatoms each independently selected from the group consisting of S and N; or a bicyclic 10-membered aromatic heterocycle containing one N-atom;
Z is C or N; $R^5$ is present where Z is C, whereby $R^5$ is halo; $R^5$ is absent where Z is N.

In an embodiment, the present invention relates to those compounds of formula (I), or any subgroup thereof as mentioned in any of the other embodiments, wherein $R^4$ is selected from the group consisting of tert-butyl, $Het^1$, aryl, $Het^2$ and $C_3$-$C_7$cycloalkyl substituted with one or more substituents selected from the group consisting of halo and $C_1$-$C_4$alkyl.

In an embodiment, the present invention relates to those compounds of formula (I), or any subgroup thereof as mentioned in any of the other embodiments, wherein $R^4$ is selected from the group consisting of tert-butyl, $Het^1$, $CH(CH_3)(CF_3)$, and $C_3$-$C_7$cycloalkyl substituted with one or more substituents selected from the group consisting of halo and $C_1$-$C_4$alkyl; in particular $R^4$ is selected from the group consisting of $Het^1$ and $C_3$-$C_7$cycloalkyl substituted with one or more substituents selected from the group consisting of halo and $C_1$-$C_4$alkyl; more in particular $R^4$ is $Het^1$.

In an embodiment, the present invention relates to those compounds of formula (I), or any subgroup thereof as mentioned in any of the other embodiments, wherein $R^4$ is selected from the group consisting of tert-butyl, aryl, $Het^2$ and $CH(CH_3)(CF_3)$; in particular $R^4$ is aryl or $Het^2$; more in particular $R^4$ is $Het^2$.

In an embodiment, the present invention relates to those compounds of formula (I), or any subgroup thereof as mentioned in any of the other embodiments, wherein Z is C or N; $R^5$ is present where Z is C, whereby $R^5$ is selected form the group consisting of $CF_3$ and halogen; $R^5$ is absent where Z is N.

In an embodiment, the present invention relates to those compounds of formula (I), or any subgroup thereof as mentioned in any of the other embodiments, wherein each $R^{1c}$ is selected independently from the group consisting of H, halogen, $C_1$-$C_6$alkyloxy, $CF_3$, and $OCF_3$.

In an embodiment, the present invention relates to those compounds of formula (I), or any subgroup thereof as mentioned in any of the other embodiments, wherein Het has formula (c) wherein each $R^{1c}$ is selected independently from the group consisting of H, halogen, $C_1$-$C_6$alkyloxy, $CF_3$, and $OCF_3$.

In an embodiment, the present invention relates to those compounds of formula (I), or any subgroup thereof as mentioned in any of the other embodiments, wherein $R^{1c}$ in the para position to N—$R^{2c}$ is selected from the group consisting of H, halogen and all other $R^{1c}$ are H. In preferred embodiment, halogen is bromo or chloro.

In an embodiment, the present invention relates to those compounds of formula (I), or any subgroup thereof as mentioned in any of the other embodiments, wherein Het has formula (c) wherein $R^{1c}$ in the para position to N—$R^{2c}$ is selected from the group consisting of H, halogen and all other $R^{1c}$ are H. In preferred embodiment, halogen is bromo or chloro.

In an embodiment, the present invention relates to those compounds of formula (I), or any subgroup thereof as mentioned in any of the other embodiments, wherein Het has formula (c) wherein $R^{2c}$ comprises a —$(CR^8R^9)_m$ chain wherein $R^8$ and $R^9$ are H and m is 2-4. Preferably $R^{10c}$ is selected from the group consisting of OH, F, $CF_2H$, $CF_3$, $SO_2R_8$, and CN. $R^8$ preferably is methyl.

In an embodiment, the present invention relates to those compounds of formula (I), or any subgroup thereof as mentioned in any of the other embodiments, wherein $R^{2c}$ comprises a —$(CR^8R^9)_m$ chain wherein $R^8$ and $R^9$ are H and m is 2-4. Preferably $R^{10c}$ is selected from the group consisting of OH, F, $CF_2H$, $CF_3$, $SO_2R_8$, and CN. $R^8$ preferably is methyl.

In an embodiment, the present invention relates to those compounds of formula (I), or any subgroup thereof as mentioned in any of the other embodiments, wherein $R^4$ is $C_3$-$C_7$cycloalkyl substituted with one or more substituents selected from the group consisting of halo and $C_1$-$C_4$alkyl; more preferably cyclopropyl substituted with halo or $C_1$-$C_4$alkyl.

In an embodiment, the present invention relates to those compounds of formula (I), or any subgroup thereof as mentioned in any of the other embodiments, wherein Z is N.

In an embodiment, the present invention relates to those compounds of formula (I), or any subgroup thereof as mentioned in any of the other embodiments, wherein $R^5$ is H.

In an embodiment, the present invention relates to those compounds of formula (I), or any subgroup thereof as mentioned in any of the other embodiments, wherein $R^4$ is selected from the group consisting of tert-butyl, $Het^1$, aryl, $Het^2$ and $C_3$-$C_7$cycloalkyl substituted with one or more substituents selected from the group consisting of halo and $C_1$-$C_4$alkyl;
$R^{10b}$ is selected from the group consisting of H, $C_1$-$C_6$alkyl, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, O-Benzyl, $NR^8SO_2R^9$, $SO_2NR^8R^9$, $SO_2R^8$ and a 4 to 6 membered saturated ring containing one oxygen atom; and
m is an integer from 2 to 6.

In an embodiment, the present invention relates to those compounds of formula (I), or any subgroup thereof as mentioned in any of the other embodiments, wherein $R^{10b}$ is selected from the group consisting of H, $C_1$-$C_6$alkyl, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, O-Benzyl, $NR^8SO_2R^9$, $SO_2NR^8R^9$, $SO_2R^8$ and a 4 to 6 membered saturated ring containing one oxygen atom.

In an embodiment, the present invention relates to those compounds of formula (I), or any subgroup thereof as mentioned in any of the other embodiments, wherein Het has formula (b) wherein $R^{10b}$ is selected from the group consisting of H, $C_1$-$C_6$alkyl, OH, CN, F, $CF_2H$, $CF_3$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, O-Benzyl, $NR^8SO_2R^9$, $SO_2NR^8R^9$, $SO_2R^8$ and a 4 to 6 membered saturated ring containing one oxygen atom.

In an embodiment, the present invention relates to those compounds of formula (I), or any subgroup thereof as mentioned in any of the other embodiments, wherein Het has formula (b) wherein at most two X are N. In a preferred embodiment, one X is N. In a more preferred embodiment, the one X that is N is located in meta position to the N—$R^{2b}$ group of the imidazole ring.

In an embodiment, the present invention relates to those compounds of formula (I), or any subgroup thereof as mentioned in any of the other embodiments, wherein Het having formula (b) has at most two X being N. In a preferred embodiment, one X is N. In a more preferred embodiment, the one X that is N is located in meta position to the N—$R^{2b}$ group of the imidazole ring.

In an embodiment, the present invention relates to those compounds of formula (I), or any subgroup thereof as mentioned in any of the other embodiments, wherein each $R^{1b}$ is selected independently from the group consisting of H, halogen and $CH_2$—$NH_2$. In a further preferred embodiment, $R^{1b}$ in the para position to C—N—$R^{2b}$ is selected from the group consisting of H, halogen and $CH_2$—$NH_2$, and all other $R^{1b}$ are H. In a further preferred embodiment said halogen is bromo or chloro. In a most preferred embodiment, at most one $R^{1b}$ is chloro, and all other $R^{1b}$ are H. In yet an even more preferred embodiment, $R^{1b}$ in the para position to C—N—$R^{2b}$ is chloro.

In an embodiment, the present invention relates to those compounds of formula (I), or any subgroup thereof as mentioned in any of the other embodiments, wherein Het has formula (b) wherein each $R^{1b}$ is selected independently from the group consisting of H, halogen and $CH_2$—$NH_2$. In a further preferred embodiment, $R^{1b}$ in the para position to C—N—$R^{2b}$ is selected from the group consisting of H, halogen and $CH_2$—$NH_2$, and all other $R^{1b}$ are H. In a further preferred embodiment said halogen is bromo or chloro. In a most preferred embodiment, at most one $R^{1b}$ is chloro, and all other $R^{1b}$ are H. In yet an even more preferred embodiment, $R^{1b}$ in the para position to C—N—$R^{2b}$ is chloro.

In an embodiment, the present invention relates to those compounds of formula (I), or any subgroup thereof as mentioned in any of the other embodiments, wherein $R^{11}$ is $C_1$-$C_6$alkyl or $C_3$-$C_7$cycloalkyl; in particular $C_1$-$C_6$alkyl.

In an embodiment, the present invention relates to those compounds of formula (I), or any subgroup thereof as mentioned in any of the other embodiments, wherein $R^{2b}$ comprises a —$(CR^8R^9)_m$—$R^{10b}$ chain wherein $R^8$ and $R^9$ are preferably H and m is 2-4. Preferably $R^{10b}$ is selected from the group consisting of OH, $C_1$-$C_6$alkyl; more preferably 2-propyl. Also preferably $R^{10b}$ is selected from the group consisting of methoxy, $SO_2R^8$, with $R^8$ preferably being methyl. Most preferably $R^{10b}$ is fluoro or $CF_3$.

In an embodiment, the present invention relates to those compounds of formula (I), or any subgroup thereof as mentioned in any of the other embodiments, wherein Het has formula (b) wherein $R^{2b}$ comprises a —$(CR^8R^9)_m$—$R^{10b}$ chain wherein $R^8$ and $R^9$ are preferably H and m is 2-4. Preferably $R^{10b}$ is selected from the group consisting of OH, $C_1$-$C_6$alkyl; more preferably 2-propyl. Also preferably $R^{10b}$ is selected from the group consisting of methoxy, $SO_2R^8$, with $R^8$ preferably being methyl. Most preferably $R^{10b}$ is fluoro or $CF_3$.

In an embodiment, the present invention relates to those compounds of formula (I), or any subgroup thereof as mentioned in any of the other embodiments, wherein $R^4$ is selected from $C_3$-$C_7$cycloalkyl substituted with one or more substituents selected from the group consisting of halo and $C_1$-$C_4$alkyl.

In an embodiment, the present invention relates to those compounds of formula (I), or any subgroup thereof as mentioned in any of the other embodiments, wherein $R^4$ is selected from the group consisting of $Het^1$ and cyclopropyl substituted with halo or $C_1$-$C_4$alkyl.

In an embodiment, the present invention relates to those compounds of formula (I), or any subgroup thereof as mentioned in any of the other embodiments, wherein $R^5$ is halogen, in particular fluoro.

In an embodiment, the present invention relates to those compounds of formula (I), or any subgroup thereof as mentioned in any of the other embodiments, wherein each $R^{1d}$ independently is selected from the group of H, halogen, $C_1$-$C_6$alkyl, $C_3$-$C_7$cycloalkyl, $C_1$-$C_6$alkyloxy, $N(R^6)_2$, $CO(R^6)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O$—$C_1$-$C_6$alkyl)_2$.

In an embodiment, the present invention relates to those compounds of formula (I), or any subgroup thereof as mentioned in any of the other embodiments, wherein Het has formula (d) wherein each $R^{1d}$ independently is selected from the group of H, halogen, $C_1$-$C_6$alkyl, $C_3$-$C_7$cycloalkyl, $C_1$-$C_6$alkyloxy, $N(R^6)_2$, $CO(R^6)$, $CH_2NH_2$, $CH_2OH$, CN, $C(=NOH)NH_2$, $C(=NOCH_3)NH_2$, $C(=NH)NH_2$, $CF_3$, $OCF_3$, $B(OH)_2$ and $B(O$—$C_1$-$C_6$alkyl)_2$.

In an embodiment, the present invention relates to those compounds of formula (I), or any subgroup thereof as mentioned in any of the other embodiments, wherein Het has formula (d) wherein at most two X are N. In a preferred embodiment, one X is N. In a more preferred embodiment, the one X that is N is located is in meta or para position to the N—$R^{2d}$. In a further preferred embodiment, X is in the position para to N—$R^{2d}$.

In an embodiment, the present invention relates to those compounds of formula (I), or any subgroup thereof as mentioned in any of the other embodiments, wherein Het having formula (d) has at most two X being N. In a preferred embodiment, one X is N. In a more preferred embodiment, the one X that is N is located is in meta or para position to the N—$R^{2d}$. In a further preferred embodiment, X is in the position para to N—$R^{2d}$.

In an embodiment, the present invention relates to those compounds of formula (I), or any subgroup thereof as mentioned in any of the other embodiments, wherein each $R^{1d}$ is selected independently from the group consisting of H or halogen. In a further preferred embodiment, $R^{1d}$ in the para position to N—$R^{2d}$ is halogen, and all other $R^{1d}$ are H. In a further preferred embodiment said halogen is bromo or chloro. In a most preferred embodiment, said halogen is chloro.

In an embodiment, the present invention relates to those compounds of formula (I), or any subgroup thereof as mentioned in any of the other embodiments, wherein Het has formula (d) wherein each $R^{1d}$ is selected independently from the group consisting of H or halogen. In a further preferred embodiment, $R^{1d}$ in the para position to N—$R^{2d}$ is halogen, and all other $R^{1d}$ are H. In a further preferred embodiment said halogen is bromo or chloro. In a most preferred embodiment, said halogen is chloro.

In an embodiment, the present invention relates to those compounds of formula (I), or any subgroup thereof as mentioned in any of the other embodiments, wherein $R^{2d}$ comprises a —$(CR^8R^9)_m$— chain wherein $R^8$ and $R^9$ are preferably H and m is 2-4. Preferably $R^{10d}$ is selected from the group consisting of OH, F, $CF_3$, $CF_2H$ and $C_1$-$C_6$alkyl; in particular 2-propyl.

In an embodiment, the present invention relates to those compounds of formula (I), or any subgroup thereof as mentioned in any of the other embodiments, wherein Het has formula (d) wherein $R^{2d}$ comprises a —$(CR^8R^9)_m$— chain wherein $R^8$ and $R^9$ are preferably H and m is 2-4. Preferably $R^{10d}$ is selected from the group consisting of OH, F, $CF_3$, $CF_2H$ and $C_1$-$C_6$alkyl; in particular 2-propyl.

In an embodiment, the present invention relates to those compounds of formula (I), or any subgroup thereof as mentioned in any of the other embodiments, wherein Het has formula (e) wherein $R^{3e}$ is selected from the group consisting of H, halogen, —$(CR^8R^9)_m$—$R^{10e}$, $C\equiv C$—$CH_2$—$R^{10e}$ and $C\equiv C$—$R^{10e}$.

In an embodiment, the present invention relates to those compounds of formula (I), or any subgroup thereof as mentioned in any of the other embodiments, wherein $R^{3e}$ is selected from the group consisting of H, halogen, —$(CR^8R^9)_m$—$R^{10e}$, $C\equiv C$—$CH_2$—$R^{10e}$ and $C\equiv C$—$R^{10e}$.

In an embodiment, the present invention relates to those compounds of formula (I), or any subgroup thereof as mentioned in any of the other embodiments, wherein Het has formula (e) wherein Y is C.

In an embodiment, the present invention relates to those compounds of formula (I), or any subgroup thereof as mentioned in any of the other embodiments, wherein Y is C.

In an embodiment, the present invention relates to those compounds of formula (I), or any subgroup thereof as mentioned in any of the other embodiments, wherein Het having formula (e) is limited to formula (e1)

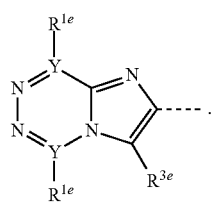

(e1)

In an embodiment, the present invention relates to those compounds of formula (I), or any subgroup thereof as mentioned in any of the other embodiments, wherein all substituents $R^{1e}$ are H.

In an embodiment, the present invention relates to those compounds of formula (I), or any subgroup thereof as mentioned in any of the other embodiments, wherein Het has formula (e) wherein all substituents $R^{1e}$ are H.

In an embodiment, the present invention relates to those compounds of formula (I), or any subgroup thereof as mentioned in any of the other embodiments, wherein at least one of $R^{1e}$ is halogen, more preferably Cl or Br.

In an embodiment, the present invention relates to those compounds of formula (I), or any subgroup thereof as mentioned in any of the other embodiments, wherein Het has formula (e) wherein at least one of $R^{1e}$ is halogen, more preferably Cl or Br.

In an embodiment, the present invention relates to those compounds of formula (I), or any subgroup thereof as mentioned in any of the other embodiments, wherein m comprises a carbon chain of 2-6 atoms, in particular 2-4 atoms, more in particular 3-5 atoms.

In an embodiment, the present invention relates to those compounds of formula (I), or any subgroup thereof as mentioned in any of the other embodiments, wherein $R^{10e}$ is selected from the group consisting of OH, $C_1$-$C_6$alkyloxy, secondary $C_1$-$C_6$alkyl; in particular OH or 2-propyl. "Secondary $C_1$-$C_6$alkyl" is intended to refer to an alkyl moiety that is attached via a non-terminal carbon atom, e.g. 2-propyl, 3-pentyl, and the like.

In an embodiment, the present invention relates to those compounds of formula (I), or any subgroup thereof as mentioned in any of the other embodiments, wherein Het has formula (e) wherein $R^{10e}$ is selected from the group consisting of OH, $C_1$-$C_6$alkyloxy, secondary $C_1$-$C_6$alkyl; in particular OH or 2-propyl. "Secondary $C_1$-$C_6$alkyl" is intended to refer to an alkyl moiety that is attached via a non-terminal carbon atom, e.g. 2-propyl, 3-pentyl, and the like.

In an embodiment, the present invention relates to those compounds of formula (I), or any subgroup thereof as mentioned in any of the other embodiments, wherein $R^{3e}$ is $C\equiv C$—$CH_2$—$R^{10e}$. Herein $R^{10e}$ preferably is $C_1$-$C_6$alkyloxy, preferably methoxy, or $C_1$-$C_6$alkyl, preferably branched alkyl.

In an embodiment, the present invention relates to those compounds of formula (I), or any subgroup thereof as mentioned in any of the other embodiments, wherein Het has formula (e) wherein $R^{3e}$ is $C\equiv C$—$CH_2$—$R^{10e}$. Herein $R^{10e}$ preferably is $C_1$-$C_6$alkyloxy, preferably methoxy, or $C_1$-$C_6$alkyl, preferably branched alkyl.

Interesting compounds of formula (I) are those compounds of formula (I) wherein one or more of the following restrictions apply:
a) Het is a heterocycle having formula (b), (d) or (e);
b) Het is a heterocycle having formula (b),
c) Het is a heterocycle having formula (c);
d) Het is a heterocycle having formula (d);
e) Z is N and $R^5$ is absent;
f) Z is C and $R^5$ is halogen;
g) $R^4$ is selected from the group consisting of $Het^1$, aryl, $Het^2$, and $C_3$-$C_7$cycloalkyl substituted with one or more substituents selected from the group consisting of halo and $C_1$-$C_4$alkyl;
h) $R^4$ is $Het^1$;
i) $R^4$ is $Het^2$;
j) $R^4$ is aryl;
k) aryl is phenyl optionally being substituted with one or more substituents each independently selected from the group consisting of halo, $C_1$-$C_4$alkyloxy, CN, $CONR^8R^9$, $COOR^8$, $SO_2R^8$, polyhalo$C_{1-4}$alkyloxy or $C_{1-4}$alkyloxy $C_{1-4}$alkyloxy;
l) aryl is phenyl optionally being substituted with one or more substituents each independently selected from the group consisting of halo, $C_1$-$C_4$alkyloxy, CN, $CONR^8R^9$, $COOR^8$, $SO_2R^8$;
m) aryl is phenyl substituted with two substituents each independently selected from the group consisting of halo, $C_1$-$C_4$alkyloxy or $C_1$-$C_4$alkyl;
n) Het is a heterocycle having formula (c-1a) wherein $R^{1c}$ is H and $R^{2c}$ is —$(CR^8R^9)_m$—$R^{10c}$ wherein $R^8$ and $R^9$ are each H, m is 3 and $R^{10c}$ represents CN or $SO_2CH_3$.

General Synthetic Schemes

The compounds of formula I may be prepared by the methods described below, using synthetic methods known in the art of organic chemistry, or modifications and derivatisations that are familiar to those skilled in the art. The starting materials used herein are commercially available or may be prepared by routine methods known in the art such as those methods disclosed in standard reference books. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene and P. G. M. Wuts, Protective Groups in Organic Chemistry, John Wiley & Sons, 1999, which are hereby incorporated by reference.

Compounds of formula I, or their pharmaceutically acceptable salts, can be prepared according to the reaction schemes discussed herein below. Unless otherwise indicated, the substituent in the schemes are defined as above. Isolation and purification of the products is accomplished by standard procedures, which are known to a chemist of ordinary skill.

Scheme 1 illustrates a method for the preparation of compounds of formula (I), wherein Het is a heterocycle of formula (b), hereby named a compound of formula I-b where $R^{1b}$, $R^{2b}$, $R^4$, $R^5$ and Z are defined as above.

Referring to scheme 1, a compound of formula I-b can be synthesized by coupling 2-hydroxymethylene imidazopyridines of formula II-a with a $N^3$-substituted 2-oxo-imidazopyridine or with a $N^3$-substituted 2-oxo-imidazobenzene of formula III in a known in the art method such as a Mitsunobu reaction which uses azadiisopropyldicarboxylate and triphenyl phosphine in a suitable solvent such as DMF (N,N-dimethylformamide) or THF (tetrahydrofuran). Alternatively, a compound of formula I-b may be prepared by displacement of Q, which is a halide, preferably chlorine II-b, or a sulfonate such as mesylate II-c in the presence of a base such as sodium hydride, potassium carbonate or cesium carbonate in a suitable solvent such as DMF or THF.

Scheme 1

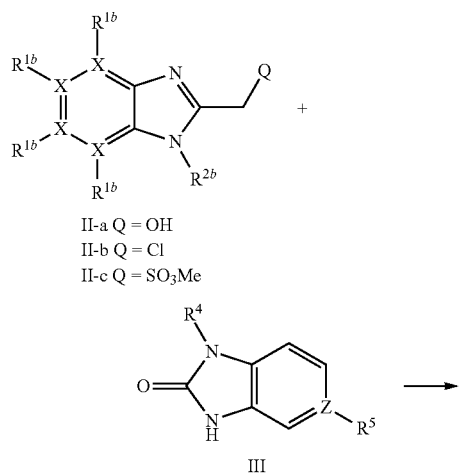

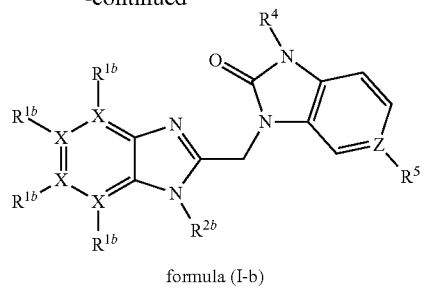

formula (I-b)

Preparation of Intermediates II-b and II-c

Treatment of the alcohol II-a with thionyl chloride provides 2-chloromethyl imidazopyridines II-b. Alternatively, alcohol II-a may be transformed to the intermediate II-c by a reaction with methane sulfonyl chloride in the presence of an organic base such as triethyl amine or diisopropyl ethyl amine in a suitable solvent such as dichloromethane (scheme 2).

Scheme 2

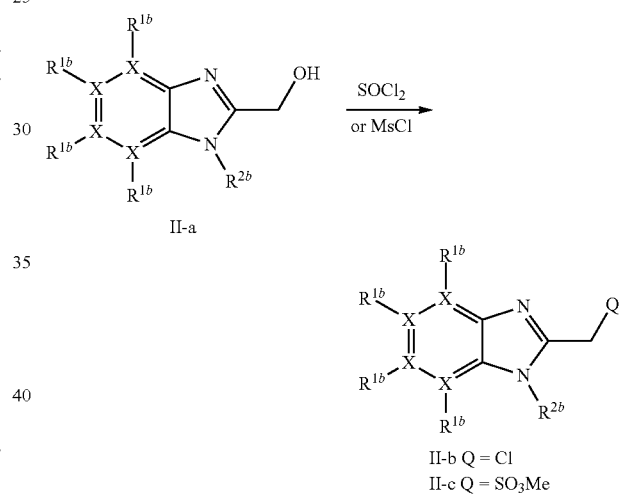

Preparation of Intermediate II-a

Intermediates of formula II-a are either commercially available or can be prepared, but not limited to, by general procedures illustrated by scheme 3, wherein $R^{1b}$, $R^{2b}$, X are defined as above. Referring to scheme 3 below, haloheteroaryls IV-b, where W is an halide preferably fluorine, can be treated with primary amines of formula V-b in the presence of a suitable base such as potassium carbonate and the like, in a suitable solvent such as ethanol or dichloromethane at a reaction temperature ranging from room temperature to 100° C. to give intermediates of formula VI-b. Hydrogenation of the nitro group using well-precedented conditions such as Pd/C, or other catalyst, under hydrogen or Fe/EtOH/$CaCl_2$ can yield diamine of formula VII-b. Alternatively, the hydrogenation of the nitro group of intermediate VIII-b using well-precedented conditions such as Pd/C, or other catalyst, under hydrogen or Fe/EtOH/$CaCl_2$ yield diamine of formula IX-b which can be treated with the aldehydes of formula X-b in the presence of suitable reducing agents such as $NaBH(OAc)_3$ (sodium triacetoxyborohydride), or $Na(CN)BH_3$ in solvents such as methylene chloride, DMF or THF, at about room temperature gives compounds of formula VII-b. The imidazole ring can be formed by treating diamines VII-b with glycolic acid or an ester like XIII-b under strong acidic conditions, such as aqueous hydrochloric acid, at elevated temperature such as reflux to yield the alcohols of formula II-a. Alternatively, diamines VII-b can be condensed with dialkoxyacetate of formula XII-b, in the presence of acetic acid, in a suitable solvent such as methanol gives the acetal II-e. The acetal of compounds II-e can be removed with acids such as hydrochloric acid to give the aldehydes of formula II-f. The resulting aldehydes of formula II-f can be reduced to alcohols using a suitable reducing agent such as $NaBH_4$ or $LiAlH_4$ in a suitable solvent such as ethanol or THF to yield the desired alcohols of formula II-a. In addition, diamines VII-b can be cyclize with dialkyl oxalate of formula XI-b in a suitable solvent such as ethanol at elevated temperature with or without microwave heating to produce imidazoles of formula II-d. Alternatively, intermediates of formula II-d may be prepared in two steps synthesis starting from diamines VII-b. Firstly diamine VII-b may be reacted with an alkyl trihaloacetimidate, preferably methyl 2,2,2-trichloro-acetimidate, in an acidic media, preferably acetic acid, at a temperature ranging between 25 and 50° C. to yield compound of formula II-g. Secondly a reaction of compounds of formula II-g with metalcarbonate, preferably sodium carbonate in a suitable solvent such as methanol, lead to intermediates of formula II-d. Intermediates of formula II-d may subsequently be reduced to the desired alcohols of formula II-a using a suitable reducing agent such as $NaBH_4$ or $LiAlH_4$ in a suitable solvent such as ethanol or THF.

Scheme 3
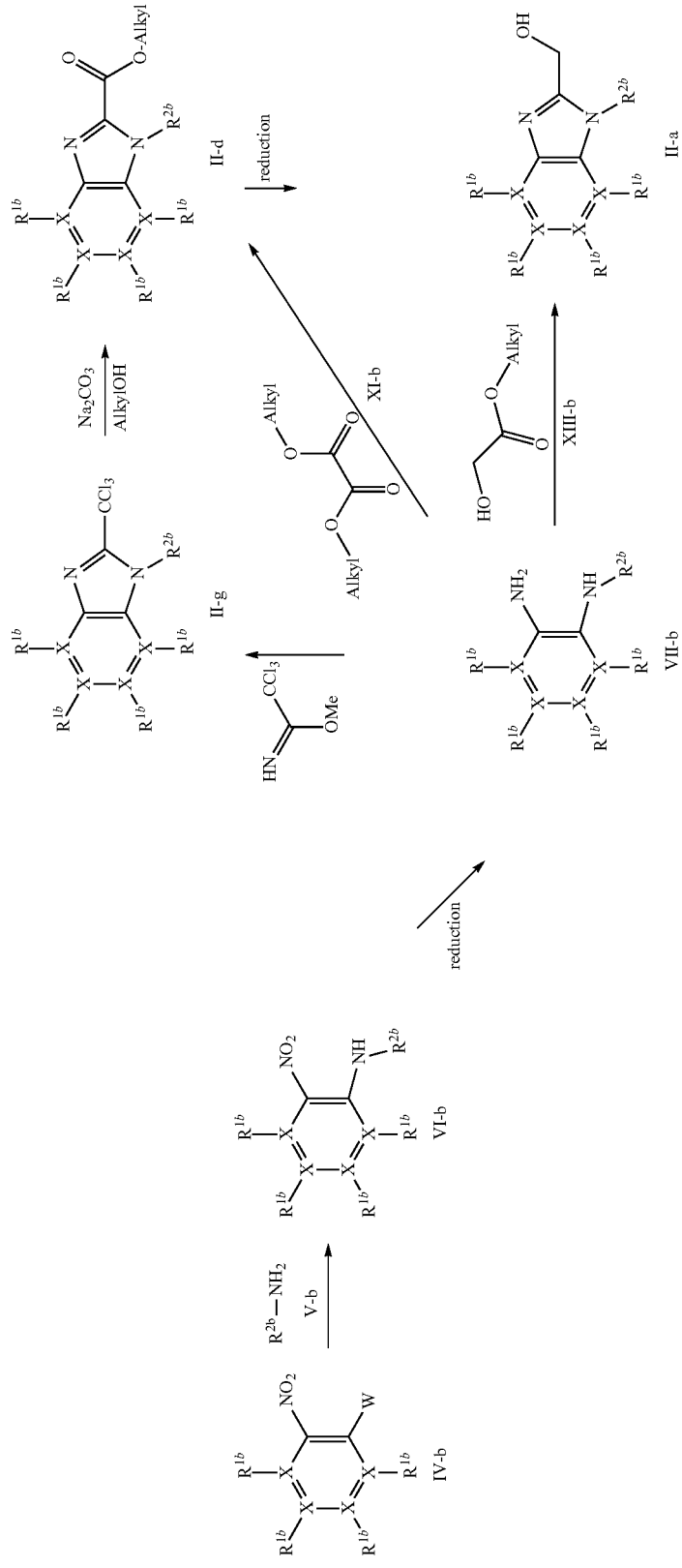

-continued
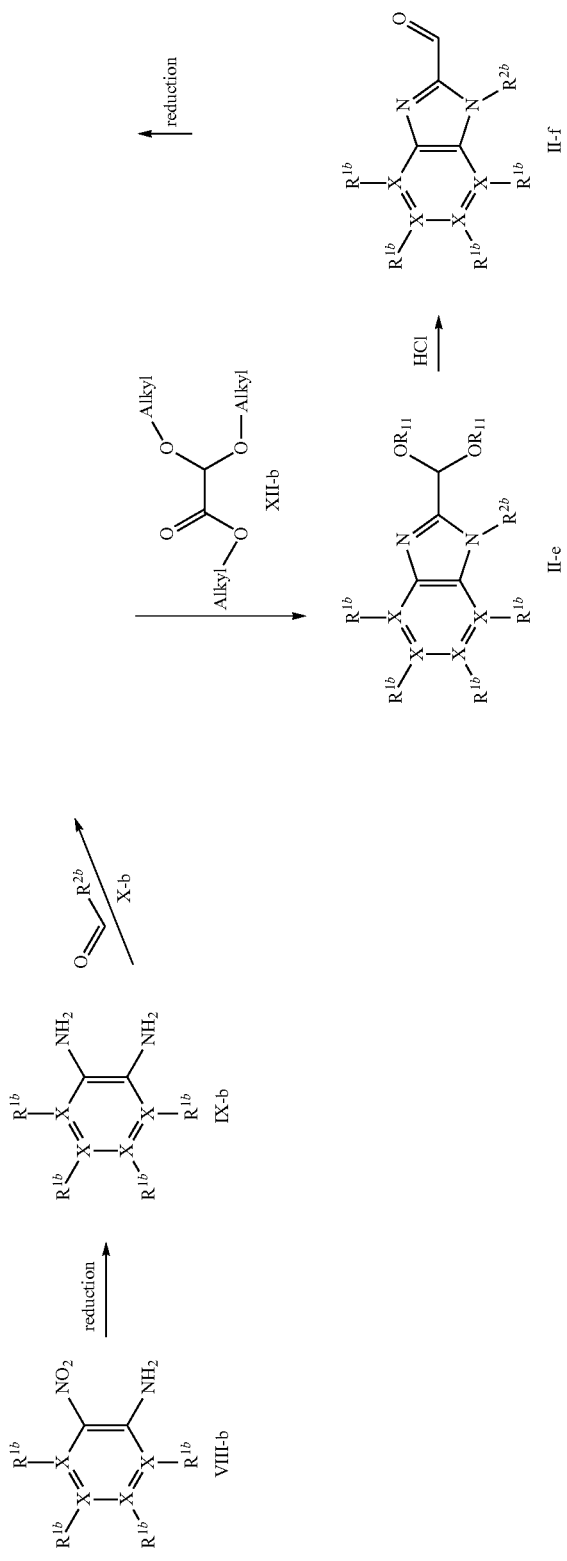

An alternative route for the preparation of intermediates of type II-a is depicted in scheme 4. Diamine IX-b may be first coupled to an alkyl glycolic acid or an ester like XIII-b under strong acidic conditions, such as aqueous hydrochloric acid, at elevated temperature such as reflux to yield the alcohols of formula XIV-b. This alcohol may be protected by a PG, where PG is a protecting group such as, but not limiting to, a trityl which consequently results in intermediates of formula XV-b. A suitable solvent for this type of reactions can be, but not limiting to, dichloromethane. The treatment of intermediate XV-b with intermediate XVI-b, wherein the LG is a leaving group, such as halide, preferably bromine, or sulfonate, in the presence of a base such as sodium hydride, potassium carbonate or cesium carbonate in a suitable solvent such as DMF or THF, gives intermediate II-h. The removal of the PG in intermediate II-h may be done in the presence of an acid such as hydrochloric acid in the presence of a solvent, not limited to, such as dioxane to yield an intermediate of formula II-a.

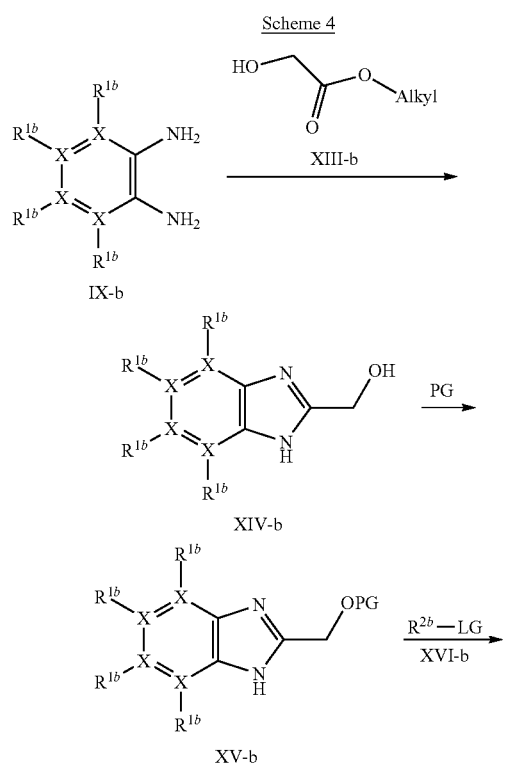

Scheme 4

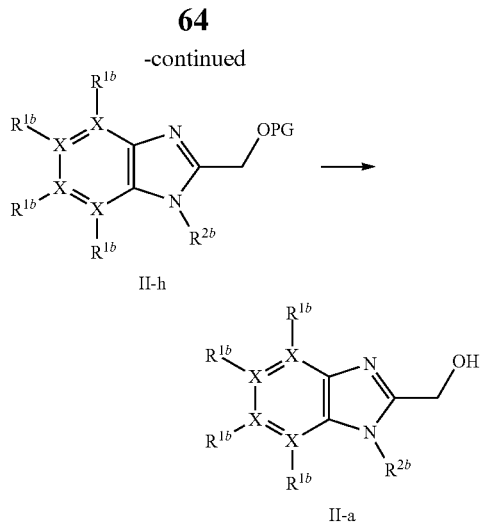

The Synthesis of a 2-oxo-imidazopyridine and a 2-oxo-imidazobenzene of formula III is shown in scheme 5. Intermediates of formula III can be synthesized using the procedure depicted in scheme 5. Displacement of W, which is a halide, preferably fluorine, or an alkoxy group, preferably methoxy, of nitro pyridine or of nitro aryl XVII with an amine, in a suitable solvent such as THF or DMF, in the presence of an organic base such as triethyl amine or diisopropyl ethyl amine, gives an intermediate of formula XVIII. Reduction of the nitro group to the amine XIX can be done in a catalytic way using hydrogen in the presence of a catalyst such as palladium or platinum, in a suitable solvent such as methanol, or in a stoichiometric way using iron in the presence of ammonium chloride or tin chloride in the presence of concentrated hydrochloric acid. The cyclisation of the resulting diamine XIX using 1,1'-carbonyldiimidazole (CDI), phosgene or triphosgene, in a solvent such as acetonitrile or THF, provides a $N^3$-substituted 2-oxo-imidazopyridine or a $N^3$-substituted 2-oxo-imidazobenzene derivative of formula III. Alternatively, an intermediate of type III may be prepared starting from commercially available dianilines XX which can be cyclized by ring closure with CDI, phosgene or triphosgene yields intermediates of type XXI. Introduction of a $R^4$ substituent (other than H) on an intermediate of formula XXI can be accomplished by a Mitsunobu reaction with commercially available alcohols, or by displacement of the LG in the intermediates of formula XXII, where LG is a leaving group such as halide, preferably bromine, or sulfonate, in the presence of a base such as sodium hydride, potassium carbonate or cesium carbonate in a suitable solvent such as DMF or THF. This will finally yield intermediates of formula III.

Scheme 5

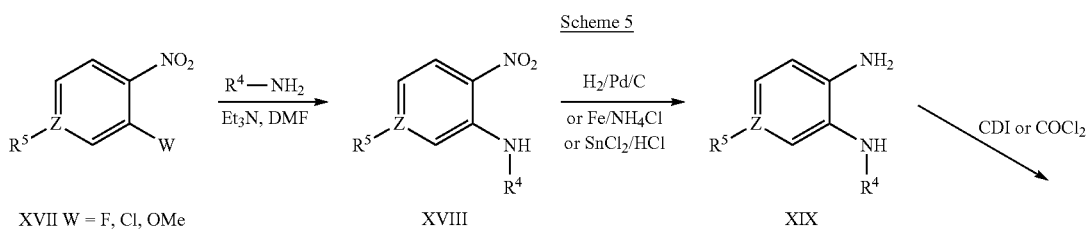

-continued

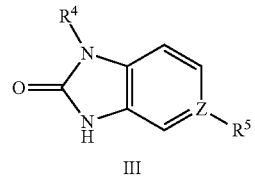
III

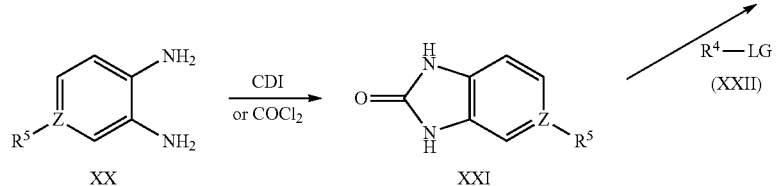

Scheme 6 illustrates a method for the preparation of compounds of formula (I), wherein Het is a heterocycle of formula (c), hereby named a compound of formula I-c, where $R^{1c}$, $R^{2c}$, $R^{3c}$, $R^4$, $R^5$ and Z are defined as above.

Referring to scheme 6, a compound of formula I-c can be synthesized by coupling a 2-hydroxymethylene indole of formula II-i with a $N^3$-substituted 2-oxo-imidazopyridine or with a $N^3$-substituted 2-oxo-imidazobenzene of formula III with a method known in the art method such as a Mitsunobu reaction which uses azadiisopropyldicarboxylate and triphenyl phosphine in a suitable solvent such as DMF or THF. Alternatively, a compound of formula I-c may be prepared by displacement of Y, which is a halide, preferably chlorine II-j, or a sulfonate such as mesylate II-k in the presence of a base such as sodium hydride, potassium carbonate or cesium carbonate in a suitable solvent such as DMF or THF.

Scheme 6

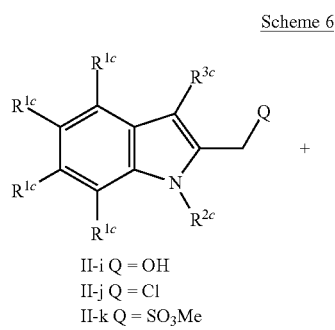

II-i Q = OH
II-j Q = Cl
II-k Q = SO₃Me

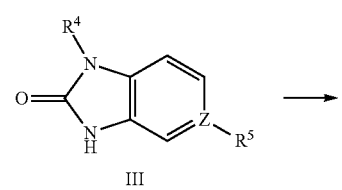
III

-continued

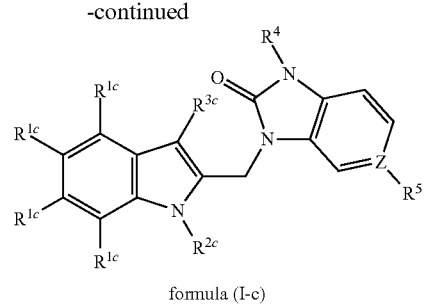
formula (I-c)

Preparation of Compound II-i

Starting materials IV-c used in this invention are commercially available, or can be synthesized, but not limited to, by methods known in the art such as Reissert synthesis or Fischer synthesis. Reaction of such indoles with $R^{2c}$-LG, where LG is a leaving group such as halide, preferably bromine, or sulfonate, in the presence of a base such as sodium hydride, potassium carbonate or cesium carbonate in a suitable solvent such as DMF or THF, gives intermediates V-c (scheme 7). The conversion of the alkyl ester of an intermediate of formula V-c to the alcohol II-i may be carried out with metal hydride such as lithium aluminum hydride or sodium borohydride in a suitable solvent such as THF, methanol or ethanol.

Alternatively, starting materials VI-c can be synthesized, but not limited to, by methods known in the art such as Reissert synthesis or Fischer synthesis. Reaction of such indoles with $R^{2c}$-LG, where LG is a leaving group such as halide, preferably bromine, or sulfonate, in the presence of a base such as sodium hydride, potassium carbonate or cesium carbonate in a suitable solvent such as DMF or THF, gives intermediates of formula VII-c. The oxidation of the methyl with selenium oxide or manganese dioxide in a suitable solvent such as dichloromethane or heptane leads to the aldehyde VIII-c. The conversion of the aldehyde VIII-c to the alcohol II-i may be carried out with metal hydride such as lithium aluminum hydride or sodium borohydride in a suitable solvent such as THF, methanol or ethanol.

Scheme 7

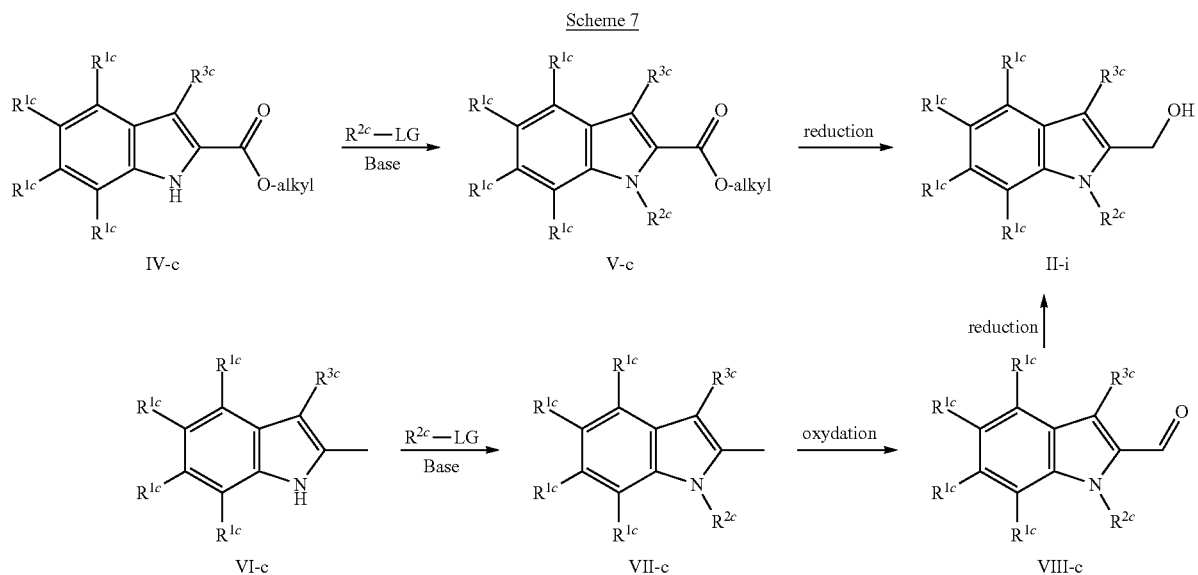

Treatment of the alcohol II-i with thionyl chloride provides 2-chloromethyl indole II-j. Alternatively, alcohol II-i may be transformed to the intermediate II-k by a reaction with methane sulfonyl chloride in the presence of an organic base such as triethyl amine or diisopropyl ethyl amine in a suitable solvent such dichloromethane (scheme 8).

Scheme 8

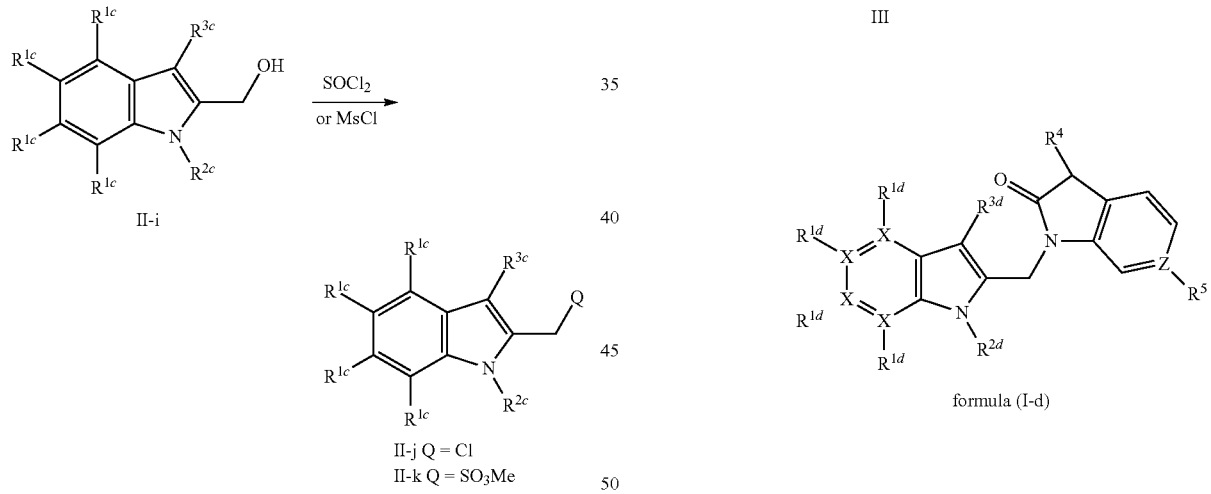

Scheme 9

Scheme 9: General synthesis of compound of formula I-d

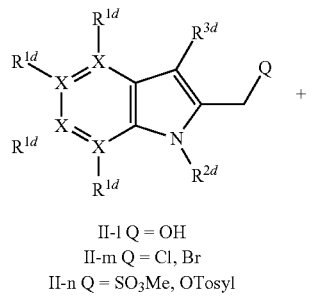

Scheme 9 illustrates a method for the preparation of compounds of formula I-d, where $R^{1d}$, $R^{2d}$, $R^{3d}$, $R^4$, $R^5$ and Z are defined as above.

A compound of formula I-d can be synthesized by coupling 2-hydroxymethylene indole II-l with a benzimidazolone III in a known in the art method such as Mitsunobu reaction which uses azadiisopropyldicarboxylate (DIAD) and triphenylphosphine in a suitable solvent such as DMF or THF. Alternatively, compounds of formula I-d may be prepared by displacement of Q, which is a halide, preferably chlorine II-m, or sulfonate such as mesylate II-n in the presence of a base such as, but not limiting to, sodium hydride, potassium carbonate or cesium carbonate in a suitable solvent such as DMF or THF.

Scheme 10

Method 1

Scheme 10: General synthesis of II-1 type intermediates

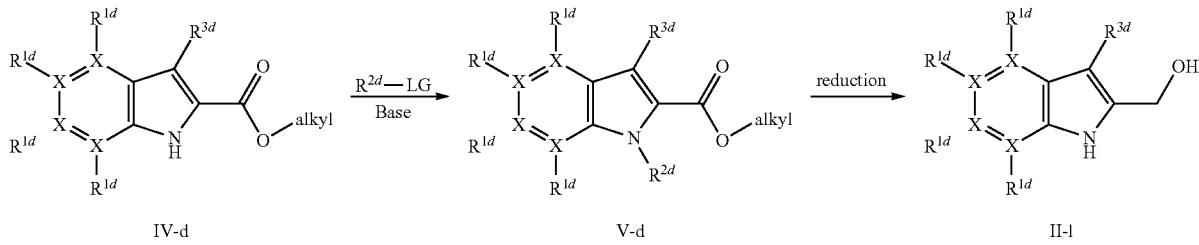

IV-d        V-d        II-1

Method 2

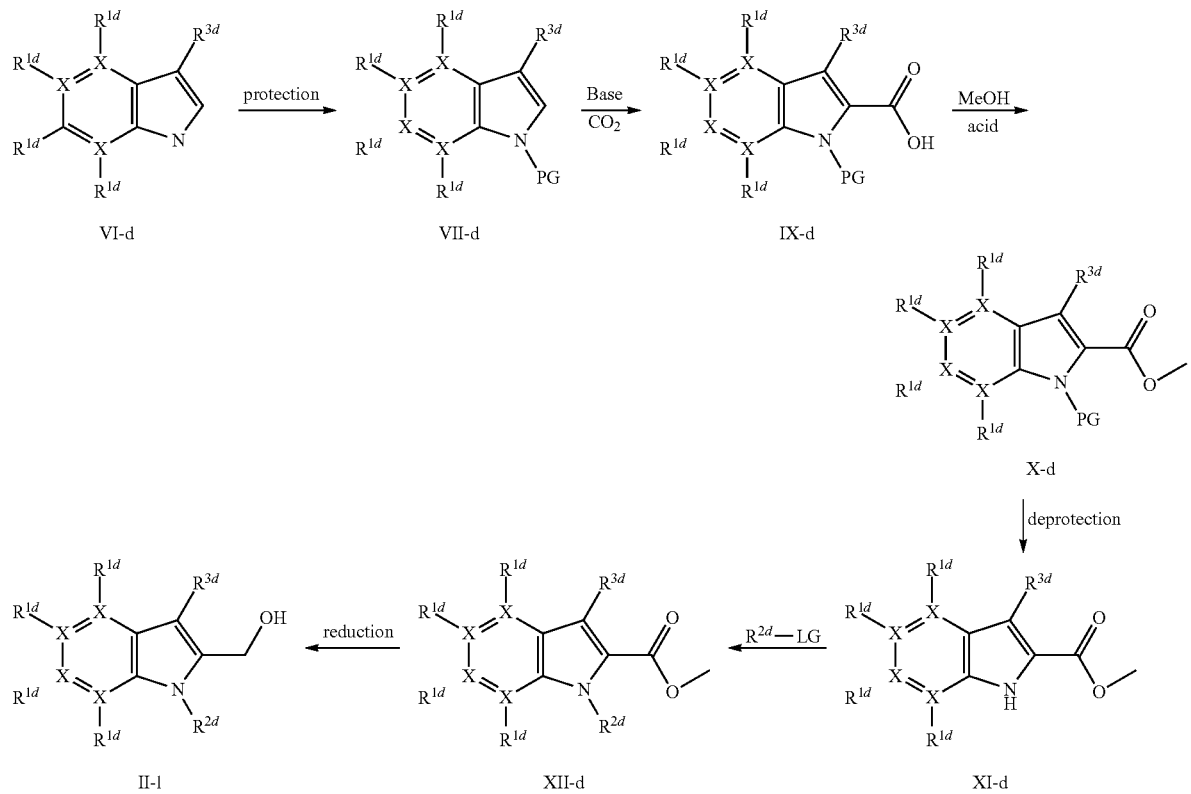

An intermediate of formula II-1 is prepared according to the methods as depicted in scheme 10.

Starting materials IV-d used in this invention, according to method 1, are commercially available, or can be synthesized, but not limited to, by methods known in the art such as Reissert synthesis or Fischer synthesis. Reaction of such an intermediate with $R^{2d}$-LG, where LG is a leaving group such as halide, preferably bromine, or sulfonate, in the presence of a base such as sodium hydride, potassium carbonate or cesium carbonate in a suitable solvent such as DMF or THF, gives an intermediate of formula V-d. The conversion of the alkyl ester of intermediate V-d to the alcohol II-1 can be done with a metal hydride such as lithium aluminum hydride or sodium borohydride in a suitable solvent such as THF or methanol.

Alternatively a II-1 type intermediate can also be synthesized as shown in scheme 10, method 2. The commercially available starting material VI-d is protected by a PG, where PG is a protecting group such as, but not limiting to, a tosyl, which consequently results in an intermediate of formula VII-d. A suitable solvent for this kind of reactions can be, but not limiting to, toluene. The metallation of intermediate VII-d followed by treatment with compound carbon dioxide, in a suitable solvent such as, but not limiting to, THF, yields intermediate IX-d. The esterification of acid in the intermediate IX-d can be performed with alcohols such methanol or ethanol in acidic conditions to yield intermediate X-d. The removal of the PG in intermediate X-d may be done in the presence of a base such as potassium carbonate or cesium carbonate in a suitable solvent such as THF and methanol to obtain indole XI-d. Reaction of indoles XI-d with $R^{2d}$-LG, where LG is a leaving group such as a halide, preferably bromine, or sulfonate, in the presence of a base such as sodium hydride, potassium carbonate or cesium carbonate in a suitable solvent such as DMF or THF, gives intermediate XII-d. The conversion of the alkyl ester of intermediate XII-d to the alcohol II-l can be carried out with a metal hydride such as lithium aluminium hydride or sodium borohydride in a suitable solvent such as THF or ethanol.

Scheme 11

Scheme 11: General synthesis of II-m and II-n type compounds

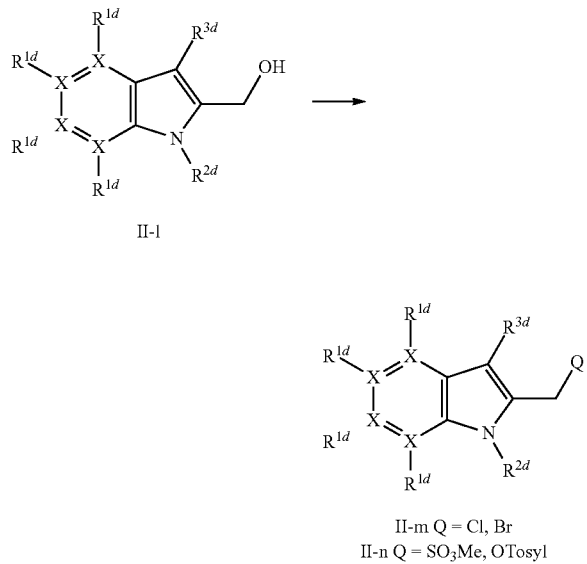

II-l

II-m Q = Cl, Br
II-n Q = SO$_3$Me, OTosyl

Treatment of the alcohol II-l with reagents like, but not limiting to, SOCl$_2$, PBr$_3$, p-TsCl (4-toluenesulfonyl chloride) or MsCl (methanesulfonyl chloride), provides 2-chloromethyl indole derivatives II-m or intermediates like II-n.

Scheme 12 illustrates a method for the preparation of compounds of formula I-e, where $R^{1c}$, $R^{3e}$, $R^4$, $R^5$, $R^{10e}$, Q, Y and Z are defined as above.

A IV-e type compound can be made by coupling 2-hydroxymethylene imidazopyridine II-o with a $N^3$-substituted benzimidazolone III in a known in the art method such as Mitsunobu reaction which use the azadiisopropyldicarboxylate and triphenylphosphine in a suitable solvent such as, but not limiting to, DMF or THF. Alternatively, compounds of formula I-e may be prepared by displacement of Q, which is a halide, II-p, preferably chlorine, or sulfonate, II-q, such as mesylate or tosylate, in the presence of base such as, but not limiting to, sodium hydride, potassium carbonate or cesium carbonate in a suitable solvent such as DMF or THF. Halogenating reagents such as, but not limited to, N-iodosuccinimide can be used to convert a IV-e type intermediate to a V-e type intermediate and CH$_3$CN can be a suitable solvent for this reaction. By coupling an alkyn to a V-e type intermediate in a known in the art method such as Sonogashira-type coupling reaction, a VI-e type intermediate can be generated. Reduction of the triple bond can be done in a catalytic way using hydrogen in the presence of the catalyst such as palladium or platinum, in a suitable solvent such as methanol, or in a stoichiometric way using iron in the presence of ammoniumchloride or tin chloride in the presence of concentrated hydrochloric acid to yield a compound of formula I-e.

Scheme 13

Scheme 13: General synthesis of II-o type compounds

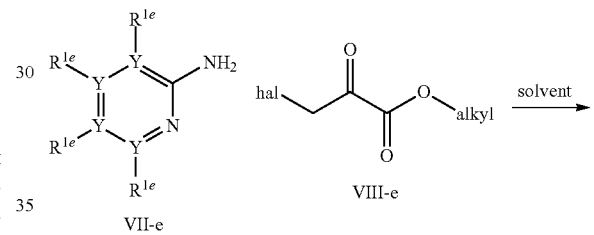

VII-e　　　VIII-e

Scheme12

Scheme 12: General synthesis of formula I-e type compounds

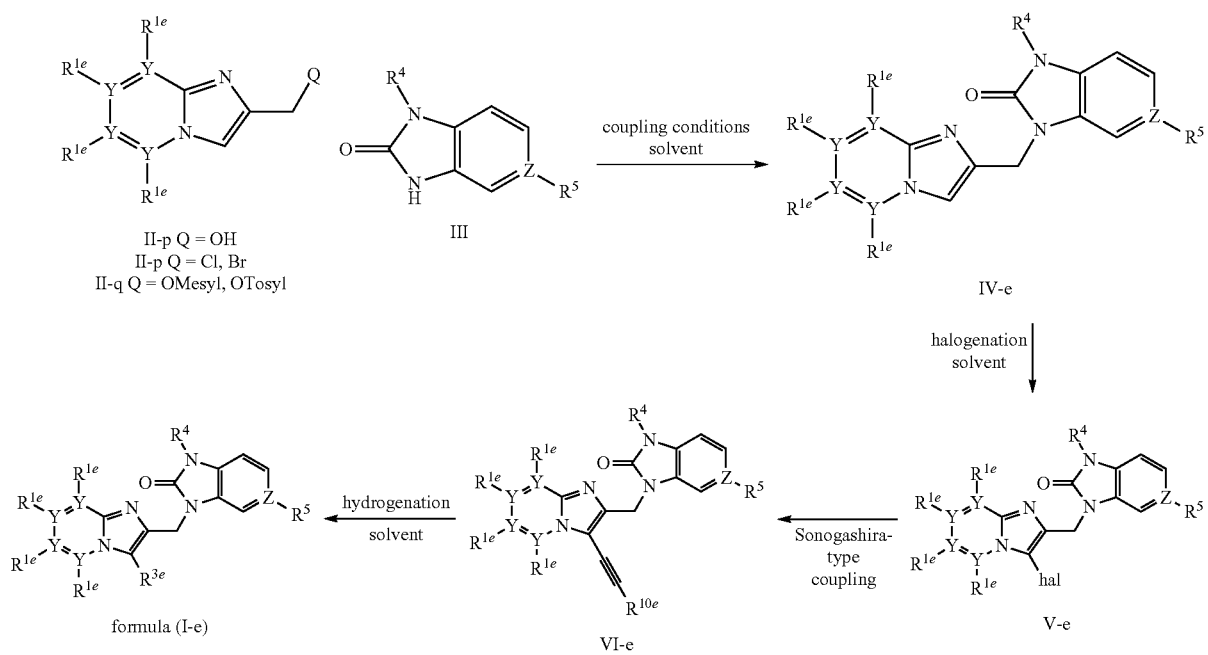

II-p Q = OH
II-p Q = Cl, Br
II-q Q = OMesyl, OTosyl

-continued

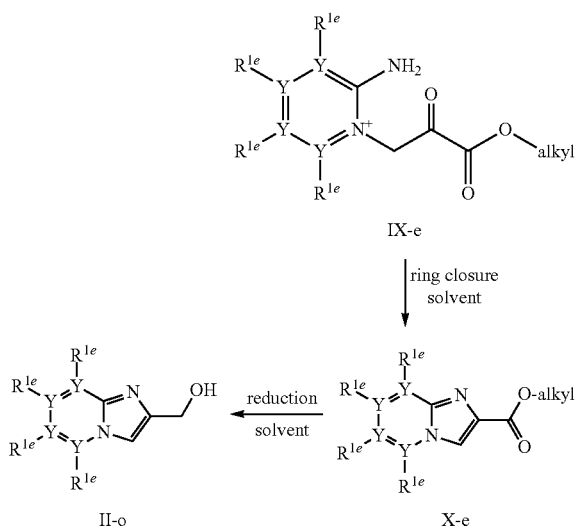

-continued

Method 2

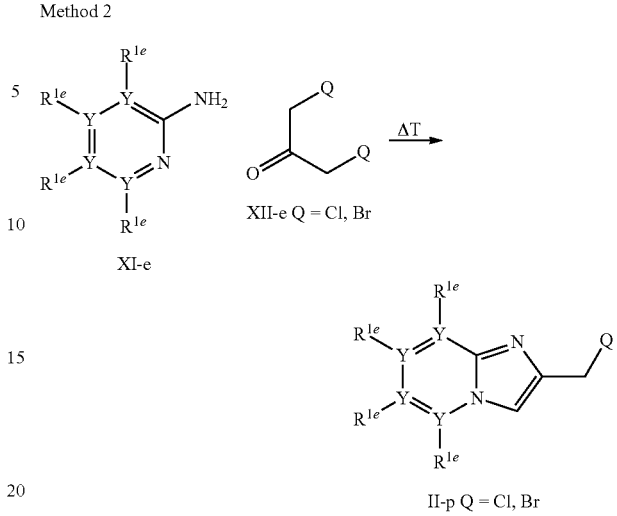

The synthesis of II-o type intermediates can generally be prepared as depicted in scheme 13. A IX-e type intermediate can be synthesized by coupling a commercially available VII-e type intermediate with a commercially available VIII-e type intermediate, of which the halogen is preferably bromine, through a base mediated coupling reaction. Possible bases to effect this reaction, but not limiting to, are $K_2CO_3$, $Cs_2CO_3$, triethylamine and sodium hydride. A suitable solvent for this type of base mediated coupling is DME (1,2-dimethoxyethane). After an intra molecular ring closure by thermal heating, an intermediate of formula X-e can be generated. The conversion of the alkyl ester of intermediate X-e to the alcohol II-o was carried out with metal hydride such as lithium aluminium hydride or sodium borohydride in a suitable solvent such as THF or methanol.

Scheme 14

Method 1

Scheme 14: General synthesis of II-p and II-q type intermediates

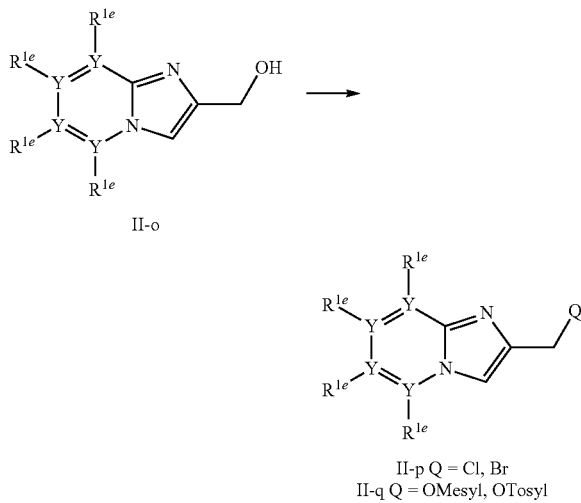

Scheme 14 shows the possibilities to synthesize II-p and II-q type intermediates. Treatment of the alcohol II-o with reagents like, but not limiting to, $SOCl_2$, $PBr_3$, p-TsCl (4-toluenesulfonyl chloride), MsCl (methane sulfonyl chloride) provides 2-chloromethyl indole II-p and to the intermediate II-q in the presence of an organic base, such as triethylamine or diisopropylethylamine in a suitable solvent such as dichloromethane. This is illustrated by method 1.

Alternatively a II-p type compound can also be generated through an inter molecular ring closure between a commercially available XI-e type compound and an also commercially available XII-e type compound. A suitable solvent for this reaction can be ethanol. This is illustrated by method 2.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

In a further aspect, the present invention concerns a pharmaceutical composition comprising a therapeutically effective amount of a compound of formula (I) as specified herein, or a compound of any of the embodiments of compounds of formula (I) as specified herein, and a pharmaceutically acceptable carrier. A therapeutically effective amount in this context is an amount sufficient to prophylaxictically act against, to stabilize or to reduce viral infection, and in particular RSV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the embodiments of compounds of formula (I) as specified herein.

Therefore, the compounds of the present invention or any embodiment thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailabilty, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Due to their antiviral properties, particularly their anti-RSV properties, the compounds of formula (I) or any embodiment thereof, and stereoisomeric forms thereof, and the pharmaceutically acceptable addition salts, and the solvates thereof, are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of the present invention or any embodiment thereof may therefore be used as medicines. Said use as a medicine or method of treatment comprises the systemic administration to viral infected subjects or to subjects susceptible to viral infections of an amount effective to combat the conditions associated with the viral infection, in particular the RSV infection.

The present invention also relates to the use of the present compounds or any embodiment thereof in the manufacture of a medicament for the treatment or the prevention of viral infections, particularly RSV infection.

The present invention furthermore relates to a method of treating a warm-blooded animal infected by a virus, or being at risk of infection by a virus, in particular by RSV, said method comprising the administration of an anti-virally effective amount of a compound of formula (I), as specified herein, or of a compound of any of the embodiments of compounds of formula (I), as specified herein.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

The invention will hereinafter be illustrated with reference to the following, non-limiting examples.

EXPERIMENTAL PART

Hereinafter, the term 'eq.' means equivalent, 'THF' means tetrahydrofuran, 'Psi' means pound-force per square inch, 'DMF' means N,N-dimethylformamide, 'DMSO' means dimethyl sulfoxide, 'DIEA' means diisopropylethylamine, 'DIAD' means diisopropyl azodicarboxylate, 'HOAc' or 'AcOH' means acetic acid, 'RP' means reversed phase, 'EtOAc' means ethyl acetate, 'Pd(dppf)Cl$_2$CH$_2$Cl$_2$' means [1,1'-bis(diphenylphosphino)ferrocene]palladium chloride complex with dichloro-methane, 'TPP' means triphenylphosphine, 'm-cPBA' means 3-chlorobenzene-carboperoxoic acid, 'Cu(OAc)$_2$' means copper(II) acetate, 'EtOH' means ethanol, 'MeOH' means methanol, 'MeCN' means methyl cyanide, 'CDT' means 1,1'-carbonyldiimidazole, 'KOEt' means potassium ethoxide, and 'HPLC' means High Performance Liquid Chromatography.

LCMS (Liquid Chromatography/Mass Spectrometry)

LCMS was done using either of the following methods:

General Method A

The LC measurement was performed using an Acquity UPLC (Waters) ('UPLC' means Ultra Performance Liquid Chromatography) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

General Method B

The LC measurement was performed using an Acquity UPLC (Waters) system comprising a binary pump, a sample organizer, a column heater (set at 55° C.), a diode-array detector (DAD) and a column as specified in the respective methods below. All the flow from the column went to a MS spectrometer. The MS detector was configured with an electrospray ionization source. Mass spectra were acquired by scanning from 120 to 1000 in 0.1 seconds. The capillary needle voltage was 3.0 kV and the source temperature was maintained at 150° C. Nitrogen was used as the nebulizer gas. Data acquisition was performed with a Waters-Micromass MassLynx-Openlynx data system.

Method 1

In addition to the general method A: Reversed phase UPLC was carried out on a bridged ethylsiloxane/silica hybrid (BEH) C18 column (1.7 µm, 2.1×50 mm; Waters Acquity) with a flow rate of 0.8 ml/min. Two mobile phases (10 mM ammonium acetate in H$_2$O/acetonitrile 95/5; mobile phase B: acetonitrile) were used to run a gradient condition from 95% A and 5% B to 5% A and 95% B in 1.3 minutes and hold for 0.3 minutes. An injection volume of 0.5 µl was used. Cone voltage was 10 V for positive ionization mode and 20 V for negative ionization mode.

Method 2

In addition to the general method B: Reversed phase UPLC (Ultra Performance Liquid Chromatography) was carried out on a Acquity UPLC HSS T3 column (1.8 µm, 2.1×100 mm; Waters Acquity) with a flow rate of 0.8 ml/min. Two mobile phases (A: 10 mM ammonium acetate in H$_2$O/acetonitrile 95/5; mobile phase B: acetonitrile) were used to run a gradient condition from 95% A and 5% B to 0% A and 100% B in 2.5 minutes and subsequently to 5% A and 95% B in 0.5 minutes. An injection volume of 1 µl was used. Cone voltage was 30 V for positive ionization mode and 30 V for negative ionization mode.

NMR

For a number of compounds, $^1$H NMR spectra were recorded on a Bruker DPX-400 spectrometer operating at 400 MHz or on a Bruker DPX-360 operating at 360 MHz using CHLOROFORM-d (deuterated chloroform, CDCl$_3$) or DMSO-d$_6$ (deuterated DMSO, dimethyl-d6 sulfoxide) as solvent. Chemical shifts (δ) are reported in parts per million (ppm) relative to tetramethylsilane (TMS), which was used as internal standard.

Melting Points

For a number of compounds, melting points (m.p.) were determined with a DSC823e (Mettler-Toledo). Melting points were measured with a temperature gradient of 30° C./minute. Maximum temperature was 400° C. Values are peak values.

Synthesis of Intermediates

All the intermediates needed for the synthesis of targeted compounds of formula (I) are synthesized as described in the following schemes 15 to 22.

Scheme 15: synthesis of tert-butyl 3-(2-oxo-2,3-dihydro-1H-benzo[d]imidazol-1-yl)azetidine-1-carboxylate 15-d

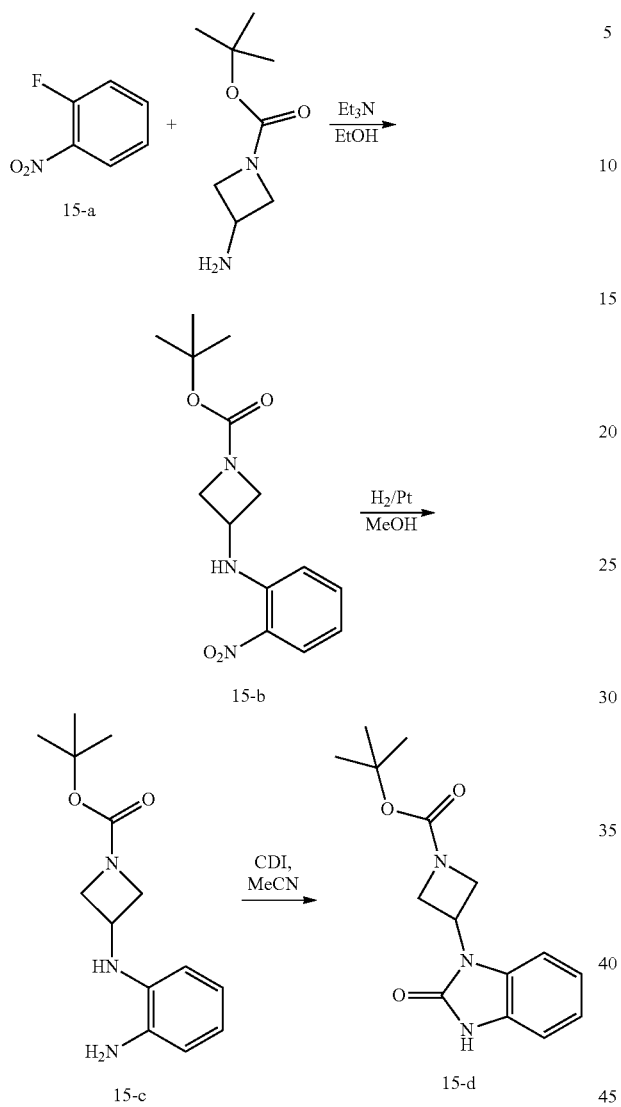

Step 1: Synthesis of tert-butyl 3-(2-nitrophenylamino)azetidine-1-carboxylate 15-d To a mixture of 2-fluoro-2-nitrobenzene, 15-a (17.278 g, 122.45 mmol, 1 eq.), triethylamine (24.782 g, 244.91 mmol, 2.0 eq.) in ethanol (170 mL) at 0° C. tert-butyl 3-aminoazetidine-1-carboxylate (23.2 g, 134.708 mmol, 1.1 eq.) was added dropwise. The resulting mixture was refluxed overnight. The mixture was cooled to room temperature and filtrated. The cake was washed with cooled ethanol and dried under vacuum. 22 g of intermediate 15-b was obtained (61.5% yield).

Step 2: Synthesis of tert-butyl 3-(2-aminophenylamino)azetidine-1-carboxylate 15-c Intermediate 15-b (21.0 g, 71.595 mmol, 1 eq.) in methanol (70 mL), THF (70 mL) and ethyl acetate (70 mL) was hydrogenated (50 Psi) at 50° C. with Pt/C (2.1 g) as a catalyst for 12 hours. After uptake of H$_2$ (3 eq.), the catalyst was filtered off and the filtrate was evaporated to give intermediate 15-c (18 g, Yield 95.5%).

Step 3: Synthesis of 1-cyclopropyl-7-methyl-1H-benzo[d]imidazol-2(3H)-one 15-d Carbonyldiimidazole (15.517 g, 95.696 mmol, 1.05 eq.) was added to a solution of intermediate 15-c (24.0 g, 91.139 mmol, 1.0 eq.) in CH$_3$CN (240 mL) at 0° C. The reaction mixture was allowed to warm to 25° C. and stirred for 1 h. The solid was collected by filtration and was washed with CH$_3$CN (70 mL) to afford the title intermediate 15-d as a white powder (19.35 g, 74%).

Scheme 16: synthesis of tert-butyl 3-(5-fluoro-2-oxo-2,3-dihydro-1H-benzo[d]-imidazol-1-yl)azetidine-1-carboxylate 16-d

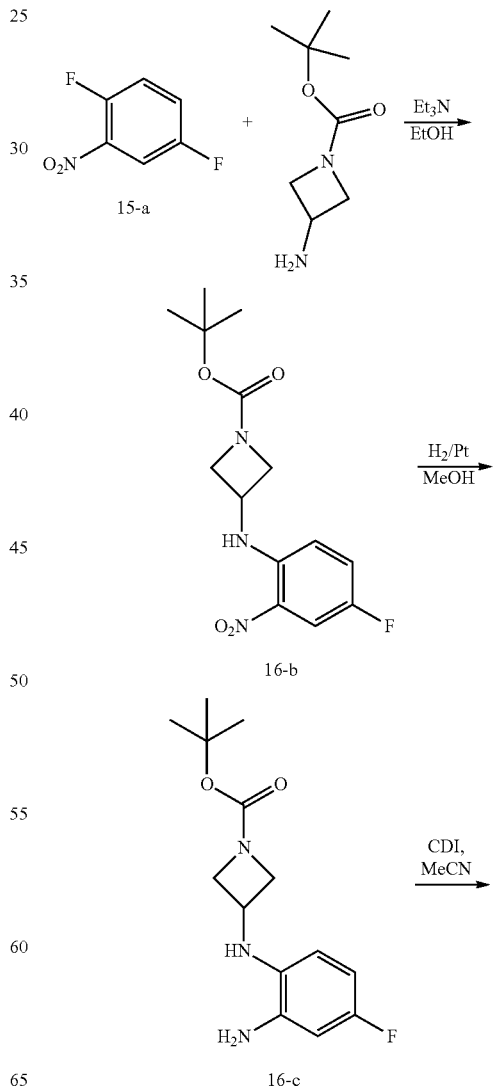

-continued

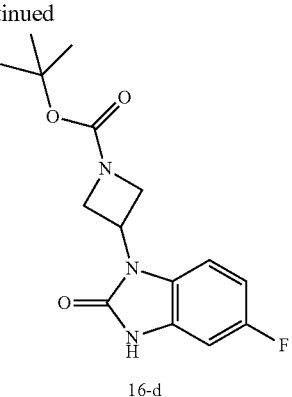
16-d

Intermediate 16-d was prepared by an analogous reaction protocol as intermediate 15-d using 1,4-difluoro-2-nitrobenzene 16-a as starting material.

Scheme 17: synthesis of tert-butyl 3-(2-oxo-2,3-dihydro-1H-imidazo[4,5-c]pyridin-1-yl)azetidine-1-carboxylate 17-d

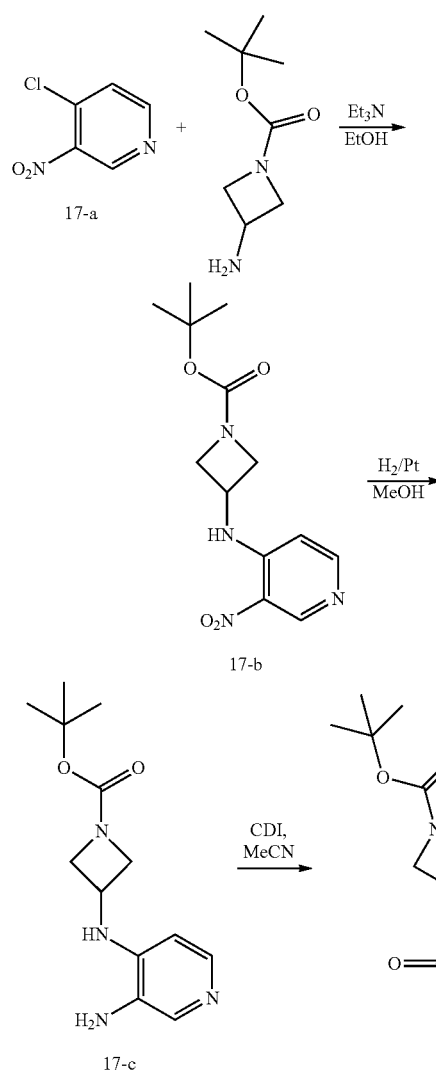

Intermediate 17-d was prepared by following an analogous reaction protocol as described for intermediate 15-d using 4-chloro-3-nitropyridine 17-a as starting material.

Scheme 18: synthesis of 1-(1-methylcyclopropyl)-1H-imidazo[4,5-c]pyridin-2(3H)-one 18-c

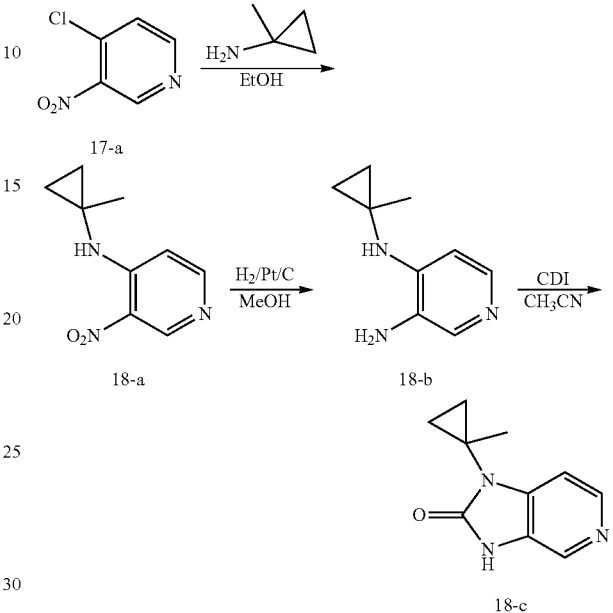

Intermediate 18-c was prepared by following an analogous reaction protocol as described for intermediate 15-d using 4-chloro-3-nitropyridine 17-a and 1-methyl-cyclopropylamine as starting material.

Scheme 19: synthesis of 1-tert-butyl-1H-imidazo[4,5-c]pyridin-2(3H)-one 19-c

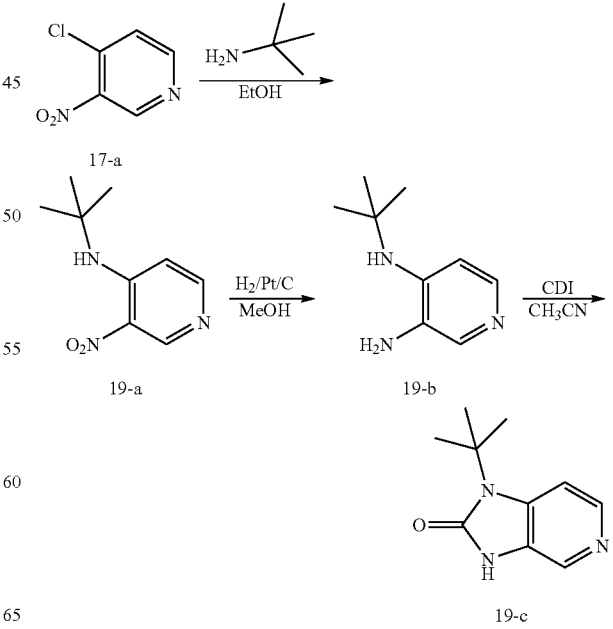

Intermediate 19-c was prepared by following an analogous reaction protocol as described for intermediate 15-d using 4-chloro-3-nitropyridine 17-a and 2-methyl-propane-2-amine as starting material.

Scheme 20: synthesis of 1-(quinolin-6-yl)-1H-imidazo[4,5-c]pyridin-2(3H)-one 20-c

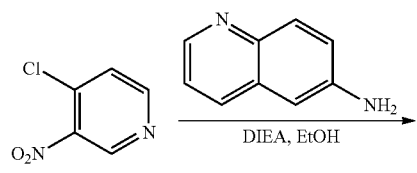

17-a

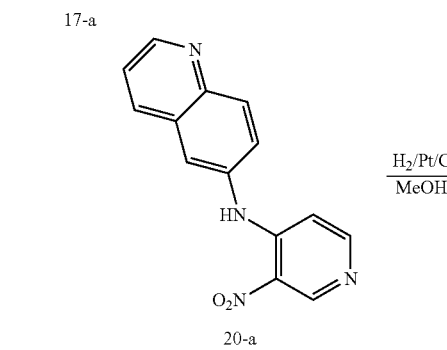

20-a

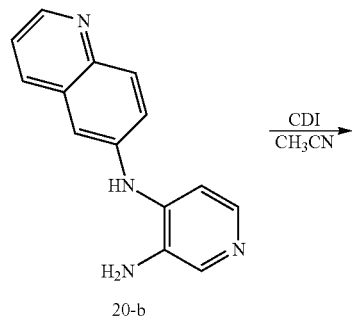

20-b

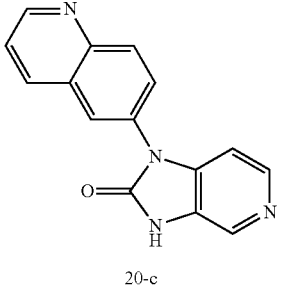

20-c

Intermediate 20-c was prepared by following an analogous reaction protocol as described for intermediate 15-d using 4-chloro-3-nitropyridine 17-a and quinolin-6-amine as starting material.

Scheme 21: synthesis of 1-(thiazol-6-yl)-1H-imidazo[4,5-c]pyridin-2(3H)-one 21-c

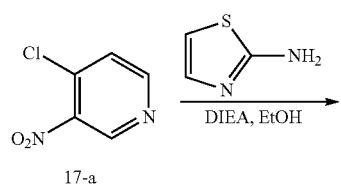

17-a

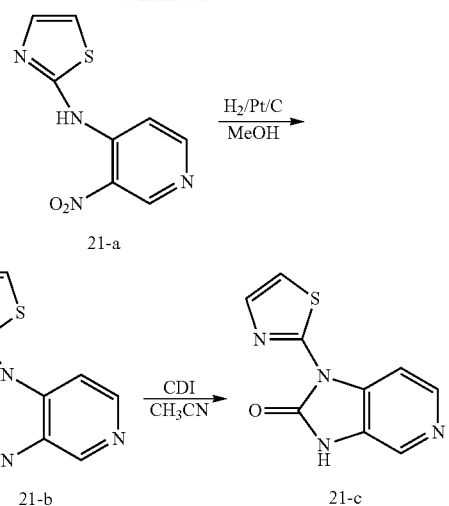

21-a 21-b      21-c

Intermediate 21-c was prepared by following an analogous reaction protocol as described for intermediate 15-d using 4-chloro-3-nitropyridine 17-a and thiazol-2-amine as starting material.

Scheme 22: synthesis of 1-(4-methoxyphenyl)-1H-imidazo[4,5-c]pyridin-2(3H)-one 22-c

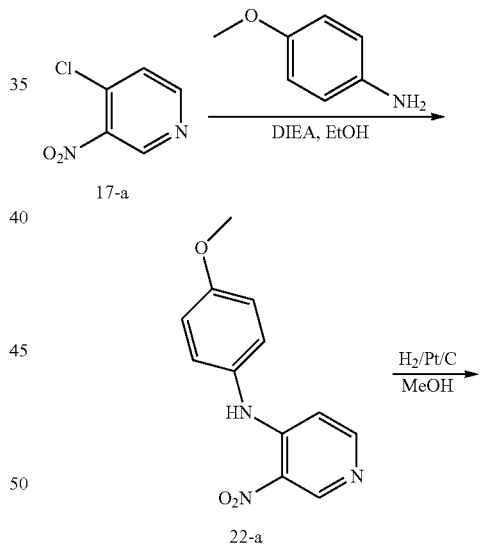

17-a 22-a

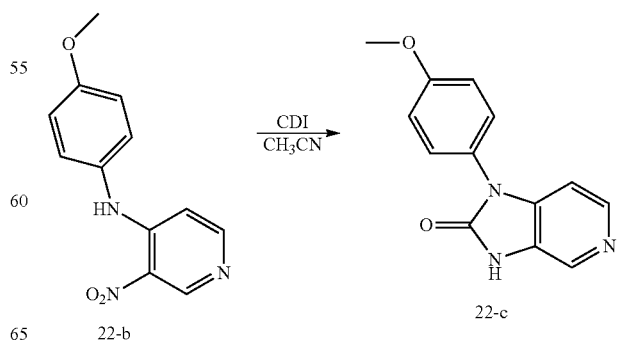

22-b        22-c

Intermediate 22-c was prepared by following an analogous reaction protocol as described for intermediate 15-d using 4-chloro-3-nitropyridine 17-a and 4-methoxyaniline as starting material.

Scheme 23: synthesis of 1-bromo-3-(methylsulfonyl)propane 23-c

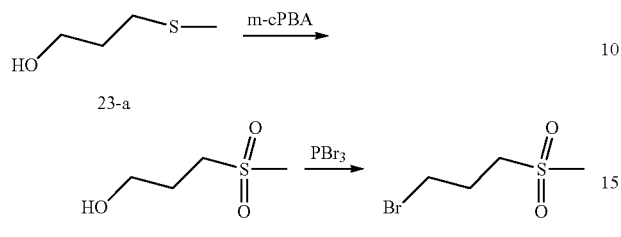

Step 1: Synthesis of 3-(methylsulfonyl)propan-1-ol 23-b

The alcohol 23-a (200 g, 1900 mmol) was dissolved in $CH_2Cl_2$ (2000 ml). The mixture was cooled to 0° C. The m-CPBA 85% in water (970 g, 5700 mmol) was added portion wise keeping the temperature between 0 to 5° C. After addition, the mixture was allowed to warm to 25° C. and stirred for 15 h. The mixture was filtered through a celite pad. The filtrate was purified by flash column (Eluent: petroleum ether:ethyl acetate=3:1 and then ethyl acetate:methanol=10:1) to yield the intermediate 23-b (75 g, 29%).

Step 2: Synthesis of 1-bromo-3-(methylsulfonyl)propane 23-c

The intermediate 23-b (75 g, 543 mmol) was dissolved in $CH_2Cl_2$ (750 ml). The mixture was cooled to 0° C. The phosphorus tribromide (53.6 ml, 570 mmol) was added drop wise keeping the temperature between 0 to 5° C. After addition, the mixture was allowed to warm to 25° C. and stirred for 15 h. The mixture was poured into ice-water. The separated organic layer was washed with brine (2×1500 mL), dried over $Na_2SO_4$, filtered and evaporated under vacuum to yield the title intermediate 23-c (77 g, 71%).

$^1$H NMR (400 MHz, CHLOROFORM-d) δ ppm 2.25-2.40 (m, 2H) 2.91 (s, 3H) 3.1-3.2 (m, 2H) 3.5-3.6 (m, 2H).

Scheme 24: Synthesis of (5-chloro-1-(3-(methylsulfonyl)propyl)-1H-indol-2-yl)-methanol 24-c

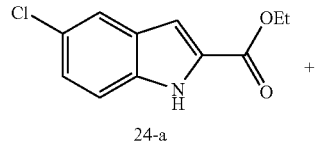

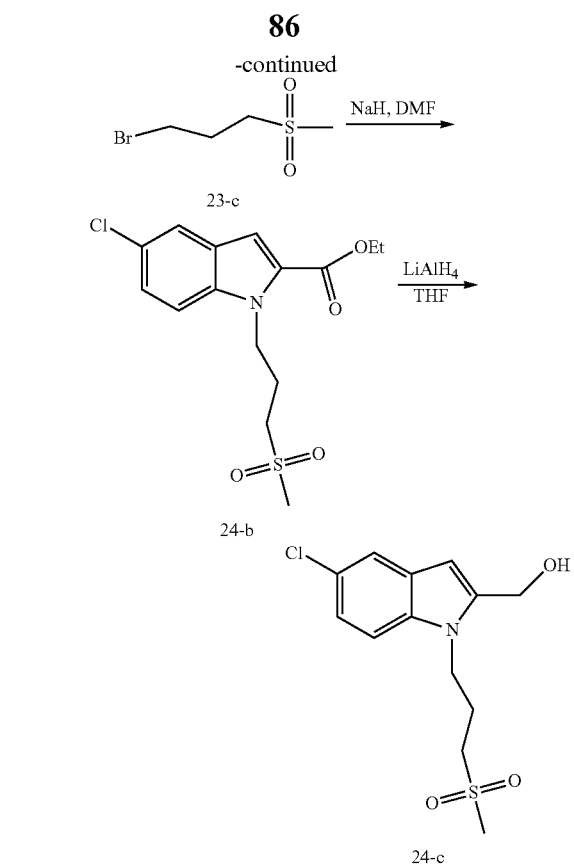

Step 1: Synthesis of ethyl 5-chloro-1-(3-(methylsulfonyl)propyl)-1H-indole-2-carboxylate 24-b Ethyl 5-bromo-1H-indole-2-carboxylate 24-a (2.3 g, 8.6 mmol) was dissolved in DMF (50 mL). The mixture was stirred at room temperature, then sodium hydride 60% suspension in mineral oil (0.52 g, 12.8 mmol) was added. The resulting mixture was stirred at room temperature for 1 hour, then 1-bromo-3-(methylsulfonyl)propane 23-c (2.6 g, 12.8 mmol) was added. The resulting mixture was stirred at room temperature overnight. The mixture was poured in ice/water solution and extracted with ethyl acetate. The organic layer was dried over $MgSO_4$ and concentrated to yield a brown crude oil. The crude was purified by column chromatography using dichloro-methane/methanol to yield the title compound 24-b (3.2 g, 96%) as a white solid.
m/z=344 (M+H)$^+$.

Step 2: Synthesis of (5-chloro-1-(3-(methylsulfonyl) propyl)-1H-indol-2-yl)methanol 24-c To a solution of intermediate 24-b (3.2 g, 8.24 mmol) in THF (100 mL) was added at room temperature lithium aluminum hydride (2M solution in THF, 5.2 mL, 10.4 mmol). The resulting mixture was stirred at room temperature overnight. The reaction mixture was quenched by addition of ethyl acetate and ethanol. The resulting mixture was poured in ice/water solution then filtered on celite. The aqueous layer was extracted with ethyl acetate (3×50 mL). The combined organic extracts were washed with brine (100 mL), dried over MgSO₄, filtered and concentrated under reduced pressure. The residue was purified by column chromatography using dichloromethane/methanol as the eluent. The intermediate 24-c was collected (2.5 g, 88%) as a white solid. m/z=302 (M+H)⁺.

The following schemes described the synthesis of intermediates needed for the synthesis of compounds of formula I.

Scheme 32: synthesis of 1-(3,4-dimethoxyphenyl)-1H-imidazo[4,5-c]pyridin-2(3H)-one 32-c.

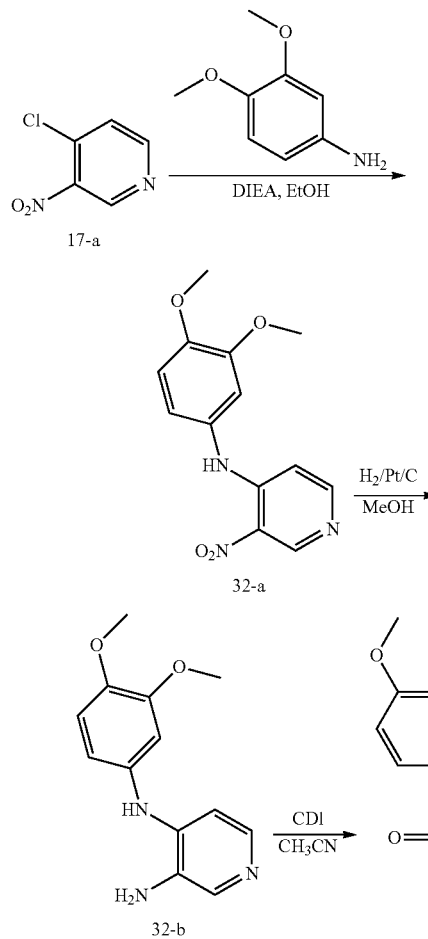

Intermediate 32-c was prepared by following an analogous reaction protocol as described for intermediate 15-d using 4-chloro-3-nitropyridine 17-a and 3,4-dimethoxyaniline as starting material.

Scheme 33: synthesis of 1-(4-methoxy-2-methylphenyl)-1H-imidazo[4,5-c]pyridin-2(3H)-one 33-c

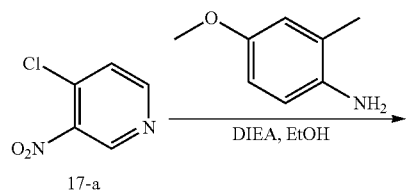

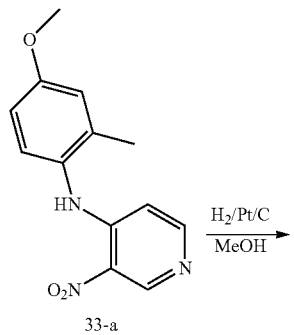

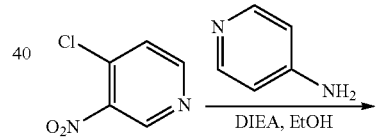

Intermediate 33-c was prepared by following an analogous reaction protocol as described for intermediate 15-d using 4-chloro-3-nitropyridine 17-a and 4-methoxy-2-methylaniline as starting material.

Scheme 34: synthesis of 1-(pyridin-4-yl)-1H-imidazo[4,5-c]pyridin-2(3H)-one 34-c

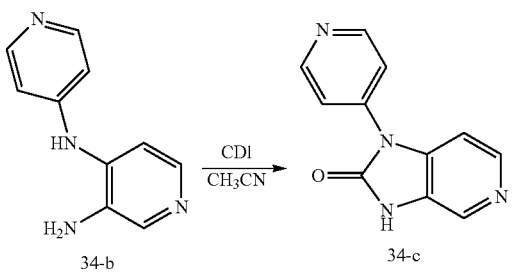

Intermediate 34-c was prepared by following an analogous reaction protocol as described for intermediate 15-d using 4-chloro-3-nitropyridine 17-a and pyridin-4-amine as starting material.

Scheme 35: synthesis of 1-(pyrimidin-4-yl)-1H-imidazo[4,5-c]pyridin-2(3H)-one 35-c

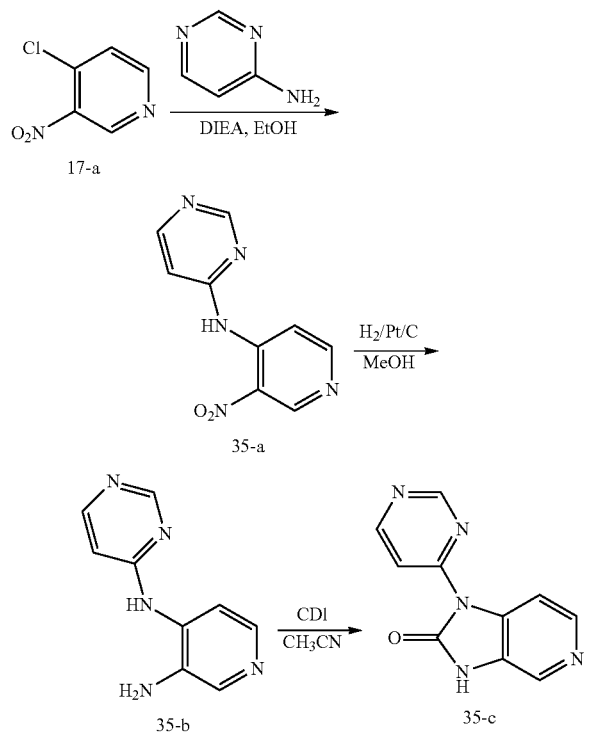

Intermediate 35-c was prepared by following an analogous reaction protocol as described for intermediate 15-d using 4-chloro-3-nitropyridine 17-a and pyrimidin-4-amine as starting material.

Scheme 36: synthesis of 1-(3-fluoropyridin-4-yl)-1H-imidazo[4,5-c]pyridin-2(3H)-one 36-c.

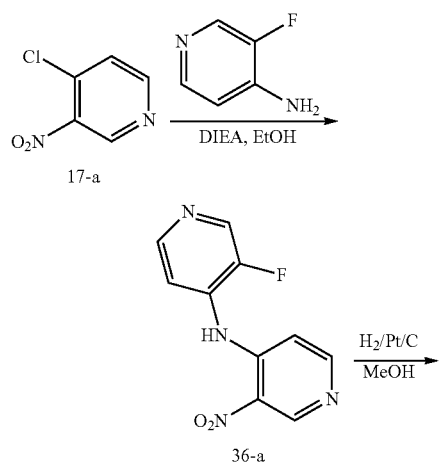

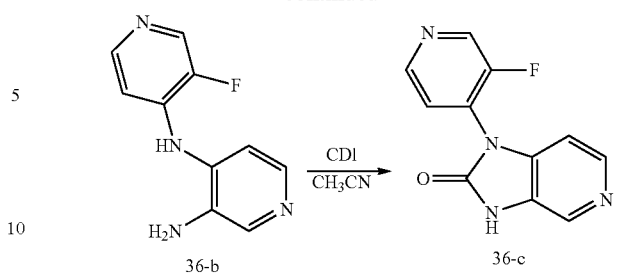

Intermediate 36-c was prepared by following an analogous reaction protocol as described for intermediate 15-d using 4-chloro-3-nitropyridine 17-a and 3-fluoropyridin-4-amine as starting material.

Scheme 37: synthesis of 5-fluoro-1-(thiazol-2-yl)-1H-benzo[d]imidazol-2(3H)-one 37-c

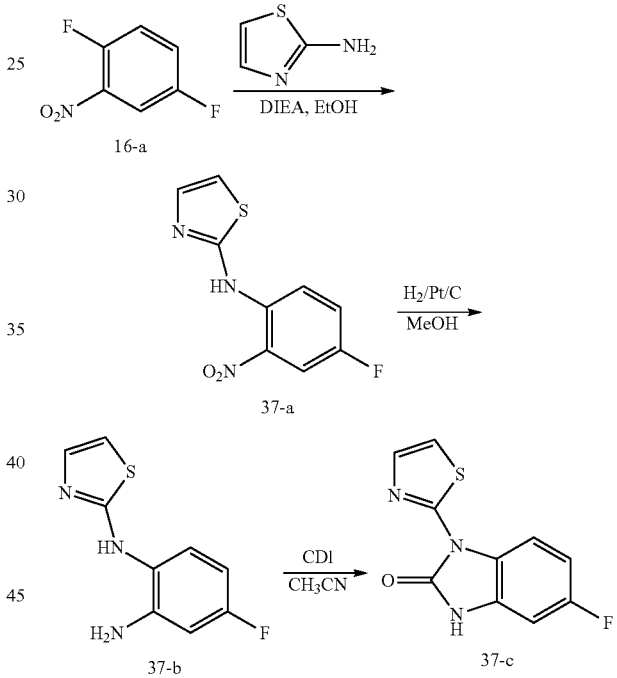

Intermediate 37-c was prepared by following an analogous reaction protocol as described for intermediate 16-d using 1,4-difluoro-2-nitrobenzene 16-a and thiazol-2-amine as starting material.

Scheme 38: synthesis of 5-fluoro-1-(pyridin-4-yl)-1H-benzo[d]imidazol-2(3H)-one 38-c

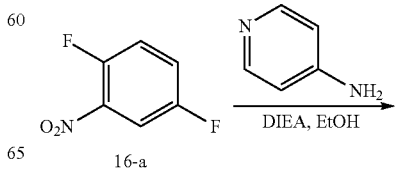

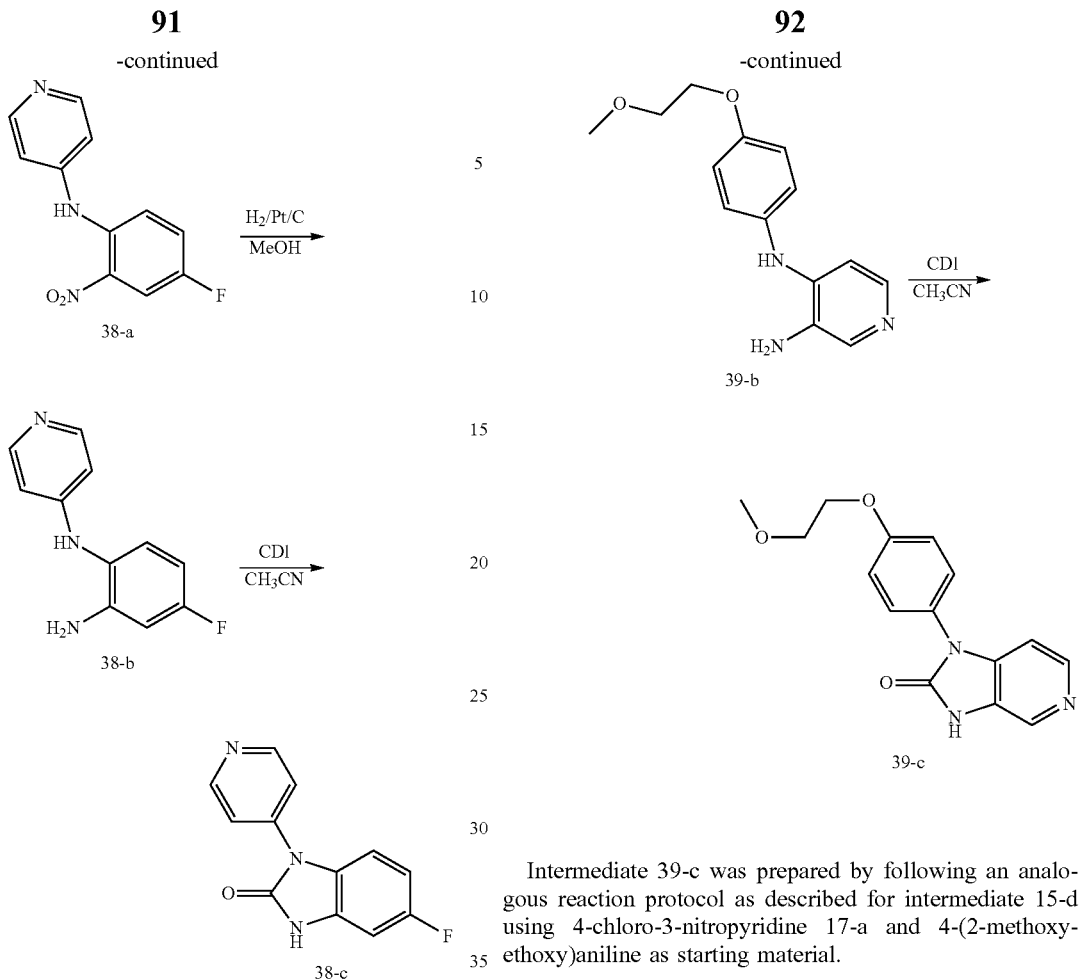

Intermediate 38-c was prepared by following an analogous reaction protocol as described for intermediate 16-d using 1,4-difluoro-2-nitrobenzene 16-a and pyridin-4-amine as starting material.

Scheme 39: synthesis of 1-(4-(2-methoxyethoxy)phenyl)-1H-imidazo[4,5-c]pyridin-2(3H)-one 39-c

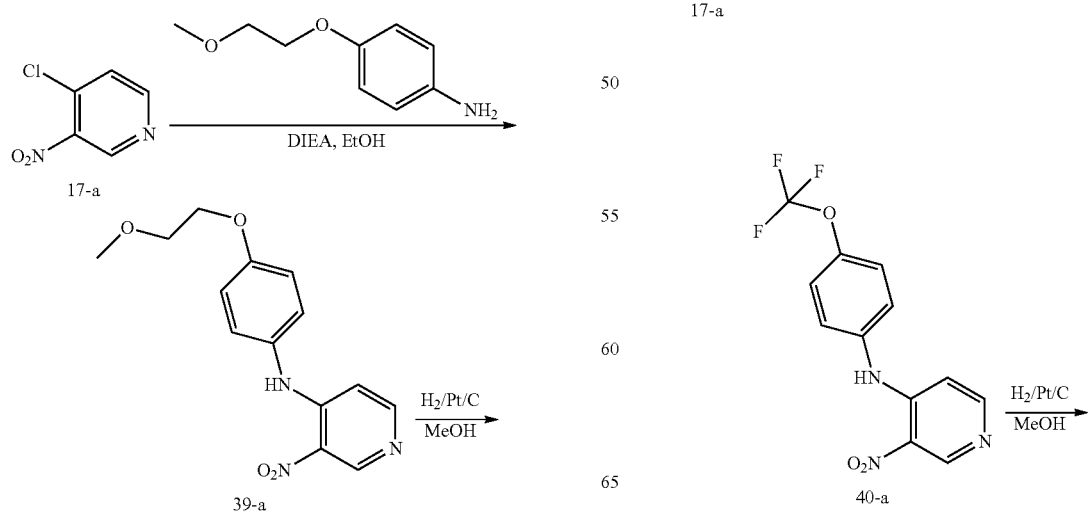

Intermediate 39-c was prepared by following an analogous reaction protocol as described for intermediate 15-d using 4-chloro-3-nitropyridine 17-a and 4-(2-methoxyethoxy)aniline as starting material.

Scheme 40: synthesis of 1-(4-(trifluoromethoxy)phenyl)-1H-imidazo[4,5-c]pyridin-2(3H)-one 40-c -continued

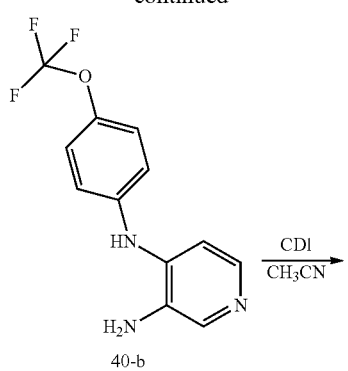
40-b

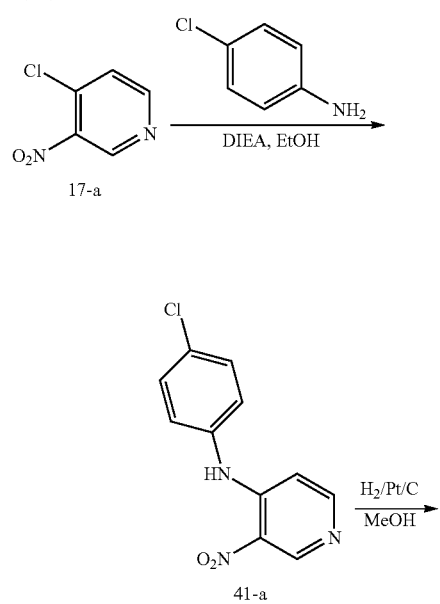
40-c

Intermediate 40-c was prepared by following an analogous reaction protocol as described for intermediate 15-d using 4-chloro-3-nitropyridine 17-a and 4-(trifluoromethoxy)aniline as starting material.

Scheme 41: synthesis of 1-(4-chlorophenyl)-1H-imidazo[4,5-c]pyridin-2(3H)-one 41-c -continued

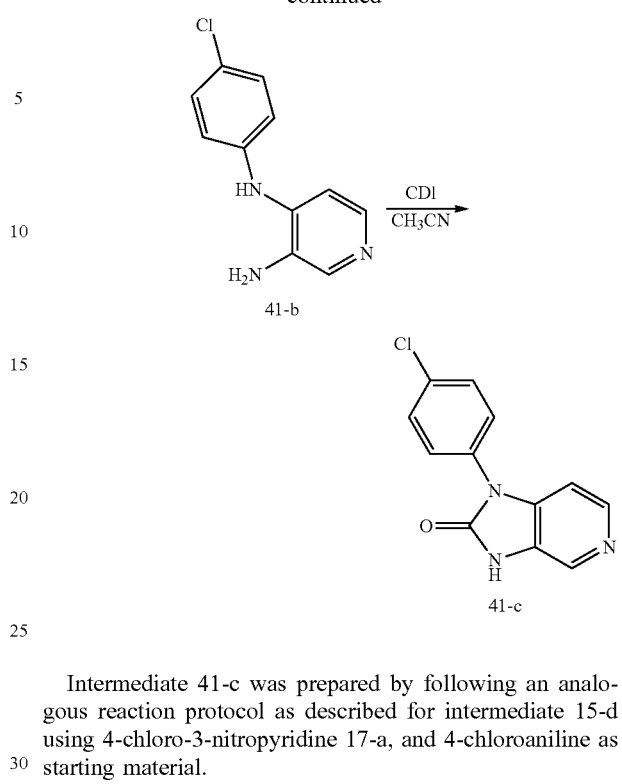
41-b 41-c

Intermediate 41-c was prepared by following an analogous reaction protocol as described for intermediate 15-d using 4-chloro-3-nitropyridine 17-a, and 4-chloroaniline as starting material.

Scheme 42: synthesis of 1-(1-methyl-1H-imidazol-2-yl)-1H-imidazo[4,5-c]pyridin-2(3H)-one 42-c

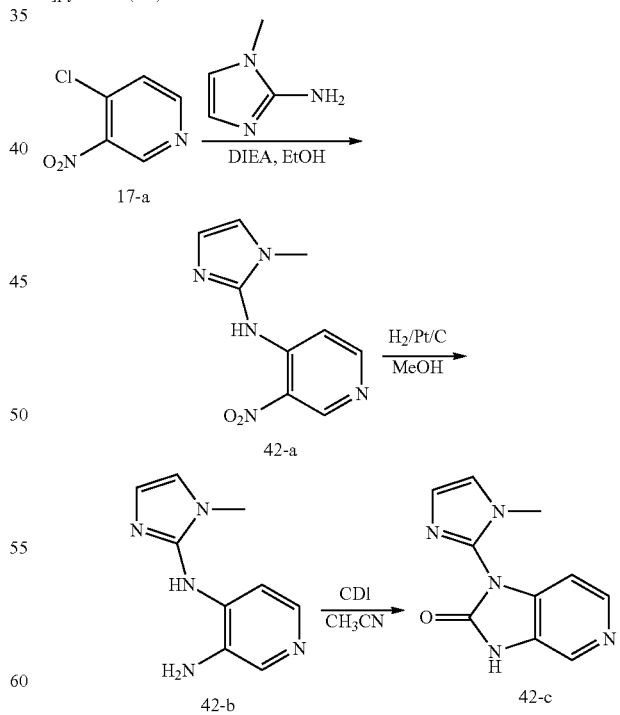
17-a 42-a 42-b    42-c

Intermediate 42-c was prepared by following an analogous reaction protocol as described for intermediate 15-d using 4-chloro-3-nitropyridine 17-a, and 1-methyl-1H-imidazol-2-amine as starting material.

Scheme 43: synthesis of 1-(oxazol-2-yl)-1H-imidazo[4,5-c]pyridin-2(3H)-one 43-c

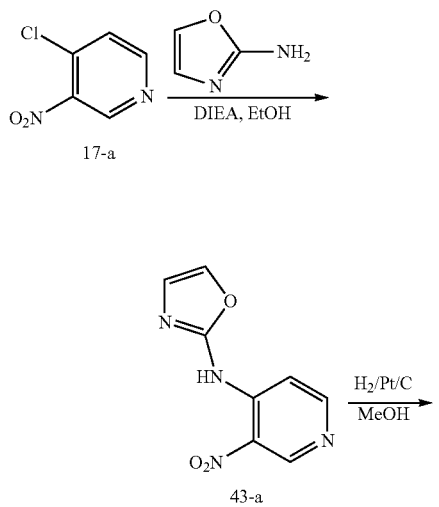

Intermediate 43-c was prepared by following an analogous reaction protocol as described for intermediate 15-d using 4-chloro-3-nitropyridine 17-a, and oxazol-2-amine as starting material.

Scheme 44: synthesis of 1-(1-methyl-1H-pyrazol-3-yl)-1H-imidazo[4,5-c]pyridin-2(3H)-one 44-c

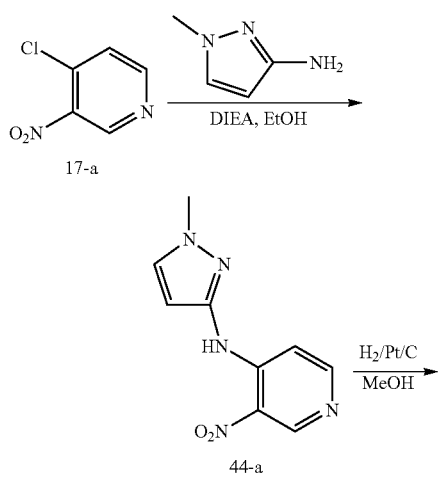

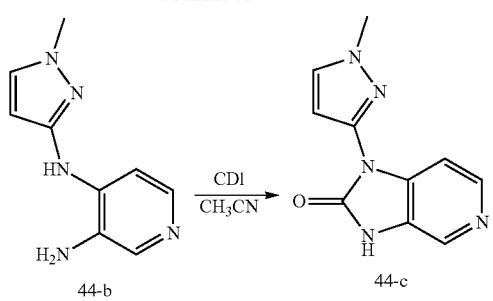

Intermediate 44-c was prepared by following an analogous reaction protocol as described for intermediate 15-d using 4-chloro-3-nitropyridine 17-a, and 1-methyl-1H-pyrazol-3-amine as starting material.

Scheme 45: synthesis of 1-(3-fluoro-4-methoxyphenyl)-1H-imidazo[4,5-c]pyridin-2(3H)-one 45-c

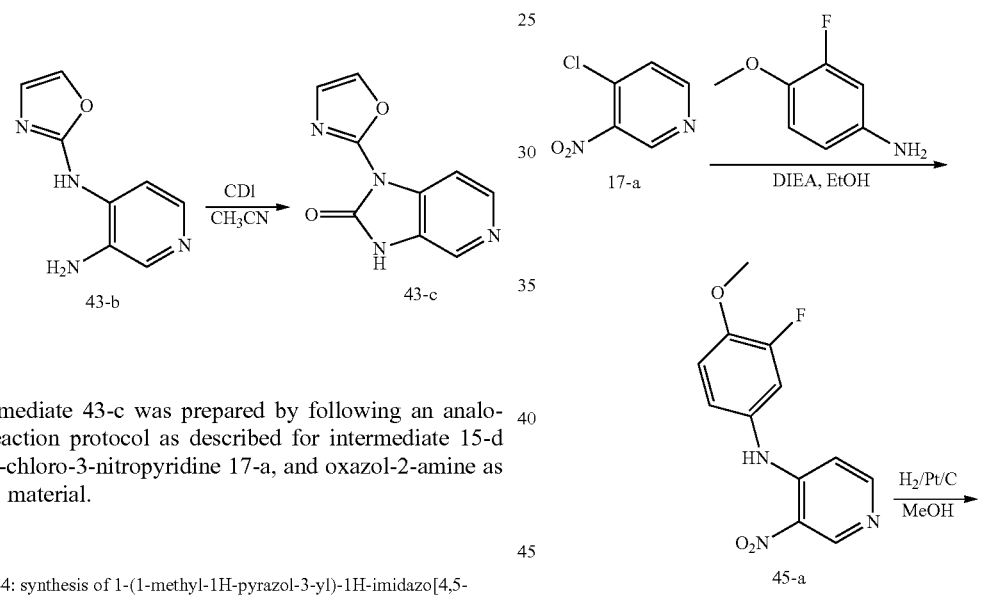

Intermediate 45-c was prepared by following an analogous reaction protocol as described for intermediate 15-d using 4-chloro-3-nitropyridine 17-a, and 3-fluoro-4-methoxyaniline as starting material.

Scheme 46: synthesis of 1-(2-fluoro-4-methoxyphenyl)-1H-imidazo[4,5-c]pyridin-2(3H)-one 46-c

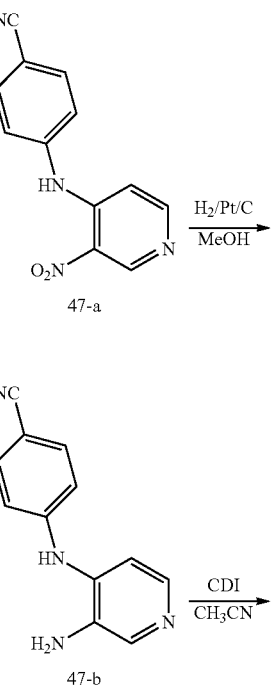

Intermediate 46-c was prepared by following an analogous reaction protocol as described for intermediate 15-d using 4-chloro-3-nitropyridine 17-a, and 2-fluoro-4-methoxyaniline as starting material.

Scheme 47: synthesis of 4-(2-oxo-2,3-dihydro-1H-imidazo[4,5-c]pyridin-1-yl)benzonitrile 47-c

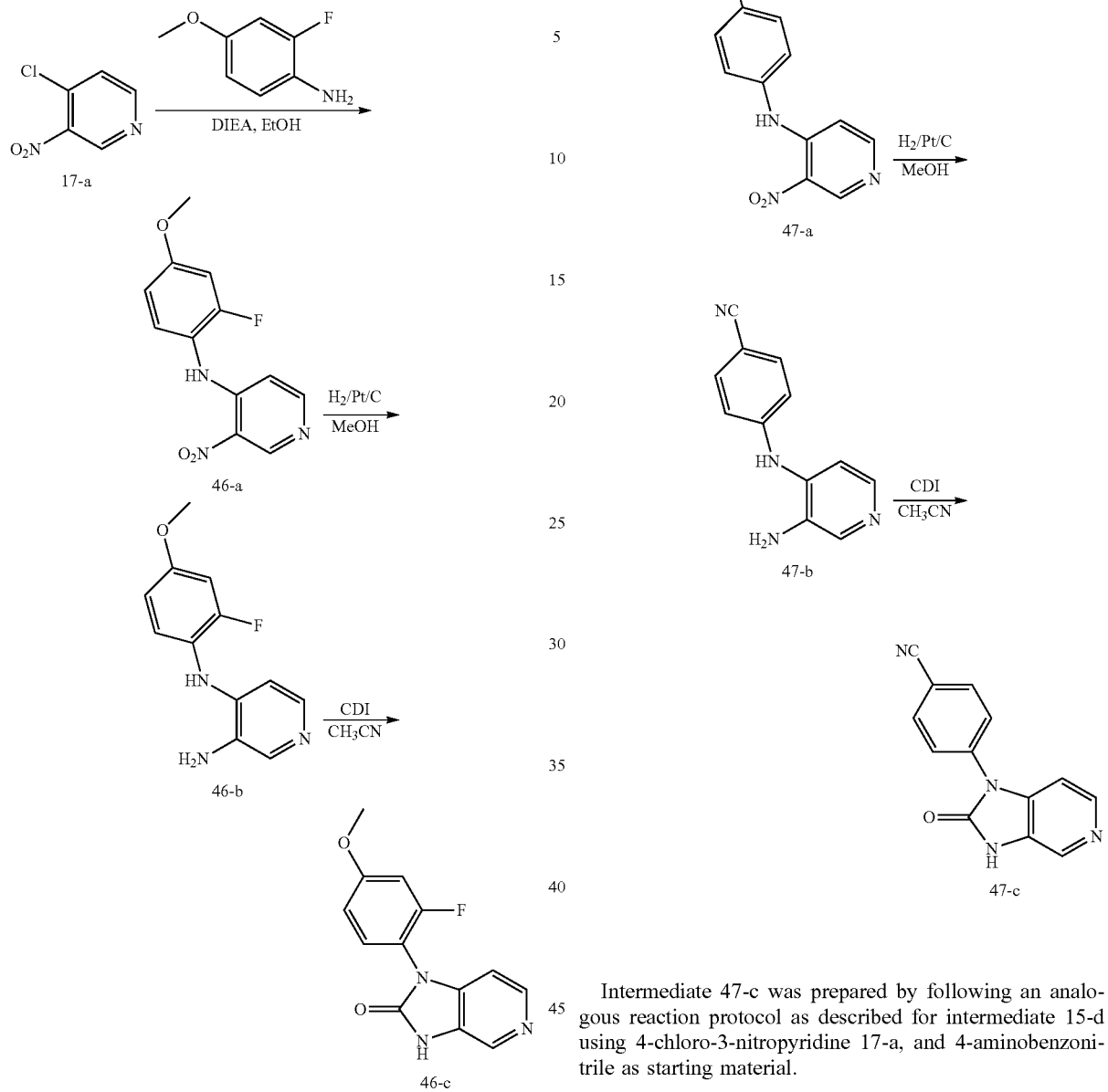

Intermediate 47-c was prepared by following an analogous reaction protocol as described for intermediate 15-d using 4-chloro-3-nitropyridine 17-a, and 4-aminobenzonitrile as starting material.

Scheme 48: synthesis of methyl 4-(2-oxo-2,3-dihydro-1H-imidazo[4,5-c]pyridin-1-yl)-benzoate 48-c

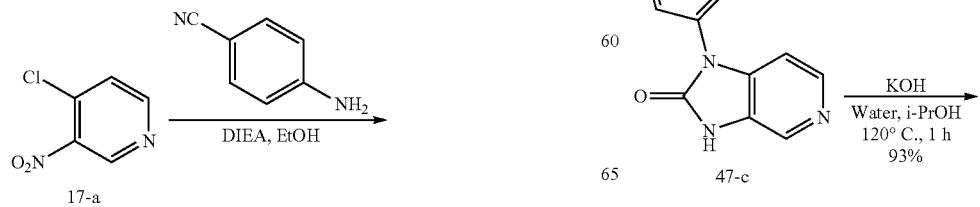

-continued

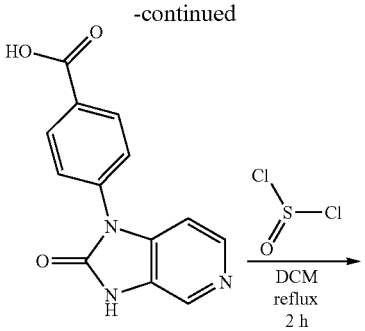

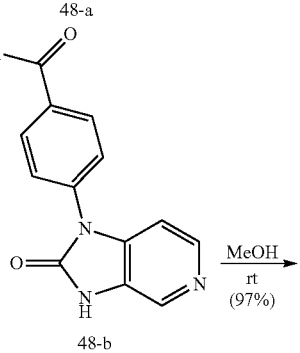

Step 1: Synthesis of 4-(2-oxo-2,3-dihydro-1H-imidazo[4,5-c]pyridin-1-yl)benzoic acid 48-a A solution of 4-(2-oxo-2,3-dihydro-1H-imidazo[4,5-c]pyridin-1-yl)benzonitrile 47-c (5 g, 21.2 mmol) in 50 mL isopropanol and 50 mL KOH solution (1.5M in water) was refluxed during 60 minutes. The solution was poured into an ice bath and neutralized to pH=7. The precipitate was filtered off and washed with water. Dried in the oven to afford a white solid (5 g, 93%).

m/z=256 (M+1)$^+$ $^1$H NMR (400 MHz, DMSO-d$_6$) δ ppm 7.17 (d, J=5.28 Hz, 1H) 7.71 (d, J=8.58 Hz, 2H) 8.12 (d, J=8.58 Hz, 2H) 8.22 (d, J=5.28 Hz, 1H) 8.32 (s, 1H)

Step 2: Synthesis of methyl 4-(2-oxo-2,3-dihydro-1H-imidazo[4,5-c]pyridin-1-yl)-benzoate 48-c To a solution of 4-(2-oxo-2,3-dihydro-1H-imidazo[4,5-c]pyridin-1-yl)benzoic acid 48-a (3 g, 12 mmol) in 100 mL DCM was added thionyl chloride (9 mL, 120 mmol, 10 eq.) at room temperature and the solution was refluxed for 16 hours. After concentration to dryness, excess MeOH was added at room temperature and stirred for 2 hours. The solution was concentrated in vacuo and crystallized with water/MeOH. The solid was filtered off and dried to give 3.1 g (98%) of title intermediate 48-c.

LCMS m/z=270 (M+H)$^+$ $^1$H NMR (400 MHz, DMSO-d$_6$) δ ppm 3.89 (s, 3H) 7.06 (d, J=5.06 Hz, 1H) 7.76 (d, J=9.02 Hz, 2H) 8.01 (d, J=4.84 Hz, 1H) 8.10 (d, J=9.02 Hz, 2H) 8.18 (s, 1H)

Scheme 49: synthesis of (5-chloro-1-(4,4,4-trifluorobutyl)-1H-pyrrolo[3,2-b]pyridin-2-yl)methanol 49-e

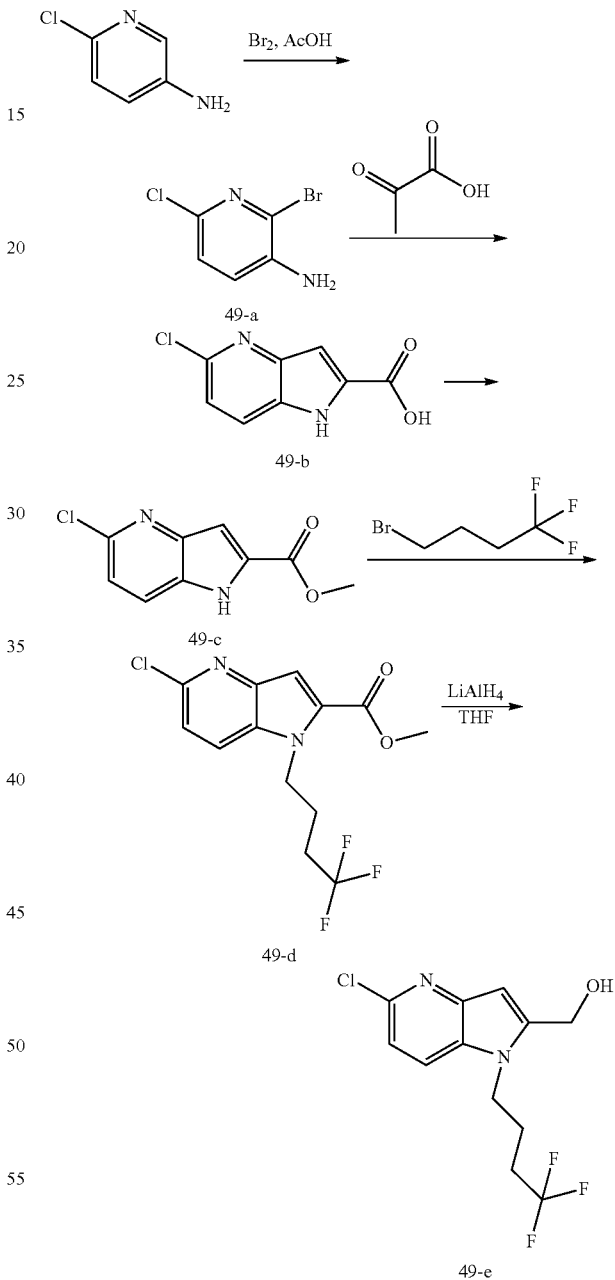

Step 1: Synthesis of 2-bromo-6-chloropyridin-3-amine 49-a

Bromine (24.86 g, 155.57 mmol) was added to a solution of 6-chloropyridin-3-amine (20.00 g, 155.57 mmol) and sodium acetate (25.52 g, 311.14 mmol) in acetic acid (383 ml). The reaction mixture was stirred at room temperature for 1 hour. Acetic acid was then evaporated. The residue was dissolved in EtOAc, washed with saturated aqueous Na₂CO₃, water and brine. The organic layer was dried over MgSO₄, filtered and evaporated, yielding 32.20 g of the desired product 49-a (99.8%).

m/z=206.96 (M+1)⁺

Step 2: Synthesis of 5-chloro-1H-pyrrolo[3,2-b]pyridine-2-carboxylic acid 49-b 2-oxopropanoic acid (36.22 g, 411.31 mmol), palladium (II)acetate (7.74 g, 34.15 mmol) and Et₃N (69.11 g, 682.94 mmol) were added to a solution of 2-bromo-6-chloropyridin-3-amine 49-a (32.20 g, 155.21 mmol) and TPP (35.83 g, 136.59 mmol) in dry DMF (300 ml). The reaction mixture was stirred at 100° C. overnight. The solvent was then evaporated, water was added and the water layer was washed with EtOAc. The water layer was acidified with conc. HCl. The precipitate was filtered off and dried, yielding 25.21 g of the wanted product 49-b (82.6%).

m/z=197.1 (M+1)⁺.

Step 3: Synthesis of methyl 5-chloro-1H-pyrrolo[3,2-b]pyridine-2-carboxylate 49-c 5-chloro-1H-pyrrolo[3,2-b]pyridine-2-carboxylic acid 49-b (25.20 g, 128.18 mmol) was added to a refluxing mixture of sulfuric acid (20 ml) and methanol (400 ml). The mixture was refluxed overnight. The mixture was then evaporated and a cold NaHCO₃ solution was added until basic pH. The precipitate was filtered off and dried, yielding 16.15 g of the desired product (59.8%).

m/z=211.17 (M+H)⁺, Cl pattern.

Step 4: Synthesis of methyl 5-chloro-1-(4,4,4-trifluorobutyl)-1H-pyrrolo[3,2-b]-pyridine-2-carboxylate 49-d To a solution of methyl 5-chloro-1H-pyrrolo[3,2-b]pyridine-2-carboxylate 49-c (2.9 g, 12.2 mmol) in DMF (50 mL) were added successively cesium carbonate (4 g, 12.2 mmol) and 4-bromo-1,1,1-trifluorobutane (2.3 g, 12.2 mmol). The resulting mixture was heated at 60° C. overnight. The reaction mixture was allowed to cool down to room temperature then poured into iced water and the product was extracted 3 times with DCM. The combined organic layers were dried over Na₂SO₄, filtered and evaporated to give the targeted product 49-d as a yellowish solid. The product was used as such in the next step.

m/z=320 (M+1)⁺

Step 5: Synthesis of (5-chloro-1-(4,4,4-trifluorobutyl)-1H-pyrrolo[3,2-b]pyridin-2-yl)-methanol 49-e To a solution of methyl 5-chloro-1-(4,4,4-trifluorobutyl)-1H-pyrrolo[3,2-b]pyridine-2-carboxylate 49-d (3.82 g, 10.8 mmol) in dry THF (100 mL) was added a 1M solution of lithium aluminumhydride (11.96 mL, 11.96 mmol) at −75°

C. The cooling bath was then removed and the reaction mixture was kept at room temperature for 3 hours. EtOAc was added, followed by a saturated NH₄Cl solution. The mixture was stirred for 30 min. The organic layer was dried over Na₂SO₄, filtered and evaporated to give a residue, which was purified by column chromatography to yield the targeted intermediate as a white powder (2.8 g, 98%).

m/z=292 (M+1)⁺

Scheme 50: synthesis of 1-(4-(methylsulfonyl)phenyl)-1H-imidazo[4,5-c]pyridin-2(3H)-one 50-c

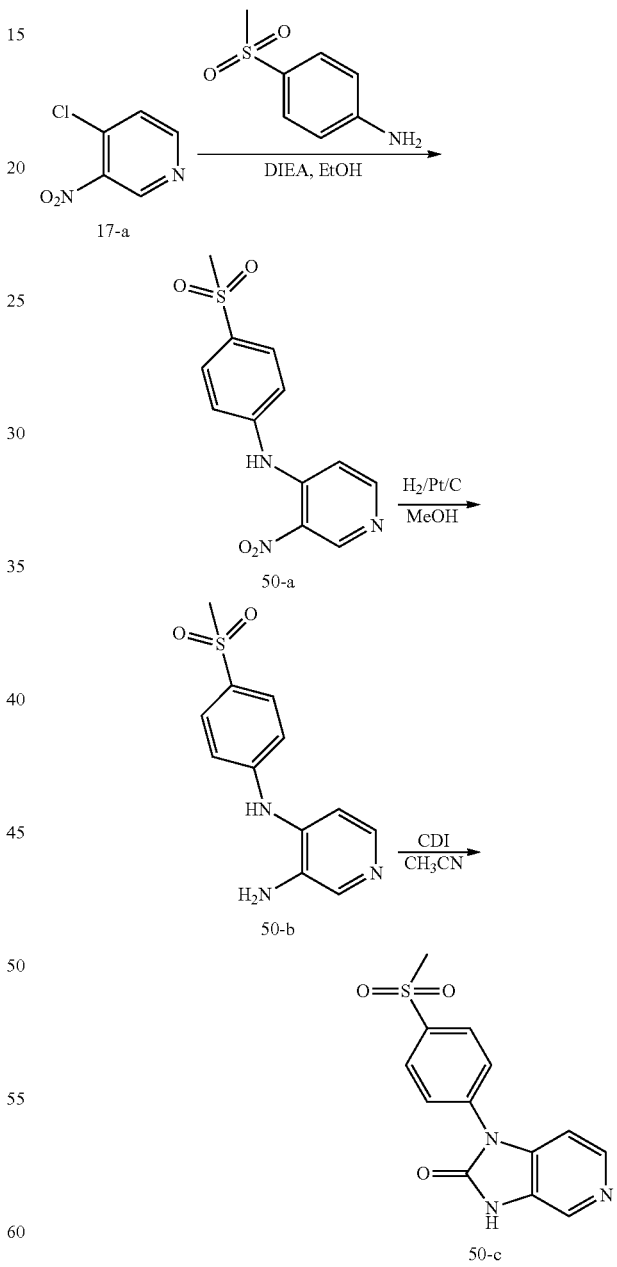

Intermediate 50-c was prepared by following an analogous reaction protocol as described for intermediate 15-d using 4-chloro-3-nitropyridine 17-a, and 4-(methylsulfonyl) aniline as starting material.

Scheme 51: synthesis of 1-p-tolyl-1H-imidazo[4,5-c]pyridin-2(3H)-one 51-c

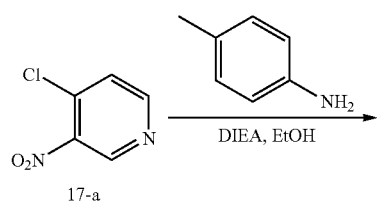
17-a

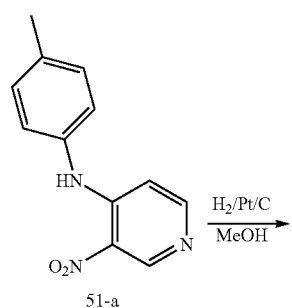
51-a

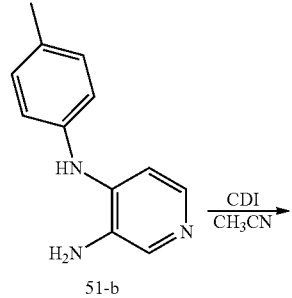
51-b

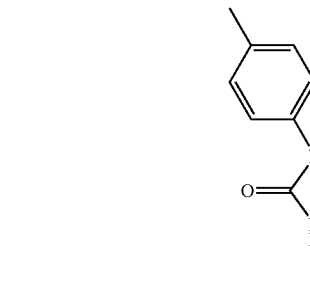
51-c

Intermediate 51-c was prepared by following an analogous reaction protocol as described for intermediate 15-d using 4-chloro-3-nitropyridine 17-a, and p-toluidine as starting material.

Scheme 52: synthesis of 1-(2,4-dimethoxyphenyl)-1H-imidazo[4,5-c]pyridin-2(3H)-one 52-c

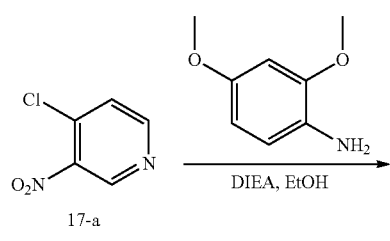
17-a

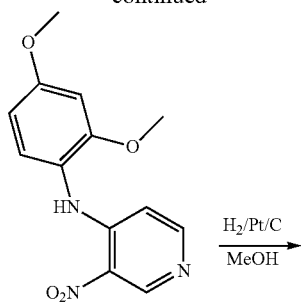
52-a

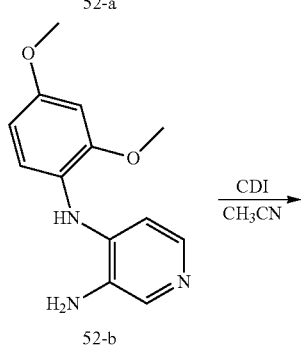
52-b

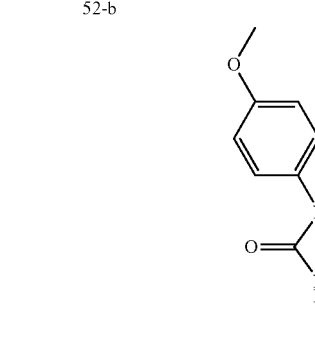
52-c

Intermediate 52-c was prepared by following an analogous reaction protocol as described for intermediate 15-d using 4-chloro-3-nitropyridine 17-a, and 2,4-dimethoxyaniline as starting material Scheme 53: synthesis of 1-(pyrimidin-2-yl)-1H-imidazo[4,5-c]pyridin-2(3H)-one 53-c

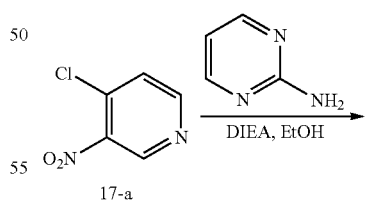
17-a

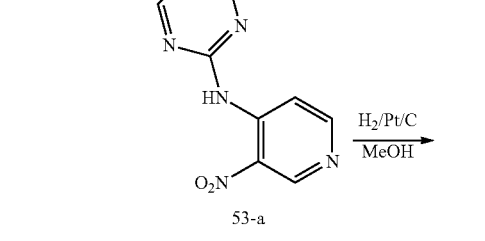
53-a

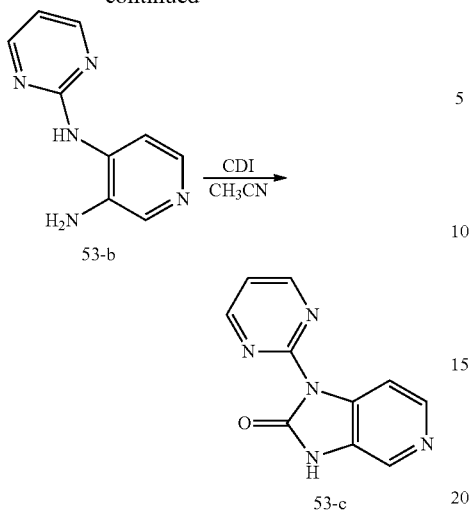

Intermediate 53-c was prepared by following an analogous reaction protocol as described for intermediate 15-d using 4-chloro-3-nitropyridine 17-a, and pyrimidin-2-amine as starting material Synthesis of Compounds Example 1

A detailed description of the synthesis of tert-butyl-3-(3-((5-chloro-1-(3-(methylsulfonyl)propyl)-1H-indol-2-yl)methyl)-2-oxo-2,3-dihydro-1H-imidazo[4,5-c]pyridin-1-yl)azetidine-1-carboxylate (P1), a representative example of the invention is given in Scheme 25.

Scheme 25

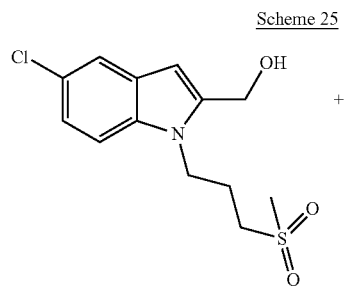

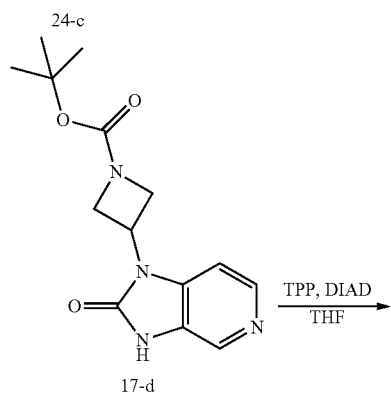

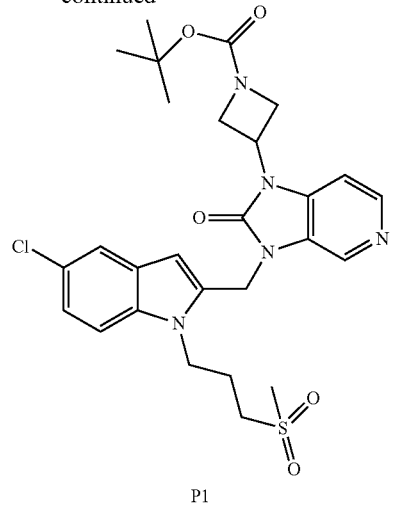

In a 100 mL dry flask, intermediate 17-d (1.9 g, 6.6 mmol), triphenylphosphine (2.08 g, 7.9 mmol, 1.2 eq) and intermediate 24-c (2 g, 6.6 mmol) were dissolved in tetrahydrofuran (THF) (60 mL). The solution was placed under $N_2$ atmosphere and diisopropylazodicarboxylate (DIAD) (1.9 mL, 9.9 mmol) was added via syringe. The reaction mixture was stirred at room temperature under nitrogen overnight. The mixture was evaporated to dryness and purified by preparative HPLC on an RP Vydac Denali C18 column (10 μm, 250 g, 5 cm) using a 0.25% $NH_4HCO_3$ in water/$CH_3CN$ solution as the eluent. After evaporation and drying in vacuo, 963 mg (25%) of a white solid was obtained.

m/z=574 (M+H)$^+$ (LCMS method 1)
MP=195° C.
$^1$H NMR (400 MHz, DMSO-d6) δ ppm 1.43 (s, 9H) 1.87-2.01 (m, 2H) 2.96 (s, 3H) 3.09-3.19 (m, 2H) 4.22-4.44 (m, 6H) 5.21-5.31 (m, 1H) 5.35 (s, 2H) 6.55 (s, 1H) 7.17 (dd, J=8.80, 1.98 Hz, 1H) 7.31 (d, J=5.28 Hz, 1H) 7.52-7.59 (m, 2H) 8.29 (d, J=5.28 Hz, 1H) 8.48 (s, 1H)

Example 2

Synthesis of tert-butyl 3-(3-((5-chloro-1-(3-(methylsulfonyl)propyl)-1H-indol-2-yl)methyl)-5-fluoro-2-oxo-2,3-dihydro-1H-benzo[d]imidazol-1-yl)azetidine-1-carboxylate (P2)

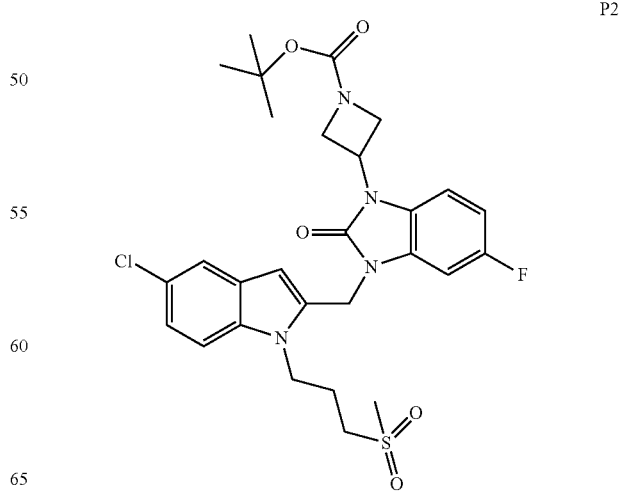

Compound P2 was prepared by following an analogous reaction protocol as described for compound P1 using intermediate 24-c and tert-butyl 3-(5-fluoro-2-oxo-2,3-dihydro-1H-benzo[d]imidazol-1-yl)azetidine-1-carboxylate 5-d as starting material.

m/z=591 (M+H)+ (LCMS Method 1)
MP=185° C.
1H NMR (400 MHz, DMSO-d6) δ ppm 1.43 (s, 9H) 1.90-2.01 (m, 2H) 2.97 (s, 3H) 3.10-3.18 (m, 2H) 4.23-4.45 (m, 6H) 5.22-5.28 (m, 1H) 5.29 (s, 2H) 6.46 (s, 1H) 6.94-7.02 (m, 1H) 7.16 (dd, J=8.69, 2.09 Hz, 1H) 7.22-7.29 (m, 2H) 7.51-7.58 (m, 2H)

Example 3

Synthesis of 1-(azetidin-3-yl)-3-((5-chloro-1-(3-(methylsulfonyl)propyl)-1H-indol-2-yl)methyl)-5-fluoro-1H-benzo[d]imidazol-2(3H)-one (P3)

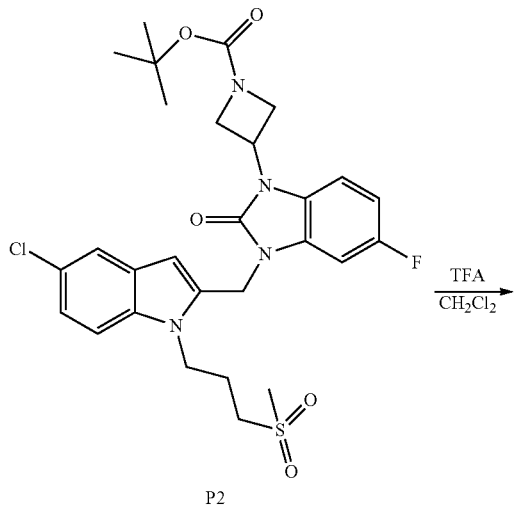

To a solution of compound P2 (800 mg, 1.353 mmol) in dichloromethane (10 mL) was added trifluoroacetic acid (1.036 ml, 13.534 mmol) at room temperature. The reaction mixture was stirred for 16 h. The reaction mixture was quenched with some iced water and the pH was basified with a saturated aqueous NaHCO3 solution. Then dichloro-methane was evaporated and the pink solid in water was stirred at room temperature for 12 hours then was filtered off. The solid was washed with water and isopropyl ether to give 536 mg of the desired compound (P3) as a beige solid (yield=78%). P3 was obtained as a trifluoroacetate salt form (0.0.17 CF3COOH).

m/z=491 (M+H)+ (LCMS method 1)
1H NMR (400 MHz, DMSO-d6) δ ppm 1.84-2.06 (m, 2H) 2.96 (s, 3H) 3.08-3.17 (m, 2H) 3.81-3.94 (m, 2H) 3.98-4.06 (m, 2H) 4.40 (t, J=7.59 Hz, 2H) 5.18-5.27 (m, 1H) 5.28 (s, 2H) 6.42 (s, 1H) 6.91-7.00 (m, 1H) 7.15 (dd, J=8.69, 2.09 Hz, 1H) 7.23 (dd, J=9.24, 2.42 Hz, 1H) 7.53 (d, J=8.80 Hz, 1H) 7.56 (d, J=1.98 Hz, 1H) 7.75 (dd, J=8.69, 4.51 Hz, 1H)

Example 4

Synthesis of 1-(azetidin-3-yl)-3-((5-chloro-1-(3-(methylsulfonyl)propyl)-1H-indol-2-yl)methyl)-1H-imidazo[4,5-c]pyridin-2(3H)-one (P4)

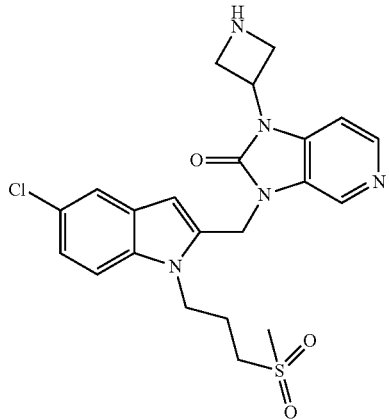

Compound P4 was prepared by an analogous reaction protocol as described for compound P3. P4 was obtained as a trifluoroacetate salt (CF3COOH).

m/z=474 (M+H)+ (LCMS Method 1)
1H NMR (400 MHz, DMSO-d6) δ ppm 1.92-2.05 (m, 2H) 2.97 (s, 3H) 3.09-3.20 (m, 2H) 4.19-4.31 (m, 2H) 4.40 (t, J=7.70 Hz, 2H) 4.55-4.66 (m, 2H) 5.32-5.46 (m, 3H) 6.56 (s, 1H) 7.17 (dd, J=9.02, 2.20 Hz, 1H) 7.52 (d, J=5.28 Hz, 1H) 7.54-7.58 (m, 2H) 8.30 (d, J=5.28 Hz, 1H) 8.49 (s, 1H) 8.73 (br. s, 1H)

Example 5

Synthesis of 3-((5-chloro-1-(3-(methylsulfonyl)propyl)-1H-indol-2-yl)methyl)-1-(1-(methylsulfonyl)azetidin-3-yl)-1H-imidazo[4,5-c]pyridin-2(3H)-one (P5)

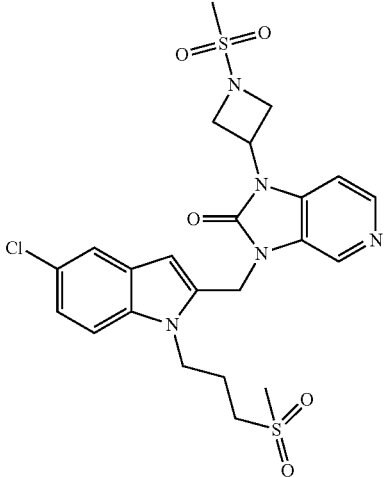 [SMILES: CS(=O)(=O)CCCn1c(Cn2c(=O)n(C3CN(S(C)(=O)=O)C3)c3ccncc32)cc2cc(Cl)ccc21]

To a solution of P4 (350 mg, 0.6 mmol) in dichloromethane (20 mL) triethyl amine (0.248 mL, 1.8 mmol) was added. The mixture was stirred at RT then methanesulfonyl chloride (0.0485 mL, 0.625 mmol) was added at room temperature. The resulting mixture was stirred at room temperature for 24 hours. A thick white precipitate was seen in the flask. The reaction mixture was washed with saturated NaHCO$_3$. The organic layer was separated, dried on MgSO$_4$ and concentrated. The resulting solid was refluxed in methanol. After cooling down to room temperature the precipitate was filtered off and dried in vacuum for 2 hours to give compound P5 (110 mg, 32%) as an off white solid.

m/z=552 (M+H)$^+$ (LCMS method 1)

MP=240° C.

$^1$H NMR (400 MHz, DMSO-d$_6$) δ ppm 1.87-2.02 (m, 2H), 2.97 (s, 3H), 3.09-3.20 (m, 5H), 4.29 (t, J=8.80 Hz, 2H), 4.39 (t, J=7.59 Hz, 2H), 4.50 (dd, J=8.91, 6.49 Hz, 2H), 5.30-5.40 (m, 3H), 6.56 (s, 1H), 7.17 (dd, J=8.69, 2.09 Hz, 1H), 7.49-7.60 (m, 3H), 8.31 (d, J=5.28 Hz, 1H), 8.48 (s, 1H)

Example 6

Synthesis of 1-(1-acetylazetidin-3-yl)-3-((5-chloro-1-(3-(methylsulfonyl)propyl)-1H-indol-2-yl)methyl)-1H-imidazo[4,5-c]pyridin-2(3H)-one (P6)

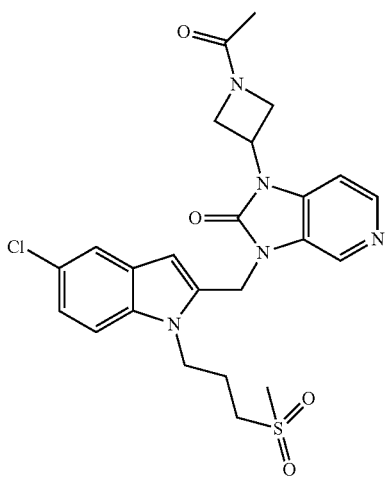

P6

Compound P6 was prepared by an analogous reaction protocol as described for compound P5 using P4 and acetyl chloride as starting material.

m/z=516 (M+H)$^+$ (LCMS method 1)

MP=252° C.

$^1$H NMR (400 MHz, DMSO-d$_6$) δ ppm 1.86 (s, 3H), 1.94 (ddd, J=15.24, 8.03, 7.76 Hz, 2H), 2.97 (s, 3H), 3.11-3.19 (m, 2H), 4.22-4.35 (m, 2H), 4.39 (t, J=7.70 Hz, 2H), 4.50-4.58 (m, 1H), 4.59-4.66 (m, 1H), 5.30 (tt, J=8.39, 5.69 Hz, 1H), 5.35 (s, 2H), 6.56 (s, 1H), 7.17 (dd, J=8.80, 1.98 Hz, 1H), 7.33 (d, J=5.28 Hz, 1H), 7.52-7.59 (m, 2H), 8.29 (d, J=5.28 Hz, 1H), 8.48 (s, 1H)

Example 7

Synthesis of 3-((5-chloro-1-(3-(methylsulfonyl)propyl)-1H-indol-2-yl)methyl)-1-(1-methylcyclopropyl)-1H-imidazo[4,5-c]pyridin-2(3H)-one (P7)

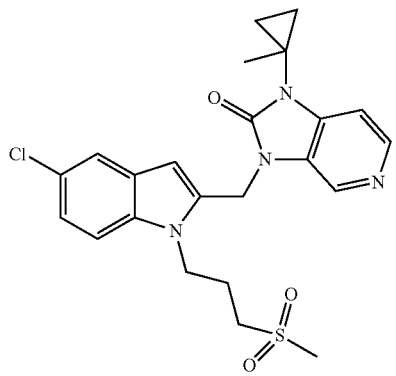

P7

Compound P7 was prepared by an analogous reaction protocol as described for compound P1 using intermediate 24-c and 1-(1-methylcyclopropyl)-1H-imidazo-[4,5-c]pyridin-2(3H)-one 18-c as starting material.

m/z=473 (M+H)$^+$ (LCMS method 1)

$^1$H NMR (400 MHz, DMSO-d$_6$) δ ppm 0.97-1.02 (m, 2H), 1.06-1.12 (m, 2H), 1.43 (s, 3H), 1.92-2.04 (m, 2H), 2.97 (s, 3H), 3.10-3.18 (m, 2H), 4.39 (t, J=7.5 Hz, 2H), 5.31 (s, 2H), 6.49 (s, 1H), 7.16 (dd, J=8.7, 2.1 Hz, 1H), 7.31 (dd, J=5.3, 0.4 Hz, 1H), 7.54 (d, J=8.8 Hz, 1H), 7.57 (d, J=2.0 Hz, 1H), 8.26 (d, J=5.1 Hz, 1H), 8.40 (s, 1H)

Example 8

Synthesis of 1-tert-butyl-3-((5-chloro-1-(3-(methylsulfonyl)propyl)-1H-indol-2-yl)methyl)-1H-imidazo[4,5-c]pyridin-2(3H)-one (P8)

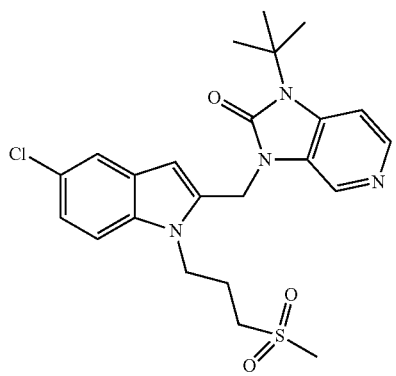

P8

Compound P8 was prepared by an analogous reaction protocol as described for compound P1 using fragment A-c and 1-tert-butyl-1H-imidazo[4,5-c]pyridin-2(3H)-one 19-c as starting material.

m/z=475 (M+H)$^+$ (LCMS method 2)

MP=226° C.

1H NMR (400 MHz, DMSO-d6) δ ppm 1.74 (s, 9H) 1.93-2.06 (m, 2H) 2.97 (s, 3H) 3.10-3.20 (m, 2H) 4.40 (t, J=7.48 Hz, 2H) 5.31 (s, 2H) 6.42 (s, 1H) 7.16 (dd, J=8.69, 2.09 Hz, 1H) 7.47-7.61 (m, 3H) 8.14 (d, J=5.72 Hz, 1H) 8.41 (s, 1H)

Example 9

Synthesis of 3-((5-chloro-1-(4,4,4-trifluorobutyl)-1H-imidazo[4,5-b]pyridin-2-yl)-methyl)-1-(1-methylcyclopropyl)-1H-imidazo[4,5-c]pyridin-2(3H)-one (P9) scheme 26

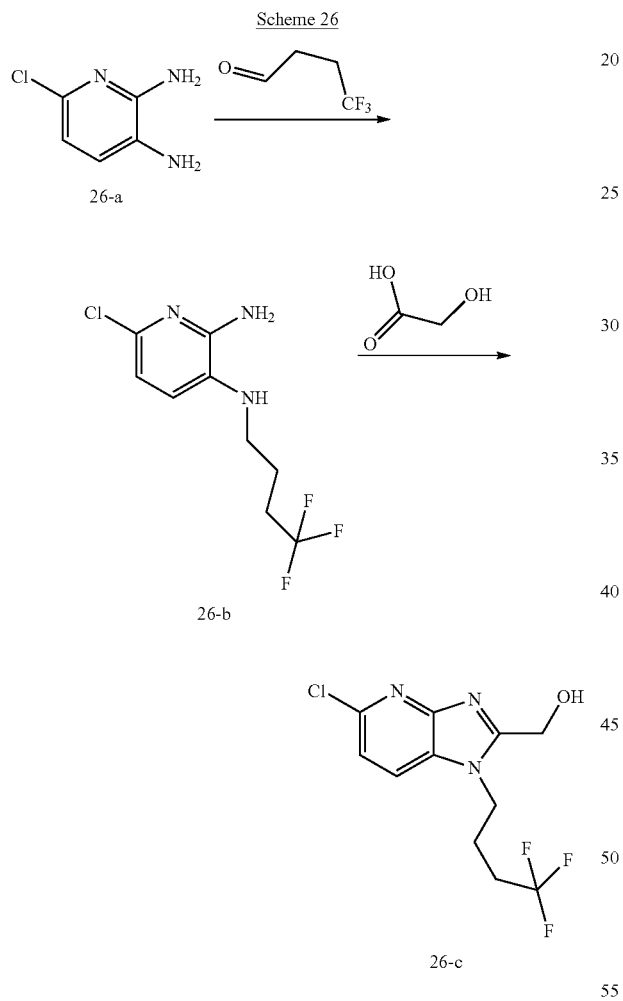

Step 1: Synthesis of 6-chloro-N³-(4,4,4-trifluorobutyl)-pyridine-2,3-diamine 26-b The intermediate 26-a (5 g, 34.82 mmol) was dissolved in dichloromethane (200 mL), acetic acid (20 drops) and 4,4,4-trifluorobutanal (4.38 g, 34.8 mmol) were added. The resulting mixture was stirred for 30 minutes and then sodium triacetoxyhydroborate (22.14 g, 104.5 mmol) was added. The reaction mixture was stirred at room temperature overnight and a solution of 50% Na₂CO₃ was added dropwise until gas evolution stopped. The organic layer was separated, dried on MgSO₄, filtrated and evaporated to dryness. The residue was purified by column chromatography using heptane/EtOAc 7/3 to pure EtOAc. Intermediate 26-b was recovered as a white solid and dried in vacuo overnight (6.16 g, 70%). m/z=254 (M+H)⁺.

Step 2: Synthesis of (5-chloro-1-(4,4,4-trifluorobutyl)-1H-imidazo[4,5-b]pyridin-2-yl)-methanol 26-c A mixture of intermediate 26-b (5.68 g, 22.46 mmol) and 2-hydroxyacetic acid (4.27 g, 56.2 mmol) was stirred at 150° C. for 4 hours. The mixture was allowed to cool down to room temperature and treated carefully with 3N hydrochloric acid. The resulting mixture was made basic with aqueous ammonia and extracted with CH₂Cl₂ (300 mL). The organic layer was dried over MgSO₄ and evaporated to dryness. The residue was purified by column chromatography on silica using CH₂Cl₂ to EtOAc. The intermediate 26-c was isolated as brown solid (4.27 g, 65%).

m/z=294 (M+H)⁺.

¹H NMR (400 MHz, CHLOROFORM-d) δ ppm 1.00 (s, 2H), 1.12-1.23 (m, 2H), 1.83-1.99 (m, 2H), 2.12-2.31 (m, 2H), 2.91 (spt, J=3.50 Hz, 1H), 4.38-4.54 (m, 2H), 5.38 (s, 2H), 7.13 (dd, J=5.27, 0.50 Hz, 1H), 7.27 (d, J=8.28 Hz, 1H), 7.61 (d, J=8.53 Hz, 1H), 8.36 (d, J=5.27 Hz, 1H), 8.77 (s, 1H)

Synthesis of 3-((5-chloro-1-(4,4,4-trifluorobutyl)-1H-imidazo[4,5-b]pyridin-2-yl)methyl)-1-(1-methylcyclopropyl)-1H-imidazo[4,5-c]pyridin-2(3H)-one (P9)

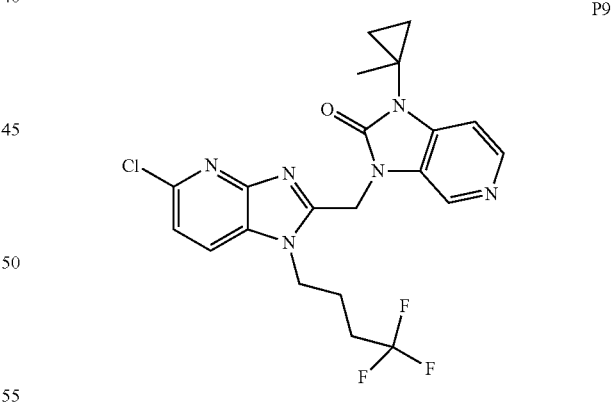

Compound P9 was prepared by an analogous reaction protocol as described for compound P1 using intermediate 26-c and 1-(1-methylcyclopropyl)-1H-imidazo-[4,5-c]pyridin-2(3H)-one 18-c as starting material.

m/z=465 (M+H)⁺ (LCMS method 2)

1H NMR (400 MHz, DMSO-d6) δ ppm 0.94-1.09 (m, 4H) 1.42 (s, 3H) 1.89-2.01 (m, 2H) 2.30-2.45 (m, 2H) 4.48 (t, J=7.59 Hz, 2H) 5.47 (s, 2H) 7.33 (d, J=5.28 Hz, 1H) 7.38 (d, J=8.36 Hz, 1H) 8.22 (d, J=8.36 Hz, 1H) 8.28 (d, J=5.28 Hz, 1H) 8.45 (s, 1H)

Example 10

Synthesis of 3-((5-chloro-1-(4-fluorobutyl)-1H-imidazo[4,5-b]pyridin-2-yl)methyl)-1-(thiazol-2-yl)-1H-imidazo[4,5-c]pyridin-2(3H)-one (P10)

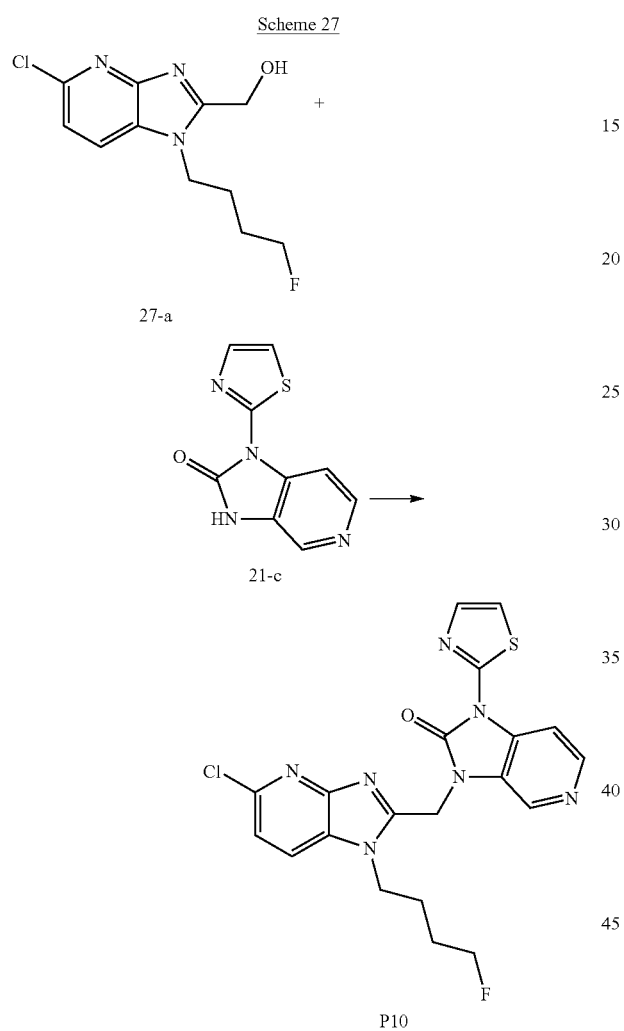

Intermediate 27-a was prepared by an analogous reaction protocol as described for intermediate 26-c using intermediate 26-a and 4-fluorobutanal as starting material. Compound P10 was prepared by an analogous reaction protocol as described for compound P1 using intermediate 27-a and 1-(thiazol-6-yl)-1H-imidazo[4,5-c]pyridin-2(3H)-one 21-c as starting material.

MP=238° C.

m/z=458 (M+H)+

$^1$H NMR (400 MHz, CHLOROFORM-d) δ ppm 1.71-1.93 (m, 2H), 4.39 (t, J=5.6 Hz, 1H), 4.42-4.48 (m, 1H), 4.51 (t, J=5.4 Hz, 1H), 5.53 (s, 1H), 7.23 (d, J=3.5 Hz, 1H), 7.27 (d, J=8.4 Hz, 1H), 7.65 (d, J=8.4 Hz, 1H), 7.70 (d, J=3.5 Hz, 1H), 8.41 (dd, J=5.4, 0.6 Hz, 1H), 8.53 (d, J=5.3 Hz, 1H), 8.91 (s, 1H)

Example 11

Synthesis of 3-((5-chloro-1-(4-fluorobutyl)-1H-indol-2-yl)methyl)-1-(thiazol-2-yl)-1H-imidazo[4,5-c]pyridin-2(3H)-one (P11)

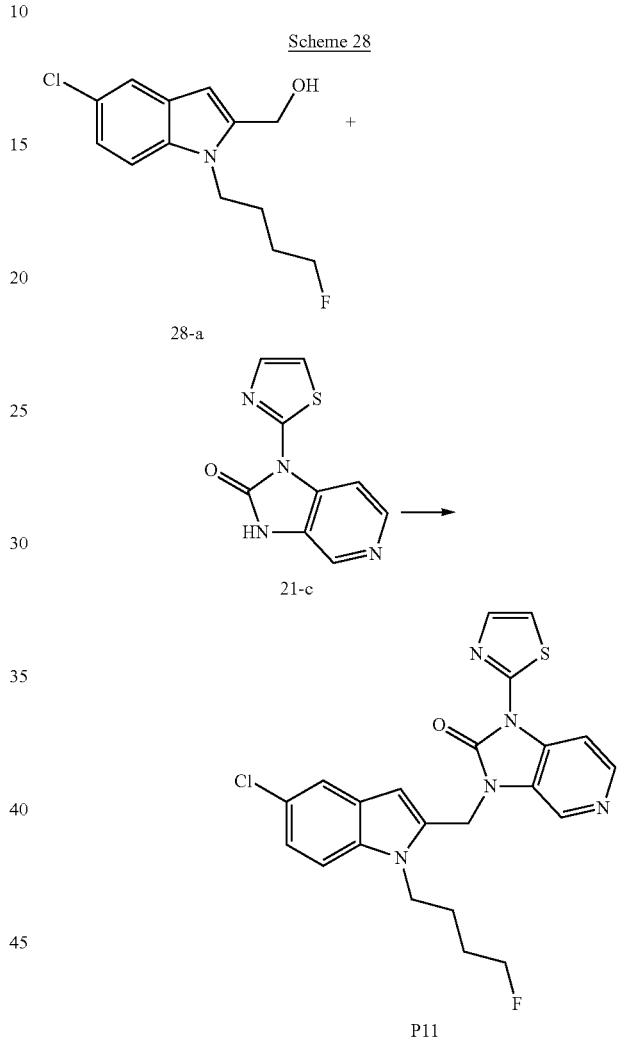

Intermediate 28-a was prepared by an analogous reaction protocol as described for intermediate 24-c using intermediate 24-a and 1-bromo-4-fluorobutane as starting material.

Compound P11 was prepared by an analogous reaction protocol as described for compound P1 using intermediate 28-a and 1-(thiazol-6-yl)-1H-imidazo[4,5-c]pyridin-2(3H)-one 21-c as starting material.

MP=240° C.

m/z=456 (M+H)+

$^1$H NMR (360 MHz, DMSO-d$_6$) δ ppm 1.51-1.64 (m, 3H), 1.69 (m, J=5.5 Hz, 1H), 4.24-4.36 (m, 3H), 4.41 (t, J=6.0 Hz, 1H), 5.48 (s, 2H), 6.64 (s, 1H), 7.15 (dd, J=8.8, 2.2 Hz, 1H), 7.52 (d, J=8.8 Hz, 1H), 7.57 (d, J=2.2 Hz, 1H), 7.63 (d, J=3.7 Hz, 1H), 7.79 (d, J=3.3 Hz, 1H), 8.33 (d, J=5.1 Hz, 1H), 8.45 (d, J=5.5 Hz, 1H), 8.63 (s, 1H)

Example 12

Synthesis of 3-((5-chloro-1-(3(methylsulfonyl)propyl)-1H-indol-2-yl)methyl)-5-fluoro-1-(1-(2-hydroxy-2-methylpropyl)azetidin-3-yl)-1H-benzo[d]imidazol-2(3H)-one (P12)

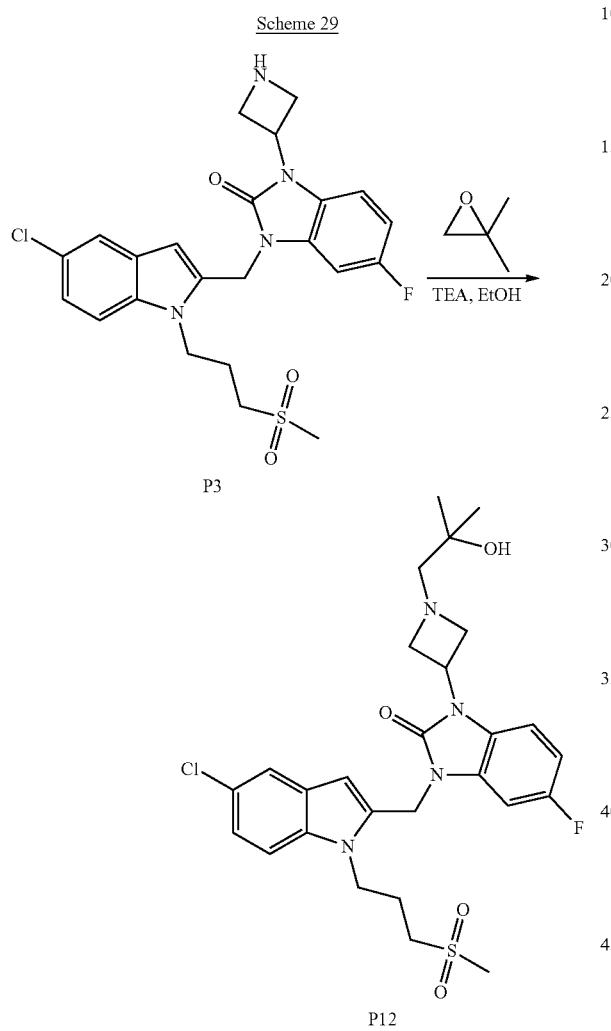

Compound P3 (150 mg, 0.3 mmol) was dissolved in ethanol (5 mL), triethylamine (133 µL, 0.88 mmol) and 2,2-dimethyloxerane (40 µL, 0.45 mmol) were added. The resulting mixture was stirred at 60° C. overnight. The reaction mixture was allowed to cool down to room temperature than evaporated to dryness. The residue was purified by column chromatography using $CH_2Cl_2$/MeOH:9/1. Compound P12 was recovered as a white solid and dried in vacuo overnight (130 mg, 78%).

m/z=463 (M+H)$^+$ $^1$H NMR (400 MHz, CHLOROFORM-d) δ ppm 1.19 (s, 6H), 2.11 (quin, J=7.59 Hz, 2H), 2.63 (br. s, 3H), 2.85 (s, 3H), 2.96-3.03 (m, 2H), 3.87-3.96 (m, 4H), 4.37-4.44 (m, 2H), 5.08 (qd, J=7.08, 6.93 Hz, 1H), 5.18 (s, 2H), 6.56 (s, 1H), 6.83 (td, J=9.13, 2.42 Hz, 1H), 6.92 (dd, J=8.36, 2.42 Hz, 1H), 7.14-7.19 (m, 1H), 7.20-7.25 (m, 1H), 7.51 (dd, J=8.58, 4.40 Hz, 1H), 7.55 (d, J=1.54 Hz, 1H)

Example 13

Synthesis of 3-((5-chloro-1-isopentyl-1H-imidazo[4,5-b]pyridin-2-yl)methyl)-1-(quinolin-6-yl)-1H-imidazo[4,5-c]pyridin-2(3H)-one (P13)

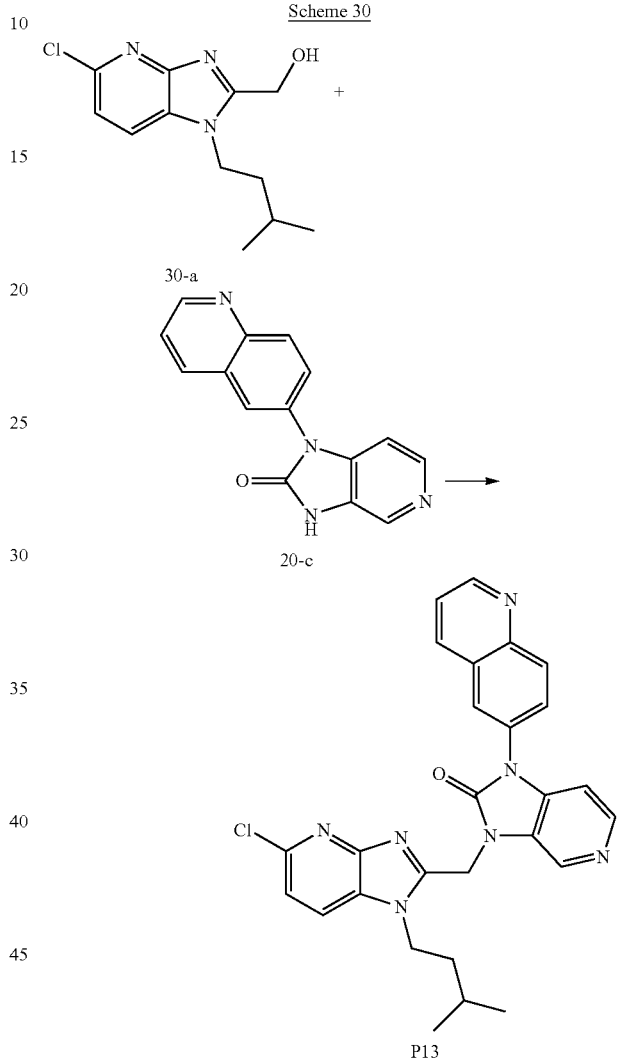

Intermediate 30-a was prepared by an analogous reaction protocol as described for intermediate 26-c using intermediate 26-a and 3-methylbutanal as starting material. Compound P13 was prepared by an analogous reaction protocol as described for compound P1 using intermediate 30-a and 1-(quinolin-6-yl)-1H-imidazo[4,5-c]pyridin-2(3H)-one 20-c as starting material.

m/z=498 (M+H)$^+$ $^1$H NMR (400 MHz, CHLOROFORM-d) δ ppm 1.00 (d, J=6.38 Hz, 6H), 1.58-1.66 (m, 2H), 1.67-1.79 (m, 1H), 4.37-4.48 (m, 2H), 5.52 (s, 2H), 7.09 (dd, J=5.50, 0.66 Hz, 1H), 7.23-7.28 (m, 1H), 7.51 (dd, J=8.36, 4.18 Hz, 1H), 7.64 (d, J=8.36 Hz, 1H), 7.84 (dd, J=9.02, 2.42 Hz, 1H), 8.01 (d, J=2.42 Hz, 1H), 8.23 (dd, J=8.47, 0.99 Hz, 1H), 8.31 (d, J=8.80 Hz, 1H), 8.38 (d, J=5.28 Hz, 1H), 8.89 (s, 1H), 9.02 (dd, J=4.29, 1.65 Hz, 1H)

Example 14

Synthesis of 4-(5-chloro-2-((1-(4-methoxyphenyl)-2-oxo-1H-imidazo[4,5-c]pyridin-3(2H)-yl)methyl)-1H-indol-1-yl)butanenitrile (P14)

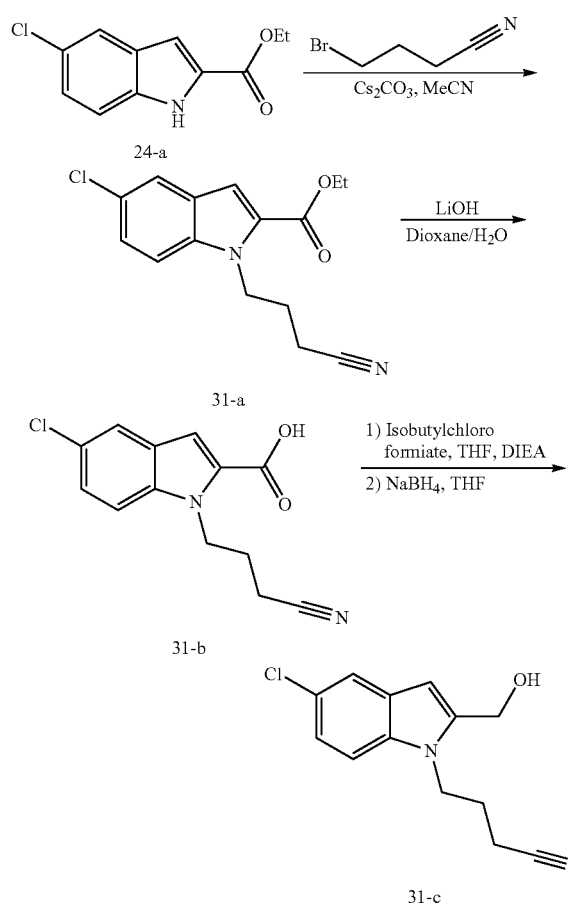

Step 1: Synthesis of ethyl 5-chloro-1-(3-cyanopropyl)-1H-indole-2-carboxylate 31-a Ethyl-5-chloroindol-2-carboxylate 24-a (33.55 g, 150 mmol) was dissolved in acetonitrile (600 mL) and stirred at room temperature. Then cesiumcarbonate (73.31 g, 225 mmol) was added and stirring was continued for 30 minutes. 4-Bromobutyronitrile (18.83 mL, 180 mmol) was added in small portions over a period of one hour and stirring was done overnight at ambient temperature. The reaction mixture was filtered and the filtrate was evaporated to dryness. The residue was dissolved in dichloro-methane and washed with water. The organic layer was dried over MgSO4, filtered and evaporated. The residue 43.5 g was used as such in the next step 99% yield.
m/z=290 (M+H)+

Step 2: Synthesis of 5-Chloro-1-(3-cyanopropyl)-1H-indole-2-carboxylic acid 31-b Ethyl 5-chloro-1-(3-cyanopropyl)indol-2-carboxylate 31-a (43.61 g, 149.97 mmol) was dissolved in 1,4-dioxane (850 mL) and stirred at room temperature. Then a solution of lithiumhydroxide (10.78 g, 450 mmol) in distilled water (150 mL) was added the stirring was continued overnight at ambient temperature. The reaction mixture was evaporated to dryness. The residue was dissolved in 500 mL water and neutralised with aqueous solution of hydrochloric acid 1N (450 mL). The white precipitate was filtered off and dried in vacuo to yield 39.8 g of the intermediate 31-b 100%.
m/z=262 (M+H)+

Step 3: Synthesis of 4-(5-chloro-2-(hydroxymethyl)-1H-indol-1-yl)butanenitrile 31-c 5-chloro-1-(3-cyanopropyl)indol-2-carboxylic acid 31-b (39.4 g, 149.98 mmol) and Hunigs base (51.69 mL, 300 mmol) were dissolved in tetrahydrofuran (550 mL) and stirred at −10° C. under a nitrogen atmosphere. Then a solution of isoButylchloroformate in tetrahydrofuran (50 ml) was added dropwise the stirring was continued for one hour at −10° C. and one hour at ambient temperature. Then sodiumborohydride (17.02 g, 450 mmol) was added portionwise at −10° C. and stirred for one hour, afterwards distilled water (200 mL) was added cautiously to the reaction mixture and stirring was continued for another hour at room temperature under a nitrogen atmosphere. The mixture was neutralised with 10% citric acid in water and then extracted with ethyl acetate. The organic layer was dried over MgSO4, filtered and evaporated. The residue was purified over silica with Heptane/dichloromethane/methanol 50/50/0→0/100/0→0/99/1 as gradient. The corresponding fractions were evaporated to yield the intermediate 31-c 23.9 g as a white powder 64%.
m/z=248 (M+H)+

Step 4: Synthesis of 4-(5-chloro-2-((1-(4-methoxyphenyl)-2-oxo-1H-imidazo[4,5-c]pyridin-3(2H)-yl)methyl)-1H-indol-1-yl)butanenitrile (P14)

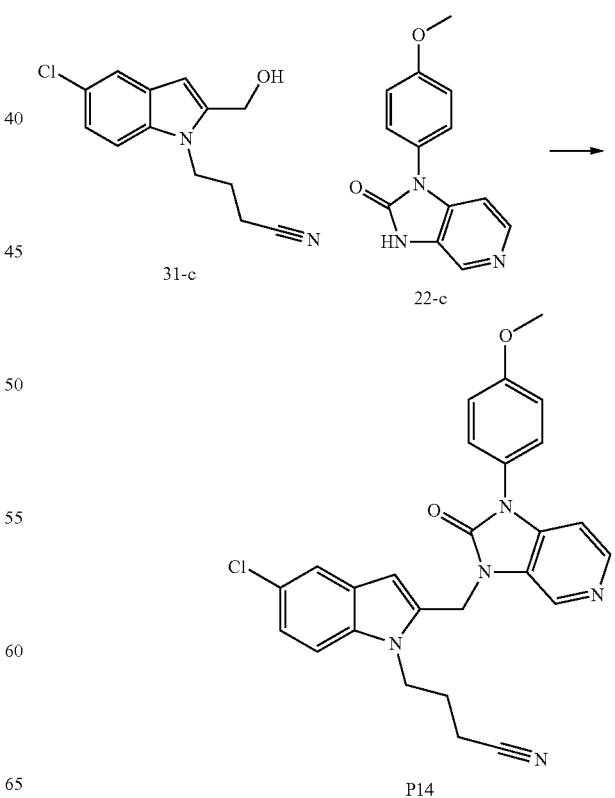

To a suspension of intermediate 31-c (3 g, 12.02 mmol), intermediate 22-c (2.9 g, 12.02 mmol) and triphenylphosphine (3.78 g, 14.43 mmol) in dry THF (90 mL) diisopropylazodicarboxylate (DIAD) (3.509 ml, 18.03 mmol) was added at room temperature dropwise. The resulting mixture was stirred overnight. The solvent was evaporated and the residue was triturated in ether. After stirring for 1 hour, the solid was filtered off and then the beige powder was crystallized in MeOH. The formed crystals were filtered off and washed with some MeOH and ether to get the title product P14 as a white powder (2.2 g, 40%).

m/z=472 (M+H)$^+$ $^1$H NMR (400 MHz, DMSO-d$_6$) δ ppm 1.95 (quin, J=7.59 Hz, 2H) 2.54 (t, J=7.50 Hz, 2H) 3.84 (s, 3H) 4.35 (t, J=7.70 Hz, 2H) 5.42 (s, 2H) 6.55 (s, 1H) 7.02 (d, J=5.28 Hz, 1H) 7.11-7.19 (m, 3H) 7.47-7.52 (m, 2H) 7.54 (d, J=8.80 Hz, 1H) 7.57 (d, J=1.98 Hz, 1H) 8.23 (d, J=5.28 Hz, 1H) 8.51 (s, 1H)

Example 15

Synthesis of 4-(5-chloro-2-((1-(3-fluoro-4-methoxyphenyl)-2-oxo-1H-imidazo[4,5-c]pyridin-3(2H)-yl)methyl)-1H-indol-1-yl)butanenitrile (P15)

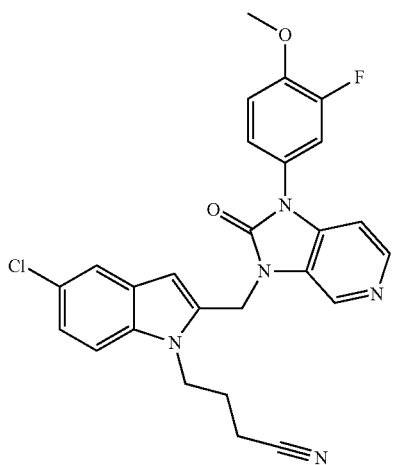 [SMILES: COc1ccc(-n2c(=O)n(Cc3cc4cc(Cl)ccc4n3CCCC#N)c3cnccc32)cc1F]

P15

Compound P15 was prepared by an analogous reaction protocol as described for compound P1 using intermediate 31-c and 1-(3-fluoro-4-methoxyphenyl)-1H-imidazo[4,5-c]pyridin-2(3H)-one 45-c as starting material.

m/z=490 (M+1)$^+$ $^1$H NMR (400 MHz, CHLOROFORM-d) δ ppm 2.01 (qd, J=7.37, 7.15 Hz, 2H), 2.36 (t, J=7.15 Hz, 2H), 3.97 (s, 3H), 4.34-4.45 (m, 2H), 5.31 (s, 2H), 6.69 (s, 1H), 6.99 (dd, J=5.28, 0.66 Hz, 1H), 7.09-7.16 (m, 1H), 7.16-7.30 (m, 4H), 7.56 (d, J=1.54 Hz, 1H), 8.32 (d, J=5.28 Hz, 1H), 8.51 (s, 1H)

Example 16

Synthesis of 3-((5-chloro-1-isopentyl-1H-imidazo[4,5-b]pyridin-2-yl)methyl)-1-(4-methoxyphenyl)-1H-imidazo[4,5-c]pyridin-2(3H)-one (P16)

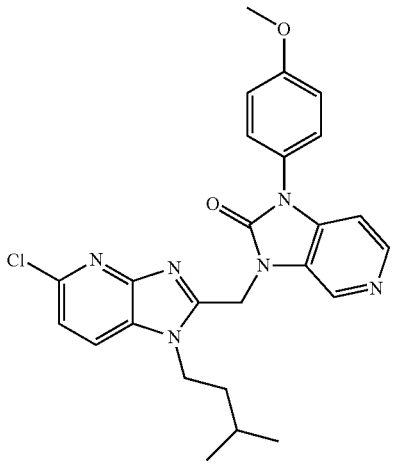 [SMILES: COc1ccc(-n2c(=O)n(Cc3nc4nc(Cl)ccc4n3CCC(C)C)c3cnccc32)cc1]

P16

Compound P16 was prepared by an analogous reaction protocol as described for compound P1 using intermediate 30-a and 1-(4-methoxyphenyl)-1H-imidazo-[4,5-c]pyridin-2(3H)-one 22-c as starting material.

m/z=477 (M+1)$^+$ $^1$H NMR (400 MHz, CHLOROFORM-d) δ ppm 0.98 (d, J=6.60 Hz, 6H), 1.52-1.63 (m, 2H), 1.68 (s, 1H), 3.88 (s, 3H), 4.34-4.46 (m, 2H), 5.48 (s, 2H), 6.93 (d, J=5.28 Hz, 1H), 7.02-7.09 (m, 2H), 7.24 (d, J=8.58 Hz, 1H), 7.33-7.41 (m, 2H), 7.62 (d, J=8.36 Hz, 1H), 8.32 (d, J=5.50 Hz, 1H), 8.82 (s, 1H)

Example 17

Synthesis of 3-((5-chloro-1-(4,4,4-trifluorobutyl)-1H-pyrrolo[3,2-b]pyridin-2-yl)-methyl)-1-(4-methoxyphenyl)-1H-imidazo[4,5-c]pyridin-2(3H)-one (P17)

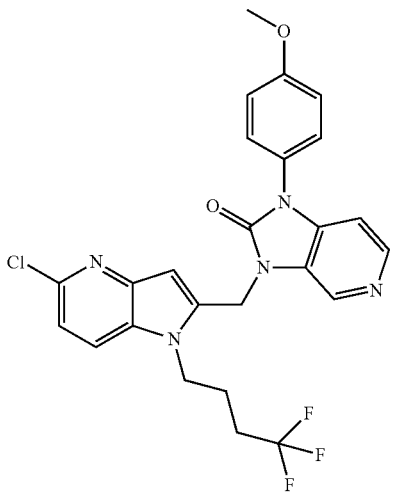 [SMILES: COc1ccc(-n2c(=O)n(Cc3cc4nc(Cl)ccc4n3CCCC(F)(F)F)c3cnccc32)cc1]

P17

Compound P17 was prepared by an analogous reaction protocol as described for compound P1 using intermediate 49-e and 1-(4-methoxyphenyl)-1H-imidazo[4,5-c]-pyridin-2(3H)-one 22-c as starting material.

m/z=516 (M+1)$^+$ $^1$H NMR (400 MHz, CHLOROFORM-d) δ ppm 1.80-1.92 (m, 2H), 2.04-2.21 (m, 2H), 3.88 (s, 3H), 4.32-4.42 (m, 2H), 5.36 (s, 2H), 6.90 (s, 1H), 6.95 (d, J=5.28 Hz, 1H), 7.05-7.11 (m, 2H), 7.16 (d, J=8.58 Hz, 1H), 7.34-7.41 (m, 2H), 7.54 (d, J=8.58 Hz, 1H), 8.31 (d, J=5.06 Hz, 1H), 8.49 (s, 1H)

Example 18

Synthesis of 3-((5-chloro-1-isopentyl-1H-imidazo[4,5-b]pyridin-2-yl)methyl)-1-(1-methylcyclopropyl)-1H-imidazo[4,5-c]pyridin-2(3H)-one (P18)

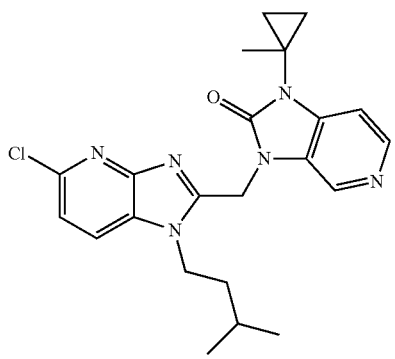 [SMILES: CC(C)CCn1c(Cn2c(=O)n(C3(C)CC3)c3ccncc32)nc2nc(Cl)ccc21]

P18

Compound P18 was prepared by an analogous reaction protocol as described for compound P1 using intermediate 30-a and 1-(1-methylcyclopropyl)-1H-imidazo[4,5-c]pyridin-2(3H)-one 18-c as starting material.

m/z=425 (M+1)$^+$ $^1$H NMR (400 MHz, CHLOROFORM-d) δ ppm 0.99 (d, J=6.60 Hz, 6H), 1.02-1.07 (m, 2H), 1.11-1.19 (m, 2H), 1.50 (s, 3H), 1.52-1.60 (m, 2H), 1.63-1.78 (m, 1H), 4.30-4.42 (m, 2H), 5.37 (s, 2H), 7.13 (d, J=5.06 Hz, 1H), 7.20 (d, J=8.36 Hz, 1H), 7.60 (d, J=8.36 Hz, 1H), 8.34 (d, J=3.74 Hz, 1H), 8.71 (br. s., 1H)

Example 19

Synthesis of 4-(5-chloro-2-((1-(3,4-dimethoxyphenyl)-2-oxo-1H-imidazo[4,5-c]pyridin-3(2H)-yl)methyl)-1H-indol-1-yl)butanenitrile (P19)

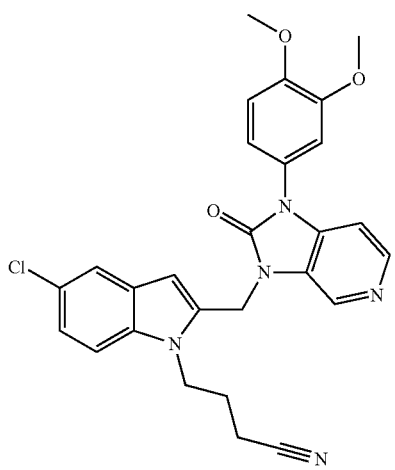

P19

Compound P19 was prepared by an analogous reaction protocol as described for compound P1 using intermediate 31-c and 1-(3,4-dimethoxyphenyl)-1H-imidazo[4,5-c]pyridin-2(3H)-one 32-c as starting material.

m/z=502 (M+1)$^+$

MP=176.51° C.

$^1$H NMR (400 MHz, DMSO-d$_6$) δ ppm 1.94 (quin, J=7.48 Hz, 2H) 2.52-2.58 (m, 2H) 3.79 (s, 3H) 3.84 (s, 3H) 4.32-4.40 (m, 2H) 5.42 (s, 2H) 6.56 (s, 1H) 7.05-7.20 (m, 5H) 7.55 (d, J=8.80 Hz, 1H) 7.57 (d, J=1.98 Hz, 1H) 8.23 (d, J=5.28 Hz, 1H) 8.51 (s, 1H)

Example 20

Synthesis of 4-(5-chloro-2-((1-(4-methoxy-2-methylphenyl)-2-oxo-1H-imidazo[4,5-c]pyridin-3(2H)-yl)methyl)-1H-indol-1-yl)butanenitrile (P20)

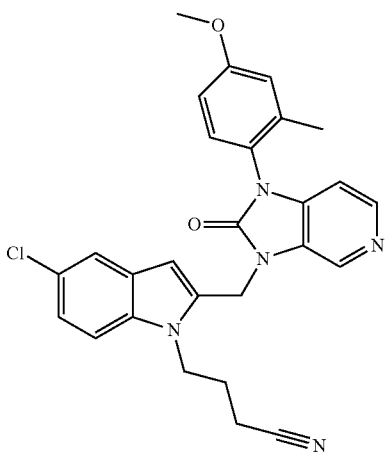 [SMILES: COc1ccc(-n2c(=O)n(Cc3cc4cc(Cl)ccc4n3CCCC#N)c3cnccc32)c(C)c1]

P20

Compound P20 was prepared by an analogous reaction protocol as described for compound P1 using intermediate 31-c and 1-(4-methoxy-2-methylphenyl)-1H-imidazo[4,5-c]pyridin-2(3H)-one 33-c as starting material.

m/z=486 (M+1)$^+$

MP=172.59° C.

$^1$H NMR (400 MHz, DMSO-d$_6$) δ ppm 1.89-2.05 (m, 2H) 2.07 (s, 3H) 2.52-2.60 (m, 2H) 3.83 (s, 3H) 4.26-4.42 (m, 2H) 5.43 (s, 2H) 6.50 (s, 1H) 6.76 (d, J=5.06 Hz, 1H) 6.96 (dd, J=8.69, 2.75 Hz, 1H) 7.06 (d, J=2.64 Hz, 1H) 7.17 (dd, J=8.69, 2.09 Hz, 1H) 7.34 (d, J=8.58 Hz, 1H) 7.55 (d, J=8.80 Hz, 1H) 7.58 (d, J=1.98 Hz, 1H) 8.21 (d, J=5.28 Hz, 1H) 8.51 (s, 1H)

Example 21

Synthesis of 4-(5-chloro-2-((2-oxo-1-(pyrimidin-2-yl)-1H-imidazo[4,5-c]pyridin-3(2H)-yl)methyl)-1H-indol-1-yl)butanenitrile (P21)

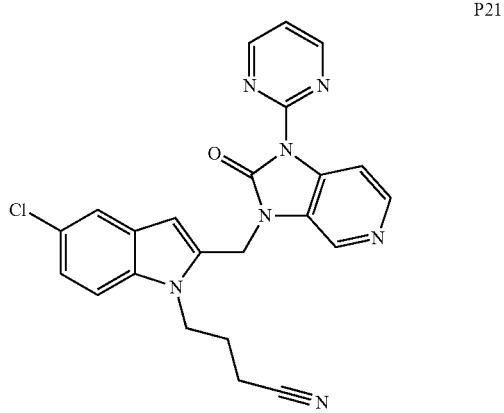

Compound P21 was prepared by an analogous reaction protocol as described for compound P1 using intermediate 31-c and 1-(pyrimidin-2-yl)-1H-imidazo[4,5-c]pyridin-2(3H)-one 53-c as starting material.

m/z=445 (M+1)$^+$ $^1$H NMR (400 MHz, DMSO-d$_6$) δ ppm 1.91 (quin, J=7.65 Hz, 2H) 2.54-2.63 (m, 2H) 4.28-4.43 (m, 2H) 5.45 (s, 2H) 6.52 (s, 1H) 7.16 (dd, J=8.69, 2.09 Hz, 1H) 7.54 (d, J=8.80 Hz, 1H) 7.57 (d, J=2.20 Hz, 1H) 7.61 (t, J=4.84 Hz, 1H) 7.77 (dd, J=5.39, 0.77 Hz, 1H) 8.33 (d, J=5.28 Hz, 1H) 8.58 (s, 1H) 9.02 (d, J=4.84 Hz, 2H)

Example 22

Synthesis of 3-((5-chloro-1-isopentyl-1H-imidazo[4,5-b]pyridin-2-yl)methyl)-1-(thiazol-2-yl)-1H-imidazo[4,5-c]pyridin-2(3H)-one (P22)

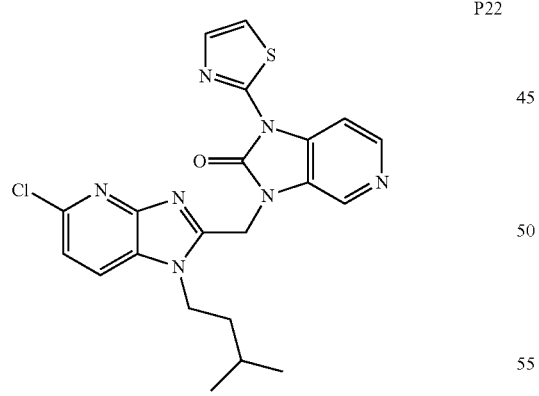

Compound P22 was prepared by an analogous reaction protocol as described for compound P1 using intermediate 30-a and 1-(thiazol-2-yl)-1H-imidazo[4,5-c]pyridin-2(3H)-one 21-c as starting material.

m/z=454 (M+1)$^+$

MP=231.23° C. and 238.22° C.

$^1$H NMR (400 MHz, DMSO-d$_6$) δ ppm 0.95 (d, J=6.38 Hz, 6H) 1.56-1.77 (m, 3H) 4.35-4.50 (m, 2H) 5.67 (s, 2H) 7.37 (d, J=8.36 Hz, 1H) 7.63 (d, J=3.52 Hz, 1H) 7.81 (d, J=3.52 Hz, 1H) 8.16 (d, J=8.36 Hz, 1H) 8.35 (d, J=5.28 Hz, 1H) 8.49 (d, J=5.28 Hz, 1H) 8.68 (s, 1H)

Example 23

Synthesis of 3-((5-chloro-1-isopentyl-1H-imidazo[4,5-b]pyridin-2-yl)methyl)-1-(pyridin-4-yl)-1H-imidazo[4,5-c]pyridin-2(3H)-one (P23)

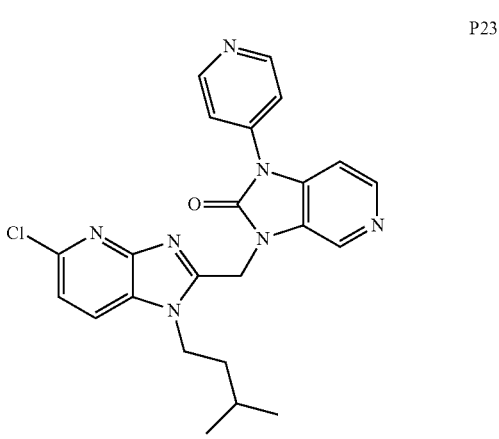

Compound P23 was prepared by an analogous reaction protocol as described for compound P1 using intermediate 30-a and 1-(pyridin-4-yl)-1H-imidazo[4,5-c]pyridin-2(3H)-one 34-c as starting material.

m/z=448 (M+1)$^+$

MP=210

$^1$H NMR (400 MHz, DMSO-d$_6$) δ ppm 0.95 (d, J=6.16 Hz, 6H) 1.57-1.75 (m, 3H) 4.34-4.49 (m, 2H) 5.60 (s, 2H) 7.37 (d, J=8.58 Hz, 1H) 7.44 (d, J=5.28 Hz, 1H) 7.70-7.80 (m, 2H) 8.16 (d, J=8.58 Hz, 1H) 8.34 (d, J=5.50 Hz, 1H) 8.62 (s, 1H) 8.75-8.85 (m, 2H)

Example 24

Synthesis of 4-(5-chloro-2-((2-oxo-1-(pyrimidin-4-yl)-1H-imidazo[4,5-c]pyridin-3(2H)-yl)methyl)-1H-indol-1-yl)butanenitrile (P24)

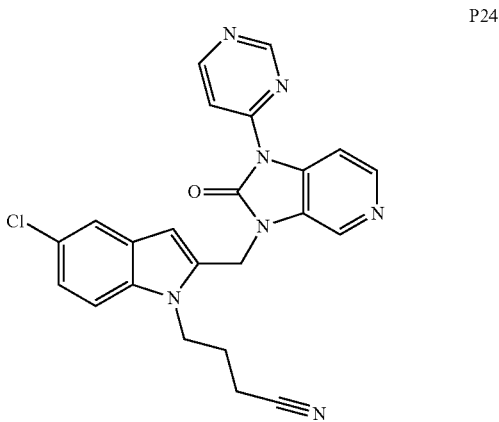

Compound P24 was prepared by an analogous reaction protocol as described for compound P1 using intermediate 31-c and 1-(pyrimidin-4-yl)-1H-imidazo[4,5-c]pyridin-2(3H)-one 35-c as starting material.

m/z=444 (M+1)⁺
MP=229.17° C.
¹H NMR (400 MHz, DMSO-d₆) δ ppm 1.98 (quin, J=7.32 Hz, 2H) 2.58 (t, J=7.37 Hz, 2H) 4.36 (t, J=7.59 Hz, 2H) 5.46 (s, 2H) 6.51 (s, 1H) 7.16 (dd, J=8.80, 1.76 Hz, 1H) 7.48-7.60 (m, 2H) 8.34 (d, J=5.28 Hz, 1H) 8.38-8.47 (m, 2H) 8.60 (s, 1H) 8.97 (d, J=5.94 Hz, 1H) 9.24 (s, 1H)

Example 25

Synthesis of 3-((5-chloro-1-isopentyl-1H-imidazo[4,5-b]pyridin-2-yl)methyl)-5-fluoro-1-(thiazol-2-yl)-1H-benzo[d]imidazol-2(3H)-one (P25)

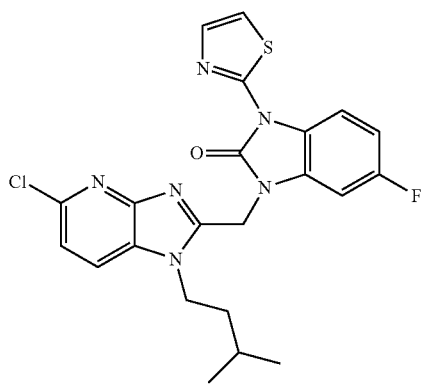

P25

Compound P25 was prepared by an analogous reaction protocol as described for compound P1 using intermediate 30-a and 5-fluoro-1-(thiazol-2-yl)-1H-benzo[d]imidazol-2(3H)-one 37-c as starting material.
m/z=471 (M+1)⁺
MP=264.42° C.
¹H NMR (400 MHz, DMSO-d₆) δ ppm 0.94 (d, J=6.38 Hz, 6H) 1.54-1.74 (m, 3H) 4.34-4.47 (m, 2H) 5.61 (s, 2H) 7.07-7.18 (m, 1H) 7.36 (d, J=8.36 Hz, 1H) 7.42 (dd, J=8.91, 2.53 Hz, 1H) 7.57 (d, J=3.52 Hz, 1H) 7.75 (d, J=3.52 Hz, 1H) 8.16 (d, J=8.36 Hz, 1H) 8.46 (dd, J=8.80, 4.84 Hz, 1H)

Example 26

Synthesis of 3-((5-chloro-1-isopentyl-1H-imidazo[4,5-b]pyridin-2-yl)methyl)-1-(3-fluoropyridin-4-yl)-1H-imidazo[4,5-c]pyridin-2(3H)-one (P26)

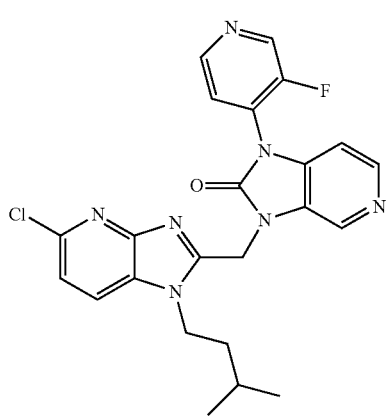 [SMILES: CC(C)CCn1c(Cn2c(=O)n(-c3ccncc3F)c3ccncc32)nc2nc(Cl)ccc21]

P26

Compound P26 was prepared by an analogous reaction protocol as described for compound P1 using intermediate 30-a and 1-(3-fluoropyridin-4-yl)-1H-imidazo[4,5-c]pyridin-2(3H)-one 36-c as starting material.
m/z=466 (M+1)⁺
MP=123.79° C.
¹H NMR (400 MHz, DMSO-d₆) δ ppm 0.94 (d, J=6.16 Hz, 6H) 1.57-1.74 (m, 3H) 4.35-4.48 (m, 2H) 5.62 (s, 2H) 7.20 (dd, J=5.06, 2.20 Hz, 1H) 7.37 (d, J=8.36 Hz, 1H) 7.83 (t, J=5.83 Hz, 1H) 8.16 (d, J=8.36 Hz, 1H) 8.33 (d, J=5.28 Hz, 1H) 8.62 (s, 1H) 8.68 (d, J=5.06 Hz, 1H) 8.93 (d, J=1.98 Hz, 1H)

Example 27

Synthesis of 4-(5-chloro-2-((6-fluoro-2-oxo-3-(thiazol-2-yl)-2,3-dihydro-1H-benzo[d]imidazol-1-yl)methyl)-1H-indol-1-yl)butanenitrile (P27)

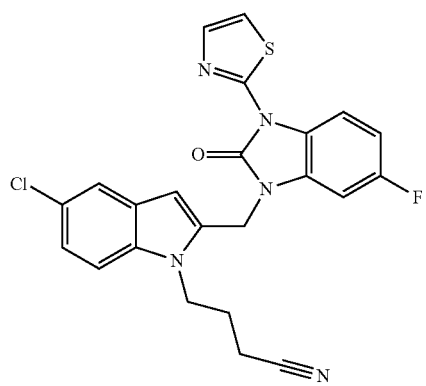

P27

Compound P27 was prepared by an analogous reaction protocol as described for compound P1 using intermediate 31-c and 5-fluoro-1-(thiazol-2-yl)-1H-benzo[d]imidazol-2(3H)-one 37-c as starting material.
m/z=466 (M+1)⁺
MP=238.29° C.
¹H NMR (400 MHz, DMSO-d₆) δ ppm 1.90-2.04 (m, 2H) 2.58 (t, J=7.37 Hz, 2H) 4.31-4.43 (m, 2H) 5.44 (s, 2H) 6.40 (s, 1H) 7.07-7.14 (m, 1H) 7.16 (dd, J=8.80, 1.98 Hz, 1H) 7.41 (dd, J=8.91, 2.53 Hz, 1H) 7.49-7.60 (m, 3H) 7.75 (d, J=3.52 Hz, 1H) 8.46 (dd, J=8.91, 4.95 Hz, 1H)

Example 28

Synthesis of 4-(5-chloro-2-((1-(4-(2-methoxy-ethoxy)phenyl)-2-oxo-1H-imidazo[4,5-c]pyridin-3(2H)-yl)methyl)-1H-indol-1-yl)butanenitrile (P28)

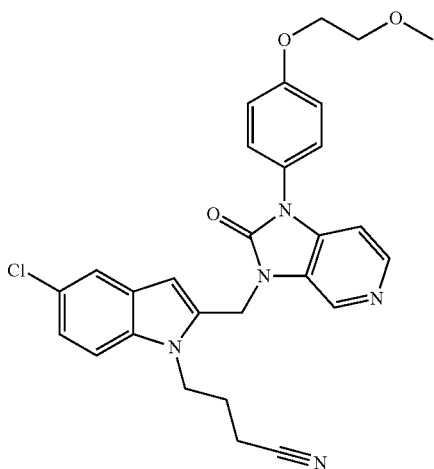 [SMILES: COCCOc1ccc(-n2c(=O)n(Cc3cc4cc(Cl)ccc4n3CCCC#N)c3cnccc32)cc1]

P28

Compound P28 was prepared by an analogous reaction protocol as described for compound P1 using intermediate 31-c and 1-(4-(2-methoxyethoxy)phenyl)-1H-imidazo[4,5-c]pyridin-2(3H)-one 39-c as starting material.

m/z=516 (M+1)$^+$ $^1$H NMR (400 MHz, DMSO-d$_6$) δ ppm 1.98 (quin, J=7.5 Hz, 2H), 2.51-2.58 (m, 2H), 3.34 (s, 3H), 3.65-3.75 (m, 2H), 4.14-4.24 (m, 2H), 4.36 (t, J=7.7 Hz, 2H), 5.40 (s, 2H), 6.53 (s, 1H), 6.99 (d, J=5.2 Hz, 1H), 7.09-7.18 (m, 3H), 7.42-7.57 (m, 4H), 8.22 (d, J=5.2 Hz, 1H), 8.46 (s, 1H)

Example 29

Synthesis of 4-(5-chloro-2-((2-oxo-1-(4-(trifluoromethoxy)phenyl)-1H-imidazo[4,5-c]pyridin-3(2H)-yl)methyl)-1H-indol-1-yl)butanenitrile (P29)

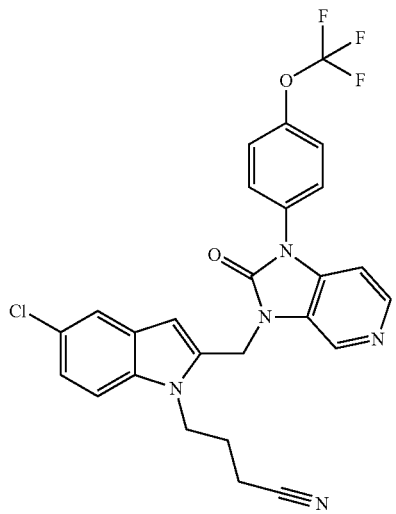 [SMILES: N#CCCCn1c(Cn2c(=O)n(-c3ccc(OC(F)(F)F)cc3)c3ccncc32)cc2cc(Cl)ccc21]

P29

Compound P29 was prepared by an analogous reaction protocol as described for compound P1 using intermediate 31-c and 1-(4-(trifluoromethoxy)phenyl)-1H-imidazo[4,5-c]pyridin-2(3H)-one 40-c as starting material.

m/z=526 (M+1)$^+$ $^1$H NMR (360 MHz, DMSO-d$_6$) δ ppm 1.97 (quin, J=7.5 Hz, 2H), 2.56 (t, J=7.5 Hz, 2H), 4.36 (t, J=7.5 Hz, 2H), 5.44 (s, 2H), 6.56 (s, 1H), 7.09-7.25 (m, 2H), 7.50-7.69 (m, 4H), 7.73-7.83 (m, 2H), 8.27 (d, J=5.5 Hz, 1H), 8.56 (s, 1H)

Example 30

Synthesis of 3-((5-chloro-1-(3-(methylsulfonyl)propyl)-1H-indol-2-yl)methyl)-1-(4-chlorophenyl)-1H-imidazo[4,5-c]pyridin-2(3H)-one (P30)

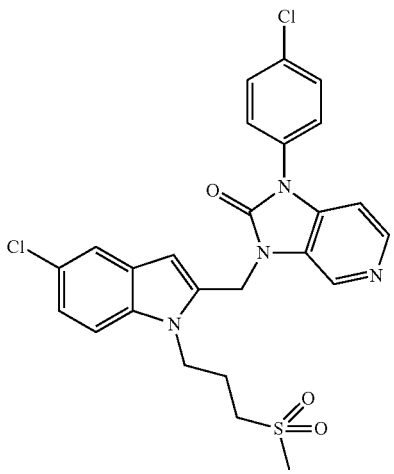 [SMILES: CS(=O)(=O)CCCn1c(Cn2c(=O)n(-c3ccc(Cl)cc3)c3ccncc32)cc2cc(Cl)ccc21]

P30

Compound P30 was prepared by an analogous reaction protocol as described for compound P1 using intermediate 24-c and 1-(4-chlorophenyl)-1H-imidazo[4,5-c]pyridin-2(3H)-one 41-c as starting material.

m/z=529 (M+1)$^+$ $^1$H NMR (360 MHz, DMSO-d$_6$) δ ppm 2.03 (m, J=7.7, 7.7 Hz, 2H), 2.94 (s, 3H), 3.15 (m, J=15.7 Hz, 2H), 4.43 (t, J=7.5 Hz, 2H), 5.43 (s, 2H), 6.62 (s, 1H), 7.10-7.23 (m, 2H), 7.52-7.61 (m, 2H), 7.67 (s, 4H), 8.26 (d, J=5.1 Hz, 1H), 8.56 (s, 1H)

Example 31

Synthesis of 3-((5-chloro-1-(4-fluorobutyl)-1H-indol-2-yl)methyl)-1-(quinolin-6-yl)-1H-imidazo[4,5-c]pyridin-2(3H)-one (P31)

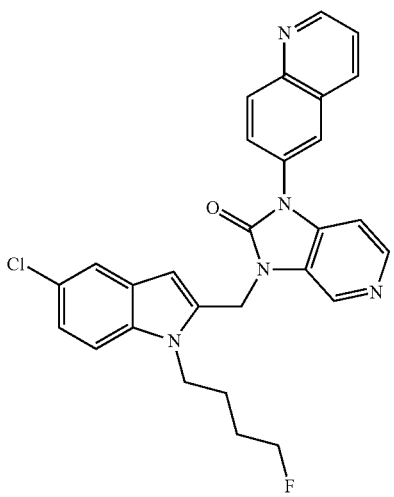 [SMILES: O=c1n(Cc2cc3cc(Cl)ccc3n2CCCCF)c2cnccc2n1-c1ccc2ncccc2c1]

P31

Compound P31 was prepared by an analogous reaction protocol as described for compound P1 using intermediate 28-a and 1-(quinolin-6-yl)-1H-imidazo[4,5-c]pyridin-2(3H)-one 20-c as starting material.

m/z=500 (M+1)⁺

$^1$H NMR (360 MHz, DMSO-d$_6$) δ ppm 1.52-1.78 (m, 4H), 4.26-4.41 (m, 3H), 4.47 (t, J=5.5 Hz, 1H), 5.47 (s, 2H), 6.69 (s, 1H), 7.16 (dd, J=8.8, 2.2 Hz, 1H), 7.28 (d, J=5.5 Hz, 1H), 7.54 (d, J=8.8 Hz, 1H), 7.60 (d, J=2.2 Hz, 1H), 7.65 (dd, J=8.4, 4.4 Hz, 1H), 8.00 (dd, J=9.1, 2.2 Hz, 1H), 8.19-8.33 (m, 3H), 8.51 (d, J=7.3 Hz, 1H), 8.58 (s, 1H), 9.02 (dd, J=4.2, 1.6 Hz, 1H)

Example 32

Synthesis of 3-((5-chloro-1-(4-fluorobutyl)-1H-indol-2-yl)methyl)-1-(4-methoxy-phenyl)-1H-imidazo[4,5-c]pyridin-2(3H)-one (P32)

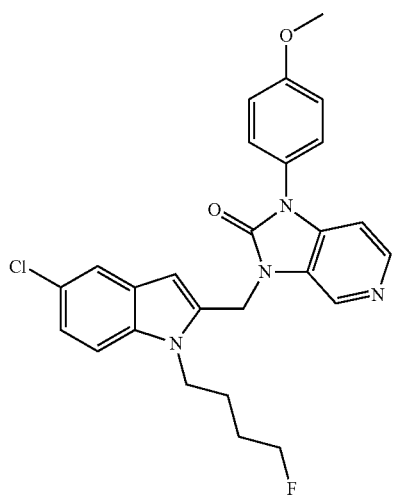 [SMILES: COc1ccc(-n2c(=O)n(Cc3cc4cc(Cl)ccc4n3CCCCF)c3cnccc32)cc1]

P32

Compound P32 was prepared by an analogous reaction protocol as described for compound P1 using intermediate 28-a and 1-(4-methoxyphenyl)-1H-imidazo[4,5-c]pyridin-2(3H)-one 22-c as starting material.

m/z=479 (M+1)⁺

MP=163° C.

$^1$H NMR (360 MHz, DMSO-d$_6$) δ ppm 1.63 (m, J=2.9, 2.9 Hz, 4H), 3.84 (s, 3H), 4.33 (m, J=5.5 Hz, 3H), 4.46 (t, J=5.9 Hz, 1H), 5.41 (s, 2H), 6.66 (s, 1H), 6.99-7.04 (m, 1H), 7.10-7.19 (m, 3H), 7.44-7.55 (m, 3H), 7.59 (d, J=2.2 Hz, 1H), 8.22 (d, J=5.5 Hz, 1H), 8.47-8.53 (m, 1H)

Example 33

Synthesis of 4-(5-chloro-2-((1-(1-methyl-1H-imidazol-2-yl)-2-oxo-1H-imidazo[4,5-c]pyridin-3(2H)-yl)methyl)-1H-indol-1-yl)butanenitrile (P33)

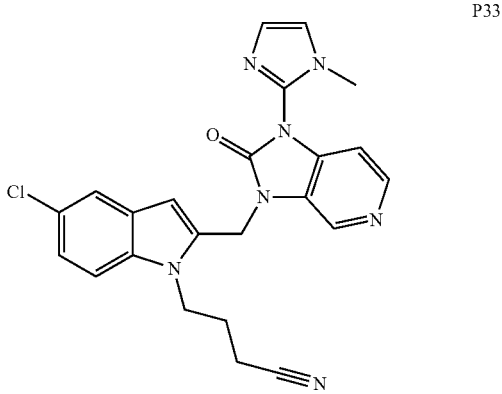

P33

Compound P33 was prepared by an analogous reaction protocol as described for compound P1 using intermediate 31-c and 1-(1-methyl-1H-imidazol-2-yl)-1H-imidazo[4,5-c]pyridin-2(3H)-one 42-c as starting material.

m/z=446 (M+1)⁺

Example 34

Synthesis of 3-((5-chloro-1-(4-fluorobutyl)-1H-indol-2-yl)methyl)-1-(4-chlorophenyl)-1H-imidazo[4,5-c]pyridin-2(3H)-one (P34)

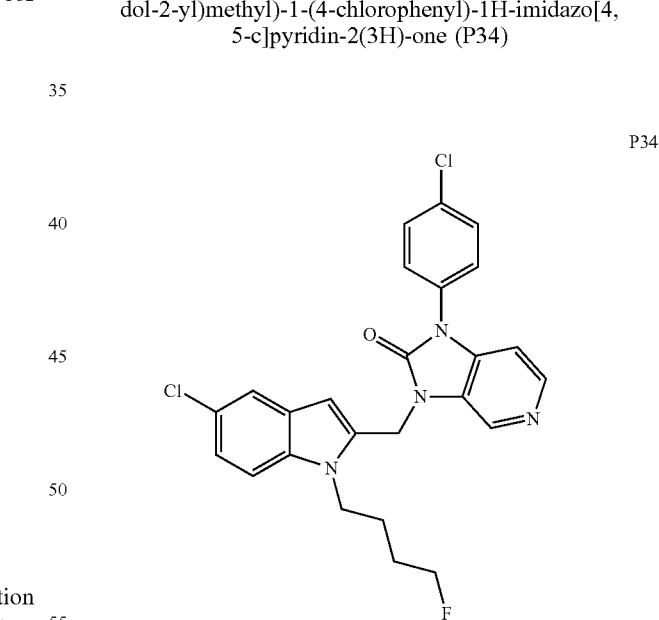

P34

Compound P34 was prepared by an analogous reaction protocol as described for compound P1 using intermediate 28-a and 1-(4-chlorophenyl)-1H-imidazo[4,5-c]pyridin-2(3H)-one 41-c as starting material.

m/z=483 (M+1)⁺

MP=168° C.

$^1$H NMR (360 MHz, DMSO-d$_6$) δ ppm 1.53-1.72 (m, 4H), 4.32 (m, J=4.4 Hz, 3H), 4.46 (t, J=5.5 Hz, 1H), 5.42 (s, 2H), 6.67 (s, 1H), 7.08-7.20 (m, 2H), 7.52 (d, J=8.8 Hz, 1H), 7.59 (d, J=1.8 Hz, 1H), 7.61-7.73 (m, 4H), 8.25 (d, J=5.5 Hz, 1H), 8.53 (s, 1H)

Example 35

Synthesis of 3-((5-chloro-1-(3-(methylsulfonyl)propyl)-1H-indol-2-yl)methyl)-1-(4-methoxyphenyl)-1H-imidazo[4,5-c]pyridin-2(3H)-one (P35)

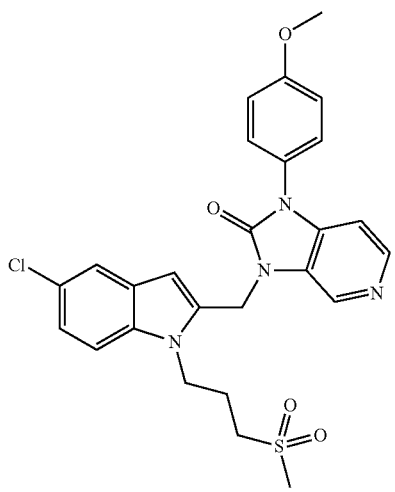 [SMILES: COc1ccc(-n2c(=O)n(Cc3cc4cc(Cl)ccc4n3CCCS(C)(=O)=O)c3cnccc32)cc1]

P35

Compound P35 was prepared by an analogous reaction protocol as described for compound P1 using intermediate 24-c and 1-(4-methoxyphenyl)-1H-imidazo[4,5-c]pyridin-2(3H)-one 22-c as starting material.

m/z=525 (M+1)$^+$
MP=215° C.
$^1$H NMR (360 MHz, DMSO-d$_6$) δ ppm 1.94-2.10 (m, 2H), 2.95 (s, 3H), 3.15 (m, J=15.4 Hz, 2H), 3.84 (s, 3H), 4.43 (t, J=7.5 Hz, 2H), 5.43 (s, 2H), 6.61 (s, 1H), 7.02 (d, J=5.1 Hz, 1H), 7.10-7.21 (m, 3H), 7.48-7.62 (m, 4H), 8.23 (d, J=5.1 Hz, 1H), 8.53 (s, 1H)

Example 36

Synthesis of 4-(5-chloro-2-((1-(1-methyl-1H-pyrazol-3-yl)-2-oxo-1H-imidazo[4,5-c]pyridin-3(2H)-yl)methyl)-1H-indol-1-yl)butanenitrile (P36)

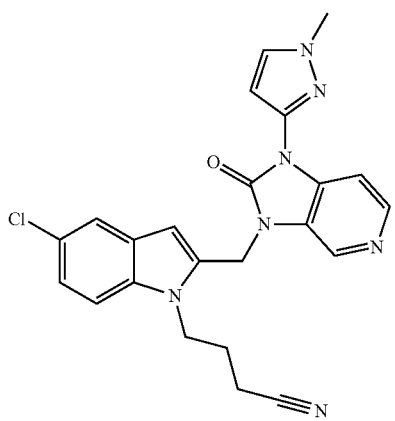 [SMILES: Cn1ccc(-n2c(=O)n(Cc3cc4cc(Cl)ccc4n3CCCC#N)c3cnccc32)n1]

P36

Compound P36 was prepared by an analogous reaction protocol as described for compound P1 using intermediate 31-c and 1-(1-methyl-1H-pyrazol-3-yl)-1H-imidazo[4,5-c]pyridin-2(3H)-one 44-c as starting material.

m/z=446 (M+1)$^+$
MP=244° C.
$^1$H NMR (360 MHz, DMSO-d$_6$) δ ppm 1.92 (quin, J=7.4 Hz, 2H), 2.56 (t, J=7.5 Hz, 2H), 3.93 (s, 3H), 4.35 (t, J=7.7 Hz, 2H), 5.44 (s, 2H), 6.46 (s, 1H), 6.71 (d, J=2.2 Hz, 1H), 7.16 (dd, J=8.8, 2.2 Hz, 1H), 7.48-7.60 (m, 2H), 7.78 (d, J=5.1 Hz, 1H), 7.88 (d, J=2.6 Hz, 1H), 8.34 (d, J=5.5 Hz, 1H), 8.54 (s, 1H)

Example 37

Synthesis of 4-(5-chloro-2-((1-(oxazol-2-yl)-2-oxo-1H-imidazo[4,5-c]pyridin-3(2H)-yl)methyl)-1H-indol-1-yl)butanenitrile (P37)

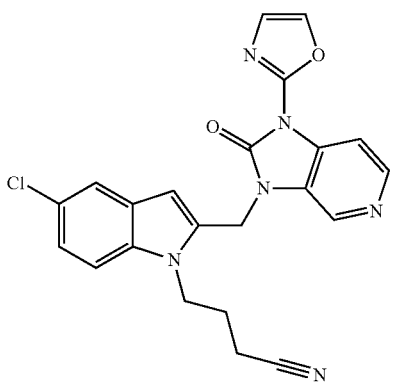 [SMILES: N#CCCCn1c(Cn2c(=O)n(-c3ncco3)c3ccncc32)cc2cc(Cl)ccc21]

P37

Compound P37 was prepared by an analogous reaction protocol as described for compound P1 using intermediate 31-c and 1-(oxazol-2-yl)-1H-imidazo[4,5-c]pyridin-2(3H)-one 43-c as starting material.

m/z=433 (M+1)$^+$
MP=234° C.
$^1$H NMR (360 MHz, DMSO-d$_6$) δ ppm 1.89-2.07 (m, 2H), 2.58 (t, J=7.5 Hz, 2H), 4.35 (m, J=15.4 Hz, 2H), 5.44 (s, 2H), 6.50 (s, 1H), 7.10-7.22 (m, 1H), 7.47 (d, J=0.7 Hz, 1H), 7.51-7.60 (m, 2H), 7.74-7.82 (m, 1H), 8.26 (d, J=1.1 Hz, 1H), 8.40 (d, J=5.1 Hz, 1H), 8.58 (s, 1H)

Example 38

Synthesis of 3-((5-chloro-1-(4-fluorobutyl)-1H-indol-2-yl)methyl)-1-(1-methyl-1H-pyrazol-3-yl)-1H-imidazo[4,5-c]pyridin-2(3H)-one (P38)

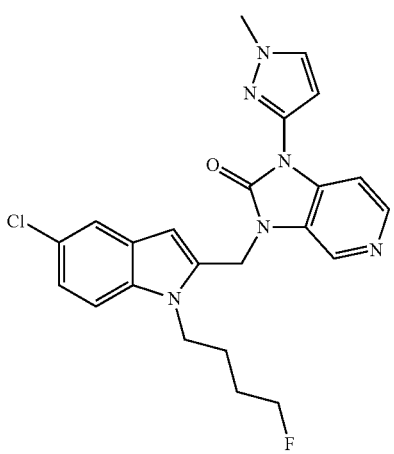 [SMILES: Cn1ccc(-n2c(=O)n(Cc3cc4cc(Cl)ccc4n3CCCCF)c3cnccc32)n1]

P38

Compound P38 was prepared by an analogous reaction protocol as described for compound P1 using intermediate 28-a and 1-(1-methyl-1H-pyrazol-3-yl)-1H-imidazo[4,5-c]pyridin-2(3H)-one 44-c as starting material.

m/z=453 (M+1)⁺
MP=169.3° C.
¹H NMR (360 MHz, DMSO-d₆) δ ppm 1.49-1.73 (m, 4H), 3.93 (s, 3H), 4.25-4.35 (m, 3H), 4.42 (t, J=6.0 Hz, 1H), 5.42 (s, 2H), 6.59 (s, 1H), 6.70 (d, J=2.2 Hz, 1H), 7.14 (dd, J=8.8, 2.2 Hz, 1H), 7.51 (d, J=8.8 Hz, 1H), 7.58 (d, J=1.8 Hz, 1H), 7.77 (d, J=5.5 Hz, 1H), 7.88 (d, J=2.2 Hz, 1H), 8.32 (d, J=5.5 Hz, 1H), 8.52 (s, 1H)

Example 39

Synthesis of 4-(5-chloro-2-((1-(4-chlorophenyl)-2-oxo-1H-imidazo[4,5-c]pyridin-3(2H)-yl)methyl)-1H-indol-1-yl)butanenitrile (P39)

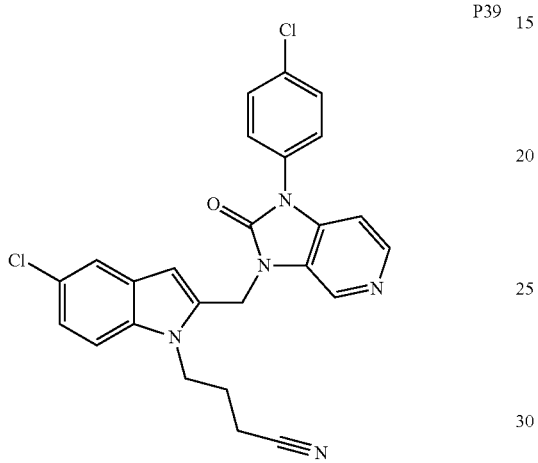

P39

Compound P39 was prepared by an analogous reaction protocol as described for compound P1 using intermediate 31-c and 1-(4-chlorophenyl)-1H-imidazo[4,5-c]pyridin-2(3H)-one 41-c as starting material.
m/z=476 (M+1)⁺
MP=210.8° C.
¹H NMR (360 MHz, DMSO-d₆) δ ppm 1.88-2.05 (m, 2H), 2.52-2.61 (m, 2H), 4.36 (t, J=7.9 Hz, 2H), 5.43 (s, 2H), 6.55 (s, 1H), 7.10-7.22 (m, 2H), 7.49-7.60 (m, 2H), 7.63-7.72 (m, 4H), 8.26 (d, J=5.5 Hz, 1H), 8.55 (s, 1H)

Example 40

Synthesis of 4-(5-chloro-2-((6-fluoro-2-oxo-3-(pyridin-4-yl)-2,3-dihydro-1H-benzo[d]imidazol-1-yl)methyl)-1H-indol-1-yl)butanenitrile (P40)

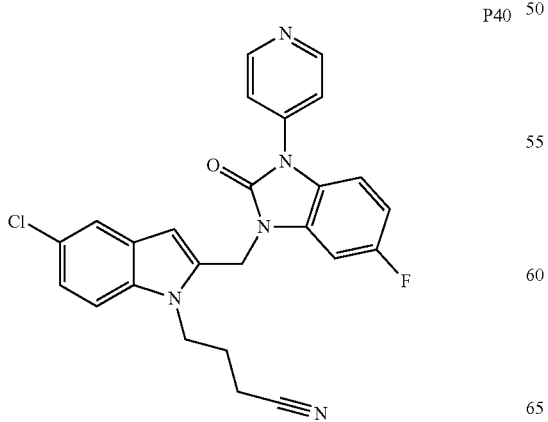

P40

Compound P40 was prepared by an analogous reaction protocol as described for compound P1 using intermediate 31-c and 5-fluoro-1-(pyridin-4-yl)-1H-benzo[d]imidazol-2(3H)-one 38-c as starting material.
m/z=461 (M+1)⁺
¹H NMR (400 MHz, DMSO-d₆) δ ppm 1.97 (quin, J=7.54 Hz, 2H) 2.56 (t, J=7.37 Hz, 2H) 4.20-4.41 (m, 2H) 5.39 (s, 2H) 6.44 (s, 1H) 6.91-7.01 (m, 1H) 7.16 (dd, J=8.80, 2.20 Hz, 1H) 7.33-7.40 (m, 2H) 7.51-7.57 (m, 2H) 7.68-7.77 (m, 2H) 8.67-8.83 (m, 2H)

Example 41

Synthesis of 4-(5-chloro-2-((1-(4-(methylsulfonyl)phenyl)-2-oxo-1H-imidazo[4,5-c]pyridin-3(2H)-yl)methyl)-1H-indol-1-yl)butanenitrile (P41)

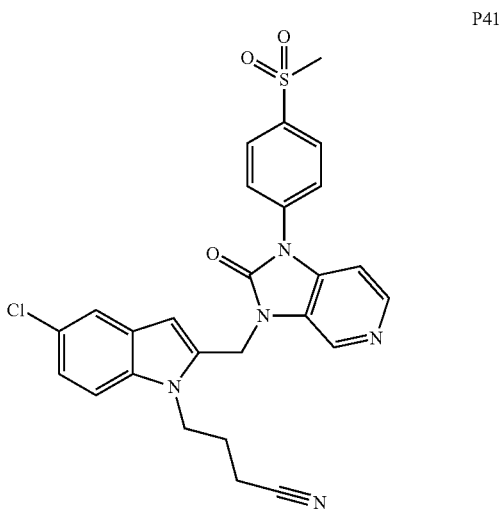

P41

Compound P41 was prepared by an analogous reaction protocol as described for compound P1 using intermediate 31-c and 1-(4-(methylsulfonyl)phenyl)-1H-imidazo[4,5-c]pyridin-2(3H)-one 50-c as starting material.
m/z=521 (M+1)⁺
¹H NMR (400 MHz, DMSO-d₆) δ ppm 1.92-2.06 (m, 2H) 2.53-2.59 (m, 2H) 3.31 (s, 3H) 4.36 (t, J=7.90 Hz, 2H) 5.45 (s, 2H) 6.56 (s, 1H) 7.09-7.22 (m, 1H) 7.29 (d, J=5.28 Hz, 1H) 7.52-7.58 (m, 2H) 7.94 (d, J=8.58 Hz, 2H) 8.16 (d, J=8.58 Hz, 2H) 8.30 (d, J=5.50 Hz, 1H) 8.57 (s, 1H)

Example 42

Synthesis of 4-(5-chloro-2-((1-(3-fluoropyridin-4-yl)-2-oxo-1H-imidazo[4,5-c]pyridin-3(2H)-yl)methyl)-1H-indol-1-yl)butanenitrile (P42)

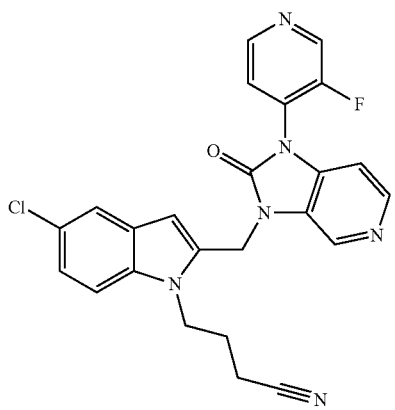 [SMILES: N#CCCCn1c(Cn2c(=O)n(-c3ccncc3F)c3ccncc32)cc2cc(Cl)ccc21]

Compound P42 was prepared by an analogous reaction protocol as described for compound P1 using intermediate 31-c and 1-(3-fluoropyridin-4-yl)-1H-imidazo[4,5-c]pyridin-2(3H)-one 36-c as starting material.

m/z=462 (M+1)$^+$ $^1$H NMR (400 MHz, DMSO-d$_6$) δ ppm 1.97 (quin, J=7.59 Hz, 2H) 2.52-2.57 (m, 2H) 4.35 (t, J=7.59 Hz, 2H) 5.46 (s, 2H) 6.56 (s, 1H) 7.14-7.20 (m, 2H) 7.55 (d, J=8.80 Hz, 1H) 7.58 (d, J=1.98 Hz, 1H) 7.81-7.88 (m, 1H) 8.31 (d, J=5.50 Hz, 1H) 8.59 (d, J=5.06 Hz, 1H) 8.92 (d, J=1.98 Hz, 1H)

Example 43

Synthesis of 4-(5-chloro-2-((2-oxo-1-(quinolin-6-yl)-1H-imidazo[4,5-c]pyridin-3(2H)-yl)methyl)-1H-indol-1-yl)butanenitrile (P43)

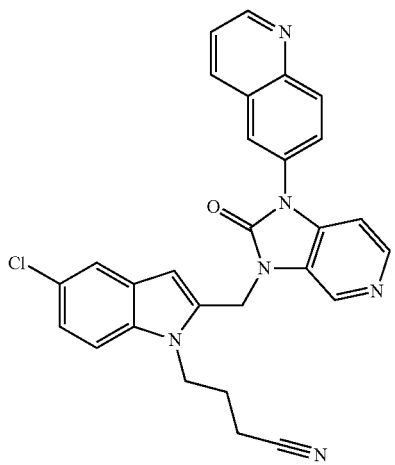 [SMILES: N#CCCCn1c(Cn2c(=O)n(-c3ccc4ncccc4c3)c3ccncc32)cc2cc(Cl)ccc21]

Compound P43 was prepared by an analogous reaction protocol as described for compound P1 using intermediate 31-c and 1-(quinolin-6-yl)-1H-imidazo[4,5-c]pyridin-2(3H)-one 20-c as starting material.

m/z=494 (M+1)$^+$ $^1$H NMR (400 MHz, DMSO-d$_6$) δ ppm 1.99 (quin, J=7.54 Hz, 2H) 2.57 (t, J=7.37 Hz, 2H) 4.19-4.51 (m, 2H) 5.48 (s, 2H) 6.59 (s, 1H) 7.18 (dd, J=8.80, 2.20 Hz, 1H) 7.28 (d, J=5.28 Hz, 1H) 7.56 (d, J=8.80 Hz, 1H) 7.58 (d, J=1.98 Hz, 1H) 7.65 (dd, J=8.36, 4.18 Hz, 1H) 8.00 (dd, J=8.91, 2.31 Hz, 1H) 8.24 (d, J=9.02 Hz, 1H) 8.27-8.31 (m, 2H) 8.50 (d, J=7.48 Hz, 1H) 8.59 (s, 1H) 9.01 (dd, J=4.18, 1.54 Hz, 1H)

Example 44

Synthesis of 3-((5-chloro-1-(4-fluorobutyl)-1H-indol-2-yl)methyl)-1-(pyridin-4-yl)-1H-imidazo[4,5-c]pyridin-2(3H)-one (P44)

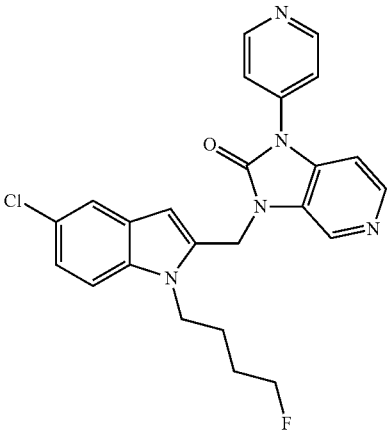 [SMILES: O=c1n(Cc2cc3cc(Cl)ccc3n2CCCCF)c2cnccc2n1-c1ccncc1]

Compound P44 was prepared by an analogous reaction protocol as described for compound P1 using intermediate 28-a and 1-(pyridin-4-yl)-1H-imidazo[4,5-c]pyridin-2(3H)-one 20-c as starting material.

m/z=451 (M+1)$^+$ $^1$H NMR (400 MHz, DMSO-d$_6$) δ ppm 1.48-1.73 (m, 4H) 4.25-4.37 (m, 3H) 4.44 (t, J=5.61 Hz, 1H) 5.43 (s, 2H) 6.66 (s, 1H) 7.15 (dd, J=8.69, 2.09 Hz, 1H) 7.40 (dd, J=5.39, 0.55 Hz, 1H) 7.52 (d, J=8.80 Hz, 1H) 7.58 (d, J=1.98 Hz, 1H) 7.70-7.76 (m, 2H) 8.30 (d, J=5.28 Hz, 1H) 8.56 (s, 1H) 8.77-8.83 (m, 2H)

Example 45

Synthesis of 4-(5-chloro-2-((1-(2-fluoro-4-methoxyphenyl)-2-oxo-1H-imidazo[4,5-c]pyridin-3(2H)-yl)methyl)-1H-indol-1-yl)butanenitrile (P45)

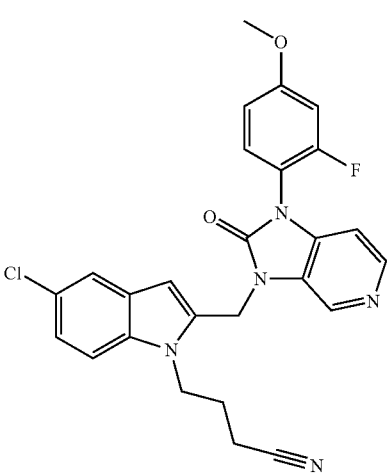 [SMILES: COc1ccc(-n2c(=O)n(Cc3cc4cc(Cl)ccc4n3CCCC#N)c3cnccc32)c(F)c1]

Compound P45 was prepared by an analogous reaction protocol as described for compound P1 using intermediate 31-c and 1-(2-fluoro-4-methoxyphenyl)-1H-imidazo[4,5-c]pyridin-2(3H)-one 46-c as starting material.

m/z=491 (M+1)+

$^1$H NMR (400 MHz, DMSO-$d_6$) δ ppm 1.79-2.03 (m, 2H) 2.52-2.56 (m, 2H) 3.87 (s, 3H) 4.22-4.45 (m, 2H) 5.41 (s, 2H) 6.51 (s, 1H) 6.91 (d, J=5.94 Hz, 1H) 6.97-7.05 (m, 1H) 7.11-7.21 (m, 2H) 7.54 (d, J=9.02 Hz, 1H) 7.57-7.63 (m, 2H) 8.23 (d, J=5.50 Hz, 1H) 8.53 (s, 1H)

Example 46

Synthesis of 4-(5-chloro-2-((2-oxo-1-p-tolyl-1H-imidazo[4,5-c]pyridin-3(2H)-yl)methyl)-1H-indol-1-yl)butanenitrile (P46)

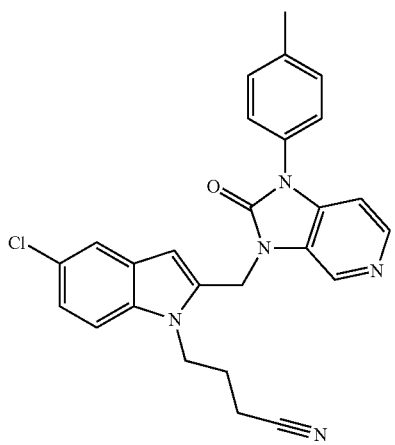 [SMILES: Cc1ccc(-n2c(=O)n(Cc3cc4cc(Cl)ccc4n3CCCC#N)c3cnccc32)cc1]

P46

Compound P46 was prepared by an analogous reaction protocol as described for compound P1 using intermediate 31-c and 1-p-tolyl-1H-imidazo[4,5-c]pyridin-2(3H)-one 51-c as starting material.

m/z=457 (M+1)+

$^1$H NMR (400 MHz, DMSO-$d_6$) δ ppm 1.94 (quin, J=7.54 Hz, 2H) 2.41 (s, 3H) 2.52-2.58 (m, 2H) 4.23-4.45 (m, 2H) 5.43 (s, 2H) 6.55 (s, 1H) 7.07 (d, J=5.50 Hz, 1H) 7.16 (dd, J=8.69, 2.09 Hz, 1H) 7.37-7.50 (m, 4H) 7.54 (d, J=8.80 Hz, 1H) 7.57 (d, J=1.98 Hz, 1H) 8.24 (d, J=5.50 Hz, 1H) 8.52 (s, 1H)

Example 47

Synthesis of 4-(5-chloro-2-((1-(2,4-dimethoxyphenyl)-2-oxo-1H-imidazo[4,5-c]pyridin-3(2H)-yl)methyl)-1H-indol-1-yl)butanenitrile (P47)

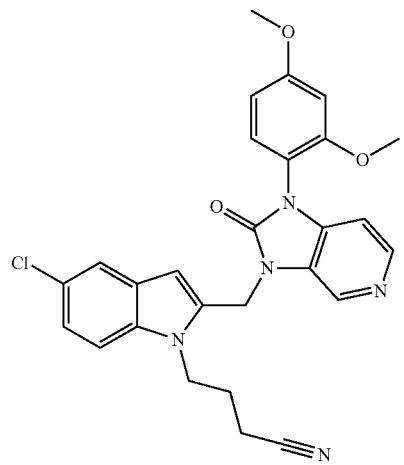 [SMILES: COc1ccc(-n2c(=O)n(Cc3cc4cc(Cl)ccc4n3CCCC#N)c3cnccc32)c(OC)c1]

P47

Compound P47 was prepared by an analogous reaction protocol as described for compound P1 using intermediate 31-c and 1-(2,4-dimethoxyphenyl)-1H-imidazo[4,5-c]pyridin-2(3H)-one 52-c as starting material.

m/z=503 (M+1)+

$^1$H NMR (400 MHz, DMSO-$d_6$) δ ppm 1.74-2.06 (m, 2H) 3.35-3.42 (m, 2H) 3.73 (s, 3H) 3.86 (s, 3H) 4.19-4.47 (m, 2H) 5.40 (s, 2H) 6.54 (s, 1H) 6.70 (dd, J=8.80, 2.64 Hz, 1H) 6.73 (d, J=4.84 Hz, 1H) 6.82 (d, J=2.64 Hz, 1H) 7.16 (dd, J=8.80, 1.98 Hz, 1H) 7.39 (d, J=8.58 Hz, 1H) 7.53 (d, J=8.80 Hz, 1H) 7.59 (d, J=2.20 Hz, 1H) 8.17 (d, J=5.28 Hz, 1H) 8.49 (s, 1H)

Example 48

Synthesis of 4-(5-chloro-2-((2-oxo-1-(pyridin-4-yl)-1H-imidazo[4,5-c]pyridin-3(2H)-yl)methyl)-1H-indol-1-yl)butanenitrile (P48)

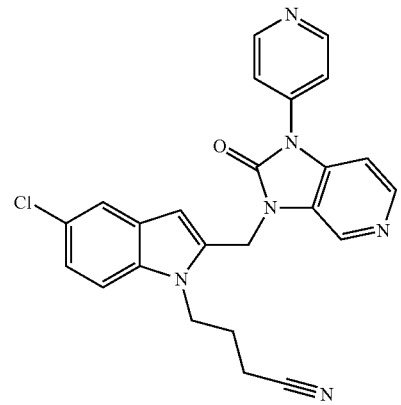

P48

Compound P48 was prepared by an analogous reaction protocol as described for compound P1 using intermediate 31-c and 1-(pyridin-4-yl)-1H-imidazo[4,5-c]pyridin-2(3H)-one 34-c as starting material.

m/z=444 (M+1)⁺

¹H NMR (400 MHz, DMSO-d₆) δ ppm 1.98 (quin, J=7.48 Hz, 2H) 2.56 (t, J=7.37 Hz, 2H) 4.27-4.42 (m, 2H) 5.45 (s, 2H) 6.54 (s, 1H) 7.17 (dd, J=8.69, 2.09 Hz, 1H) 7.41 (dd, J=5.39, 0.55 Hz, 1H) 7.51-7.59 (m, 2H) 7.71-7.77 (m, 2H) 8.32 (d, J=5.50 Hz, 1H) 8.57 (s, 1H) 8.74-8.85 (m, 2H)

Example 49

Synthesis of 4-(5-chloro-2-((2-oxo-1-(thiazol-2-yl)-1H-imidazo[4,5-c]pyridin-3(2H)-yl)methyl)-1H-indol-1-yl)butanenitrile (P49)

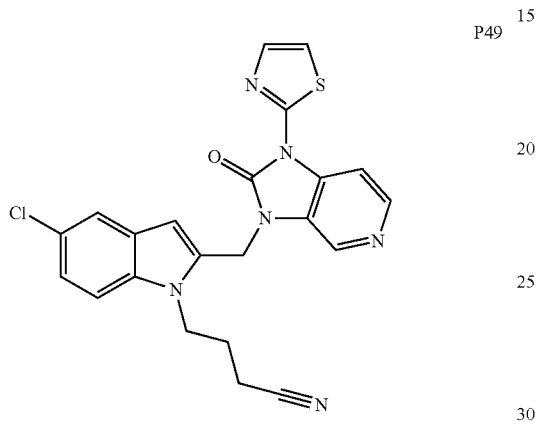

P49

Compound P49 was prepared by an analogous reaction protocol as described for compound P1 using intermediate 31-c and 1-(thiazol-2-yl)-1H-imidazo[4,5-c]pyridin-2(3H)-one 21-c as starting material.

m/z=450 (M+1)⁺

¹H NMR (400 MHz, DMSO-d₆) δ ppm 1.98 (quin, J=7.59 Hz, 2H) 2.57 (t, J=7.37 Hz, 2H) 4.36 (t, J=7.59 Hz, 2H) 5.49 (s, 2H) 6.51 (s, 1H) 7.16 (dd, J=8.69, 2.09 Hz, 1H) 7.49-7.58 (m, 2H) 7.63 (d, J=3.52 Hz, 1H) 7.79 (d, J=3.52 Hz, 1H) 8.34 (d, J=5.28 Hz, 1H) 8.47 (d, J=5.28 Hz, 1H) 8.63 (s, 1H)

Example 50

Synthesis of 4-(3-((5-chloro-1-(3-cyanopropyl)-1H-indol-2-yl)methyl)-2-oxo-2,3-dihydro-1H-imidazo[4,5-c]pyridin-1-yl)benzonitrile (P50)

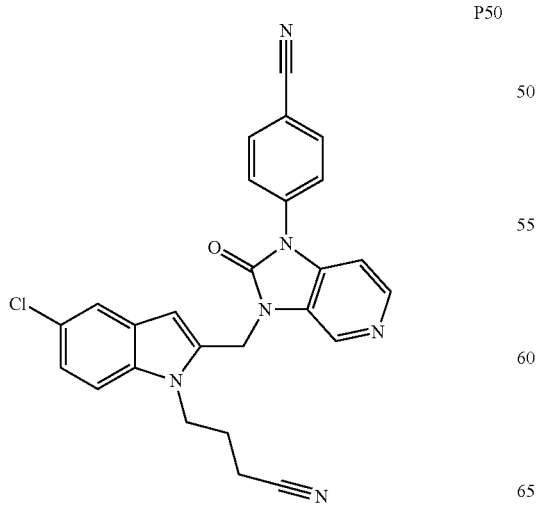

P50

Compound P50 was prepared by an analogous reaction protocol as described for compound P1 using intermediate 31-c and 4-(2-oxo-2,3-dihydro-1H-imidazo[4,5-c]pyridin-1-yl)benzonitrile 47-c as starting material.

m/z=468 (M+1)⁺

¹H NMR (400 MHz, DMSO-d₆) δ ppm 1.88-2.07 (m, 2H) 2.53-2.61 (m, 2H) 4.36 (t, J=7.70 Hz, 2H) 5.44 (s, 2H) 6.56 (s, 1H) 7.17 (dd, J=8.80, 1.98 Hz, 1H) 7.27 (d, J=5.28 Hz, 1H) 7.49-7.59 (m, 2H) 7.88 (d, J=8.58 Hz, 2H) 8.09 (d, J=8.58 Hz, 2H) 8.29 (d, J=5.50 Hz, 1H) 8.56 (s, 1H)

Example 51

Synthesis of methyl 4-(3-((5-chloro-1-(3-cyanopropyl)-1H-indol-2-yl)methyl)-2-oxo-2,3-dihydro-1H-imidazo[4,5-c]pyridin-1-yl)benzoate (P51)

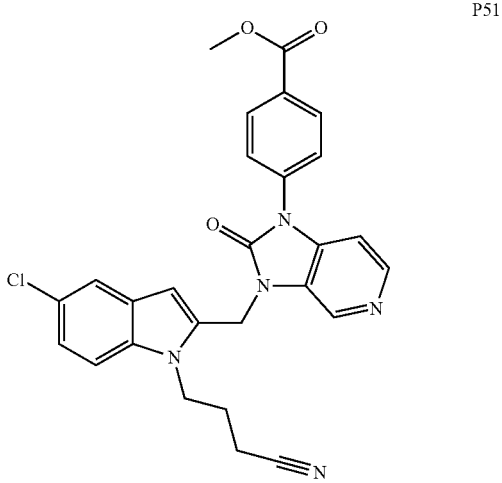

P51

Compound P51 was prepared by an analogous reaction protocol as described for compound P1 using intermediate 31-c and methyl 4-(2-oxo-2,3-dihydro-1H-imidazo[4,5-c]pyridin-1-yl)benzoate 48-c as starting material.

m/z=501 (M+1)⁺

¹H NMR (400 MHz, DMSO-d₆) δ ppm 1.89-2.13 (m, 2H) 2.58 (t, J=7.37 Hz, 2H) 3.92 (s, 3H) 4.26-4.43 (m, 2H) 5.50 (s, 2H) 6.58 (s, 1H) 7.18 (dd, J=8.69, 2.09 Hz, 1H) 7.50-7.60 (m, 3H) 7.78-7.87 (m, 2H) 8.17-8.25 (m, 2H) 8.50 (d, J=6.16 Hz, 1H) 8.79 (s, 1H)

Example 52

Synthesis of 4-(3-((5-chloro-1-(3-cyanopropyl)-1H-indol-2-yl)methyl)-2-oxo-2,3-dihydro-1H-imidazo[4,5-c]pyridin-1-yl)benzoic acid (P52)

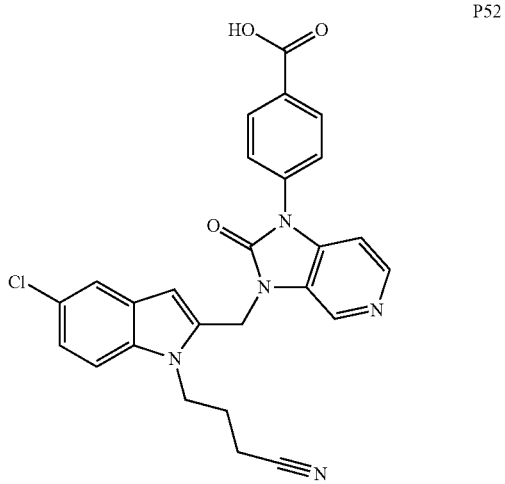

Compound P51(650 mg, 1.17 mmol) was dissolved in 75 mL THF/Water (3:1) and a excess LiOH (112 mg, 4.68 mmol, 4 eq.) was added at room temperature. After two days stirring at room temperature the solution was adjusted till pH=6 with HCl (6M in water). The solid was filtered off and further crystallized in MeOH/water to give the title compound P52 (335 mg, 60%).

m/z=487 (M+1)$^+$ $^1$H NMR (400 MHz, DMSO-d$_6$) δ ppm 1.87-2.04 (m, 2H) 2.53-2.59 (m, 2H) 4.21-4.50 (m, 2H) 5.43 (s, 2H) 6.50 (s, 1H) 7.17 (dd, J=8.58, 1.98 Hz, 1H) 7.25 (d, J=5.72 Hz, 1H) 7.44-7.62 (m, 2H) 7.77 (d, J=7.70 Hz, 2H) 8.08-8.20 (m, 2H) 8.28 (d, J=5.50 Hz, 1H) 8.55 (s, 1H)

Example 53

Synthesis of 4-(3-((5-chloro-1-(3-cyanopropyl)-1H-indol-2-yl)methyl)-2-oxo-2,3-dihydro-1H-imidazo[4,5-c]pyridin-1-yl)-N-cyclopropylbenzamide (P53)

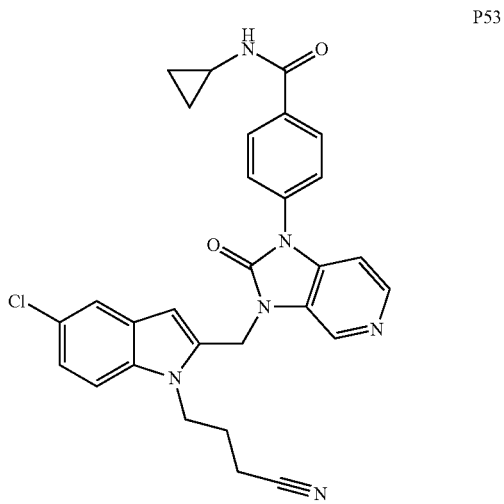

To a solution of compound P52 (220 mg, 0.439 mmol) in 40 mL DMF, was added cyclopropylamine (0.092 mL, 1.32 mmol, 3 eq.), triethylamine (0.183 mL, 1.32 mmol, 3 eq.) and diethyl cyanophosphonate (0.2 mL, 1.32 mmol, 3 eq.) at room temperature. After 16 hours the solution was concentrated in vacuo and taken up in diethyl ether.

The solid was filtered off and further crystallized in Diisopropyl ether/acetonitrile to yield the title compound P53 (160 mg, 68%) as a white solid.

m/z=526 (M+1)$^+$ $^1$H NMR (400 MHz, DMSO-d$_6$) δ ppm 0.49-0.66 (m, 2H) 0.69-0.77 (m, 2H) 1.80-2.10 (m, 2H) 2.53-2.63 (m, 2H) 2.75-3.01 (m, 1H) 4.14-4.50 (m, 2H) 5.44 (s, 2H) 6.55 (s, 1H) 7.12-7.20 (m, 2H) 7.55 (d, J=8.80 Hz, 1H) 7.57 (d, J=1.98 Hz, 1H) 7.70 (d, J=8.58 Hz, 2H) 8.03 (d, J=8.80 Hz, 2H) 8.28 (d, J=5.28 Hz, 1H) 8.55 (s, 1H) 8.58 (d, J=3.96 Hz, 1H)

Antiviral Activity

Black 96-well clear-bottom microtiter plates (Corning, Amsterdam, The Netherlands) were filled in duplicate using a customized robot system with serial 4-fold dilutions of compound in a final volume of 50 μl culture medium [RPMI medium without phenol red, 10% FBS, 0.04% gentamycin (50 mg/ml) and 0.5% DMSO]. Then, 100 μl of a HeLa cell suspension (5×10$^4$ cells/ml) in culture medium was added to each well followed by the addition of 50 μl rgRSV224 (MOI=0.02) virus in culture medium using a multidrop dispenser (Thermo Scientific, Erembodegem, Belgium). rgRSV224 virus is an engineered virus that includes an additional GFP gene (Hallak et al, 2000) and was in-licensed from the NIH (Bethesda, Md., USA). Medium, virus- and mock-infected controls were included in each test. Cells were incubated at 37° C. in a 5% CO$_2$ atmosphere. Three days post-virus exposure, viral replication was quantified by measuring GFP expression in the cells by a MSM laser microscope (Tibotec, Beerse, Belgium). The EC$_{50}$ was defined as the 50% inhibitory concentration for GFP expression. In parallel, compounds were incubated for three days in a set of white 96-well microtitier plates (Corning) and the cytotoxicity of compounds in HeLa cells was determined by measuring the ATP content of the cells using the ATPlite kit (PerkinElmer, Zaventem, Belgium) according to the manufacturer's instructions. The CC50 was defined as the 50% concentration for cytotoxicity.

REFERENCES

Hallak L K, Spillmann D, Collins P L, Peeples M E. Glycosaminoglycan sulfation requirements for respiratory syncytial virus infection. J. Virol. 740, 10508-10513 (2000).

The following compounds were prepared according to the working examples.

| | Structure | WT activity pEC$_{50}$ | Tox CC$_{50}$ |
|---|---|---|---|
| P1 | 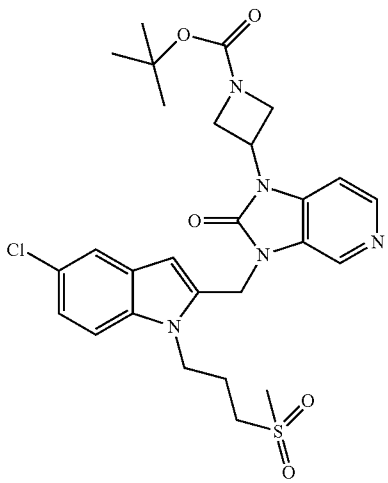 | 8.3 | 4.3 |
| P2 | 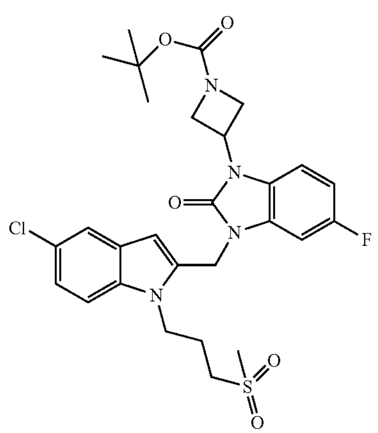 | 7.9 | 5.0 |
| P3 | (·0.17 CF$_3$COOH) | 7.0 | 4.9 |
| P4 | (·CF$_3$COOH) | 7.5 | <4.0 |
| P5 | | 8.8 | 4.0 |
| P6 | | 8.4 | <4.6 |

145
-continued
| | Structure | WT activity pEC50 | Tox CC50 |
|---|---|---|---|
| P7 | 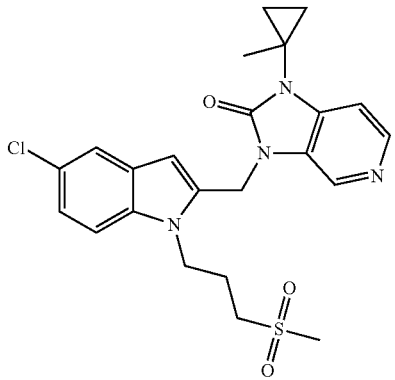 | 9.3 | 4.3 |
| P8 | 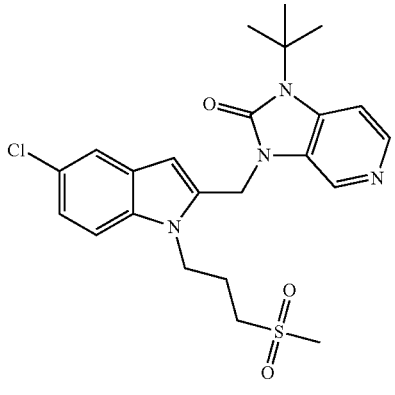 | 8.6 | 4.4 |
| P9 | 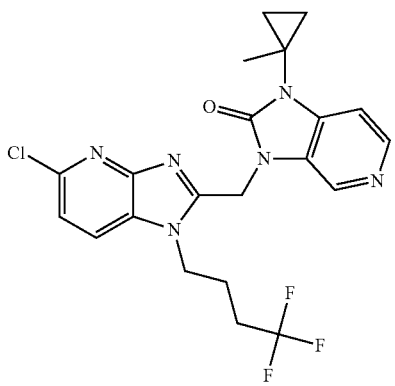 | 9.0 | <4.0 |
146
-continued
| | Structure | WT activity pEC50 | Tox CC50 |
|---|---|---|---|
| P10 | 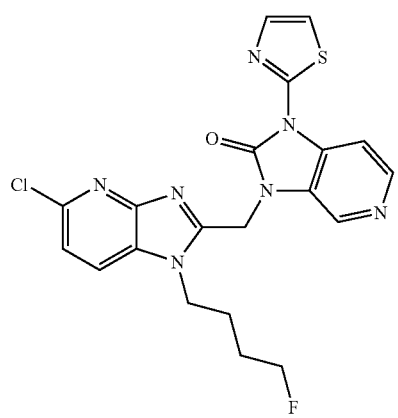 | n.d. | n.d. |
| P11 | 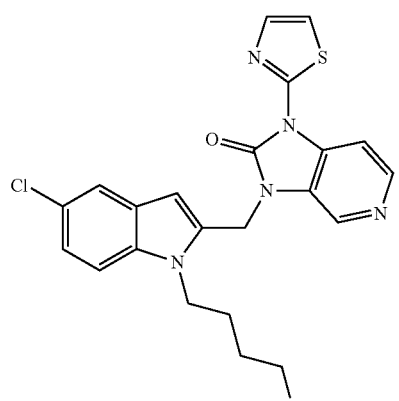 | 7.9 | <4.6 |
| P12 | 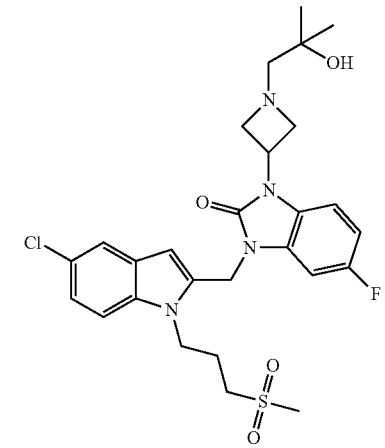 | 7.4 | 4.9 |

-continued
| Structure | WT activity pEC$_{50}$ | Tox CC$_{50}$ |
|---|---|---|
| P13 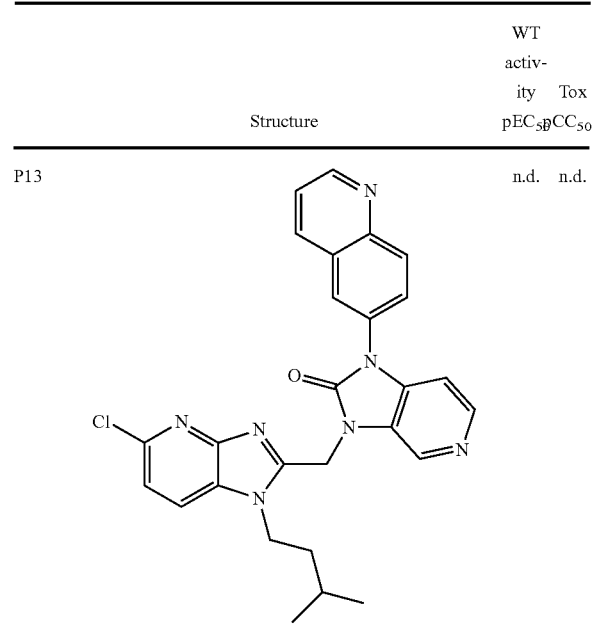 | n.d. | n.d. |
| P14 | 9.4 | 4.9 |
| P15 | 9 | <4 |
-continued
| Structure | WT activity pEC$_{50}$ | Tox CC$_{50}$ |
|---|---|---|
| P16 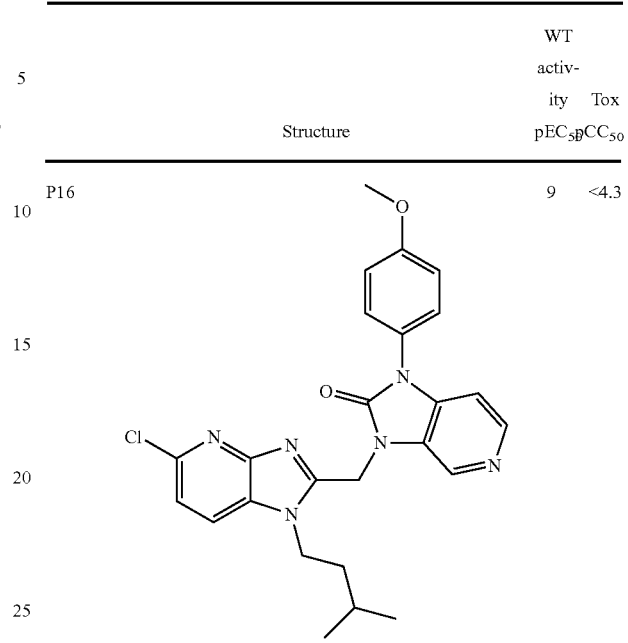 | 9 | <4.3 |
| P17 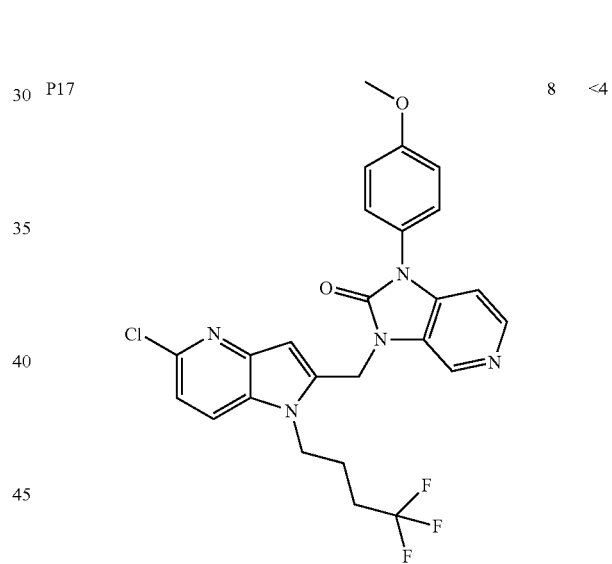 | 8 | <4 |
| P18 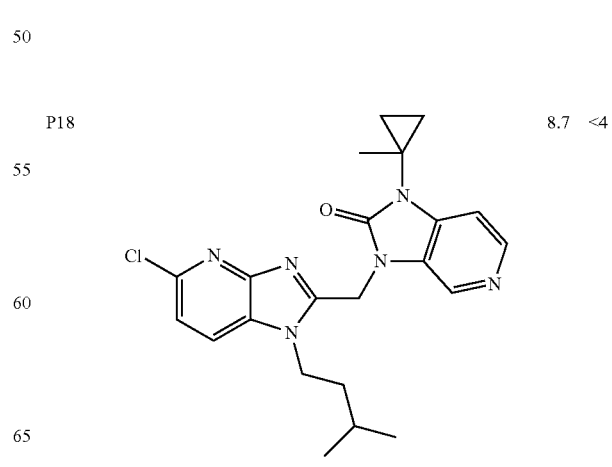 | 8.7 | <4 |

-continued

| | Structure | WT activity pEC₅₀ | Tox CC₅₀ |
|---|---|---|---|
| P19 | | 9.9 | <4 |
| P20 | | 9.4 | <4 |
| P21 | | 8.2 | <4 |
| P22 | 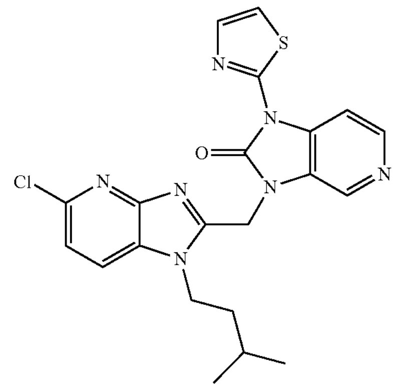 | 8.4 | 4.6 |
| P23 | 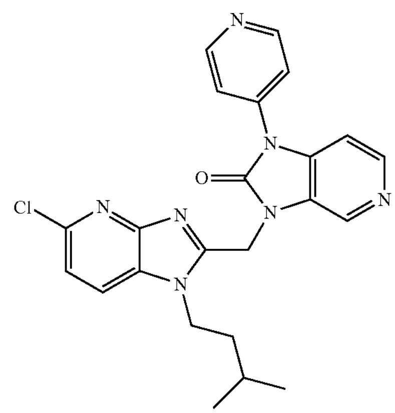 | 8.1 | <4 |
| P24 | 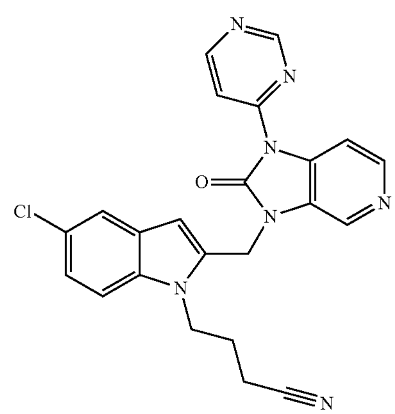 | 8 | <4.3 |
| P25 | 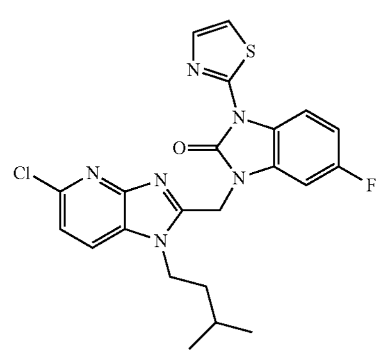 | 7.8 | <4.3 |

-continued
| | Structure | WT activity pEC50 | Tox CC50 |
|---|---|---|---|
| P26 | 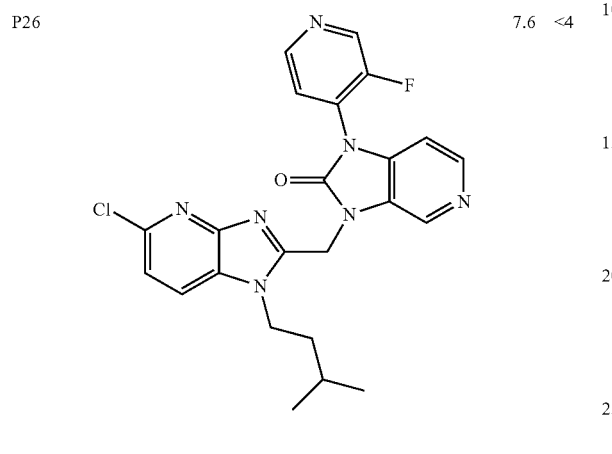 | 7.6 | <4 |
| P27 | 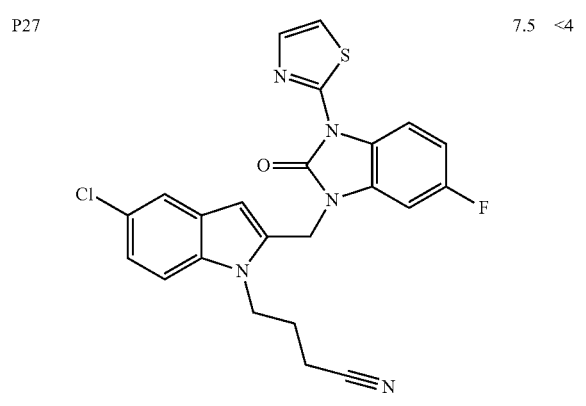 | 7.5 | <4 |
| P28 | 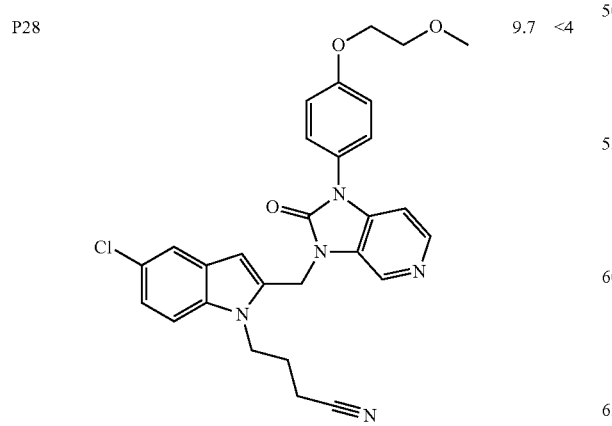 | 9.7 | <4 |
-continued
| | Structure | WT activity pEC50 | Tox CC50 |
|---|---|---|---|
| P29 | 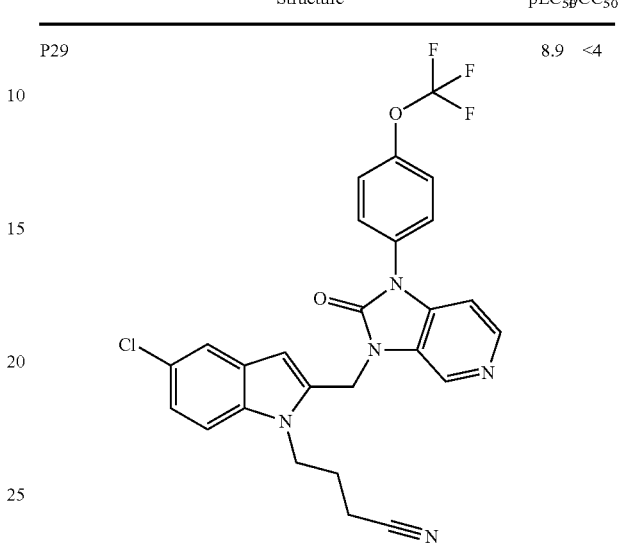 | 8.9 | <4 |
| P30 | 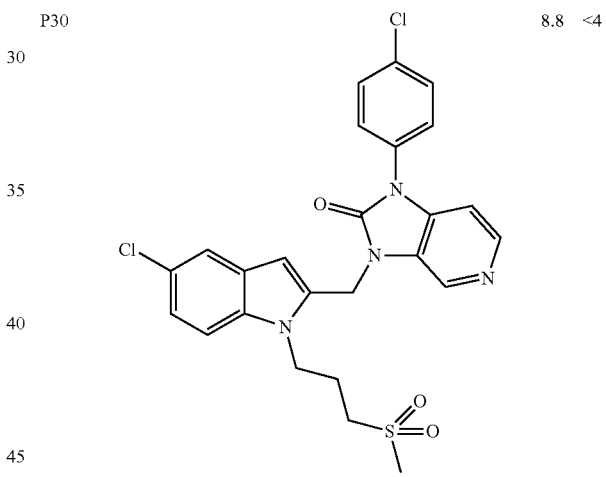 | 8.8 | <4 |
| P31 | 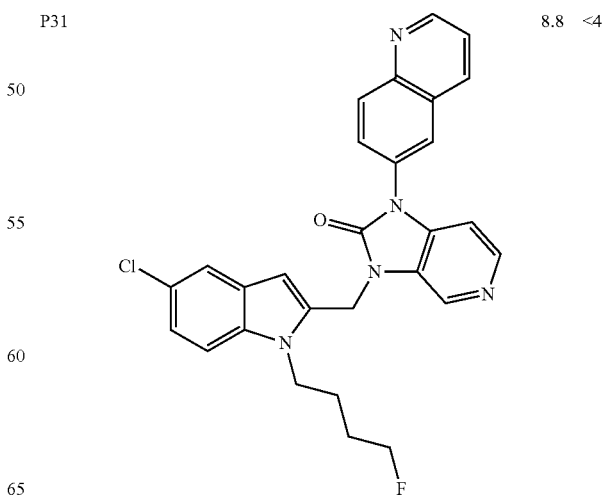 | 8.8 | <4 |

| Structure | WT activity pEC$_{50}$ | Tox CC$_{50}$ |
|---|---|---|
| P32 | 8.4 | 4.1 |
| P33 | 8 | <4 |
| P34 | 7.5 | <4 |
| P35 | 9.5 | 4.5 |
| P36 | 8.8 | 4.2 |
| P37 | 8.8 | <4 |

| Structure | WT activity pEC50 | Tox CC50 |
|---|---|---|
| P38 | 8.8 | <4 |
| P39 | 8.4 | 4.6 |
| P40 | — | <4 |
| P41 | 9.7 | <4 |
| P42 | 9.5 | <4 |
| P43 | 9.4 | <4 |

-continued
| | Structure | WT activity pEC$_{50}$ | Tox CC$_{50}$ |
|---|---|---|---|
| P44 | 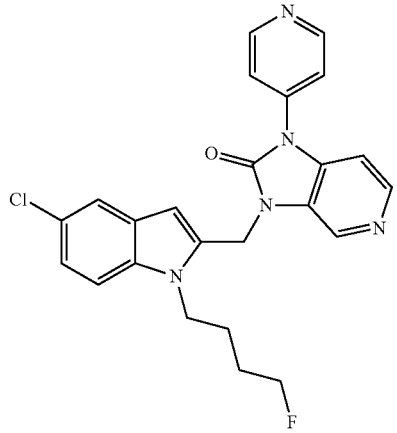 | 9 | <4 |
| P45 | 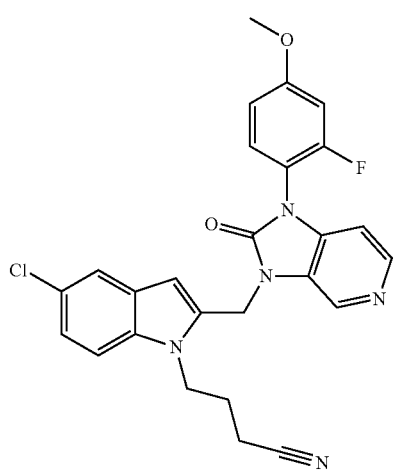 | 9 | 4.8 |
| P46 | 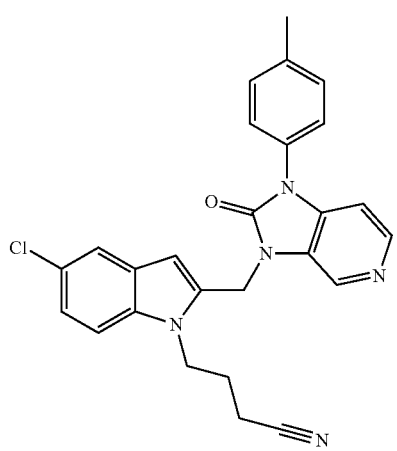 | 8.9 | <4 |
-continued
| | Structure | WT activity pEC$_{50}$ | Tox CC$_{50}$ |
|---|---|---|---|
| P47 | 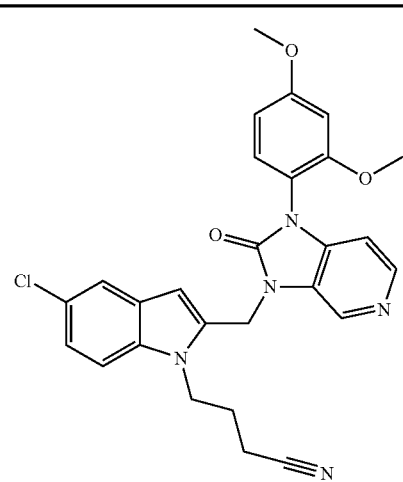 | 8.8 | <4 |
| P48 | 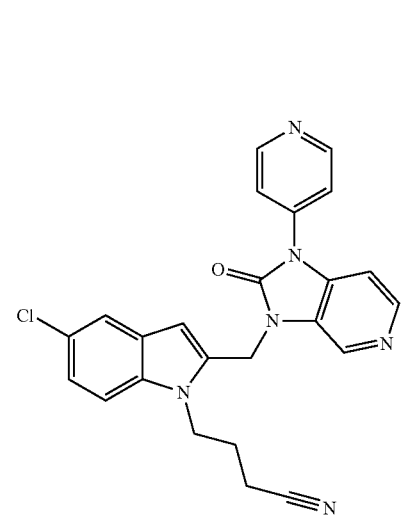 [SMILES: N#CCCCn1c(Cn2c(=O)n(-c3ccncc3)c3ccncc32)cc2cc(Cl)ccc21] | 8.6 | <4 |
| P49 | 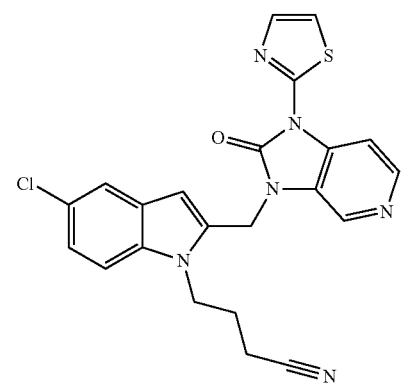 [SMILES: N#CCCCn1c(Cn2c(=O)n(-c3nccs3)c3ccncc32)cc2cc(Cl)ccc21] | 8.2 | <4.6 |

| | Structure | WT activity pEC$_{50}$ | Tox CC$_{50}$ |
|---|---|---|---|
| P50 | 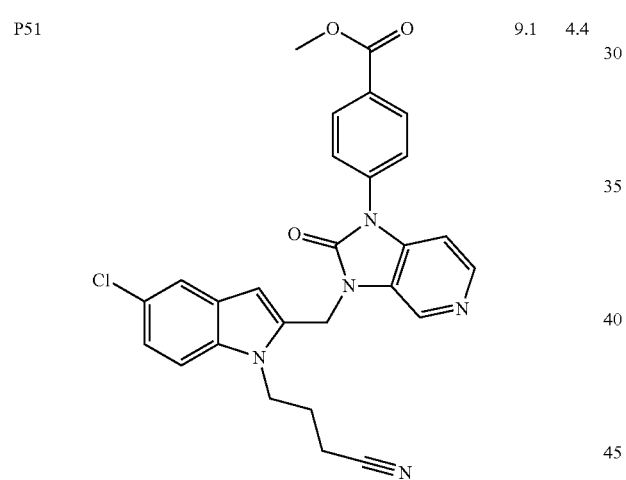 | — | — |
| P51 | 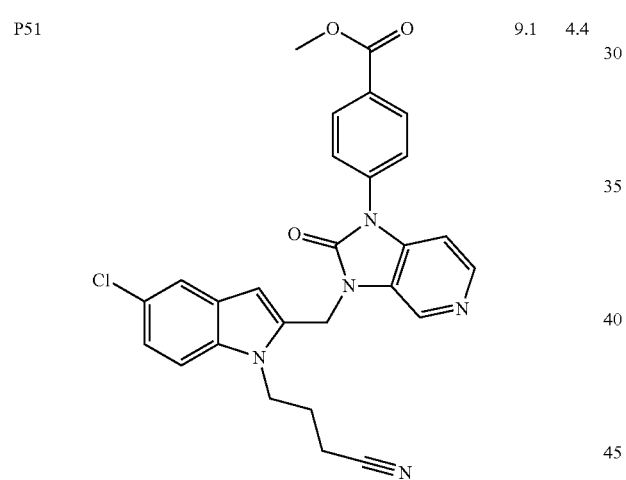 | 9.1 | 4.4 |
| P52 | 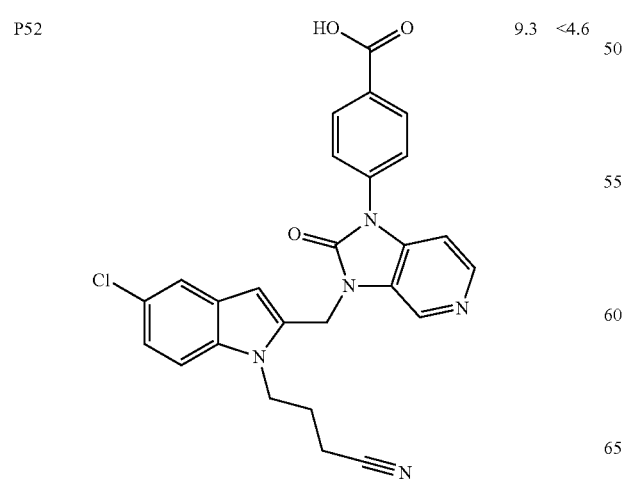 | 9.3 | <4.6 |
| P53 | 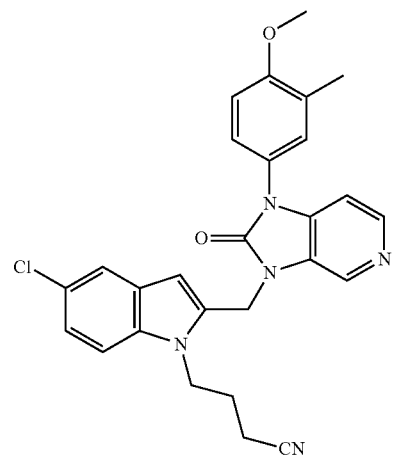 | 9.3 | 4.6 |
The following compounds can be prepared according to the working examples:
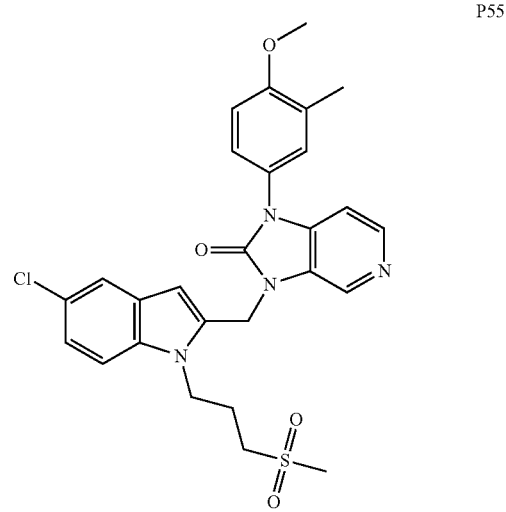
P54
P55

-continued

P56

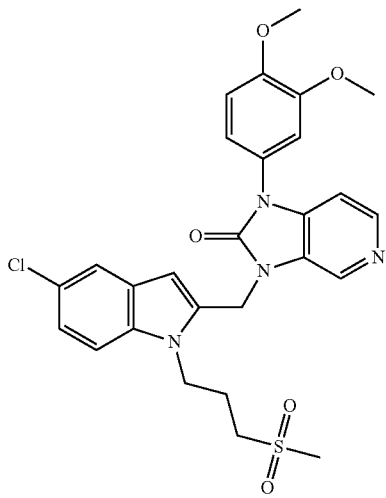

Composition Examples

"Active ingredient" (a.i.) as used throughout these examples relates to a compound of Formula (I), including any stereoisomeric form thereof, or a pharmaceutically acceptable addition salt or a solvate thereof; in particular to any one of the exemplified compounds.

Typical examples of recipes for the formulation of the invention are as follows:
1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:
1. A compound of Formula (I),

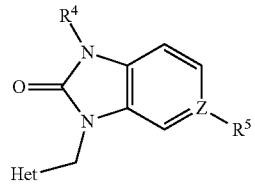

formula (I)

or a stereoisomeric form thereof, wherein
Het is a heterocycle having formula (cc):

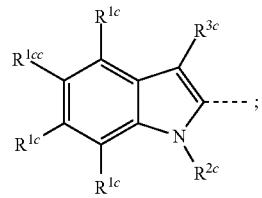

(cc)

m is an integer from 2 to 6;
wherein $R^{1cc}$ is chloro and each $R^{1c}$ is H;
$R^{3c}$ is selected from the group consisting of H, halogen, $C_1$-$C_6$alkyl, $C_3$-$C_7$cycloalkyl, $C_1$-$C_6$alkyloxy and $CO(R^{7c})$;
$R^{2c}$ is —$(CR^8R^9)_m$—$R^{10c}$;
$R^{7c}$ is selected from the group consisting of OH, O($C_1$-$C_6$alkyl), $NH_2$, $NHSO_2N(C_1$-$C_6$alkyl$)_2$, $NHSO_2NHCH_3$, $NHSO_2(C_1$-$C_6$alkyl), $NHSO_2(C_3$-$C_7$cycloalkyl), $N(C_1$-$C_6$-alkyl$)_2$, $NR^8R^9$ and $NR^9R^{10c}$;
each $R^8$ and $R^9$ are independently selected from the group consisting of H, $C_1$-$C_{10}$alkyl and $C_3$-$C_7$cycloalkyl; or $R^8$ and $R^9$ taken together form a 4 to 6 membered aliphatic ring that optionally contains one or more heteroatoms selected from the group consisting of N, S and O;
$R^{10c}$ is selected from the group consisting of H, $R^{11}$, OH, CN, F, $CF_2H$, $CF_3$, $C(=NOH)NH_2$, $CONR^8R^9$, $COOR^8$, $CONR^8SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, $SO_2R^8$ and a 4 to 6 membered saturated ring containing one oxygen atom;
$R^{11}$ is selected from the group consisting of $C_1$-$C_6$ alkyl, $C_3$-$C_7$cycloalkyl, phenyl, pyridinyl and pyrazolyl; each optionally substituted with one or more substituents each independently selected from the group consisting of $CF_3$, $CH_3$, $OCH_3$, $OCF_3$ and halogen;
$R^4$ is selected from the group consisting of tert-butyl, $Het^1$, aryl, $Het^2$, $CH(CH_3)(CF_3)$, and $C_3$-$C_7$cycloalkyl substituted with one or more substituents selected from the group consisting of halo and $C_1$-$C_4$alkyl;
aryl represents phenyl or naphthalenyl; wherein said phenyl or naphthalenyl is optionally substituted with one or more substituents each independently selected from the group consisting of halo, $C_1$-$C_4$alkyloxy, $C_1$-$C_4$alkyl, OH, CN, $CF_2H$, $CF_3$, $CF_3O$, $CONR^8R^9$, $COOR^8$, $CON(R^8)SO_2R^9$, $CON(R^8)SO_2N(R^8R^9)$, $NR^8R^9$, $NR^8COOR^9$, $OCOR^8$, $NR^8SO_2R^9$, $SO_2NR^8R^9$, SO$_2$R$^8$, OCONR$^8$R$^9$, OCONR$^8$R$^{12}$, N(R$^8$)CON(R$^8$R$^9$), N(R$^8$)COOR$^{12}$ and C$_{1-4}$alkyloxyC$_{1-4}$alkyloxy;

Het$^1$ represents a 4 to 6 membered saturated ring containing one N atom, optionally being substituted with one or more substituents each independently selected from the group consisting of halo, C$_1$-C$_4$alkyloxy, SO$_2$R$^8$, C$_1$-C$_4$alkylcarbonyl, CO(aryl), COHet$^2$, C$_1$-C$_4$alkyloxycarbonyl, pyridinyl, CF$_3$, SO$_2$N(C$_1$-C$_4$alkyl)$_2$, SO$_2$NH(C$_1$-C$_4$alkyl), (C=O)NH(C$_{1-4}$alkyl), (C=S)NH(C$_{1-4}$alkyl), C$_1$-C$_4$alkyl and C$_1$-C$_4$alkyl substituted with one hydroxy; or Het$^1$ represents a 4 to 6 membered saturated ring containing one O atom, substituted with one or more substituents each independently selected from the group consisting of halo, C$_1$-C$_4$alkyloxy, CF$_3$, NH(C=O)(C$_{1-4}$alkyl), (C=O)NH(C$_{1-4}$alkyl) and C$_1$-C$_4$alkyl; or Het$^1$ represents a bicyclic 7 to 11 membered non-aromatic heterocycle containing one or two heteroatoms each independently selected from the group consisting of O, S and N, optionally substituted with one or more substituents each independently selected from the group consisting of halo, C$_1$-C$_4$alkyloxy, SO$_2$R$^8$, C$_1$-C$_4$alkylcarbonyl, CO(aryl), COHet$^2$, C$_1$-C$_4$alkyloxycarbonyl, pyridinyl, CF$_3$, SO$_2$N(C$_1$-C$_4$alkyl)$_2$, SO$_2$NH(C$_1$-C$_4$alkyl), (C=O)NH(C$_{1-4}$alkyl), (C=S)NH(C$_{1-4}$alkyl), C$_1$-C$_4$alkyl and C$_1$-C$_4$alkyl substituted with one hydroxy;

Het$^2$ represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N; said Het$^2$ optionally being substituted with one or more substituents each independently selected from the group consisting of halo, C$_1$-C$_4$alkyloxy, C$_1$-C$_4$alkyl, OH, CN, CF$_2$H, CF$_3$, CONR$^8$R$^9$, COOR$^8$, CON(R$^8$)SO$_2$R$^9$, CON(R$^8$)SO$_2$N(R$^8$R$^9$), NR$^8$R$^9$, NR$^8$COOR$^9$, OCOR$^8$, NR$^8$SO$_2$R$^9$, SO$_2$NR$^8$R$^9$, SO$_2$R$^8$, OCONR$^8$R$^9$, OCONR$^8$R$^{12}$, N(R$^8$)CON(R$^8$R$^9$), and N(R$^8$)COOR$^{12}$;

Z is N; and R$^5$ is absent; and pharmaceutically acceptable addition salts thereof.

2. The compound according to claim 1, wherein
Het is a heterocycle having formula (cc);
each R$^8$ and R$^9$ are independently chosen from the group consisting of H and C$_1$-C$_{10}$alkyl;
R$^{3c}$ is selected from the group consisting of H, halogen and C$_1$-C$_6$alkyl;
R$^{10c}$ is selected from the group consisting of H, C$_1$-C$_6$alkyl, OH, CN, F, CF$_2$H, CF$_3$, NR$^8$R$^9$, SO$_2$NR$^8$R$^9$ and SO$_2$R$^8$;
aryl represents phenyl or naphthalenyl; said aryl optionally being substituted with one or more substituents each independently selected from the group consisting of halo, C$_1$-C$_4$alkyloxy, C$_1$-C$_4$alkyl, OH, CN, CF$_2$H, CF$_3$, CONR$^8$R$^9$, NR$^8$R$^9$, NR$^8$COOR$^9$, SO$_2$NR$^8$R$^9$, SO$_2$R$^8$, OCONR$^8$R$^9$, OCONR$^8$R$^{12}$ and N(R$^8$)COOR$^{12}$;

Het$^1$ represents a 4 to 6 membered saturated ring containing one N atom, optionally being substituted with one or more substituents each independently selected from the group consisting of halo, C$_1$-C$_4$alkyloxy, CF$_3$, SO$_2$R$^8$, C$_1$-C$_4$alkylcarbonyl, C$_1$-C$_4$alkyloxycarbonyl, pyridinyl, SO$_2$N(C$_1$-C$_4$alkyl)$_2$, SO$_2$NH(C$_1$-C$_4$alkyl), (C=O)NH(C$_{1-4}$alkyl), (C=S)NH(C$_{1-4}$alkyl), C$_1$-C$_4$alkyl and C$_1$-C$_4$alkyl substituted with one hydroxy; or Het$^1$ represents a 4 to 6 membered saturated ring containing one O atom, substituted with one or more substituents each independently selected from the group consisting of halo, C$_1$-C$_4$alkyloxy, CF$_3$, NH(C=O)(C$_{1-4}$alkyl), (C=O)NH(C$_{1-4}$alkyl) and C$_1$-C$_4$alkyl; and Het$^2$ represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N; said Het$^2$ optionally being substituted with one or more substituents each independently selected from the group consisting of halo, C$_1$-C$_4$alkyloxy, C$_1$-C$_4$alkyl, OH, CN, CF$_2$H, CF$_3$, CONR$^8$R$^9$, NR$^8$R$^9$, NR$^8$COOR$^9$, SO$_2$NR$^8$R$^9$, SO$_2$R$^8$, OCONR$^8$R$^9$, OCONR$^8$R$^{12}$ and N(R$^8$)COOR$^{12}$;

and a pharmaceutically acceptable addition salt thereof.

3. The compound according to claim 1, wherein R$^4$ is selected from the group consisting of Het$^1$, aryl, Het$^2$, and C$_3$-C$_7$cycloalkyl substituted with one or more substituents selected from the group consisting of halo and C$_1$-C$_4$alkyl.

4. The compound according to claim 3 wherein R$^4$ is Het$^1$.

5. The compound according to claim 3 wherein R$^4$ is Het$^2$.

6. The compound according to claim 3 wherein R$^4$ is aryl.

7. The compound according to claim 6 wherein aryl is phenyl optionally being substituted with one or more substituents each independently selected from the group consisting of halo, C$_1$-C$_4$alkyloxy, C$_1$-C$_4$alkyl, CN, CONR$^8$R$^9$, COOR$^8$ and SO$_2$R$^8$.

8. The compound according to claim 7 wherein aryl is phenyl substituted with two substituents each independently selected from the group consisting of halo, C$_1$-C$_4$alkyloxy and C$_1$-C$_4$alkyl.

9. The compound according to claim 8 wherein Het is of formula (c-1a)

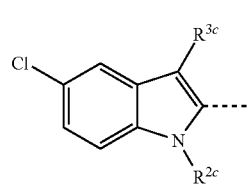

(c-1a)

wherein R$^{3c}$ is H and R$^{2c}$ is —(CR$^8$R$^9$)$_m$—R$^{10c}$; wherein R$^8$ and R$^9$ are each H; m is 3; and R$^{10c}$ represents CN or SO$_2$CH$_3$.

10. The compound according to claim 1 wherein aryl is phenyl optionally being substituted with one or more substituents each independently selected from the group consisting of halo, C$_1$-C$_4$alkyloxy, C$_1$-C$_4$alkyl, CN, CONR$^8$R$^9$, COOR$^8$, SO$_2$R$^8$, CF$_3$O and C$_{1-4}$alkyloxyC$_{1-4}$alkyloxy.

11. The compound according to claim 1 wherein the compound is

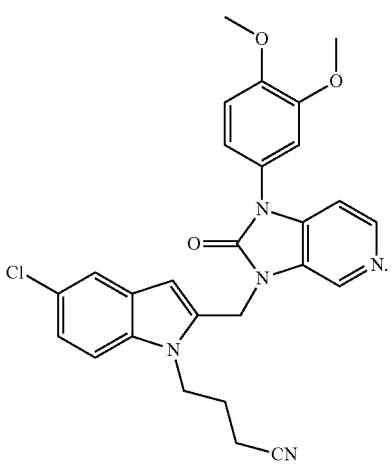 [SMILES: COc1ccc(-n2c(=O)n(Cc3cc4cc(Cl)ccc4n3CCCC#N)c3cnccc32)cc1OC]

12. A pharmaceutical composition comprising a pharmaceutically acceptable carrier, and as active ingredient a therapeutically effective amount of a compound as defined in claim 1.

13. A method of treating a respiratory syncytial viral (RSV) infection comprising administering to a subject in need of treatment an anti-virally effective amount of a compound as claimed in claim 1.

14. A compound selected from the group consisting of:
tert-Butyl-3-(3-((5-chloro-1-(3-(methyl-sulfonyl)propyl)-1H-indol-2-yl)methyl)-2-oxo-2;3-dihydro-1H-imidazo[4;5-c]pyridin-1-yl)azetidine-1-carboxylate;
tert-Butyl 3-(3-((5-chloro-1-(3-(methylsulfonyl)propyl)-1H-indol-2-yl)methyl)-5-fluoro-2-oxo-2;3-dihydro-1H-benzo[d]imidazol-1-yl)azetidine-1-carboxylate;
1-(Azetidin-3-yl)-3-((5-chloro-1-(3-(methylsulfonyl)propyl)-1H-indol-2-yl)methyl)-5-fluoro-1H-benzo[d]imidazol-2(3H)-one;
1-(Azetidin-3-yl)-3-((5-chloro-1-(3-(methylsulfonyl)propyl)-1H-indol-2-yl)methyl)-1H-imidazo[4;5-c]pyridin-2(3H)-one;
3-((5-Chloro-1-(3-(methylsulfonyl)propyl)-1H-indol-2-yl)methyl)-1-(1-(methylsulfonyl)azetidin-3-yl)-1H-imidazo[4;5-c]pyridin-2(3H)-one;
1-(1-Acetylazetidin-3-yl)-3-((5-chloro-1-(3-(methylsulfonyl)propyl)-1H-indol-2-yl)methyl)-1H-imidazo[4;5-c]pyridin-2(3H)-one;
3-((5-Chloro-1-(3-(methylsulfonyl)propyl)-1H-indol-2-yl)methyl)-1-(1-methylcyclopropyl)-1H-imidazo[4;5-c]pyridin-2(3H)-one;
1-tert-Butyl-3-((5-chloro-1-(3-(methylsulfonyl)propyl)-1H-indol-2-yl)methyl)-1H-imidazo[4;5-c]pyridin-2(3H)-one;
3-((5-Chloro-1-(4-fluorobutyl)-1H-indol-2-yl)methyl)-1-(thiazol-2-yl)-1H-imidazo[4;5-c]pyridin-2(3H)-one;
3-((5-Chloro-1-(3(methylsulfonyl)propyl)-1H-indol-2-yl)methyl)-5-fluoro-1-(1-(2-hydroxy-2-methylpropyl)azetidin-3-yl)-1H-benzo[d]imidazol-2(3H)-one;
4-(5-Chloro-2-((1-(4-methoxyphenyl)-2-oxo-1H-imidazo[4;5-c]pyridin-3(2H)-yl)methyl)-1H-indol-1-yl)butanenitrile;
4-(5-Chloro-2-((1-(3-fluoro-4-methoxyphenyl)-2-oxo-1H-imidazo[4;5-c]pyridin-3(2H)-yl)methyl)-1H-indol-1-yl)butanenitrile;
4-(5-Chloro-2-((1-(3;4-dimethoxyphenyl)-2-oxo-1H-imidazo[4;5-c] pyridin-3(2H)-yl)methyl)-1H-indol-1-yl)butanenitrile;
4-(5-Chloro-2-((1-(4-methoxy-2-methylphenyl)-2-oxo-1H-imidazo[4;5-c] pyridin-3(2H)-yl)methyl)-1H-indol-1-yl)butanenitrile;
4-(5-Chloro-2-((2-oxo-1-(pyrimidin-2-yl)-1H-imidazo[4;5-c]pyridin-3(2H)-yl)methyl)-1H-indol-1-yl)butanenitrile;
4-(5-Chloro-2-((2-oxo-1-(pyrimidin-4-yl)-1H-imidazo[4;5-c]pyridin-3(2H)-yl)methyl)-1H-indol-1-yl)butanenitrile;
4-(5-Chloro-2-((6-fluoro-2-oxo-3-(thiazol-2-yl)-2;3-dihydro-1H-benzo[d]imidazol-1-yl)methyl)-1H-indol-1-yl)butanenitrile;
4-(5-Chloro-2-((1-(4-(2-methoxyethoxy)phenyl)-2-oxo-1H-imidazo[4;5-c] pyridin-3(2H)-yl)methyl)-1H-indol-1-yl)butanenitrile;
4-(5-Chloro-2-((2-oxo-1-(4-(trifluoromethoxy)phenyl)-1H-imidazo[4;5-c]pyridin-3(2H)-yl)methyl)-1H-indol-1-yl)butanenitrile;
3-((5-Chloro-1-(3-(methylsulfonyl)propyl)-1H-indol-2-yl)methyl)-1-(4-chlorophenyl)-1H-imidazo[4;5-c]pyridin-2(3H)-one;
3-((5-Chloro-1-(4-fluorobutyl)-1H-indol-2-yl)methyl)-1-(quinolin-6-yl)-1H-imidazo[4;5-c]pyridin-2(3H)-one;
3-((5-Chloro-1-(4-fluorobutyl)-1H-indol-2-yl)methyl)-1-(4-methoxy-phenyl)-1H-imidazo[4;5-c]pyridin-2(3H)-one;
4-(5-Chloro-2-((1-(1-methyl-1H-imidazol-2-yl)-2-oxo-1H-imidazo[4;5-c] pyridin-3(2H)-yl)methyl)-1H-indol-1-yl)butanenitrile;
3-((5-Chloro-1-(4-fluorobutyl)-1H-indol-2-yl)methyl)-1-(4-chlorophenyl)-1H-imidazo[4;5-c]pyridin-2(3H)-one;
3-((5-Chloro-1-(3-(methylsulfonyl)propyl)-1H-indol-2-yl)methyl)-1-(4-methoxyphenyl)-1H-imidazo[4;5-c]pyridin-2(3H)-one;
4-(5-Chloro-2-((1-(1-methyl-1H-pyrazol-3-yl)-2-oxo-1H-imidazo[4;5-c] pyridin-3(2H)-yl)methyl)-1H-indol-1-yl)butanenitrile;
4-(5-Chloro-2-((1-(oxazol-2-yl)-2-oxo-1H-imidazo[4;5-c]pyridin-3(2H)-yl)methyl)-1H-indol-1-yl)butanenitrile;
3-((5-Chloro-1-(4-fluorobutyl)-1H-indol-2-yl)methyl)-1-(1-methyl-1H-pyrazol-3-yl)-1H-imidazo[4;5-c]pyridin-2(3H)-one;
4-(5-Chloro-2-((1-(4-chlorophenyl)-2-oxo-1H-imidazo[4;5-c]pyridin-3(2H)-yl)methyl)-1H-indol-1-yl)butanenitrile;
4-(5-Chloro-2-((6-fluoro-2-oxo-3-(pyridin-4-yl)-2;3-dihydro-1H-benzo[d]imidazol-1-yl)methyl)-1H-indol-1-yl)butanenitrile;
4-(5-Chloro-2-((1-(4-(methylsulfonyl)phenyl)-2-oxo-1H-imidazo[4;5-c] pyridin-3(2H)-yl)methyl)-1H-indol-1-yl)butanenitrile;
4-(5-Chloro-2-((1-(3-fluoropyridin-4-yl)-2-oxo-1H-imidazo[4;5-c]pyridin-3(2H)-yl)methyl)-1H-indol-1-yl)butanenitrile;
4-(5-Chloro-2-((2-oxo-1-(quinolin-6-yl)-1H-imidazo[4;5-c]pyridin-3(2H)-yl)methyl)-1H-indol-1-yl)butanenitrile;
3-((5-Chloro-1-(4-fluorobutyl)-1H-indol-2-yl)methyl)-1-(pyridin-4-yl)-1H-imidazo[4;5-c]pyridin-2(3H)-one;
4-(5-Chloro-2-((1-(2-fluoro-4-methoxyphenyl)-2-oxo-1H-imidazo[4;5-c]pyridin-3(2H)-yl)methyl)-1H-indol-1-yl)butanenitrile;
4-(5-Chloro-2-((2-oxo-1-p-tolyl-1H-imidazo[4;5-c]pyridin-3(2H)-yl)methyl)-1H-indol-1-yl)butanenitrile;

4-(5-Chloro-2-((1-(2;4-dimethoxyphenyl)-2-oxo-1H-imidazo[4;5-c]pyridin-3(2H)-yl)methyl)-1H-indol-1-yl)butanenitrile;

4-(5-Chloro-2-((2-oxo-1-(pyridin-4-yl)-1H-imidazo[4;5-c]pyridin-3(2H)-yl)methyl)-1H-indol-1-yl)butanenitrile;

4-(5-Chloro-2-((2-oxo-1-(thiazol-2-yl)-1H-imidazo[4;5-c]pyridin-3(2H)-yl)methyl)-1H-indol-1-yl)butanenitrile;

4-(3-((5-Chloro-1-(3-cyanopropyl)-1H-indol-2-yl)methyl)-2-oxo-2;3-dihydro-1H-imidazo[4;5-c]pyridin-1-yl)benzonitrile;

Methyl 4-(3-((5-chloro-1-(3-cyanopropyl)-1H-indol-2-yl)methyl)-2-oxo-2;3-dihydro-1H-imidazo[4;5-c]pyridin-1-yl)benzoate;

4-(3-((5-Chloro-1-(3-cyanopropyl)-1H-indol-2-yl)methyl)-2-oxo-2;3-dihydro-1H-imidazo[4;5-c]pyridin-1-yl)benzoic acid;

4-(3-((5-Chloro-1-(3-cyanopropyl)-1H-indol-2-yl)methyl)-2-oxo-2;3-dihydro-1H-imidazo[4;5-c]pyridin-1-yl)-N-cyclopropylbenzamide;

4-[5-Chloro-2-[[1-(4-methoxy-3-methyl-phenyl)-2-oxo-imidazo[4;5-c]pyridin-3-yl]methyl]indol-1-yl]butanenitrile;

3-[[5-Chloro-1-(3-methylsulfonylpropyl)indol-2-yl]methyl]-1-(4-methoxy-3-methyl-phenyl)imidazo[4;5-c]pyridin-2-one;

3-[[5-Chloro-1-(3-methylsulfonylpropyl)indol-2-yl]methyl]-1-(3;4-dimethoxyphenyl)imidazo[4;5-c]pyridin-2-one; and pharmaceutically acceptable addition salts thereof.

15. A method of treating a respiratory syncytial viral (RSV) infection comprising administering to a subject in need of treatment an anti-virally effective amount of a compound as claimed in claim 3.

16. A method of treating a respiratory syncytial viral (RSV) infection comprising administering to a subject in need of treatment an anti-virally effective amount of a compound as claimed in claim 9.

17. A method of treating a respiratory syncytial viral (RSV) infection comprising administering to a subject in need of treatment an anti-virally effective amount of a compound as claimed in claim 11.

18. A method of treating a respiratory syncytial viral (RSV) infection comprising administering to a subject in need of treatment an anti-virally effective amount of a compound as claimed in claim 14.

* * * * *